(12) United States Patent
Velten et al.

(10) Patent No.: US 11,827,616 B2
(45) Date of Patent: Nov. 28, 2023

(54) HETEROCYCLIC COMPOUNDS AS PESTICIDES

(71) Applicant: Discovery Purchaser Corporation, Wilmington, DE (US)

(72) Inventors: Robert Velten, Langenfeld (DE); Alexander Arlt, Cologne (DE); Niels Boehnke, Berlin (DE); Kerstin Ilg, Cologne (DE); Sebastian Horstmann, Leverkusen (DE); Arnoldus Vermeer, Monheim (DE); Karin Horn, Duesseldorf (DE); Ulrich Goergens, Ratingen (DE); Daniela Portz, Vettweiss (DE); Andreas Turberg, Haan (DE)

(73) Assignee: DISCOVERY PURCHASER CORPORATION, Wilmington, DE (US)

( * ) Notice: Subject to any disclaimer, the term of this patent is extended or adjusted under 35 U.S.C. 154(b) by 612 days.

(21) Appl. No.: 16/609,754

(22) PCT Filed: Apr. 26, 2018

(86) PCT No.: PCT/EP2018/060678
§ 371 (c)(1),
(2) Date: Oct. 31, 2019

(87) PCT Pub. No.: WO2018/202524
PCT Pub. Date: Nov. 8, 2018

(65) Prior Publication Data
US 2020/0062729 A1 Feb. 27, 2020

(51) Int. Cl.
| | | |
|---|---|---|
| *A01N 43/40* | (2006.01) | |
| *A01N 43/60* | (2006.01) | |
| *C07D 213/64* | (2006.01) | |
| *A61K 31/4545* | (2006.01) | |
| *A61K 31/44* | (2006.01) | |
| *A61K 31/496* | (2006.01) | |
| *C07D 405/14* | (2006.01) | |
| *A61K 31/4436* | (2006.01) | |
| *A61K 31/443* | (2006.01) | |
| *A61K 31/444* | (2006.01) | |
| *A61K 31/4439* | (2006.01) | |
| *C07D 401/12* | (2006.01) | |
| *C07D 405/12* | (2006.01) | |
| *C07D 409/12* | (2006.01) | |
| *A01P 7/04* | (2006.01) | |
| *A61P 33/14* | (2006.01) | |
| *A01P 7/00* | (2006.01) | |
| *A61P 33/00* | (2006.01) | |
| *C07D 401/04* | (2006.01) | |

(52) U.S. Cl.
CPC .......... *C07D 401/04* (2013.01); *A01N 43/40* (2013.01); *A01N 43/60* (2013.01); *A01P 7/00* (2021.08); *A01P 7/04* (2021.08); *A61K 31/44* (2013.01); *A61K 31/443* (2013.01); *A61K 31/444* (2013.01); *A61K 31/4436* (2013.01); *A61K 31/4439* (2013.01); *A61K 31/4545* (2013.01); *A61K 31/496* (2013.01); *A61P 33/00* (2018.01); *A61P 33/14* (2018.01); *C07D 213/64* (2013.01); *C07D 401/12* (2013.01); *C07D 405/12* (2013.01); *C07D 405/14* (2013.01); *C07D 409/12* (2013.01)

(58) Field of Classification Search
CPC .. C07D 401/04; C07D 213/64; C07D 401/12; C07D 405/12; C07D 409/12; A01N 43/40; A01N 43/60; A61P 33/00; A61P 33/14
See application file for complete search history.

(56) References Cited

U.S. PATENT DOCUMENTS 7,247,756 B2 * 7/2007 Theodoridis .......... C07C 217/58
568/634
8,946,234 B2 2/2015 Maue et al.
(Continued)

FOREIGN PATENT DOCUMENTS

CN 101337937 A 1/2009
CN 101337940 A 1/2009
(Continued)

OTHER PUBLICATIONS

PCT International Search Report for PCT/EP2018/060678, dated Jul. 12, 2018.
Baur, et al., "Polydisperse Ethoxylated Fatty Alcohol Surfactants as Accelerators of Cuticular Penetration. 1. Effects of Ethoxy Chain Length and the Size of the Penetrants," Pesticide Science, (1997), vol. 51: 131-152.
(Continued)

*Primary Examiner* — John Pak
(74) *Attorney, Agent, or Firm* — MCBEE MOORE & VANIK IP, LLC; Susan McBee; Kurt Buechle

(57) ABSTRACT

The invention relates to novel compounds of the formula (I)

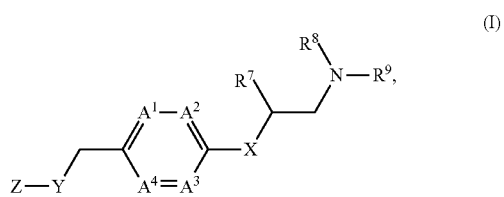

in which Z, Y, $A^1$, $A^2$, $A^3$, $A^4$, X, $R^7$, $R^8$ and $R^9$ have the meanings mentioned above,
and processes and intermediates for the preparation thereof, and their use for controlling animal pests, in particular insects.

21 Claims, No Drawings

(56) References Cited

U.S. PATENT DOCUMENTS

| | | |
|---|---|---|
| 2003/0092739 A1 | 5/2003 | Yeh et al. |
| 2006/0052599 A1 | 3/2006 | Ishibashi et al. |
| 2014/0275503 A1 | 9/2014 | Giampietro et al. |
| 2015/0099766 A1 | 4/2015 | Maue et al. |
| 2015/0238641 A1 | 8/2015 | Lin et al. |
| 2015/0259317 A1 | 9/2015 | Fliri et al. |

FOREIGN PATENT DOCUMENTS

| | | | |
|---|---|---|---|
| CN | 101715774 A | | 6/2010 |
| CN | 102046601 | * | 5/2011 |
| CN | 102391261 A | | 3/2012 |
| CN | 103109816 A | | 5/2013 |
| CN | 103232431 A | | 8/2013 |
| CN | 103265527 A | | 8/2013 |
| CN | 103524422 A | | 1/2014 |
| EP | 0135894 A2 | | 4/1985 |
| EP | 0678504 A2 | | 10/1995 |
| EP | 2050734 A1 | | 4/2009 |
| EP | 2236507 A1 | | 10/2010 |
| EP | 2647626 A1 | | 10/2013 |
| WO | 1998/48800 A1 | | 11/1998 |
| WO | 2002017712 A2 | | 3/2002 |
| WO | 03/064386 A1 | | 8/2003 |
| WO | 2003/084917 A1 | | 10/2003 |
| WO | 2003/106457 A1 | | 12/2003 |
| WO | 2004/041264 A1 | | 5/2004 |
| WO | 2004/089925 A1 | | 10/2004 |
| WO | 2004/099160 A1 | | 11/2004 |
| WO | 2005/049572 A1 | | 6/2005 |
| WO | 2005/082089 A2 | | 9/2005 |
| WO | 2006/003494 A2 | | 1/2006 |
| WO | 2006/043635 A1 | | 4/2006 |
| WO | 2006/058649 A1 | | 6/2006 |
| WO | 2006/078619 A1 | | 7/2006 |
| WO | 2006/105304 A2 | | 10/2006 |
| WO | 2007040280 A1 | | 4/2007 |
| WO | 2007040282 A1 | | 4/2007 |
| WO | 2008/073461 A2 | | 6/2008 |
| WO | 2008/073929 A1 | | 6/2008 |
| WO | 2008/073936 A1 | | 6/2008 |
| WO | 2009/145360 A1 | | 12/2009 |
| WO | 2010/13299 A1 | | 2/2010 |
| WO | 2010/043377 A1 | | 4/2010 |
| WO | 2010/051926 A2 | | 5/2010 |
| WO | 2010/054024 A2 | | 5/2010 |
| WO | 2010052161 A2 | | 5/2010 |
| WO | 2010/071885 A1 | | 6/2010 |
| WO | 2011/044181 A1 | | 4/2011 |
| WO | 2011/085575 A1 | | 7/2011 |
| WO | 2012/029672 A1 | | 3/2012 |
| WO | 2012/034403 A1 | | 3/2012 |
| WO | 2012/038851 A1 | | 3/2012 |
| WO | 2012/082566 A1 | | 6/2012 |
| WO | 2013/019621 A1 | | 2/2013 |
| WO | 2013/050317 A1 | | 4/2013 |
| WO | 2013/144213 A1 | | 10/2013 |
| WO | 2013/161312 A1 | | 10/2013 |
| WO | 2013/162715 A2 | | 10/2013 |
| WO | 2013/162716 A2 | | 10/2013 |
| WO | 2014/028669 A1 | | 2/2014 |
| WO | 2014/116684 A1 | | 7/2014 |
| WO | 2014/179144 A1 | | 11/2014 |
| WO | 2014/201206 A1 | | 12/2014 |
| WO | 2014/207240 A1 | | 12/2014 |
| WO | 2015/058021 A1 | | 4/2015 |
| WO | 2015/058028 A1 | | 4/2015 |
| WO | 2015/089139 A1 | | 6/2015 |
| WO | 2016/040185 A1 | | 3/2016 |
| WO | 2016/044789 A1 | | 3/2016 |
| WO | 2016/059097 A1 | | 4/2016 |

OTHER PUBLICATIONS

Major, et al., "2-[(2-N-methyl-N-methoxyaminoethyl)-(p-methoxybenzyl)Amino]Pyridine. An Hydroxylamine Analog of Pyrilamine," Journal of Organic Chemistry, (1957), vol. 22: 579-581.

Draber, et al., "Chemie der Pflanzenschutz-und Schädlingsbekämpfungsmittel", vol. 2, Springer Verlag, (1970), pp. 401-412.

"The Pesticide Manual" (16th ed., British Crop Protection Council 2012) or can be searched for on the Internet (e.g. http://www.alanwood.net/pesticides).

Registry (STN) [online], Feb. 10, 2017, [Search Date Mar. 1, 2022], CAS Registry Nos. 2069157-54-4, 1808619-81-9, 179843-77-6, 1797667-76-5, 179323-06-8, 1797122-57-6, 1445377-72-9, 1445200-02-1, 1428012-80-9, 1427969-88-7, 1394748-01-6 (11 pages).

* cited by examiner

HETEROCYCLIC COMPOUNDS AS PESTICIDES

CROSS-REFERENCE TO RELATED APPLICATIONS

This application is the National Stage entry of International Application No. PCT/EP2018/060678, filed 26 Apr. 2018, which claims priority to European Patent Application No. 17169375.7, filed 4 May 2017.

BACKGROUND

Field

The present invention relates to novel heterocyclic compounds, to processes and intermediates for the preparation thereof, and their use for controlling animal pests, in particular insects.

Description of Related Art

Heterocycle derivatives having fungicidal properties have already been described in the literature, for example in WO2014/179144.

Heterocycle derivatives having pharmaceutical properties have already been described in the literature, for example in WO2005/082089, WO2008073929, WO2009/145360.

Modern pesticides have to meet many demands, for example in relation to efficacy, persistence and spectrum of their action and possible use. Questions of toxicity and of combinability with other active compounds or formulation auxiliaries play a role, as does the question of the cost and complexity involved in the synthesis of an active compound. In addition, resistances can occur. For all these reasons alone, the search for novel pesticides cannot be considered complete, and there is a constant need for novel compounds having improved properties compared to the known compounds, at least in relation to individual aspects.

SUMMARY

It was an object of the present invention to provide compounds which widen the spectrum of the pesticides under various aspects.

This object, and further objects which are not stated explicitly but can be discerned or derived from the connections discussed herein, are achieved by novel compounds of the formula (I)

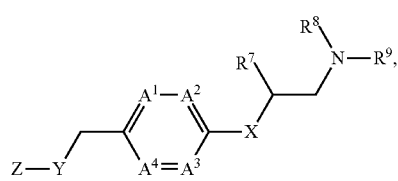

(I)

in which (configuration 1)
Z represents optionally substituted naphthyl, dibenzo[b,d]furanyl, dibenzo[b,d]thiophenyl, carbazolyl, indanyl, benzothiophenyl, benzofuranyl, indolyl, fluorenyl, phenanthrenyl, anthracenyl or represents a phenyl of the substructure formula (II)

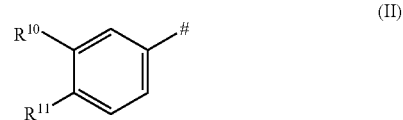

(II)

and the substituted phenyl of the substructure formula (II) may optionally carry up to two further substituents selected from the group consisting of halogen, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylsulfanyl, $(C_3-C_6)$-cycloalkyl and $(C_3-C_6)$-halocycloalkyl, Y represents O, S, —$CH_2$—, —$NR^5$,
$A^1$ represents N or —$CR^1$,
$A^2$ represents N or —$CR^2$,
$A^3$ represents N or —$CR^3$,
$A^4$ represents N or —$CR^4$,
where at least one and at most two of the atoms $A_1$, $A_2$, $A_3$ and $A_4$ in the aromatic ring represent N,
X represents oxygen, sulfanyl, sulfinyl, sulfonyl, —$CH_2$, carbonyl, —CHOH or —$NR^6$,
$R^1$, $R^2$, $R^3$ and $R^4$ each independently of one another represent hydrogen, halogen, nitro, cyano, aminocarbonyl, aminosulfonyl, in each case optionally substituted $(C_1-C_4)$-alkyl, $(C_2-C_4)$-alkenyl, $(C_2-C_4)$-alkynyl, $(C_3-C_6)$-cycloalkyl, $(C_1-C_4)$-alkoxy, $(C_2-C_4)$-alkenyloxy, $(C_2-C_4)$-alkynyloxy, $(C_3-C_6)$-cycloalkoxy, N-mono-$(C_1-C_4)$-alkylamino, N-mono-$(C_3-C_6)$-cycloalkylamino, N,N-di-$(C_1-C_4)$-alkylamino, N,N-di-$(C_3-C_6)$-cycloalkylamino, N,N—$(C_3-C_6)$-cycloalkyl-$(C_1-C_4)$-alkylamino, N—$(C_1-C_4)$-alkanoylamino, N—$(C_3-C_6)$-cycloalkanoylamino, N—$(C_1-C_4)$-alkanoyl-N—$(C_1-C_4)$-alkylamino, N—$(C_3-C_6)$-cycloalkanoyl-N—$(C_1-C_4)$-alkylamino, N—$(C_3-C_6)$-cycloalkanoyl-N—$(C_3-C_6)$-cycloalkylamino, N—$(C_1-C_4)$-alkanoyl-N—$(C_3-C_6)$-cycloalkylamino, $(C_1-C_4)$-alkoxycarbonyl, $(C_3-C_6)$-cycloalkoxycarbonyl, $(C_1-C_4)$-alkanoyl, $(C_3-C_6)$-cycloalkanoyl, $(C_1-C_4)$-alkylsulfanyl, $(C_1-C_4)$-alkylsulfinyl, $(C_1-C_4)$-alkylsulfonyl, $(C_3-C_6)$-cycloalkylsulfanyl, $(C_3-C_6)$-cycloalkylsulfinyl, $(C_3-C_6)$-cycloalkylsulfonyl, N—$(C_1-C_4)$-alkylaminocarbonyl, N—$(C_3-C_6)$-cycloalkylaminocarbonyl, N,N-di-$(C_1-C_4)$-alkylaminocarbonyl, N,N-di-$(C_3-C_6)$-cycloalkylaminocarbonyl, N,N—$(C_3-C_6)$-cycloalkyl-$(C_1-C_4)$-alkylaminocarbonyl, —CH=N—O—[$(C_1-C_4)$-alkyl], —CH=N—O—[$(C_3-C_6)$-cycloalkyl], —C[$(C_1-C_4)$-alkyl]=N—O—[$(C_1-C_4)$-alkyl], —C[$(C_3-C_6)$-cycloalkyl]=N—O—[$(C_1-C_4)$-alkyl], —C[$(C_1-C_4)$-alkyl]=N—O—[$(C_3-C_6)$-cycloalkyl], —C [$(C_3-C_6)$-cycloalkyl]=N—O—[$(C_3-C_6)$-cycloalkyl], $R^5$ represents hydrogen or optionally substituted $(C_1-C_4)$-alkyl, $(C_3-C_6)$-cycloalkyl, $(C_1-C_3)$-alkanoyl, $R^6$ represents hydrogen or optionally substituted $(C_1-C_4)$-alkyl, $(C_3-C_6)$-cycloalkyl, $(C_1-C_4)$-alkanoyl or a ring closure with $R^8$ formed by 1 to 3 $CH_2$ groups, $R^7$ represents hydrogen or optionally substituted $(C_1-C_4)$-alkyl, $(C_3-C_6)$-cycloalkyl or a ring closure with $R^8$ formed by 1 to 3 $CH_2$ groups, $R^8$ represents hydrogen or represents optionally substituted $(C_1-C_4)$-alkyl, $(C_2-C_4)$-alkenyl, $(C_2-C_4)$-alkynyl, $(C_3-C_6)$-cycloalkyl or together with $R^6$ or $R^7$ is closed in a ring formed by 1 to 3 $CH_2$ groups or together with $R^9$ is closed in a 4- to 6-membered heterocyclic ring which, in the case of a 5- or 6-membered heterocyclic ring, may comprise further heteroatoms, and which is optionally mono- or polysubstituted by identical or different halogen substituents, cyano or by ($C_1$-$C_4$)-alkyl, ($C_3$-$C_6$)-cycloalkyl, ($C_1$-$C_4$)-alkoxy, each of which is optionally mono- or polysubstituted by identical or different halogen substituents, $R^9$ represents in each case optionally substituted ($C_1$-$C_4$)-alkyl, ($C_3$-$C_6$)-cycloalkyl, ($C_2$-$C_4$)-alkenyl, ($C_2$-$C_4$)-alkynyl, N-mono-($C_1$-$C_4$)-alkylamino, N,N-di-($C_1$-$C_4$)-alkylamino, ($C_1$-$C_4$)-alkoxy, ($C_2$-$C_4$)-alkenyloxy, ($C_2$-$C_4$)-alkynyloxy, ($C_3$-$C_6$)-cycloalkoxy, ($C_1$-$C_4$)-alkylcarbonyl, ($C_1$-$C_4$)-alkylsulfinyl, ($C_1$-$C_4$)-alkylsulfonyl, ($C_1$-$C_4$)-alkoxycarbonyl, in the case that $R^7$ represents hydrogen or optionally substituted ($C_1$-$C_4$)-alkyl, ($C_3$-$C_6$)-cycloalkyl or in the case that $R^7$ together with $R^8$ forms a 5- or 6-membered ring, or $R^9$ represents in each case optionally substituted ($C_1$-$C_4$)-alkyl, ($C_3$-$C_6$)-cycloalkyl, ($C_2$-$C_4$)-alkenyl, ($C_2$-$C_4$)-alkynyl, N-mono-($C_1$-$C_4$)-alkylamino, N,N-di-($C_1$-$C_4$)-alkylamino, ($C_1$-$C_4$)-alkoxy, ($C_2$-$C_4$)-alkenyloxy, ($C_2$-$C_4$)-alkynyloxy, ($C_3$-$C_6$)-cycloalkoxy, ($C_1$-$C_4$)-alkylsulfinyl, ($C_1$-$C_4$)-alkylsulfonyl, in the case that $R^7$ forms a 4-membered ring together with $R^8$, or $R^8$ and $R^9$ represent a 4- to 6-membered heterocyclic ring closure which, in the case of a 5- or 6-membered heterocyclic ring, may comprise further heteroatoms and is optionally mono- or polysubstituted by identical or different halogen substituents, cyano or by ($C_1$-$C_4$)-alkyl, ($C_3$-$C_6$)-cycloalkyl, ($C_1$-$C_4$)-alkoxy, each of which is optionally mono- or polysubstituted by identical or different halogen substituents, $R^{10}$ represents halogen, nitro, cyano, —$SF_5$ or represents phenyl, pyrid-2-yl, pyrid-3-yl, pyrid-4-yl, thiophen-2-yl, thiophen-3-yl, ($C_1$-$C_4$)-alkyl, ($C_1$-$C_4$)-alkenyl, ($C_1$-$C_4$)-alkynyl, ($C_3$-$C_6$)-cycloalkyl, ($C_1$-$C_4$)-alkoxy, ($C_2$-$C_4$)-alkenyloxy, ($C_2$-$C_4$)-alkynyloxy, ($C_3$-$C_6$)-cycloalkoxy, ($C_1$-$C_4$)-alkylsulfanyl, ($C_1$-$C_4$)-alkylsulfinyl, ($C_1$-$C_4$)-alkylsulfonyl, ($C_3$-$C_6$)-cycloalkylsulfanyl, ($C_3$-$C_6$)-cycloalkylsulfinyl, ($C_3$-$C_6$)-cycloalkylsulfonyl, —CH=N—O—[($C_1$-$C_4$)-alkyl], —C[($C_1$-$C_4$)-alkyl]=N—O—[($C_1$-$C_4$)-alkyl], optionally mono- or polysubstituted by identical or different substituents from the group consisting of halogen, cyano, nitro, —$SF_5$, ($C_1$-$C_4$)-alkyl, ($C_2$-$C_4$)-alkenyl, ($C_2$-$C_4$)-alkynyl, ($C_1$-$C_4$)-haloalkyl, ($C_2$-$C_4$)-haloalkenyl, ($C_1$-$C_4$)-alkoxy, ($C_1$-$C_4$)-haloalkoxy, ($C_2$-$C_4$)-alkenyloxy, ($C_2$-$C_4$)-haloalkenyloxy, ($C_2$-$C_4$)-alkynyloxy, ($C_3$-$C_6$)-cycloalkoxy, ($C_3$-$C_6$)-halocycloalkoxy, ($C_3$-$C_6$)-cycloalkyl, ($C_3$-$C_6$)-halocycloalkyl, ($C_1$-$C_4$)-alkylsulfanyl, ($C_1$-$C_4$)-alkylsulfinyl, ($C_1$-$C_4$)-alkylsulfonyl, ($C_1$-$C_4$)-haloalkylsulfonyl, ($C_1$-$C_4$)-haloalkylsulfanyl, ($C_1$-$C_4$)-haloalkylsulfinyl, ($C_3$-$C_6$)-cycloalkylsulfanyl, ($C_3$-$C_6$)-cycloalkylsulfinyl, ($C_3$-$C_6$)-cycloalkylsulfonyl, $C_6$-,$C_{10}$-,$C_{14}$-aryl, $C_6$-,$C_{10}$-,$C_{14}$-aryloxy, benzyl, benzyloxy, benzylthio, $C_6$-,$C_{10}$-,$C_{14}$-arylthio, $C_6$-,$C_{10}$-,$C_{14}$-arylamino, benzylamino, heterocyclyl and trialkylsilyl, $R^{11}$ represents hydrogen, halogen, cyano or nitro or represents in each case optionally substituted ($C_1$-$C_4$)-alkyl, ($C_3$-$C_5$)-cycloalkyl, ($C_1$-$C_4$)-alkoxy, ($C_1$-$C_4$)-alkylsulfanyl, ($C_1$-$C_4$)-alkylsulfinyl, ($C_1$-$C_4$)-alkylsulfonyl, —CH=N—O—[($C_1$-$C_4$)-alkyl], —C[($C_1$-$C_4$)-alkyl]=N—O—[($C_1$-$C_4$)-alkyl], and salts, metal complexes, N-oxides and tautomeric forms of the compounds of the formula (I), with the proviso, that the compound 1-[4-(6-{2-[3-(chloromethyl)phenyl]ethyl}pyridin-3-yl)piperazin-1-yl]ethanone is excluded.

DETAILED DESCRIPTION OF A PREFERRED EMBODIMENT

The excluded compound was specifically disclosed in WO2009145360 as intermediate for the preparation of a pharmaceutically active compound.

The compounds according to the invention are defined in general terms by the formula (I). Preferred substituents or ranges of the radicals given in the formulae mentioned above and below are illustrated hereinafter:

Configuration 2:

Z preferably represents optionally substituted naphthyl, dibenzo[b,d]furanyl, dibenzo[b,d]thiophenyl, indan-4-yl, benzothiophen-4-yl, benzofuran-4-yl, indol-4-yl or represents substituted phenyl of the substructure formula (II), where the phenyl of the substructure formula (II) preferably carries no further substituents apart from $R^{10}$ and $R^{11}$.

Y preferably represents O, S, —$NR^5$, $R^1$, $R^2$, $R^3$ and $R^4$ preferably each independently of one another represent a substituent selected from the group consisting of hydrogen, halogen, nitro, cyano, or represent ($C_1$-$C_4$)-alkyl, ($C_2$-$C_4$)-alkenyl, ($C_2$-$C_4$)-alkynyl, ($C_3$-$C_6$)-cycloalkyl, ($C_1$-$C_4$)-alkoxy, ($C_2$-$C_4$)-alkenyloxy, ($C_2$-$C_4$)-alkynyloxy, ($C_3$-$C_6$)-cycloalkoxy, ($C_1$-$C_4$)-alkoxycarbonyl, ($C_3$-$C_6$)-cycloalkoxycarbonyl, N-mono-($C_1$-$C_4$)-alkylamino, N,N-di-($C_1$-$C_4$)-alkylamino, ($C_1$-$C_4$)-alkylsulfanyl, ($C_1$-$C_4$)-alkylsulfinyl, ($C_1$-$C_4$)-alkylsulfonyl, ($C_3$-$C_6$)-cycloalkylsulfanyl, ($C_3$-$C_6$)-cycloalkylsulfinyl, ($C_3$-$C_6$)-cycloalkylsulfonyl, each of which is optionally mono- or polysubstituted by identical or different substituents from the group consisting of halogen, cyano, nitro, ($C_1$-$C_4$)-alkyl, ($C_1$-$C_4$)-haloalkyl, ($C_1$-$C_4$)-alkoxy, ($C_1$-$C_4$)-haloalkoxy, ($C_3$-$C_6$)-cycloalkyl, ($C_3$-$C_6$)-halocycloalkyl, $R^5$ preferably represents hydrogen or represents ($C_1$-$C_4$)-alkyl, ($C_3$-$C_4$)-cycloalkyl, ($C_1$-$C_3$)-alkanoyl, optionally mono- or polysubstituted by identical or different halogen substituents, $R^6$ preferably represents hydrogen or represents ($C_1$-$C_4$)-alkyl, ($C_3$-$C_4$)-cycloalkyl, ($C_1$-$C_4$)-alkanoyl, optionally mono- or polysubstituted by identical or different halogen substituents, or a ring closure with $R^8$ formed by 1 to 3 $CH_2$ groups, $R^7$ preferably represents hydrogen or represents ($C_1$-$C_4$)-alkyl, ($C_3$-$C_4$)-cycloalkyl, optionally mono- or polysubstituted by identical or different halogen substituents, or a ring closure with $R^8$ formed by 1 to 3 $CH_2$ groups, $R^8$ preferably represents hydrogen or represents ($C_1$-$C_4$)-alkyl, ($C_2$-$C_4$)-alkenyl, ($C_2$-$C_4$)-alkynyl, ($C_3$-$C_4$)-cycloalkyl, optionally mono- or polysubstituted by identical or different substituents from the group consisting of halogen, nitro and cyano, or a ring closure together with $R^6$ or $R^7$ formed by 1 to 3 $CH_2$ groups, or a 4- to 6-membered heterocyclic ring closure together with $R^9$ which, in the case of a 5- or 6-membered heterocyclic ring, may comprise further heteroatoms selected from the group consisting of N and O and which is optionally mono- or polysubstituted by identical or different substituents from the group consisting of halogen, ($C_1$-$C_4$)-alkyl and ($C_1$-$C_4$)-haloalkyl, $R^9$ preferably represents $(C_1-C_4)$-alkyl, $(C_2-C_4)$-alkenyl, $(C_3-C_4)$-cycloalkyl, $(C_1-C_4)$-alkoxy, $(C_2-C_4)$-alkenyloxy, $(C_3-C_6)$-cycloalkoxy, $(C_1-C_4)$-alkylcarbonyl, $(C_1-C_4)$-alkylsulfinyl, $(C_1-C_4)$-alkylsulfonyl, $(C_1-C_4)$-alkoxycarbonyl, each of which is optionally mono- or polysubstituted by identical or different substituents from the group consisting of halogen, cyano, nitro or $(C_3-C_6)$-cycloalkyl, in the case that $R^7$ represents hydrogen or $(C_1-C_4)$-alkyl, $(C_3-C_4)$-cycloalkyl, optionally mono- or polysubstituted by identical or different halogen substituents or in the case that $R^7$ with $R^8$ forms a 5- or 6-membered ring, or $R^9$ preferably represents $(C_1-C_4)$-alkyl, $(C_2-C_4)$-alkenyl, $(C_3-C_4)$-cycloalkyl, $(C_1-C_4)$-alkoxy, $(C_2-C_4)$-alkenyloxy, $(C_3-C_4)$-cycloalkoxy, $(C_1-C_4)$-alkylsulfinyl, $(C_1-C_4)$-alkylsulfonyl, in each case optionally mono- or polysubstituted by identical or different substituents from the group consisting of halogen, cyano, nitro or $(C_3-C_6)$-cycloalkyl, in the case that $R^7$ forms a 4-membered ring together with $R^8$, or $R^8$ and $R^9$ preferably represent a 4- to 6-membered heterocyclic ring closure which, in the case of a 5- or 6-membered heterocyclic ring, may contain further heteroatoms selected from the group consisting of N, O and which is optionally mono- or polysubstituted by identical or different substituents from the group consisting of halogen, $(C_1-C_4)$-alkyl and $(C_1-C_4)$-haloalkyl, $R^{10}$ preferably represents halogen or represents phenyl, pyrid-2-yl, pyrid-3-yl, pyrid-4-yl, thiophen-2-yl, thiophen-3-yl, $(C_1-C_4)$-alkyl, $(C_1-C_4)$-alkenyl, $(C_1-C_4)$-alkynyl, $(C_3-C_6)$-cycloalkyl, $(C_1-C_4)$-alkoxy, $(C_2-C_4)$-alkenyloxy, $(C_2-C_4)$-alkynyloxy, $(C_3-C_6)$-cycloalkoxy, $(C_1-C_4)$-alkylsulfanyl, $(C_1-C_4)$-alkylsulfinyl, $(C_1-C_4)$-alkylsulfonyl, $(C_3-C_6)$-cycloalkylsulfanyl, $(C_3-C_6)$-cycloalkylsulfinyl, $(C_3-C_6)$-cycloalkylsulfonyl, —CH=N—O—[$(C_1-C_4)$-alkyl], —C[$(C_1-C_4)$-alkyl]=N—O—[$(C_1-C_4)$-alkyl], optionally mono- or polysubstituted by identical or different substituents from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy, $(C_3-C_6)$-cycloalkyl, $(C_3-C_6)$-halocycloalkyl, $R^{11}$ preferably represents hydrogen, halogen, cyano or nitro or represents $(C_1-C_4)$-alkyl, $(C_1-C_4)$-alkoxy, $(C_1-C_4)$-alkylsulfanyl, $(C_1-C_4)$-alkylsulfinyl, $(C_1-C_4)$-alkylsulfonyl, $(C_3-C_5)$-cycloalkyl, —CH=N—O—[$(C_1-C_4)$-alkyl], —C[$(C_1-C_4)$-alkyl]=N—O—[$(C_1-C_4)$-Alkyl], optionally mono- or polysubstituted by identical or different substituents from the group consisting of halogen, cyano, nitro, $(C_1-C_4)$-alkoxy and $(C_3-C_6)$-cycloalkyl.

Substituents not mentioned in Configuration 2 are as defined in Configuration 1.

Configuration 3:

Z particularly preferably represents naphthyl, dibenzo[b,d]furanyl, dibenzo[b,d]thiophenyl, optionally mono- or polysubstituted by identical or different substituents from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylsulfanyl, $(C_1-C_4)$-haloalkylsulfanyl, $(C_3-C_6)$-cycloalkyl, $(C_3-C_6)$-halocycloalkyl, $(C_1-C_4)$-alkylcarbonyl, $(C_1-C_4)$-haloalkylcarbonyl, or represents substituted phenyl of the substructure formula (II), at least one of the atoms $A_3$ or $A_4$ in the aromatic ring particularly preferably represents nitrogen, $R^1$, $R^2$, $R^3$ and $R^4$ each independently of one another particularly preferably represent a substituent selected from the group consisting of hydrogen, halogen, $(C_1-C_4)$-alkyl, $(C_1-C_4)$-haloalkyl, $(C_2-C_4)$-alkenyl, $(C_2-C_4)$-haloalkenyl, $(C_1-C_4)$-alkoxy, $(C_1-C_4)$-haloalkoxy, $(C_3-C_6)$-cycloalkyl, $(C_3-C_6)$-halocycloalkyl, $(C_1-C_4)$-alkylsulfanyl, $(C_1-C_4)$-alkylsulfinyl and $(C_1-C_4)$-alkylsulfonyl, $R^6$ particularly preferably represents hydrogen, $(C_1-C_4)$-alkyl or a ring closure with $R^8$ formed by 1 to 3 $CH_2$ groups, $R^7$ particularly preferably represents hydrogen, $(C_1-C_4)$-alkyl, $(C_3-C_4)$-cycloalkyl or a ring closure with $R^8$ formed by 1 to 3 $CH_2$ groups, $R^8$ particularly preferably represents hydrogen or represents $(C_1-C_4)$-alkyl, $(C_2-C_4)$-alkenyl, $(C_2-C_4)$-alkynyl, $(C_3-C_4)$-cycloalkyl, optionally mono- or polysubstituted by identical or different substituents from the group consisting of halogen, or a ring closure together with $R^6$ or $R^7$ formed by 1 to 3 $CH_2$ groups, or a 4- to 6-membered heterocyclic ring closure together with $R^9$ which is formed by 3 to 5 $CH_2$ groups and which is optionally mono- or polysubstituted by identical or different substituents from the group consisting of halogen, $(C_1-C_4)$-alkyl and $(C_1-C_4)$-haloalkyl, $R^9$ particularly preferably represents $(C_1-C_4)$-alkyl, $(C_3-C_6)$-cycloalkyl, $(C_1-C_6)$-alkoxy, $(C_1-C_6)$-alkylcarbonyl, each of which is optionally mono- or polysubstituted by identical or different substituents from the group consisting of halogen, cyano, nitro or $(C_3-C_6)$-cycloalkyl, in the case that $R^7$ represents hydrogen or represents $(C_1-C_4)$-alkyl, $(C_3-C_4)$-cycloalkyl or in the case that $R^7$ together with $R^8$ forms a 5- or 6-membered ring, or $R^9$ particularly preferably represents $(C_1-C_4)$-alkyl, $(C_3-C_4)$-cycloalkyl, $(C_1-C_4)$-alkoxy, each of which is optionally mono- or polysubstituted by identical or different substituents from the group consisting of halogen, cyano, nitro or $(C_3-C_6)$-cycloalkyl, in the case that $R^7$ together with $R^8$ forms a 4-membered ring, or $R^8$ and $R^9$ particularly preferably represent a 4- to 6-membered heterocyclic ring closure which is formed by 3 to 5 $CH_2$ groups and which is optionally mono- or polysubstituted by identical or different substituents from the group consisting of halogen, $(C_1-C_4)$-alkyl and $(C_1-C_4)$-haloalkyl, $R^{10}$ particularly preferably represents halogen or represents phenyl, pyrid-2-yl, pyrid-3-yl, pyrid-4-yl, thiophen-2-yl, thiophen-3-yl, optionally mono- or polysubstituted by identical or different substituents from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy, $(C_3-C_6)$-cycloalkyl, $(C_3-C_6)$-halocycloalkyl, or represents $(C_1-C_4)$-alkyl, $(C_1-C_4)$-alkenyl, $(C_1-C_4)$-alkynyl, $(C_3-C_6)$-cycloalkyl, $(C_1-C_4)$-alkoxy, $(C_2-C_4)$-alkenyloxy, $(C_2-C_4)$-alkynyloxy, $(C_3-C_6)$-cycloalkoxy, $(C_1-C_4)$-alkylsulfanyl, $(C_1-C_4)$-alkylsulfinyl, $(C_1-C_4)$-alkylsulfonyl, $(C_3-C_6)$-cycloalkylsulfanyl, $(C_3-C_6)$-cycloalkylsulfinyl, $(C_3-C_6)$-cycloalkylsulfonyl, —CH=N—O—[$(C_1-C_4)$-alkyl], —C[$(C_1-C_4)$-alkyl]=N—O—[$(C_1-C_4)$-alkyl, optionally mono- or polysubstituted by identical or different substituents from the group consisting of halogen, cyano, nitro, $R^{11}$ particularly preferably represents hydrogen, halogen, cyano or nitro or represents $(C_1-C_4)$-alkyl, $(C_1-C_4)$-alkoxy, $(C_1-C_4)$-alkylsulfanyl, $(C_1-C_4)$-alkylsulfinyl, $(C_1-C_4)$-alkylsulfonyl, $(C_3-C_5)$-cycloalkyl, optionally mono- or polysubstituted by identical or different substituents from the group consisting of halogen, cyano, and $(C_3-C_6)$-cycloalkyl.

Substituents not mentioned in Configuration 3 are as defined in Configuration 1 or Configuration 2.

Configuration 4:

Z very particularly preferably represents naphthyl, dibenzo[b,d]furanyl, dibenzo[b,d]thiophenyl, optionally mono- or polysubstituted by identical or different substituents from the group consisting of halogen, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylsulfanyl, $(C_1-C_4)$-haloalkylsulfanyl, $(C_3-C_6)$-cycloalkyl, or represents substituted phenyl of the substructure formula (II), Y very particularly preferably represents oxygen, X very particularly preferably represents oxygen or —$NR^6$.

Substituents not mentioned in Configuration 4 are as defined in Configuration 1, Configuration 2 or Configuration 3.

Configuration 5:

Z especially preferably represents naphthyl which is optionally mono- or polysubstituted by identical or different substituents from the group consisting of halogen, cyano, $(C_1-C_4)$-alkyl, $(C_1-C_4)$-haloalkyl, or represents unsubstituted dibenzo[b,d]furanyl or dibenzo[b,d]thiophenyl or represents substituted phenyl of the substructure formula (II), $R^1$, $R^2$, $R^3$ and $R^4$ especially preferably represent a substituent selected from the group consisting of hydrogen, halogen, $(C_1-C_4)$-alkyl, $(C_1-C_4)$-haloalkyl, $(C_1-C_4)$-alkoxy and $(C_1-C_4)$-alkylsulfanyl, $R^6$ especially preferably represents hydrogen, $(C_1-C_3)$-alkyl or a ring closure with $R^8$ formed by 1 to 2 $CH_2$ groups, $R^7$ especially preferably represents hydrogen or a ring closure with $R^8$ formed by 1 to 3 $CH_2$ groups, $R^8$ especially preferably represents hydrogen or represents $(C_1-C_4)$-alkyl, optionally mono- or polysubstituted by identical or different halogen substituents, or a ring closure together with $R^6$ formed by 1 or 2 $CH_2$ groups or a ring closure together with $R^7$ formed by 1 to 3 $CH_2$ groups or a 4- to 6-membered heterocyclic ring closure together with $R^9$ which is formed by 3 to 5 $CH_2$ groups and which is optionally mono- or polysubstituted by identical or different substituents from the group consisting of halogen, $(C_1-C_4)$-alkyl and $(C_1-C_4)$-haloalkyl, $R^9$ especially preferably represents $(C_1-C_6)$-alkyl, $(C_3-C_6)$-cycloalkyl or $(C_1-C_6)$-alkoxy, each of which is optionally mono- or polysubstituted by identical or different substituents from the group consisting of halogen, cyano and $(C_3-C_6)$-cycloalkyl, or $R^8$ and $R^9$ especially preferably represent a 4- to 6-membered heterocyclic ring closure which is formed by 3 to 5 $CH_2$ groups and which is optionally mono- or polysubstituted by identical or different substituents from the group consisting of halogen, $(C_1-C_4)$-alkyl and $(C_1-C_4)$-haloalkyl, $R^{10}$ especially preferably represents halogen, $(C_1-C_4)$-alkyl, $(C_1-C_4)$-alkoxy, $(C_1-C_4)$-haloalkoxy or represents phenyl which is optionally mono- or polysubstituted by identical or different substituents from the group consisting of halogen, cyano, $(C_1-C_4)$-alkyl, $(C_1-C_4)$-haloalkyl, $(C_1-C_4)$-alkoxy and $(C_1-C_4)$-haloalkoxy, $R^{11}$ especially preferably represents hydrogen, halogen, nitro or cyano or represents $(C_1-C_4)$-alkyl, $(C_3-C_5)$-cycloalkyl or $(C_1-C_4)$-alkoxy, optionally mono- or polysubstituted by identical or different halogen substituents.

Substituents not mentioned in Configuration 5 are as defined in Configuration 1, Configuration 2, Configuration 3 or Configuration 4.

Configuration 6:

Z with emphasis represents a naphthyl of the substructure formula (III):

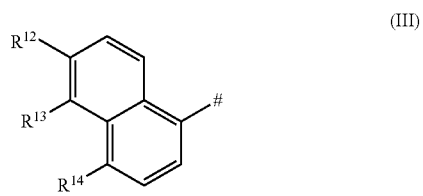

or represents unsubstituted dibenzo[b,d]furanyl or dibenzo[b,d]thiophenyl or represents substituted phenyl of the substructure formula (II).

$R^1$ with emphasis represents hydrogen, halogen, $(C_1-C_4)$-alkyl or $(C_1-C_4)$-alkoxy, $R^2$ with emphasis represents hydrogen, halogen or $(C_1-C_4)$-haloalkyl, $R^3$ with emphasis represents hydrogen, halogen, $(C_1-C_4)$-alkoxy or $(C_1-C_4)$-alkylsulfanyl, $R^4$ with emphasis represents hydrogen or halogen, $R^6$ with emphasis represents hydrogen, or represents a piperazine ring closure with $R^8$, $R^7$ with emphasis represents hydrogen, or represents a pyrrolidine ring closure with $R^8$, $R^8$ with emphasis represents hydrogen, $(C_1-C_4)$-alkyl or represents a piperazine ring closure together with $R^6$ or represents a pyrrolidine ring closure together with $R^7$ or represents a piperidine ring closure together with $R^9$, $R^9$ with emphasis represents $(C_1-C_4)$-alkyl or $(C_1-C_4)$-alkoxy, each of which is optionally mono- or polysubstituted by identical or different substituents from the group consisting of halogen and cyano, or $R^8$ and $R^9$ with emphasis represent a piperidine ring closure, $R^{10}$ with emphasis represents halogen, $(C_1-C_4)$-alkyl, $(C_1-C_4)$-alkoxy, $(C_1-C_4)$-haloalkoxy or represents a phenyl of the substructure formula (IV):

$R^{11}$ with emphasis represents hydrogen or halogen or represents $(C_1-C_4)$-alkyl or $(C_1-C_4)$-alkoxy, optionally mono- or polysubstituted by identical or different halogen substituents, $R^{12}$, $R^{13}$ and $R^{14}$ with emphasis each independently of one another represent hydrogen or halogen, $R^{15}$ with emphasis represents hydrogen, halogen, cyano, $(C_1-C_4)$-alkyl, $(C_1-C_4)$-haloalkyl, $(C_1-C_4)$-alkoxy or $(C_1-C_4)$-haloalkoxy.

Substituents not mentioned in Configuration 6 are as defined in Configuration 1, Configuration 2, Configuration 3, Configuration 4 or Configuration 5.

In a preferred embodiment, the invention relates to the compounds of the formula (I)
where Z has the meanings described in Configuration (1) and
where Y, $A^1$, $A^2$, $A^3$, $A^4$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (2) or Configuration (3) or Configuration (4) or Configuration (5) or Configuration (6).

In a further preferred embodiment, the invention relates to the compounds of the formula (I)
where Z has the meanings described in Configuration (2) and
where Y, $A^1$, $A^2$, $A^3$, $A^4$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (1) or Configuration (3) or Configuration (4) or Configuration (5) or Configuration (6).

In a further preferred embodiment, the invention relates to the compounds of the formula (I)
where Z has the meanings described in Configuration (3) and
where Y, $A^1$, $A^2$, $A^3$, $A^4$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (1) or Configuration (2) or Configuration (4) or Configuration (5) or Configuration (6).

In a further preferred embodiment, the invention relates to the compounds of the formula (I)
where Z has the meanings described in Configuration (4) and
where Y, $A^1$, $A^2$, $A^3$, $A^4$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (1) or Configuration (2) or Configuration (3) or Configuration (5) or Configuration (6).

In a further preferred embodiment, the invention relates to the compounds of the formula (I)
where Z has the meanings described in Configuration (5) and
where Y, $A^1$, $A^2$, $A^3$, $A^4$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (1) or Configuration (2) or Configuration (3) or Configuration (4) or Configuration (6).

In a further preferred embodiment, the invention relates to the compounds of the formula (I)
where Z has the meanings described in Configuration (6) and
where Y, $A^1$, $A^2$, $A^3$, $A^4$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (1) or Configuration (2) or Configuration (3) or Configuration (4) or Configuration (5).

In a preferred embodiment, the invention relates to the compounds of the formula (I)
where Y has the meanings described in Configuration (1) and
where Z, $A^1$, $A^2$, $A^3$, $A^4$, X, R, $R^2$, $R^3$ $R^4$ $R^5$, $R^6$, $R^7$, $R^8$, $R^9$, $R^{10}$ and $R^{11}$ have the meanings described above, in particular the meanings described in Configuration (2) or Configuration (3) or Configuration (4) or Configuration (5) or Configuration (6).

In a further preferred embodiment, the invention relates to the compounds of the formula (I)
where Y has the meanings described in Configuration (2) and
where Z, $A^1$, $A^2$, $A^3$, $A^4$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (1) or Configuration (3) or Configuration (4) or Configuration (5) or Configuration (6).

In a further preferred embodiment, the invention relates to the compounds of the formula (I)
where Y has the meanings described in Configuration (4) and
where Z, $A^1$, $A^2$, $A^3$, $A^4$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (1) or Configuration (2) or Configuration (3) or Configuration (5) or Configuration (6).

In a preferred embodiment, the invention relates to the compounds of the formula (I)
where $A^3$ and $A^4$ have the meanings described in Configuration (1) and
where Z, Y, $A^1$, $A^2$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (2) or Configuration (3) or Configuration (4) or Configuration (5) or Configuration (6).

In a further preferred embodiment, the invention relates to the compounds of the formula (I)
where $A^3$ and $A^4$ have the meanings described in Configuration (3) and
where Z, Y, $A^1$, $A^2$, X, $R^1$, $R^2$, $R^3$, $R^4$ $R^5$, $R^6$, $R^7$, $R^8$, $R^9$, $R^{10}$ and $R^{11}$ have the meanings described above, in particular the meanings described in Configuration (1) or Configuration (2) or Configuration (4) or Configuration (5) or Configuration (6).

In a preferred embodiment, the invention relates to the compounds of the formula (I)
where $R^1$, $R^2$, $R^3$ and $R^4$ have the meanings described in Configuration (1) and
where Z, Y, $A^1$, $A^2$, $A^3$, $A^4$, X, R, $R^6$, $R^7$, R, $R^9$, $R^{10}$ and $R^{11}$ have the meanings described above, in particular the meanings described in Configuration (2) or Configuration (3) or Configuration (4) or Configuration (5) or Configuration (6).

In a further preferred embodiment, the invention relates to the compounds of the formula (I)
where $R^1$, $R^2$, $R^3$ and $R^4$ have the meanings described in Configuration (2) and
where Z, Y, $A^1$, $A^2$, $A^3$, $A^4$, X, $R^5$, $R^6$, $R^7$, R, $R^9$, $R^{10}$ and $R^{11}$ have the meanings described above, in particular the meanings described in Configuration (1) or Configuration (3) or Configuration (4) or Configuration (5) or Configuration (6).

In a further preferred embodiment, the invention relates to the compounds of the formula (I)
where $R^1$, $R^2$, $R^3$ and $R^4$ have the meanings described in Configuration (3) and
where Z, Y, $A^1$, $A^2$, $A^3$, $A^4$, X, $R^5$, $R^6$, $R^7$, R, $R^9$, $R^{10}$ and $R^{11}$ have the meanings described above, in particular the meanings described in Configuration (1) or Configuration (2) or Configuration (4) or Configuration (5) or Configuration (6).

In a further preferred embodiment, the invention relates to the compounds of the formula (I)
where $R^1$, $R^2$, $R^3$ and $R^4$ have the meanings described in Configuration (5) and
where Z, Y, $A^1$, $A^2$, $A^3$, $A^4$, X, $R^5$, $R^6$, $R^7$, R, $R^9$, $R^{10}$ and $R^{11}$ have the meanings described above, in particular the meanings described in Configuration (1) or Configuration (2) or Configuration (3) or Configuration (4) or Configuration (6).

In a further preferred embodiment, the invention relates to the compounds of the formula (I)
where $R^1$, $R^2$, $R^3$ and $R^4$ have the meanings described in Configuration (6) and
where Z, Y, $A^1$, $A^2$, $A^3$, $A^4$, X, $R^5$, $R^6$, $R^7$, R, $R^9$, $R^{10}$ and $R^{11}$ have the meanings described above, in particular the meanings described in Configuration (1) or Configuration (2) or Configuration (3) or Configuration (4) or Configuration (5).

In a preferred embodiment, the invention relates to the compounds of the formula (I)
where X has the meanings described in Configuration (1) and
where Z, Y, $A^1$, $A^2$, $A^3$, $A^4$, $R^1$, $R^2$, $R^3$, $R^4$ $R^5$, $R^6$, $R^7$, R, $R^9$, $R^{10}$ and $R^{11}$ have the meanings described above, in particular the meanings described in Configuration (2) or Configuration (3) or Configuration (4) or Configuration (5) or Configuration (6).

In a further preferred embodiment, the invention relates to the compounds of the formula (I)
where X has the meanings described in Configuration (3) and
where Z, Y, $A^1$, $A^2$, $A^3$, $A^4$, $R^1$, $R^2$, $R^3$, $R^4$ $R^5$, $R^6$, $R^7$, R, $R^9$, $R^{10}$ and $R^{11}$ have the meanings described above, in particular the meanings described in Configuration (1) or Configuration (2) or Configuration (4) or Configuration (5) or Configuration (6).

In a preferred embodiment, the invention relates to the compounds of the formula (I)
where $R^6$ has the meanings described in Configuration (1) and
where Z, Y, $A^1$, $A^2$, $A^3$, $A^4$, X, $R^1$, $R^2$, $R^3$, $R^4$ $R^5$, $R^7$, $R^8$, $R^9$, $R^{10}$ and $R^{11}$ have the meanings described above, in particular the meanings described in Configuration (2) or Configuration (3) or Configuration (4) or Configuration (5) or Configuration (6).

In a further preferred embodiment, the invention relates to the compounds of the formula (I)
where $R^6$ has the meanings described in Configuration (2) and
where Z, Y, $A^1$, $A^2$, $A^3$, $A^4$, X, $R^1$, $R^2$, $R^3$, $R^4$ $R^5$, $R^7$, $R^8$, $R^9$, $R^{10}$ and $R^{11}$ have the meanings described above, in particular the meanings described in Configuration (1) or Configuration (3) or Configuration (4) or Configuration (5) or Configuration (6).

In a further preferred embodiment, the invention relates to the compounds of the formula (I)
where $R^6$ has the meanings described in Configuration (3) and
where Z, Y, $A^1$, $A^2$, $A^3$, $A^4$, X, $R^1$, $R^2$, $R^3$, $R^4$ $R^5$, $R^7$, $R^8$, $R^9$, $R^{10}$ and $R^{11}$ have the meanings described above, in particular the meanings described in Configuration (1) or Configuration (2) or Configuration (4) or Configuration (5) or Configuration (6).

In a further preferred embodiment, the invention relates to the compounds of the formula (I)
where $R^6$ has the meanings described in Configuration (6) and
where Z, Y, $A^1$, $A^2$, $A^3$, $A^4$, X, $R^1$, $R^2$, $R^3$, $R^4$ $R^5$, $R^7$, $R^8$, $R^9$, $R^{10}$ and $R^{11}$ have the meanings described above, in particular the meanings described in Configuration (1) or Configuration (2) or Configuration (3) or Configuration (4) or Configuration (5).

In a preferred embodiment, the invention relates to the compounds of the formula (I)
where $R^7$ has the meanings described in Configuration (1) and
where Z, Y, $A^1$, $A^2$, $A^3$, $A^4$, X, $R^1$, $R^2$, $R^3$, $R^4$ $R^5$, $R^6$, $R^8$, $R^9$, $R^{10}$ and $R^{11}$ have the meanings described above, in particular the meanings described in Configuration (2) or Configuration (3) or Configuration (4) or Configuration (5) or Configuration (6).

In a further preferred embodiment, the invention relates to the compounds of the formula (I)
where $R^7$ has the meanings described in Configuration (2) and
where Z, Y, $A^1$, $A^2$, $A^3$, $A^4$, X, $R^1$, $R^2$, $R^3$, $R^4$ $R^5$, $R^6$, $R^8$, $R^9$, $R^{10}$ and $R^{11}$ have the meanings described above, in particular the meanings described in Configuration (1) or Configuration (3) or Configuration (4) or Configuration (5) or Configuration (6).

In a further preferred embodiment, the invention relates to the compounds of the formula (I)
where $R^7$ has the meanings described in Configuration (3) and
where Z, Y, $A^1$, $A^2$, $A^3$, $A^4$, X, $R^1$, $R^2$, $R^3$, $R^4$ $R^5$, $R^6$, $R^8$, $R^9$, $R^{10}$ and $R^{11}$ have the meanings described above, in particular the meanings described in Configuration (1) or Configuration (2) or Configuration (4) or Configuration (5) or Configuration (6).

In a further preferred embodiment, the invention relates to the compounds of the formula (I)
where $R^7$ has the meanings described in Configuration (5) and
where Z, Y, $A^1$, $A^2$, $A^3$, $A^4$, X, $R^1$, $R^2$, $R^3$, $R^4$ $R^5$, $R^6$, $R^8$, $R^9$, $R^{10}$ and $R^{11}$ have the meanings described above, in particular the meanings described in Configuration (1) or Configuration (2) or Configuration (3) or Configuration (4) or Configuration (6).

In a further preferred embodiment, the invention relates to the compounds of the formula (I)
where $R^7$ has the meanings described in Configuration (6) and
where Z, Y, $A^1$, $A^2$, $A^3$, $A^4$, X, $R^1$, $R^2$, $R^3$, $R^4$ $R^5$, $R^6$, R, $R^9$, $R^{10}$ and $R^{11}$ have the meanings described above, in particular the meanings described in Configuration (1) or Configuration (2) or Configuration (3) or Configuration (4) or Configuration (5).

In a preferred embodiment, the invention relates to the compounds of the formula (I)
where $R^8$ has the meanings described in Configuration (1) and
where Z, Y, $A^1$, $A^2$, $A^3$, $A^4$, X, $R^1$, $R^2$, $R^3$, $R^4$ $R^5$, $R^6$, $R^7$, $R^9$, $R^{10}$ and $R^{11}$ have the meanings described above, in particular the meanings described in Configuration (2) or Configuration (3) or Configuration (4) or Configuration (5) or Configuration (6).

In a further preferred embodiment, the invention relates to the compounds of the formula (I)
where $R^8$ has the meanings described in Configuration (2) and
where Z, Y, $A^1$, $A^2$, $A^3$, $A^4$, X, $R^1$, $R^2$, $R^3$, $R^4$ $R^5$, $R^6$, $R^7$, $R^9$, $R^{10}$ and $R^{11}$ have the meanings described above, in particular the meanings described in Configuration (1) or Configuration (3) or Configuration (4) or Configuration (5) or Configuration (6).

In a further preferred embodiment, the invention relates to the compounds of the formula (I)
where $R^8$ has the meanings described in Configuration (3) and where Z, Y, $A^1$, $A^2$, $A^3$, $A^4$, X, $R^1$, $R^2$, $R^3$, $R^4$ $R^5$, $R^6$, $R^7$, $R^9$, $R^{10}$ and $R^{11}$ have the meanings described above, in particular the meanings described in Configuration (1) or Configuration (2) or Configuration (4) or Configuration (5) or Configuration (6).

In a further preferred embodiment, the invention relates to the compounds of the formula (I)
where $R^8$ has the meanings described in Configuration (5) and
where Z, Y, $A^1$, $A^2$, $A^3$, $A^4$, X, $R^1$, $R^2$, $R^3$, $R^4$ $R^5$, $R^6$, $R^7$, $R^9$, $R^{10}$ and $R^{11}$ have the meanings described above, in particular the meanings described in Configuration (1) or Configuration (2) or Configuration (3) or Configuration (4) or Configuration (6).

In a further preferred embodiment, the invention relates to the compounds of the formula (I)
where $R^8$ has the meanings described in Configuration (6) and
where Z, Y, $A^1$, $A^2$, $A^3$, $A^4$, X, $R^1$, $R^2$, $R^3$, $R^4$ $R^5$, $R^6$, $R^1$, $R^9$, $R^{10}$ and $R^{11}$ have the meanings described above, in particular the meanings described in Configuration (1) or Configuration (2) or Configuration (3) or Configuration (4) or Configuration (5).

In a preferred embodiment, the invention relates to the compounds of the formula (I)
where $R^9$ has the meanings described in Configuration (1) and
where Z, Y, $A^1$, $A^2$, $A^3$, $A^4$, X, $R^1$, $R^2$, $R^3$, $R^4$ $R^5$, $R^6$, $R^7$, $R^9$, $R^{10}$ and $R^{11}$ have the meanings described above, in particular the meanings described in Configuration (2) or Configuration (3) or Configuration (4) or Configuration (5) or Configuration (6).

In a further preferred embodiment, the invention relates to the compounds of the formula (I)
where $R^9$ has the meanings described in Configuration (2) and
where Z, Y, $A^1$, $A^2$, $A^3$, $A^4$, X, $R^1$, $R^2$, $R^3$, $R^4$ $R^5$, $R^6$, $R^7$, $R^9$, $R^{10}$ and $R^{11}$ have the meanings described above, in particular the meanings described in Configuration (1) or Configuration (3) or Configuration (4) or Configuration (5) or Configuration (6).

In a further preferred embodiment, the invention relates to the compounds of the formula (I)
where $R^9$ has the meanings described in Configuration (3) and
where Z, Y, $A^1$, $A^2$, $A^3$, $A^4$, X, $R^1$, $R^2$, $R^3$, $R^4$ $R^5$, $R^6$, $R^7$, $R^8$, $R^{10}$ and $R^{11}$ have the meanings described above, in particular the meanings described in Configuration (1) or Configuration (2) or Configuration (4) or Configuration (5) or Configuration (6).

In a further preferred embodiment, the invention relates to the compounds of the formula (I)
where $R^9$ has the meanings described in Configuration (5) and
where Z, Y, $A^1$, $A^2$, $A^3$, $A^4$, X, $R^1$, $R^2$, $R^3$, $R^4$ $R^5$, $R^6$, $R^7$, $R^9$, $R^{10}$ and $R^{11}$ have the meanings described above, in particular the meanings described in Configuration (1) or Configuration (2) or Configuration (3) or Configuration (4) or Configuration (6).

In a further preferred embodiment, the invention relates to the compounds of the formula (I)
where $R^9$ has the meanings described in Configuration (6) and
where Z, Y, $A^1$, $A^2$, $A^3$, $A^4$, X, $R^1$, $R^2$, $R^3$, $R^4$ $R^5$, $R^6$, $R^7$, R, $R^{10}$ and $R^{11}$ have the meanings described above, in particular the meanings described in Configuration (1) or Configuration (2) or Configuration (3) or Configuration (4) or Configuration (5).

In a preferred embodiment, the invention relates to the compounds of the formula (I)
where $R^{10}$ and $R^{11}$ have the meanings described in Configuration (1) and
where Z, Y, $A^1$, $A^2$, $A^3$, $A^4$, X, $R^1$, $R^2$, $R^3$, $R^4$ $R^5$, $R^6$, $R^1$, $R^8$ and $R^9$ have the meanings described above, in particular the meanings described in Configuration (2) or Configuration (3) or Configuration (4) or Configuration (5) or Configuration (6).

In a further preferred embodiment, the invention relates to the compounds of the formula (I)
where $R^{10}$ and $R^{11}$ have the meanings described in Configuration (2) and
where Z, Y, $A^1$, $A^2$, $A^3$, $A^4$, X, $R^1$, $R^2$, $R^3$, $R^4$ $R^5$, $R^6$, $R^1$, $R^8$ and $R^9$ have the meanings described above, in particular the meanings described in Configuration (1) or Configuration (3) or Configuration (4) or Configuration (5) or Configuration (6).

In a further preferred embodiment, the invention relates to the compounds of the formula (I)
where $R^{10}$ and $R^{11}$ have the meanings described in Configuration (3) and
where Z, Y, $A^1$, $A^2$, $A^3$, $A^4$, X, $R^1$, $R^2$, $R^3$, $R^4$ $R^5$, $R^6$, $R^1$, $R^8$ and $R^9$ have the meanings described above, in particular the meanings described in Configuration (1) or Configuration (2) or Configuration (4) or Configuration (5) or Configuration (6).

In a further preferred embodiment, the invention relates to the compounds of the formula (I)
where $R^{10}$ and $R^{11}$ have the meanings described in Configuration (5) and
where Z, Y, $A^1$, $A^2$, $A^3$, $A^4$, X, $R^1$, $R^2$, $R^3$, $R^4$ $R^5$, $R^6$, $R^1$, $R^8$ and $R^9$ have the meanings described above, in particular the meanings described in Configuration (1) or Configuration (2) or Configuration (3) or Configuration (4) or Configuration (6).

In a further preferred embodiment, the invention relates to the compounds of the formula (I)
where $R^{10}$ and $R^{11}$ have the meanings described in Configuration (6) and
where Z, Y, $A^1$, $A^2$, $A^3$, $A^4$, X, $R^1$, $R^2$, $R^3$, $R^4$ $R^5$, $R^6$, $R^1$, $R^8$ and $R^9$ have the meanings described above, in particular the meanings described in Configuration (1) or Configuration (2) or Configuration (3) or Configuration (4) or Configuration (5).

Definitions

The person skilled in the art is aware that, if not stated explicitly, the expressions "a" or "an" as used in the present application may, depending on the situation, mean "one (1)", "one (1) or more" or "at least one (1)".

It is obvious to the person skilled in the art that examples given in the present application are not to be considered as limiting, but rather merely describe some embodiments in more detail.

For all the structures described herein, such as ring systems and groups, adjacent atoms must not be —O—O— or —O—S—.

Structures having a variable number of possible carbon atoms (C atoms) may be referred to in the present application as $C_{lower\ limit\ of\ carbon\ atoms}$-$C_{upper\ limit\ of\ carbon\ atoms}$ structures ($C_{LL}$-$C_{UL}$ structures), in order thus to be stipulated more specifically. Example: an alkyl group may consist of 3 to 10 carbon atoms and in that case corresponds to $C_3$-$C_{10}$-alkyl. Ring structures composed of carbon atoms and heteroatoms may be referred to as "LL- to UL-membered"

structures. One example of a 6-membered ring structure is toluene (a 6-membered ring structure substituted by a methyl group).

If a collective term for a substituent, for example $C_{LL}$-$C_{UL}$-alkyl, is at the end of a composite substituent, for example $C_{LL}$-$C_{UL}$-Cycloalkyl-$C_{LL}$-$C_{UL}$-alkyl, the constituent at the start of the composite substituent, for example the $C_{LL}$-$C_{UL}$-Cycloalkyl, may be mono- or polysubstituted identically or differently and independently by the latter substituent, $C_{LL}$-$C_{UL}$-alkyl. All the collective terms used in this application for chemical groups, cyclic systems and cyclic groups can be stipulated more specifically through the addition "$C_{LL}$-$C_{UL}$" or "LL- to UL-membered". Unless defined differently, the definition of collective terms also applies to these collective terms in composite substituents Example: the definition of $C_{LL}$-$C_{UL}$-alkyl also applies to $C_{LL}$-$C_{UL}$-alkyl as part of a composite substituent, for example $C_{LL}$-$C_{UL}$-cycloalkyl-$C_{LL}$-$C_{UL}$-alkyl.

In the definitions of the symbols given in the above formulae, collective terms which are generally representative of the following substituents were used:

halogen refers to the elements of the 7th main group, preferably fluorine, chlorine, bromine and iodine, more preferably fluorine, chlorine and bromine and still more preferably fluorine and chlorine.

Examples of heteroatom are N, O, S, P, B, Si. Preferably, the term "heteroatom" relates to N, S and O.

Unless defined differently elsewhere, "alkyl"—on its own or as part of a chemical group—represents straight-chain or branched hydrocarbons preferably having 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is also given to alkyls having 1 to 4 carbon atoms such as, inter alia, methyl, ethyl, ethyl, n-propyl, isopropyl, n-butyl, isobutyl, s-butyl or t-butyl. Unless defined differently elsewhere, "alkenyl"—on its own or as part of a chemical group—represents straight-chain or branched hydrocarbons preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preference is also given to alkenyls having 2 to 4 carbon atoms such as, inter alia, 2-propenyl, 2-butenyl or 1-methyl-2-propenyl.

Unless defined differently elsewhere, "alkynyl"—on its own or as part of a chemical group—represents straight-chain or branched hydrocarbons preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is also given to alkynyls having 2 to 4 carbon atoms such as, inter alia, ethynyl, 2-propynyl or 2-butynyl-2-propenyl.

Unless defined differently elsewhere, "cycloalkyl"—on its own or as part of a chemical group—represents mono-, bi- or tricyclic hydrocarbons preferably having 3 to 10 carbons, for example cyclopropyl, cyclobutyl, cyclopentyl, cyclohexyl, cycloheptyl, cyclooctyl, bicyclo[2.2.1]heptyl, bicyclo[2.2.2]octyl or adamantyl. Preference is also given to cycloalkyls having 3, 4, 5, 6 or 7 carbon atoms such as, inter alia, cyclopropyl or cyclobutyl. Unless defined differently elsewhere, "alkylcycloalkyl" represents mono-, bi- or tricyclic alkylcycloalkyl preferably having 4 to 10 or 4 to 7 carbon atoms, for example methylcyclopropyl, ethylcyclopropyl, isopropylcyclobutyl, 3-methylcyclopentyl and 4-methylcyclohexyl. Preference is also given to alkylcycloalkyls having 4, 5 or 7 carbon atoms such as, inter alia, ethylcyclopropyl or 4-methylcyclohexyl.

Unless defined differently elsewhere, "hydroxyalkyl" represents a straight-chain or branched alcohol preferably having 1 to 6 carbon atoms, for example methanol, ethanol, n-propanol, isopropanol, n-butanol, isobutanol, s-butanol and t-butanol. Preference is also given to hydroxyalkyl groups having 1 to 4 carbon atoms.

Unless defined differently elsewhere, "alkoxy" represents straight-chain or branched O-alkyl preferably having 1 to 6 carbon atoms such as, for example, methoxy, ethoxy, n-propoxy, isopropoxy, n-butoxy, isobutoxy, s-butoxy and t-butoxy. Preference is also given to alkoxy groups having 1 to 4 carbon atoms. Unless defined differently elsewhere, "alkylsulfanyl" represents straight-chain or branched S-alkyl preferably having 1 to 6 carbon atoms, for example methylthio, ethylthio, n-propylthio, isopropylthio, n-butylthio, isobutylthio, s-butylthio and t-butylthio. Preference is also given to alkylsulfanyl groups having 1 to 4 carbon atoms.

Unless defined differently elsewhere, "alkylsulfinyl" represents straight-chain or branched alkylsulfinyl preferably having 1 to 6 carbon atoms, for example methylsulfinyl, ethylsulfinyl, n-propylsulfinyl, isopropylsulfinyl, n-butylsulfinyl, isobutylsulfinyl, s-butylsulfinyl and t-butylsulfinyl. Preference is also given to alkylsulfinyl groups having 1 to 4 carbon atoms.

Unless defined differently elsewhere, "alkylsulfonyl" represents straight-chain or branched alkylsulfonyl preferably having 1 to 6 carbon atoms, for example methylsulfonyl, ethylsulfonyl, n-propylsulfonyl, isopropylsulfonyl, n-butylsulfonyl, isobutylsulfonyl, s-butylsulfonyl and t-butylsulfonyl. Preference is also given to alkylsulfonyl groups having 1 to 4 carbon atoms.

Unless defined differently elsewhere, "alkylcarbonyl" represents straight-chain or branched alkyl-C(=O) preferably having 2 to 7 carbon atoms such as methylcarbonyl, ethylcarbonyl, n-propylcarbonyl, isopropylcarbonyl, s-butylcarbonyl and t-butylcarbonyl. Preference is also given to alkylcarbonyls having 1 to 4 carbon atoms.

Unless defined differently elsewhere, "alkoxycarbonyl"—alone or as a constituent of a chemical group—represents straight-chain or branched alkoxycarbonyl, preferably having 1 to 6 carbon atoms or having 1 to 4 carbon atoms in the alkoxy moiety, for example methoxycarbonyl, ethoxycarbonyl, n-propoxycarbonyl, isopropoxycarbonyl, s-butoxycarbonyl and t-butoxycarbonyl.

Unless defined differently elsewhere, "alkylaminocarbonyl" represents straight-chain or branched alkylaminocarbonyl having preferably 1 to 6 carbon atoms or 1 to 4 carbon atoms in the alkyl moiety, for example methylaminocarbonyl, ethylaminocarbonyl, n-propylaminocarbonyl, isopropylaminocarbonyl, s-butylaminocarbonyl and t-butylaminocarbonyl. The alkylaminocarbonyl groups according to the invention may be substituted by one or more identical or different radicals.

Unless defined differently elsewhere, "N,N-dialkylaminocarbonyl" represents straight-chain or branched N,N-dialkylaminocarbonyl having preferably 1 to 6 carbon atoms or 1 to 4 carbon atoms in the alkyl moiety, for example N,N-dimethylaminocarbonyl, N,N-diethylaminocarbonyl, N,N-di(n-propylamino)carbonyl, N,N-di(isopropylamino)carbonyl and N,N-di-(s-butylamino)carbonyl.

Unless defined differently elsewhere, "N,N-dialkylamino" represents straight-chain or branched N,N-dialkylamino having preferably 1 to 6 carbon atoms or 1 to 4 carbon atoms in the alkyl moiety, for example N,N-dimethylamino-1, N,N-diethylamino, N,N-di(n-propylamino), N,N-di(isopropylamino) and N,N-di-(s-butylamino). Unless defined differently elsewhere, "alkanoyl" or else "alkylcarbonyl" represents straight-chain or branched alkyl radical having 1 to 6 carbon atoms which carries a doubly attached oxygen atom in the 1-position and is attached via the 1-position. Examples include: formyl, acetyl, propionyl, n-butyryl, i-butyryl, pivaloyl, n-hexanoyl.

Unless defined differently elsewhere, "aryl" represents a mono-, bi- or polycyclic aromatic system having preferably 6 to 14, especially 6 to 10, ring carbon atoms, for example phenyl, naphthyl, anthryl, phenanthrenyl, preferably phenyl. In addition, aryl also represents polycyclic systems such as tetrahydronaphthyl, indenyl, indanyl, fluorenyl, biphenyl, where the bonding site is on the aromatic system.

Examples of substituted aryls are the arylalkyls, which may likewise be substituted by one or more identical or different radicals in the $C_1$-$C_4$-alkyl and/or $C_6$-$C_{14}$-aryl moiety. Examples of such arylalkyls include benzyl and 1-phenylethyl.

Unless defined differently elsewhere, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted, where the bonding site is on a ring atom. Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulfur atoms. If the heterocyclyl radical or the heterocyclic ring is optionally substituted, it may be fused to other carbocyclic or heterocyclic rings. In the case of optionally substituted heterocyclyl, the invention also embraces polycyclic systems, for example 8-azabicyclo [3.2.1]octanyl or 1-azabicyclo[2.2.1]heptyl. In the case of optionally substituted heterocyclyl, the invention also embraces spirocyclic systems, for example 1-oxa-5-azaspiro [2.3]hexyl.

Heterocyclyl groups according to the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

The term "optionally substituted" groups/substituents, such as a substituted alkyl, alkenyl, alkynyl, alkoxy, alkylsulfanyl, alkylsulfinyl, alkylsulfonyl, cycloalkyl, aryl, phenyl, benzyl, heterocyclyl and heteroaryl radical, denotes, for example, a substituted radical derived from an unsubstituted base structure, where the substituents are, for example, one (1) substituent or a plurality of substituents, preferably 1, 2, 3, 4, 5, 6 or 7, selected from a group consisting of amino, hydroxy, halogen, nitro, cyano, isocyano, mercapto, isothiocyanato, $C_1$-$C_4$-carboxy, carboxamide, $SF_5$, aminosulfonyl, $C_1$-$C_4$-alkyl, $C_3$-$C_4$-cycloalkyl, $C_2$-$C_4$-alkenyl, $C_5$-$C_6$-cycloalkenyl, $C_2$-$C_4$-alkynyl, N-mono-$C_1$-$C_4$-alkylamino, N,N-di-$C_1$-$C_4$-alkylamino, N—$C_1$-$C_4$-alkanoylamino, $C_1$-$C_4$-alkoxy, $C_2$-$C_4$-alkenyloxy, $C_2$-$C_4$-alkynyloxy, $C_3$-$C_4$-cycloalkoxy, $C_5$-$C_6$-cycloalkenyloxy, $C_1$-$C_4$-alkoxycarbonyl, $C_2$-$C_4$-alkenyloxycarbonyl, $C_2$-$C_4$-alkynyloxycarbonyl, $C_6$-,$C_{10}$-,$C_{14}$-aryloxycarbonyl, $C_1$-$C_4$-alkanoyl, $C_2$-$C_4$-alkenylcarbonyl, $C_2$-$C_4$-alkynylcarbonyl, $C_6$-,$C_{10}$-,$C_{14}$-arylcarbonyl, $C_1$-$C_4$-alkylsulfanyl, $C_3$-$C_4$-cycloalkylsulfanyl, $C_1$-$C_4$-alkylthio, $C_2$-$C_4$-alkenylthio, $C_5$-$C_6$-cycloalkenylthio, $C_2$-$C_4$-alkynylthio, $C_1$-$C_4$-alkylsulfenyl and $C_1$-$C_4$-alkylsulfinyl, where both enantiomers of the $C_1$-$C_4$-alkylsulfinyl group are included, $C_1$-$C_4$-alkylsulfonyl, N-mono-$C_1$-$C_4$-alkylaminosulfonyl, N,N-di-$C_1$-$C_4$-alkylaminosulfonyl, $C_1$-$C_4$-alkylphosphinyl, $C_1$-$C_4$-alkylphosphonyl, where for $C_1$-$C_4$-alkylphosphinyl and $C_1$-$C_4$-alkylphosphonyl both enantiomers are included, N—$C_1$-$C_4$-alkylaminocarbonyl, N,N-di-$C_1$-$C_4$-alkylaminocarbonyl, N—$C_1$-$C_4$-alkanoylaminocarbonyl, N—$C_1$-$C_4$-alkanoyl-N—$C_1$-$C_4$-alkylaminocarbonyl, —CH=N—O—[($C_1$-$C_4$)-alkyl], —C[($C_1$-$C_4$)-alkyl]=N—O—[($C_1$-$C_4$)-alkyl, $C_6$-,$C_{10}$-,$C_{14}$-aryl, $C_6$-,$C_{10}$-,$C_{14}$-aryloxy, benzyl, benzyloxy, benzylthio, $C_6$-,$C_{10}$-,$C_{14}$-arylthio, $C_6$-,$C_{10}$-,$C_{14}$-arylamino, benzylamino, heterocyclyl and trialkylsilyl, substituents attached via a double bond such as $C_1$-$C_4$-alkylidene (e.g. methylidene or ethylidene), an oxo group, an imino group and a substituted imino group. If two or more radicals form one or more rings, these may be carbocyclic, heterocyclic, saturated, partially saturated, unsaturated, for example also aromatic and further-substituted.

The substituents mentioned by way of example ("first substituent level") may, if they contain hydrocarbonaceous components, optionally have further substitution therein ("second substituent level"), for example by one or more of the substituents each independently selected from halogen, hydroxyl, amino, nitro, cyano, isocyano, azido, acylamino, an oxo group and an imino group. The term "optionally substituted" group preferably embraces just one or two substituent levels.

Unless defined differently elsewhere, the halogen-substituted chemical groups (such as, for example, alkyl, cycloalkyl or alkoxy) are mono- or polysubstituted by halogen up to the maximum possible number of substituents. Such groups are also referred to as halo groups (such as, for example, haloalkyl). In the case of polysubstitution by halogen, the halogen atoms may be identical or different, and may all be bonded to one carbon atom or may all be bonded to a plurality of carbon atoms. Here, halogen represents in particular fluorine, chlorine, bromine or iodine, preferably fluorine, chlorine or bromine and more preferably fluorine. More particularly, halogen-substituted groups are monohalocycloalkyl such as 1-fluorocyclopropyl, 2-fluorocyclopropyl or 1-fluorocyclobutyl, monohaloalkyl such as 2-chloroethyl, 2-fluoroethyl, 1-chloroethyl, 1-fluoroethyl, chloromethyl, or fluoromethyl; perhaloalkyl such as trichloromethyl or trifluoromethyl or $CF_2CF_3$, polyhaloalkyl such as difluoromethyl, 2-fluoro-2-chloroethyl, dichloromethyl, 1,1,2,2-tetrafluoroethyl or 2,2,2-trifluoroethyl. Further examples of haloalkyls are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl, 3,3,3-trifluoropropyl and pentafluoro-t-butyl. Preference is given to haloalkyls having 1 to 4 carbon atoms and 1 to 9, preferably 1 to 5, identical or different halogen atoms selected from fluorine, chlorine and bromine. Particular preference is given to haloalkyls having 1 or 2 carbon atoms and 1 to 5 identical or different halogen atoms selected from fluorine and chlorine, such as, inter alia, difluoromethyl, trifluoromethyl or 2,2-difluoroethyl. Further examples of compounds substituted by halogen are haloalkoxy such as $OCF_3$, $OCHF_2$, $OCH_2F$, $OCF_2CF_3$, $OCH_2CF_3$, $OCH_2CHF_2$ and $OCH_2CH_2Cl$, haloalkylsulfanyls such as difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio, haloalkylsulfinyls such as difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl, haloalkylsulfinyls such as difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl, haloalkylsulfonyl groups such as difluoromethylsulfonyl, trifluoromethylsulfonyl, trichloromethylsulfonyl, chlorodifluoromethylsulfonyl, 1-fluoroethylsulfonyl, 2-fluoroethylsulfonyl, 2,2-difluoroethylsulfonyl, 1,1,2,2-tetrafluoroethylsulfonyl, 2,2,2-trifluoroethylsulfonyl and 2-chloro-1,1,2-trifluoroethylsulfonyl.

Unless defined differently elsewhere, in the case of radicals having carbon atoms preference is given to those having 1 to 4 carbon atoms, in particular 1 or 2 carbon atoms. Preference is generally given to substituents from the group of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given here to the substituents methyl, methoxy, fluorine and chlorine.

Unless defined differently elsewhere, substituted amino such as mono- or disubstituted amino is a radical from the group of the substituted amino radicals N-substituted, for example, by one or two identical or different radicals from the group of alkyl, hydroxyl, amino, alkoxy, acyl and aryl; preferably N-mono- and N,N-dialkylamino (e.g. methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (e.g. N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and saturated N-heterocycles; preference is given to alkyl radicals having 1 to 4 carbon atoms; aryl is preferably phenyl or substituted phenyl; acyl is as defined further down, preferably $(C_1-C_4)$alkanoyl. The same applies to substituted hydroxylamino or hydrazino.

Substituted amino also includes quaternary ammonium compounds (salts) having four organic substituents on the nitrogen atom.

Unless defined differently elsewhere, optionally substituted phenyl is preferably phenyl which is unsubstituted or mono- or polysubstituted, preferably up to trisubstituted, by identical or different radicals from the group of halogen, $C_1-C_4$-alkyl, $C_1-C_4$-alkoxy, $C_1-C_4$-alkoxy-$C_1-C_4$-alkoxy, $C_1-C_4$-alkoxy-$C_1-C_4$-alkyl, $C_1-C_4$-haloalkyl, $C_1-C_4$-haloalkoxy, $C_1-C_4$-alkylsulfanyl, $C_1-C_4$-haloalkylsulfanyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl, 4-heptafluorophenyl.

Unless defined differently elsewhere, optionally substituted cycloalkyl is preferably cycloalkyl, which is unsubstituted or mono- or polysubstituted, preferably up to trisubstituted, by identical or different radicals from the group of halogen, cyano, $C_1-C_4$-alkyl, $C_1-C_4$-alkoxy, $C_1-C_4$-alkoxy-$C_1-C_4$-alkoxy, $C_1-C_4$-alkoxy-$C_1-C_4$-alkyl, $C_1-C_4$-haloalkyl and $C_1-C_4$-haloalkoxy, especially substituted by one or two $C_1-C_4$-alkyl radicals.

Compounds according to the invention may occur in preferred embodiments. Individual embodiments described herein may be combined with one another. Not included are combinations which contravene the laws of nature and which the person skilled in the art would therefore rule out on the basis of his/her expert knowledge. Ring structures having three or more adjacent oxygen atoms, for example, are excluded.

Isomers

Depending on the nature of the substituents, the compounds of the formula (I) may take the form of geometric and/or optically active isomers or corresponding isomer mixtures in different compositions. These stereoisomers are, for example, enantiomers, diastereomers, atropisomers or geometric isomers. The invention therefore encompasses both pure stereoisomers and any desired mixtures of these isomers.

Methods and Uses

The invention also relates to methods for controlling animal pests where compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection compositions.

In the context of the present application, the term "pesticide" in each case also always encompasses the term "crop protection composition".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are carried out on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) can preferably be used as pesticides. They are active against normally sensitive and resistant species and also against all or specific stages of development. The aforementioned pests include:
pests from the phylum of the Arthropoda, in particular
from the class of the Arachnida, for example *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici;*
from the class of the Chilopoda, for example *Geophilus* spp., *Scutigera* spp.;
from the order or the class of the Collembola, for example *Onychiurus armatus; Sminthurus viridis*; from the class of the Diplopoda, for example *Blaniulus guttulatus;*
from the class of the Insecta, for example from the order of the Blattodea, e.g. *Blatta orientalis, Blattella asahinai, Blattella germanica, Leucophaea maderae, Loboptera decipiens, Neostylopyga rhombifolia,* Panchlora spp., Parcoblatta spp., *Periplaneta* spp., e.g. *Periplaneta americana, Periplaneta australasiae, Pycnoscelus surinamensis, Supella longipalpa;*
from the order of the Coleoptera, for example *Acalymma vittatum, Acanthoscelides obtectus, Adoretus* spp., *Aethina tumida, Agelastica alni, Agrilus* spp., e.g. *Agrilus planipennis, Agrilus coxalis, Agrilus bilineatus, Agrilus anxius, Agriotes* spp., e.g. *Agriotes linneatus, Agriotes mancus, Alphitobius diaperinus, Amphimallon solstitialis, Anobium punctatum, Anoplophora* spp., e.g. *Anoplophora glabripennis, Anthonomus* spp., e.g. *Anthonomus grandis, Anthrenus* spp., *Apion* spp., *Apogonia* spp., *Atomaria* spp., e.g. *Atomaria linearis, Attagenus* spp., *Baris caerulescens, Bruchidius obtectus, Bruchus* spp., e.g. *Bruchus pisorum, Bruchus rufimanus, Cassida* spp., *Cerotoma trifurcata, Ceutorrhynchus* spp., e.g. *Ceutorrhynchus assimilis, Ceutorrhynchus quadridens, Ceutorrhynchus rapae, Chaetocnema* spp., e.g. *Chaetocnema confinis, Chaetocnema denticulata, Chaetocnema ectypa, Cleonus mendicus, Conoderus* spp., *Cosmopolites* spp., e.g. *Cosmopolites sordidus, Costelytra zealandica, Ctenicera* spp., *Curculio* spp., e.g. *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus fumissi, Dendroctonus* spp., e.g. *Dendroctonus ponderosae, Dermestes* spp., *Diabrotica* spp., e.g. *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., e.g. *Epilachna borealis, Epilachna varivestis, Epitrix* spp., e.g. *Epitrix cucumeris,*

*Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., e.g. *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., e.g. *Leucoptera coffeella, Limonius ectypus, Lissorhoptrus oryzophilus, Listronotus* (=*Hyperodes*) spp., *Lixus* spp., *Luperodes* spp., *Luperomorpha xanthodera, Lyctus* spp., *Megacyllene* spp., e.g. *Megacyllene robiniae, Megascelis* spp., *Melanotus* spp., e.g. *Melanotus longulus oregonensis, Meligethes aeneus, Melolontha* spp., e.g. *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., e.g. *Otiorhynchus cribricollis, Otiorhynchus ligustici, Otiorhynchus ovatus, Otiorhynchus rugosostriarus, Otiorhynchus sulcatus, Oulema* spp., e.g. *Oulema melanopus, Oulema oryzae, Oxycetonia jucunda, Phaedon cochleariae, Phyllophaga* spp., *Phyllophaga helleri, Phyllotreta* spp., e.g. *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., e.g. *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., e.g. *Scolytus multistriatus, Sinoxylon perforans, Sitophilus* spp., e.g. *Sitophilus granarius, Sitophilus linearis, Sitophilus oryzae, Sitophilus zeamais, Sphenophorus* spp., *Stegobium paniceum, Stemechus* spp., e.g. *Stemechus paludatus, Symphyletes* spp., *Tanymecus* spp., e.g. *Tanymecus dilaticollis, Tanymecus indicus, Tanymecus palliatus, Tenebrio molitor, Tenebrioides mauretanicus, Tribolium* spp., e.g. *Tribolium audax, Tribolium castaneum, Tribolium confusum, Trogoderma* spp., *Tychius* spp., *Xylotrechus* spp., *Zabrus* spp., e.g. *Zabrus tenebrioides;* from the order of the Dermaptera, for example *Anisolabis maritime, Forficula auricularia, Labidura riparia;* from the order of the Diptera, for example *Aedes* spp., e.g. *Aedes aegypti, Aedes albopictus, Aedes sticticus, Aedes vexans, Agromyza* spp., e.g. *Agromyza frontella, Agromyza parvicornis, Anastrepha* spp., *Anopheles* spp., e.g. *Anopheles quadrimaculatus, Anopheles gambiae, Asphondylia* spp., *Bactrocera* spp., e.g. *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., e.g. *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., e.g. *Culex pipiens, Culex quinquefasciatus, Culicoides* spp., *Culiseta* spp., *Cuterebra* spp., *Dacus oleae, Dasineura* spp., e.g. *Dasineura brassicae, Delia* spp., e.g. *Delia antiqua, Delia coarctata, Delia florilega, Delia platura, Delia radicum, Dermatobia hominis, Drosophila* spp., e.g. *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., e.g. *Liriomyza brassicae, Liriomyza huidobrensis, Liriomyza sativae, Lucilia* spp., e.g. *Lucilia cuprina, Lutzomyia* spp., *Mansonia* spp., *Musca* spp., e.g. *Musca domestica, Musca domestica vicina, Oestrus* spp., *Oscinella frit, Paratanytarsus* spp., *Paralauterborniella subcincta, Pegomya oder Pegomyia* spp., e.g. *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., e.g. *Rhagoletis cingulata, Rhagoletis completa, Rhagoletis fausta, Rhagoletis indifferens, Rhagoletis mendax, Rhagoletis pomonella, Sarcophaga* spp., *Simulium* spp., e.g. *Simulium meridionale, Stomoxys* spp., *Tabanus* spp., *Tetanops* spp., *Tipula* spp., e.g. *Tipula paludosa, Tipula simplex, Toxotrypana curvicauda;* from the order of the Hemiptera, for example *Acizzia acaciaebaileyanae, Acizzia dodonaeae, Acizzia uncatoides, Acrida turrita, Acyrthosipon* spp., e.g. *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., e.g. *Amrasca bigutulla, Amrasca devastans, Anuraphis cardui, Aonidiella* spp., e.g. *Aonidiella aurantii, Aonidiella citrina, Aonidiella inomata, Aphanostigma piri, Aphis* spp., e.g. *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis vibumiphila, Arboridia apicalis, Arytainilla* spp., *Aspidiella* spp., *Aspidiotus* spp., e.g. *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., e.g. *Cacopsylla pyricola, Calligypona marginata, Capulinia* spp., *Cameocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., e.g. *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., e.g. *Dysaphis apiifolia, Dysaphis plantaginea, Dysaphis tulipae, Dysmicoccus* spp., *Empoasca* spp., e.g. *Empoasca abrupta, Empoasca fabae, Empoasca maligna, Empoasca solana, Empoasca stevensi, Eriosoma* spp., e.g. *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., e.g. *Icerya purchasi, Idiocerus* spp., *Idioscopus* spp., *Laodelphax striatellus, Lecanium* spp., e.g. *Lecanium comi* (=*Parthenoleca-* nium comi), Lepidosaphes spp., e.g. Lepidosaphes ulmi, Lipaphis erysimi, Lopholeucaspis japonica, Lycorma delicatula, Macrosiphum spp., e.g. Macrosiphum euphorbiae, Macrosiphum lilii, Macrosiphum rosae, Macrosteles facifrons, Mahanarva spp., Melanaphis sacchari, Metcalfiella spp., Metcalfa pruinosa, Metopolophium dirhodum, Monellia costalis, Monelliopsis pecanis, Myzus spp., e.g. Myzus ascalonicus, Myzus cerasi, Myzus ligustri, Myzus ornatus, Myzus persicae, Myzus nicotianae, Nasonovia ribisnigri, Neomaskellia spp., Nephotettix spp., e.g. Nephotettix cincticeps, Nephotettix nigropictus, Nettigonicla spectra, Nilaparvata lugens, Oncometopia spp., Orthezia praelonga, Oxya chinensis, Pachypsylla spp., Parabemisia myricae, Paratrioza spp., e.g. Paratrioza cockerelli, Parlatoria spp., Pemphigus spp., e.g. Pemphigus bursarius, Pemphigus populivenae, Peregrinus maidis, Perkinsiella spp., Phenacoccus spp., e.g. Phenacoccus madeirensis, Phloeomyzus passerinii, Phorodon humuli, Phylloxera spp., e.g. Phylloxera devastatrix, Phylloxera notabilis, Pinnaspis aspidistrae, Planococcus spp., e.g. Planococcus citri, Prosopidopsylla flava, Protopulvinaria pyriformis, Pseudaulacaspis pentagona, Pseudococcus spp., e.g. Pseudococcus calceolariae, Pseudococcus comstocki, Pseudococcus longispinus, Pseudococcus maritimus, Pseudococcus vibumi, Psyllopsis spp., Psylla spp., e.g. Psylla buxi, Psylla mali, Psylla pyri, Pteromalus spp., Pulvinaria spp., Pyrilla spp., Quadraspidiotus spp., e.g. Quadraspidiotus juglansregiae, Quadraspidiotus ostreaeformis, Quadraspidiotus pemiciosus, Quesada gigas, Rastrococcus spp., Rhopalosiphum spp., e.g. Rhopalosiphum maidis, Rhopalosiphum oxyacanthae, Rhopalosiphum padi, Rhopalosiphum rufiabdominale, Saissetia spp., e.g. Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata spp., Sogatella furcifera, Sogatodes spp., Stictocephala festina, Siphoninus phillyreae, Tenalaphara malayensis, Tetragonocephela spp., Tinocallis caryaefoliae, Tomaspis spp., Toxoptera spp., e.g. Toxoptera aurantii, Toxoptera citricidus, Trialeurodes vaporariorum, Trioza spp., e.g. Trioza diospyri, Typhlocyba spp., Unaspis spp., Viteus vitifolii, Zygina spp.;

from the suborder of the Heteroptera, for example, Aelia spp., Anasa tristis, Antestiopsis spp., Boisea spp., Blissus spp., Calocoris spp., Campylomma livida, Caveleius spp., Cimex spp., e.g. Cimex adjunctus, Cimex hemipterus, Cimex lectularius, Cimex pilosellus, Collaria spp., Creontiades dilutus, Dasynus piperis, Dichelops furcatus, Diconocoris hewetti, Dysdercus spp., Euschistus spp., e.g. Euschistus heros, Euschistus servus, Euschistus tristigmus, Euschistus variolarius, Eurydema spp., Eurygaster spp., Halyomorpha halys, Heliopeltis spp., Horcias nobilellus, Leptocorisa spp., Leptocorisa varicornis, Leptoglossus occidentalis, Leptoglossus phyllopus, Lygocoris spp., e.g. Lygocoris pabulinus, Lygus spp., e.g. Lygus elisus, Lygus hesperus, Lygus lineolaris, Macropes excavatus, Megacopta cribraria, Miridae, Monalonion atratum, Nezara spp., e.g. Nezara viridula, Nysius spp., Oebalus spp., Pentomidae, Piesma quadrata, Piezodorus spp., e.g. Piezodorus guildinii, Psallus spp., Pseudacysta persea, Rhodnius spp., Sahlbergella singularis, Scaptocoris castanea, Scotinophora spp., Stephanitis nashi, Tibraca spp., Triatoma spp.;

from the order of the Hymenoptera, for example, Acromyrmex spp., Athalia spp., e.g. Athalia rosae, Atta spp., Camponotus spp., Dolichovespula spp., Diprion spp., e.g. Diprion similis, Hoplocampa spp., e.g. Hoplocampa cookei, Hoplocampa testudinea, Lasius spp., Linepithema (Iridiomyrmex) humile, Monomorium pharaonis, Paratrechina spp., Paravespula spp., Plagiolepis spp., Sirex spp., e.g. Sirex noctilio, Solenopsis invicta, Tapinoma spp., Technomyrmex albipes, Urocerus spp., Vespa spp., e.g. Vespa crabro, Wasmannia auropunctata, Xeris spp.;

from the order of the Isopoda, for example Armadillidium vulgare, Oniscus asellus, Porcellio scaber; from the order of the Isoptera, for example, Coptotermes spp., e.g. Coptotermes formosanus, Cornitermes cumulans, Cryptotermes spp., Incisitermes spp., Kalotermes spp., Microtermes obesi, Nasutitermis spp., Odontotermes spp., Porotermes spp., Reticulitermes spp., e.g. Reticulitermes flavipes, Reticulitermes hesperus;

from the order of the Lepidoptera, for example Achroia grisella, Acronicta major, Adoxophyes spp., e.g. Adoxophyes orana, Aedia leucomelas, Agrotis spp., e.g. Agrotis segetum, Agrotis ipsilon, Alabama spp., e.g. Alabama argillacea, Amyelois transitella, Anarsia spp., Anticarsia spp., e.g. Anticarsia gemmatalis, Argyroploce spp., Autographa spp., Barathra brassicae, Blastodacna atra, Borbo cinnara, Bucculatrix thurberiella, Bupalus piniarius, Busseola spp., Cacoecia spp., Caloptilia theivora, Capua reticulana, Carpocapsa pomonella, Carposina niponensis, Cheimatobia brumata, Chilo spp., e.g. Chilo plejadellus, Chilo suppressalis, Choreutis pariana, Choristoneura spp., Chrysodeixis chalcites, Clysia ambiguella, Cnaphalocerus spp., Cnaphalocrocis medinalis, Cnephasia spp., Conopomorpha spp., Conotrachelus spp., Copitarsia spp., Cydia spp., e.g. Cydia nigricana, Cydia pomonella, Dalaca noctuides, Diaphania spp., Diparopsis spp., Diatraea saccharalis, Dioryctria spp., e.g. Dioryctria zimmermani, Earias spp., Ecdytolopha aurantium, Elasmopalpus lignosellus, Eldana saccharina, Ephestia spp., e.g. Ephestia elutella, Ephestia kuehniella, Epinotia spp., Epiphyas postvittana, Erannis spp., Erschoviella musculana, Etiella spp., Eudocima spp., Eulia spp., Eupoecilia ambiguella, Euproctis spp., e.g. Euproctis chrysorrhoea, Euxoa spp., Feltia spp., Galleria mellonella, Gracillaria spp., Grapholitha spp., e.g. Grapholita molesta, Grapholita prunivora, Hedylepta spp., Helicoverpa spp., e.g. Helicoverpa armigera, Helicoverpa zea, Heliothis spp., e.g. Heliothis virescens, Hofmannophila pseudospretella, Homoeosoma spp., Homona spp., Hyponomeuta padella, Kakivoria flavofasciata, Lampides spp., Laphygma spp., Laspeyresia molesta, Leucinodes orbonalis, Leucoptera spp., e.g. Leucoptera coffeella, Lithocolletis spp., e.g. Lithocolletis blancardella, Lithophane antennata, Lobesia spp., e.g. Lobesia botrana, Loxagrotis albicosta, Lymantria spp., e.g. Lymantria dispar, Lyonetia spp., e.g. Lyonetia clerkella, Malacosoma neustria, Maruca testulalis, Mamestra brassicae, Melanitis leda, Mocis spp., Monopis obviella, Mythimna separata, Nemapogon cloacellus, Nymphula spp., Oiketicus spp., Omphisa spp., Operophtera spp., Oria spp., Orthaga spp., Ostrinia spp., e.g. Ostrinia nubilalis, Panolis flammea, Parnara spp., Pectinophora spp., e.g. Pectinophora gossypiella, Perileucoptera spp., Phthorimaea spp., e.g. Phthorimaea operculella, Phyllocnistis citrella,

*Phyllonorycter* spp., e.g. *Phyllonorycter blancardella, Phyllonorycter crataegella, Pieris* spp., e.g. *Pieris rapae, Platynota stultana, Plodia interpunctella, Plusia* spp., *Plutella xylostella* (=*Plutella maculipennis*), *Podesia* spp., e.g. *Podesia syringae, Prays* spp., *Prodenia* spp., *Protoparce* spp., *Pseudaletia* spp., e.g. *Pseudaletia unipuncta, Pseudoplusia includens, Pyrausta nubilalis, Rachiplusia nu, Schoenobius* spp., e.g. *Schoenobius bipunctifer, Scirpophaga* spp., e.g. *Scirpophaga innotata, Scotia segetum, Sesamia* spp., e.g. *Sesamia inferens, Sparganothis* spp., *Spodoptera* spp., e.g. *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., e.g. *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., e.g. *Gryllotalpa gryllotalpa, Hieroglyphus* spp., *Locusta* spp., e.g. *Locusta migratoria, Melanoplus* spp., e.g. *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., e.g. *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., e.g. *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., e.g. *Thrips palmi, Thrips tabaci;* from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp., e.g. *Scutigerella immaculata;* pests from the phylum of the Mollusca, for example from the class of the Bivalvia, e.g. *Dreissena* spp.;

and also from the class of the Gastropoda, for example *Arion* spp., e.g. *Arion ater rufus, Biomphalaria* spp., *Bulinus* spp., *Deroceras* spp., e.g. *Deroceras laeve, Galba* spp., *Lymnaea* spp., *Oncomelania* spp., *Pomacea* spp., *Succinea* spp.;

plant pests from the phylum of the Nematoda, i.e. phytoparasitic nematodes, in particular *Aglenchus* spp., e.g. *Aglenchus agricola, Anguina* spp., e.g. *Anguina tritici, Aphelenchoides* spp., e.g. *Aphelenchoides arachidis, Aphelenchoides fragariae, Belonolaimus* spp., e.g. *Belonolaimus gracilis, Belonolaimus longicaudatus, Belonolaimus nortoni, Bursaphelenchus* spp., e.g. *Bursaphelenchus cocophilus, Bursaphelenchus eremus, Bursaphelenchus xylophilus, Cacopaurus* spp., e.g. *Cacopaurus pestis, Criconemella* spp., e.g. *Criconemella curvata, Criconemella onoensis, Criconemella ornata, Criconemella rusium, Criconemella xenoplax* (=*Mesocriconema xenoplax*), *Criconemoides* spp., e.g. *Criconemoides femiae, Criconemoides onoense, Criconemoides ornatum, Ditylenchus* spp., e.g. *Ditylenchus dipsaci, Dolichodorus* spp., *Globodera* spp., e.g. *Globodera pallida, Globodera rostochiensis, Helicotylenchus* spp., e.g. *Helicotylenchus dihystera, Hemicriconemoides* spp., *Hemicycliophora* spp., *Heterodera* spp., e.g. *Heterodera avenae, Heterodera glycines, Heterodera schachtii, Hirschmaniella* spp., *Hoplolaimus* spp., *Longidorus* spp., e.g. *Longidorus africanus, Meloidogyne* spp., e.g. *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., e.g. *Paratrichodorus minor, Paratylenchus* spp., *Pratylenchus* spp., e.g. *Pratylenchus penetrans, Pseudohalenchus* spp., *Psilenchus* spp., *Punctodera* spp., *Quinisulcius* spp., *Radopholus* spp., e.g. *Radopholus citrophilus, Radopholus similis, Rotylenchulus* spp., *Rotylenchus* spp., *Scutellonema* spp., *Subanguina* spp., *Trichodorus* spp., e.g. *Trichodorus obtusus, Trichodorus primitivus, Tylenchorhynchus* spp., e.g. *Tylenchorhynchus annulatus, Tylenchulus* spp., e.g. *Tylenchulus semipenetrans, Xiphinema* spp., e.g. *Xiphinema index.*

The compounds of the formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). They can, as the case may be, also be used as intermediates or precursors for the synthesis of other active compounds.

Formulations

The present invention further relates to formulations and application forms prepared therefrom as pesticides, for example drench, drip and spray liquors, comprising at least one compound of the formula (I). Optionally, the application forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemical active compounds.

Preference is given to formulations or application forms comprising at least one auxiliary, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the application forms prepared from these formulations (for example ready-to-use pesticides such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulfoxide, and water.

In principle, it is possible to use all suitable carriers. Suitable carriers include more particularly the following: e.g. ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the application forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and application forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, and natural phospholipids such as cephalins and lecithins and synthetic phospholipids. Further auxiliaries may be mineral and vegetable oils.

It is possible if appropriate for still further auxiliaries to be present in the formulations and the application forms derived therefrom. Examples of such additives are fragrances, protective colloids, binders, adhesives, thickeners, thixotropic agents, penetrants, retention promoters, stabilizers, sequestrants, complexing compositions, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and hence to increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the application forms prepared from the formulations (in particular pesticides) may vary within wide ranges. The concentration of the compound of the formula (I) in the application forms may typically be between 0.00000001% and 95% by weight of the compound of the formula (I), preferably between 0.00001% and 1% by weight, based on the weight of the application form. Application is accomplished in a customary manner appropriate for the application forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated levels of water or soil salinity. It is also possible to improve flowering and fruiting performance, optimize germination capacity and root development, facilitate harvesting and improve harvest yields, influence maturation, improve the quality and/or the nutritional value of the harvested products, prolong storage life and/or improve the processibility of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used to improve plant properties, for example growth, yield and quality of the harvested material.

In a particular embodiment according to the invention, the compounds of the formula (I) are present in formulations or in the application forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active compounds specified here by their common names are known and are described for example in "The Pesticide Manual" (16th ed., British Crop Protection Council 2012) or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, for example spinosyns, e.g. spinetoram and spinosad.

(6) Glutamate-gated chloride channel (GluCl) allosteric modulators, for example avermectins/milbemycins, e.g. abamectin, emamectin benzoate, lepimectin and milbemectin.

(7) Juvenile hormone mimetics, for example juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulfuryl fluoride or borax or tartar emetic or methyl isocyanate generator, e.g. diazomet and metam.

(9) Chordotonal organ modulators, e.g. pymetrozine or flonicamide.

(10) Mite growth inhibitors, for example clofentezine, hexythiazox and diflovidazin or etoxazole.

(11) Microbial disruptors of the insect gut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis* and B.t. plant proteins: Cry1Ab, Cry1Ac, Cry1Fa, Cry1A.105, Cry2Ab, VIP3A, mCry3A, Cry3Ab, Cry3Bb, Cry34Ab1/35Ab1.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists, for example chromafenozide, halofenozide, methoxyfenozide and tebufenozide.

(19) Octopamine receptor agonists, for example amitraz.

(20) Mitochondrial complex III electron transport inhibitors, for example hydramethylnon or acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spirodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilides, for example pyflubumide.

(28) Ryanodine receptor modulators, for example diamides, e.g. chlorantraniliprole, cyantraniliprole and flubendiamide, further active compounds, for example afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyrifluquinazon, pyriminostrobin, spirobudiclofen, tetramethylfluthrin, tetraniliprole, tetrachlorantraniliprole, tioxazafen, thiofluoximate, triflumezopyrim and iodomethane; additionally preparations based on *Bacillus firmus* (I-1582, BioNeem, Votivo), and the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457) (CAS 637360-23-7), 2-chloro-N—[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N—[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N—[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N—[3-chloro-1-(3-pyridinyl)-1H-pyrazol-4-yl]-N-ethyl-3-[(3,3,3-trifluoropropyl)sulfinyl]propanamide, (+)-N—[3-chloro-1-(3-pyridinyl)-1H-pyrazol-4-yl]-N-ethyl-3-[(3,3,3-trifluoropropyl)sulfinyl]propanamide and (−)-N—[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N—[4-chloro-2-methyl-6-[(methylamino)thioxomethyl]phenyl]-1-(3-chloro-2-pyridinyl)-1H-pyrazole-5-carboxamide (Liudaibenjiaxuanan, known from CN 103109816 A) (CAS 1232543-85-9); N—[4-chloro-2-[[(1,1-dimethylethyl)amino]carbonyl]-6-methylphenyl]-1-(3-chloro-2- pyridinyl)-3-(fluoromethoxy)-1H-pyrazole-5-carboxamide (known from WO 2012/034403 A1) (CAS 1268277-22-0), N—[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)pyrimidine (known from CN 101337940 A) (CAS 1108184-52-6); (2E)- and 2(Z)-2-[2-(4-cyanophenyl)-1-[3-(trifluoromethyl)phenyl]ethylidene]-N—[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxycarbonyl) [4-[(trifluoromethyl)thio]phenyl]amino]carbonyl]indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-1-[N—[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8), N—[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9) and N—[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7).

Fungicides

The active compounds specified here by their common names are known and described, for example, in "Pesticide Manual" (16th Ed. British Crop Protection Council) or searchable on the Internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimefon, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-ylthiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2- chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) mefentrifluconazole, (1.082) ipfentrifluconazole.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N—[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N—[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N—[1-(2,4-dichlorophenyl)-1-methoxypropan-2-yl]-3-(difluoromethyl)-1-methyl-1H-pyrazole-4-carboxamide, (2.042) N—[2-chloro-6-(trifluoromethyl)benzyl]-N-cyclopropyl-3-(difluoromethyl)-5-fluoro-1-methyl-1H-pyrazole-4-carboxamide, (2.043) N—[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N—[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N—[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain at complex III, for example (3.001) ametoctradin, (3.002) amisulbrom, (3.003)

azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3 S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dim- ethylphenyl)-1H-pyrazol-1-yl]-2-methylbenzylbenzyl} carbamate.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl} piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-

(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM 1-1562, or *Bacillus firmus*, strain I-1582 (Accession number CNCM 1-1582), or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), Pasteuria penetrans, Pasteuria spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KVO1, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum* rifai T39 (Accession number CNCM 1-952).

Examples of viruses which are used or can be used as biological pesticides are: *Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include: *Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), pyrethrum/pyrethrins, *Quassia amara*, *Quercus*, Quillaja, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, *Brassicaceae* extract, especially oilseed rape powder or mustard powder.

Safener as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N—({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The inventive treatment of the plants and parts of plants with the compounds of the formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having novel properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants to phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidal active compounds, for example imidazolinones, sulfonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other vegetable species, cotton, tobacco, oilseed rape, and also fruit plants (the fruits being apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Plant Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, meaning that the compounds of the formula (I) are applied to the foliage, in which case the treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) according to the invention are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from infestation by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from infestation by pests, by treating the seed with one of the compounds of the formula (I). The method according to the invention for protecting seed and germinating plants against infestation by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) according to the invention for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when a compound of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Compounds of the formula (I) can also be used in combination with signalling technology compositions, leading to better colonization by symbionts, for example rhizobia, mycorrhizae and/or endophytic bacteria or fungi, and/or to optimized nitrogen fixation.

The compounds of the formula (I) are suitable for the protection of seed of any plant variety which is used in agriculture, in greenhouses, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and methods for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting agents, dispersants, emulsifiers, antifoams, preservatives, secondary thickeners, adhesives, gibberellins, and also water.

Suitable dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting compositions which may be present in the seed-dressing formulations usable in accordance with the invention are all substances which promote wetting and which are customary for the formulation of agrochemically active compounds. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of agrochemically active compounds. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Useful secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Useful gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schaidlingsbekimpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute application forms thereof, can also be used to dress seed of transgenic plants.

For the treatment of seed with the seed-dressing formulations usable in accordance with the invention, or the application forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) having favourable endotherm toxicity are suitable for controlling parasites which occur in animal husbandry and animal keeping in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of the formula (I) are administered to mammals.

In another specific embodiment, the compounds of the formula (I) are administered to birds, namely caged birds or particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal keeping is enabled and better animal well-being is achievable.

In relation to the field of animal health, the term "control" or "controlling" in the present context means that the compounds of the formula (I) are effective in reducing the incidence of the particular parasite in an animal infected with such parasites to an innocuous degree. More specifically, "controlling" in the present context means that the compounds of the formula (I) kill the respective parasite, inhibit its growth, or inhibit its proliferation.

The arthropods include, for example, but are not limited to, from the order of Anoplurida, for example *Haematopinus* spp., *Linognathus* spp., *Pediculus* spp., *Phtirus* spp. and *Solenopotes* spp.;

from the order of Mallophagida and the suborders Amblycerina and Ischnocerina, for example, *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp;

from the order of Diptera and the suborders Nematocerina and Brachycerina, for example *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example *Ceratophyllus* spp., *Ctenocephalides* spp., *Pulex* spp., *Tunga* spp., *Xenopsylla* spp.;

from the order of Heteropterida, for example *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the subclass of Acari (Acarina) and the order of Metastigmata, for example from the family of Argasidae such as *Argas* spp., *Ornithodorus* spp., *Otobius* spp., from the family of Ixodidae such as *Amblyomma* spp., *Dermacentor* spp., *Haemaphysalis* spp., *Hyalomma* spp., *Ixodes* spp., *Rhipicephalus* (*Boophilus*) spp., *Rhipicephalus* spp. (the original genus of multihost ticks); from the order of Mesostigmata such as *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example, *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example, *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (*Flagellata*), such as:

Metamonada: from the order of Diplomonadida, for example *Giardia* spp., *Spironucleus* spp.

Parabasala: from the order of Trichomonadida, for example *Histomonas* spp., *Pentatrichomonas* spp., *Tetratrichomonas* spp., *Trichomonas* spp., *Tritrichomonas* spp.

Euglenozoa: from the order of Trypanosomatida, for example *Leishmania* spp., *Trypanosoma* spp.

Sarcomastigophora (*Rhizopoda*) such as Entamoebidae, for example, *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, nematodes, Pentastoma and Platyhelminthes (e.g. Monogenea, cestodes and trematodes).

Exemplary helminths include, but are not limited to:

Monogenea: e.g.: *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

From the order of Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example, *Linguatula* spp.

In the veterinary field and in animal keeping, the compounds of the formula (I) are administered by methods generally known in the art, such as via the enteral, parenteral, dermal or nasal route in the form of suitable preparations. Administration may be prophylactic, metaphylactic or therapeutic.

Thus, one embodiment of the present invention relates to the compounds of the formula (I) for use as a medicament.

A further aspect relates to the compounds of the formula (I) for use as an antiendoparasitic agent.

A further specific aspect of the invention relates to the compounds of the formula (I) for use as an antihelminthic agent, especially for use as a nematicide, platyhelminthicide, acanthocephalicide or pentastomicide.

A further specific aspect of the invention relates to the compounds of the formula (I) for use as an antiprotozoic agent.

A further aspect relates to the compounds of the formula (I) for use as an antiectoparasitic agent, especially an arthropodicide, very particularly an insecticide or an acaricide.

Further aspects of the invention are veterinary medicine formulations comprising an effective amount of at least one compound of the formula (I) and at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) with other active compounds, especially with endo- and ectoparasiticides, are provided for the field of veterinary medicine.

In the field of animal health, "mixture" means not just that two (or more) different active compounds are formulated in a common formulation and are correspondingly employed together, but also relates to products comprising formulations separated for each active compound. Accordingly, when more than two active compounds are to be employed, all active compounds can be formulated in a common formulation or all active compounds can be formulated in separate formulations; likewise conceivable are mixed forms in which some of the active compounds are formulated together and some of the active compounds are formulated separately. Separate formulations allow the separate or successive application of the active compounds in question.

The active compounds specified here by their common names are known and are described, for example, in the "Pesticide Manual" (see above) or can be searched for on the Internet (e.g.: http://www.alanwood.net/pesticides).

Illustrative active compounds from the group of the ectoparasiticides as mixing components include, without any intention that this should constitute a restriction, the insecticides and acaricides listed in detail above. Further usable active compounds are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multisite) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in the case of Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators;

- active compounds having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;
- compounds from other classes, for example butacarb, dimetilan, cloethocarb, phosphocarb, pirimiphos(-ethyl), parathion(-ethyl), methacrifos, isopropyl o-salicylate, trichlorfon, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos;
- organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;
- pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs),
- neonicotinoids, e.g. nithiazine
- dicloromezotiaz, triflumezopyrim
- macrocyclic lactones, e.g. nemadectin, ivermectin, latidectin, moxidectin, selamectin, eprinomectin, doramectin, emamectin benzoate; milbemycin oxime
- triprene, epofenonane, diofenolan;
- biologicals, hormones or pheromones, for example natural products, e.g. thuringiensin, codlemone or neem components
- dinitrophenols, e.g. dinocap, dinobuton, binapacryl;
- benzoylureas, e.g. fluazuron, penfluron,
- amidine derivatives, e.g. chlormebuform, cymiazole, demiditraz
- beehive varroa acaricides, for example organic acids, e.g. formic acid, oxalic acid.

Illustrative active compounds from the group of the endoparasiticides, as mixing components, include, but are not limited to, anthelmintically active compounds and antiprotozoic active compounds.

The active anthelmintic ingredients include, but are not limited to, the following active nematicidal, trematicidal and/or cestocidal ingredients:

- from the class of the macrocyclic lactones, for example: eprinomectin, abamectin, nemadectin, moxidectin, doramectin, selamectin, lepimectin, latidectin, milbemectin, ivermectin, emamectin, milbemycin;
- from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;
- from the class of the depsipeptides, preferably cyclic depsipeptides, especially 24-membered cyclic depsipeptides, for example: emodepside, PF1022A;
- from the class of the tetrahydropyrimidines, for example: morantel, pyrantel, oxantel;
- from the class of the imidazothiazoles, for example: butamisole, levamisole, tetramisole;
- from the class of the aminophenylamidines, for example: amidantel, deacylated amidantel (dAMD), tribendimidine;
- from the class of the aminoacetonitriles, for example: monepantel;
- from the class of the paraherquamides, for example: paraherquamide, derquantel;
- from the class of the salicylanilides, for example: tribromsalan, bromoxanide, brotianide, clioxanide, closantel, niclosamide, oxyclozanide, rafoxanide;
- from the class of the substituted phenols, for example: nitroxynil, bithionol, disophenol, hexachlorophene, niclofolan, meniclopholan;
- from the class of the organophosphates, for example: trichlorfon, naphthalofos, dichlorvos/DDVP, crufomate, coumaphos, haloxon;
- from the class of the piperazinones/quinolines, for example: praziquantel, epsiprantel;
- from the class of the piperazines, for example: piperazine, hydroxyzine;
- from the class of the tetracyclines, for example: tetracycline, chlortetracycline, doxycycline, oxytetracycline, rolitetracycline;
- from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Antiprotozoic active compounds include, but are not limited to, the following active compounds:

- from the class of the triazines, for example: diclazuril, ponazuril, letrazuril, toltrazuril;
- from the class of polyether ionophores, for example: monensin, salinomycin, maduramicin, narasin;
- from the class of the macrocyclic lactones, for example: milbemycin, erythromycin;
- from the class of the quinolones, for example: enrofloxacin, pradofloxacin;
- from the class of the quinines, for example: chloroquine;
- from the class of the pyrimidines, for example: pyrimethamine;

from the class of the sulfonamides, for example: sulfaquinoxaline, trimethoprim, sulfaclozin;

from the class of the thiamines, for example: amprolium;

from the class of the lincosamides, for example: clindamycin;

from the class of the carbanilides, for example: imidocarb;

from the class of the nitrofurans, for example: nifurtimox;

from the class of the quinazolinone alkaloids, for example: halofuginone;

from various other classes, for example: oxamniquin, paromomycin;

from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host.

The pathogens can be transmitted either mechanically (for example trachoma by non-stinging flies) onto a host or after injection into a host (for example malaria parasites by mosquitoes).

Examples of vectors and the diseases or pathogens they transmit are:

1) Mosquitoes

Anopheles: malaria, filariasis;

Culex: Japanese encephalitis, filariasis, other viral diseases, transmission of other worms;

Aedes: yellow fever, dengue fever, other viral diseases, filariasis;

Simuliidae: transmission of worms, especially *Onchocerca volvulus;*

Psychodidae: transmission of leishmaniasis

2) Lice: skin infections, epidemic typhus;

3) Fleas: plague, endemic typhus, tapeworms;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borelliosis such as *Borrelia bungdorferi* sensu lato., *Borrelia duttoni*, tick-borne encephalitis, Q fever (*Coxiella burnetii*), babesia (*Babesia canis canis*), ehrlichiosis.

Examples of vectors in the context of the present invention are insects, for example aphids, flies, leafhoppers or thrips, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, Psychodidae such as *Phlebotomus*, Lutzomyia, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against infestation or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, glues, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) take the form of a ready-to-use pesticide, meaning that they can be applied to the material in question without further modifications. Useful further insecticides or fungicides especially include those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling compositions.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

Preparation Processes

The compounds according to the invention can be prepared by customary methods known to those skilled in the art.

Reaction Scheme I - Method A

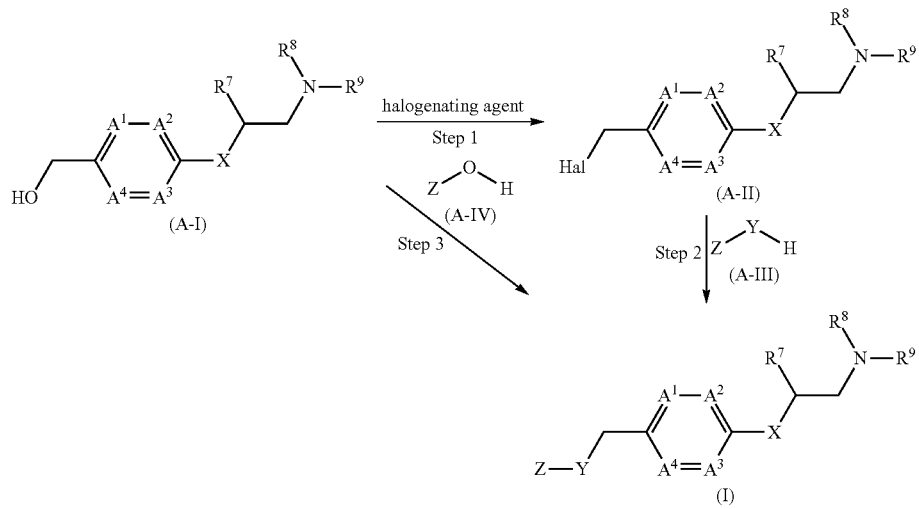

Compounds of the formula (I) can be prepared, for example, according to Reaction Scheme I in one or two steps. The radicals $A^1$, $A^2$, $A^3$, $A^4$, Z, X, $R^5$, $R^7$, $R^8$ and $R^9$ have the meanings mentioned above and optionally further meanings relevant for the preparation processes, which meanings are evident from the text or context. Y represents O, S or $NR^5$. Hal represents chlorine or bromine.

For example, using halogenating agents, alcohols of the formula (A-I) can be converted into benzyl halides of the formula (A-II). These then react in the presence of basic reaction auxiliaries in a second reaction step with compounds of the formula (A-III) in a nucleophilic substitution reaction to give compounds of the formula (I).

For compounds of the formula (I) in which Y represents oxygen, this reaction may alternatively also be carried out in a one-step process. Here, the benzyl alcohol of the formula (A-I) is activated in situ in the presence of a trialkyl- or triarylphosphane and an azodicarboxylate and reacts with an alcohol of the formula (A-IV) in a nucleophilic substitution reaction to give compounds of the formula (I).

Method A—Step 1:

The compounds of the formula (A-I) are known (e.g. [6-(4-ethylpiperazin-1-yl)pyridin-3-yl]methanol from WO2010/132999, tert-butyl 4-[3-chloro-5-(hydroxymethyl) pyridin-2-yl]piperazine-1-carboxylate from EP2050734 and tert-butyl 3-{[3-fluoro-5-(hydroxymethyl)pyridin-2-yl] amino}pyrrolidine-1-carboxylate from US2006/0052599) or can be obtained by known preparation processes. Further processes for their preparation have been described in this application, inter alia of (6-{2-[methoxy(methyl)amino] ethoxy}pyridin-3-yl)methanol and (3-fluoro-5-{2-[methoxy (methyl)amino]ethoxy}pyridin-2-yl)methanol (see also Schemes II and VI).

For the halogenation reaction, numerous reaction conditions have been described. They are known to those skilled in the art. Houben-Weyl, *Methoden der Organischen Chemie* [Methods of Organic Chemistry], Volume V/3 (Georg Thieme Verlag Stuttgart), p. 760 gives a review for Hal=Cl, and Houben-Weyl, *Methoden der Organischen Chemie*, Volume V/4 (Georg Thieme Verlag Stuttgart), p. 361 for Hal=Br. Preference is given to preparing the benzyl chlorides of the formula (A-II) in which Hal represents chlorine.

They can be prepared, for example, in the presence of thionyl chloride from the benzyl alcohols of the formula (A-I). The reaction can be carried out in a suitable inert solvent or diluent, for example toluene or dichloromethane, and optionally in the presence of catalytic amounts of N,N-dimethylformamide (cf., for example, 5-(chloromethyl)-2-(2,2,3,3-tetrafluoropropoxy)pyridine from WO2013/161312).

Method A—Step 2:

The compounds of the formula (A-III) are known, commercially available or can be obtained by known preparation processes (see, for example, WO2002017712 for 5,6-dichloro-1-naphthol). Further processes for their preparation have been described in the present application (see, for example, the preparation of 6-fluoro-3'-(trifluoromethoxy) biphenyl-3-ol and 4-chloro-3-methoxyphenol).

With heating in the presence of a basic reaction auxiliary such as, for example, potassium carbonate or caesium carbonate, the halides of the formula (A-II) react in a nucleophilic substitution reaction with compounds of the formula (A-III) to give compounds of the formula (I) in which Y represents O, S or $NR^5$. The reaction is optionally carried out in the presence of an inert solvent or diluent. Examples which may be mentioned are N,N-dimethylformamide, N-methyl-2-pyrrolidone and acetonitrile. For Y=O or $NR^5$, the reaction is preferably carried out at temperatures of 50-120° C., for Y=S at room temperature (see WO2015/089139 for Y=O, WO2013/019621 and WO2005/049572 for Y=$NR^5$, WO2012/082566 for Y=S).

Method A—Step 3:

The compounds of the formula (A-IV) are known, commercially available or can be obtained by known preparation processes. Further processes for their preparation are described in the present application (see, for example, the preparation of 6-fluoro-3'-(trifluoromethoxy)biphenyl-3-ol or 4-chloro-3-methoxyphenol).

The benzyl alcohols of the formula (A-I) react in the presence of a trialkyl- or triarylphosphane and an azodicarboxylate with an alcohol of the formula (A-IV) in a nucleophilic substitution reaction to give compounds of the formula (I) in which Y represents oxygen. This reaction is known to those skilled in the art as the "Mitsunobu reaction". The phosphane used is preferably triphenylphosphane, and the azodicarboxylate used is preferably diethyl azodicarboxylate. The reaction takes place in the presence of an inert solvent or diluent such as, for example, tetrahydrofuran. (see, for example, WO2016/044789).

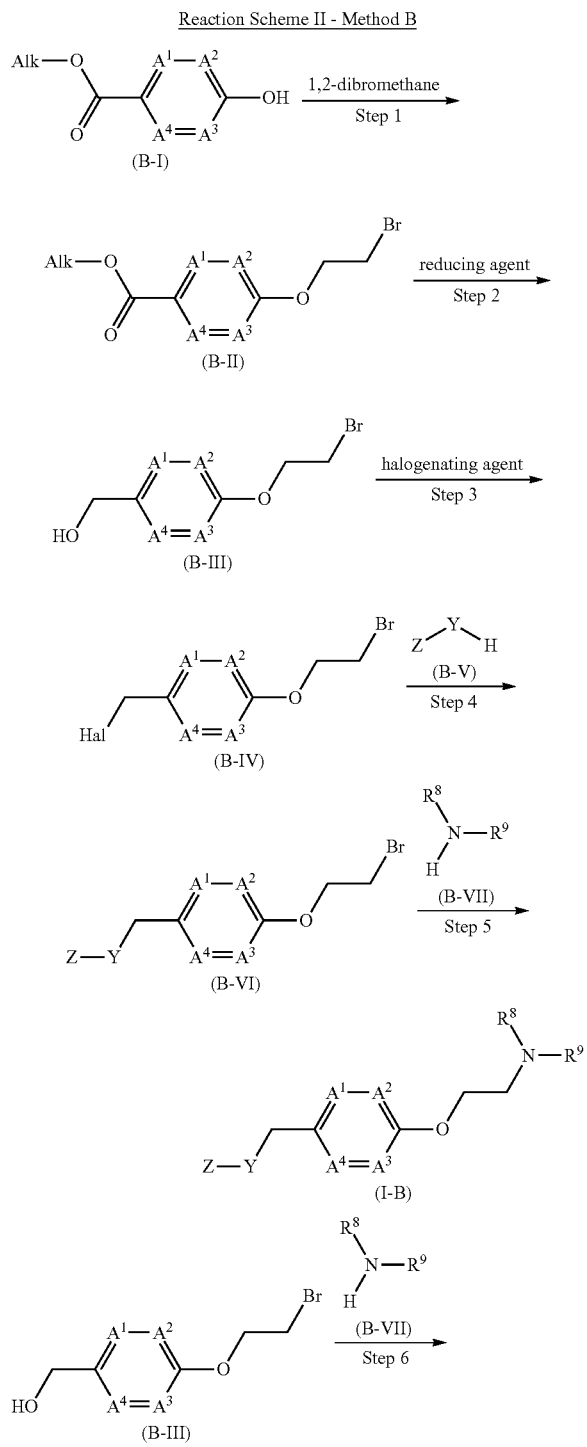

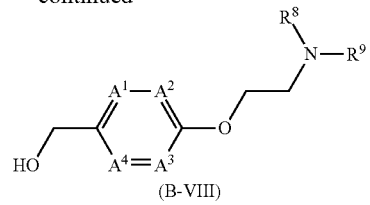

Compounds of the formula (I-B) can be prepared, for example, according to Reaction Scheme II. The radicals $A^1$, $A^2$, $A^3$, $A^4$, Z, $R^5$, $R^8$ and $R^9$ have the meanings mentioned above (where this process does not allow ring formation between $R^8$ and $R^6$ or R) and optionally further meanings relevant for the preparation processes which are evident from the text and the context. Y represents O, S or $NR^5$. Hal represents chlorine or bromine. Alk represents $(C_1-C_3)$-alkyl.

For example, alcohols of the formula (B-I) can react with 1,2-dibromoethane in the presence of basic reaction auxiliaries in a nucleophilic substitution reaction to give compounds of the formula (B-II). In a subsequent step, the alkyl ester function in compounds of the formula (B-II) can be reduced using a reducing agent to give benzyl alcohols of the formula (B-III). Using halogenating agents, benzyl alcohols of the formula (B-III) can then be converted into benzyl halides of the formula (B-IV). These can then react in the presence of basic reaction auxiliaries in a further reaction step with compounds of the formula (B-V) in a nucleophilic substitution reaction to give compounds of the formula (B-VI). In a further nucleophilic substitution reaction, amines of the formula (B-VII) can be reacted with the bromides of the formula (B-VI) to give compounds of the formula (I-B).

Method B—Step 1:

The compounds of the formula (B-I) are known, commercially available or can be obtained by known preparation processes (see, for example, WO2011/044181 for methyl 3-fluoro-5-hydroxypyridine-2-carboxylate).

The alcohols of the formula (B-I) react with 1,2-dibromomethane in the presence of a basic auxiliary such as, for example, potassium carbonate or caesium carbonate, and optionally in the presence of a catalytic amount of potassium iodide, in a nucleophilic substitution reaction. The reaction is optionally carried out in the presence of an inert solvent or diluent. Examples which may be mentioned are N,N-dimethylformamide, N-methyl-2-pyrrolidone and acetonitrile. The reaction is carried out at elevated temperature, preferably at 50° C. to 120° C. (for examples in which $A^1$ to $A^4$ represent —CH, see, for example, WO1998/48800).

Method B—Step 2:

The esters of the formula (B-II) react in the presence of a suitable reducing agent such as, for example, sodium borohydride or diisobutylaluminium hydride, to give benzyl alcohols of the formula (B-III). If the reaction is carried out in the presence of sodium borohydride, a suitable solvent or diluent such as, for example, ethanol or methanol is employed. Here, the reaction is preferably carried out at temperatures of from 0° C. to 50° C. If diisobutylaluminium hydride is used, the reaction is carried out in a suitable inert solvent, for example toluene or dichloromethane. Here, the reaction is preferably carried out at temperatures of from −78° C. to +30° C. (see, for example, the synthesis, described in the present application, of methyl 5-(2-bromoethoxy)-3-fluoropyridine-2-carboxylate). If diisobutylaluminium hydride is used, a mixture of the benzyl alcohols of the formula (B-III) with the analogous benzaldehydes may be obtained. In this case, in a second step, the aldehyde function is reduced to give the benzyl alcohols of the formula (B-III). This reaction can be carried out in the presence of sodium hydride under the conditions mentioned above.

Method B—Step 3:

For the halogenation reaction, numerous reaction conditions have been described. They are known to the person skilled in the art and have already been described under Step 1 of Method A.

Method B—Step 4:

The compounds of the formula (B-V) are known, commercially available or can be obtained by known preparation processes. Further processes for their preparation are described in the present application (see, for example, the preparation of 6-fluoro-3'-(trifluoromethoxy)biphenyl-3-ol or 4-chloro-3-methoxyphenol).

With heating in the presence of a basic reaction auxiliary such as, for example, potassium carbonate or caesium carbonate, the halides of the formula (B-IV) react in a nucleophilic substitution reaction with compounds of the formula (B-V) to give compounds of the formula (B-VI). The reaction is optionally carried out in the presence of an inert solvent or diluent. Examples which may be mentioned are N,N-dimethylformamide, N-methyl-2-pyrrolidone and acetonitrile. The reaction is preferably carried out at temperatures of from 50° C. to 120° C.

Method B—Step 5:

The compounds of the formula (B-VII) are known, commercially available or can be obtained by known preparation processes (see, for example, EP0678504 for 1-(aminooxy) propane). Some are also known as their hydrochlorides or hydrobromides and are commercially available.

Under heating, the bromides of the formula (B-VI) react in a nucleophilic substitution reaction with compounds of the formula (B-VII) to give compounds of the formula (I-B). The reaction is optionally carried out in the presence of an inert solvent or diluent. Examples which may be mentioned are N,N-dimethylformamide, N-methyl-2-pyrrolidone, acetonitrile and tetrahydrofuran. The reaction is optionally carried out in the presence of a basic reaction auxiliary such as, for example, potassium carbonate, caesium carbonate or N,N-diisopropylethylamine. The reaction is preferably carried out at temperatures of from 10° C. to 120° C. (without basic reaction auxiliary: WO2006/078619, in the presence of $K_2CO_3$: WO2010/071885, in the presence of N,N-diisopropylethylamine: WO2006/105304)

Method B—Step 6:

Under heating, the bromides of the formula (B-III) react in a nucleophilic substitution reaction with compounds of the formula (B-VII) to give compounds of the formula (B-VIII). The reaction conditions correspond to those described in Step 5. These can be converted into compounds of the formula (I-B) using Method A.

Reaction Scheme III - Method C

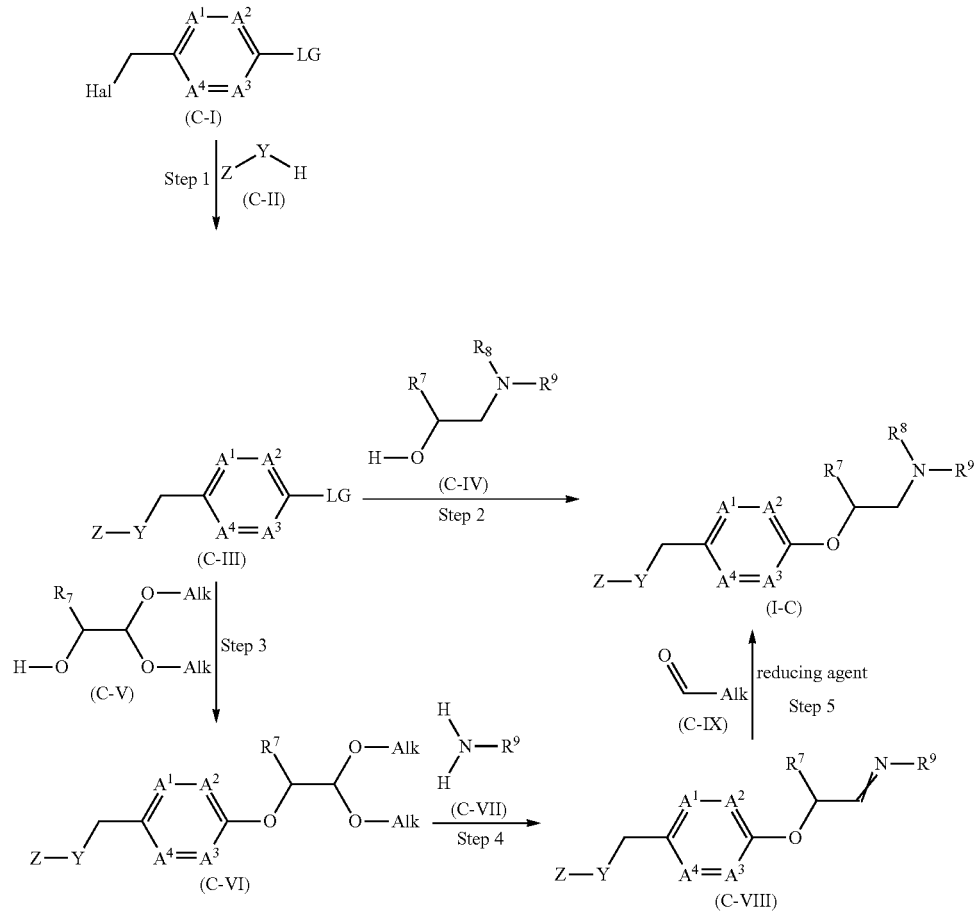

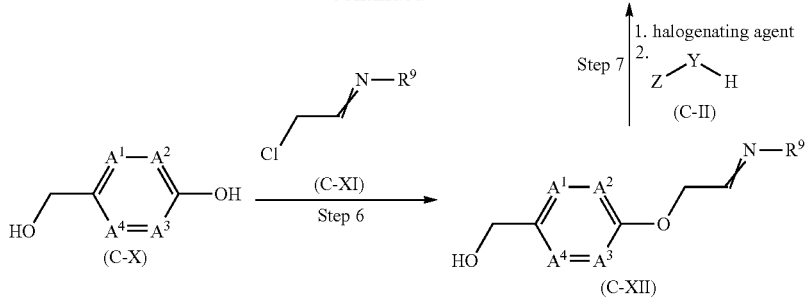

Compounds of the formula (I-C) can be prepared, for example, according to Reaction Scheme III. The radicals $A^1$, $A^2$, $A^3$, $A^4$, Z, $R^5$, $R^7$, $R^8$ and $R^9$ have the meanings mentioned above and optionally further meanings relevant for the preparation processes, which meanings are evident from the text or context. Y represents O, S or $NR^5$. Hal represents chlorine or bromine. LG represents fluorine or chlorine. Alk represents $(C_1-C_5)$-alkyl.

For example, compounds of the formula (C-I) can react with compounds of the formula (C-II) in the presence of basic reaction auxiliaries in a nucleophilic substitution reaction to give compounds of the formula (C-III). In a subsequent step, the compounds of the formula (C-III) can be converted directly in a nucleophilic aromatic substitution reaction with compounds of the formula (C-IV) to give compounds of the formula (I-C). Alternatively, the compounds of the formula (C-III) can react in a nucleophilic aromatic substitution reaction with compounds of the formula (C-V) to give compounds of the formula (C-VI). These can be condensed with amines of the formula (C-VII) or their hydrochlorides or hydrobromides to give compounds of the formula (C-VIII). The compounds of the formula (C-VIII) can then be reduced in a first step and reacted in a reductive amination reaction with aldehydes of the formula (C-IX) in a second step, to give compounds of the formula (I-C).

According to a further route for preparing compounds of the formula (C-VIII), benzyl alcohols of the formula (C-X) can be reacted with chlorides of the formula (C-XI), which initially affords compounds of the formula (C-XII). After conversion of the alcohol into a halogen using a halogenating agent, this halogenated intermediate can react in a nucleophilic substitution reaction with compounds of the formula (C-II) to give compounds of the formula (C-VIII).

Method C—Step 1:
The benzyl halides of the formula (C-I) are known, commercially available or can be obtained by known preparation processes (see, for example, EP0366085 for 2-chloro-5-(chloromethyl)pyridine or WO2014/028669 for 5-(bromomethyl)-2-chloropyrimidine).

With heating in the presence of a basic reaction auxiliary such as, for example, potassium carbonate or caesium carbonate, the benzyl halides of the formula (C-I) react in a nucleophilic substitution reaction with compounds of the formula (C-II) to give compounds of the formula (C-III). The reaction is optionally carried out in the presence of an inert solvent or diluent. Examples which may be mentioned are N,N-dimethylformamide, N-methyl-2-pyrrolidone and acetonitrile. The reaction is preferably carried out at temperatures of from 10° C. to 120° C. (see, for example, US2003/0092739).

Method C—Step 2:
The alcohols of the formula (C-IV) are known, commercially available or can be obtained by known preparation processes (see, for example, Journal of Organic Chemistry, 1957, 22, 579 for 2-[methoxy(methyl)amino]ethanol).

In the presence of a basic reaction auxiliary such as, for example, sodium hydride, the compounds of the formula (C-III) react in a nucleophilic aromatic substitution reaction with alcohols of the formula (C-IV) to give compounds of the formula (I-C). The reaction is carried out in the presence of an inert solvent or diluent. Examples which may be mentioned are N,N-dimethylformamide, N-methyl-2-pyrrolidone and tetrahydrofuran. The reaction is preferably carried out at temperatures of from 0° C. to 120° C. (see, for example, EP2236507 for LG=Cl or EP0135894 for LG=F).

Method C—Step 3:
The compounds of the formula (C-III) react in a nucleophilic aromatic substitution reaction with compounds of the formula (C-V) to give acetals of the formula (C-VI). This reaction takes place under the conditions described in Step 2 of Method C.

Method C—Step 4:
The compounds of the formula (C-VII) are known, commercially available or can be obtained by known preparation processes (see, for example, EP0678504 for 1-(aminooxy) propane). Some are also known as their hydrochlorides or hydrobromides and are commercially available.

The acetals of the formula (C-VI) react, optionally in the presence of an acid such as, for example, para-toluenesulfonic acid (see, for example, WO2012/038851), or of a dehydrating reagent such as, for example, magnesium sulfate (see, for example, WO2010/054024), with compounds of the formula (C-VII) or their hydrochlorides or hydrobromides in a condensation reaction, to give compounds of the formula (C-VIII). The reaction is carried out in the presence of an inert solvent or diluent. Examples which may be mentioned are ethanol, methanol, acetonitrile, tetrahydrofuran and water, and also mixtures of these solvents. The reaction is preferably carried out at temperatures of from 10° C. to 80° C.

Method C—Step 5:
The aldehydes of the formula (C-IX) are known, commercially available or can be obtained by known preparation processes.

The compounds of the formula (C-VIII) can be converted in a two-step one-pot reaction into compounds of the formula (I-C). In the first step, the compounds of the formula (C-VIII) initially react in the presence of a reducing agent such as, for example, sodium cyanoborohydride to give an intermediate of the general formula (I-C) in which $R^8$ represents hydrogen. The reaction is carried out in the presence of a solvent or diluent such as, for example, acetic acid at temperatures of from 10° C. to 80° C.

In the second step, this intermediate reacts in the presence of a reducing agent with aldehydes of the formula (C-IX) in a reductive alkylation to give compounds of the formula (I-C) in which $R^8$ represents $(C_1-C_6)$-alkyl which is optionally substituted at $C_2$ to $C_6$. The reaction is carried out in the presence of a solvent or diluent such as, for example, acetic acid at temperatures of from 10° C. to 80° C.

Method C—Step 6:

The compounds of the formula (C-X) and of the formula (C-XI) are known, commercially available or can be obtained by known preparation processes. Further processes for their preparation are described in the present application, for example of 2-fluoro-6-(hydroxymethyl)pyridin-3-ol.

In the presence of a basic reaction auxiliary such as, for example, potassium carbonate or caesium carbonate, the compounds of the formula (C-X) react in a nucleophilic substitution reaction with chlorides of the formula (C-XI) to give compounds of the formula (C-XII). The reaction is optionally carried out in the presence of an inert solvent or diluent. Examples which may be mentioned are N,N-dimethylformamide, N-methyl-2-pyrrolidone and acetonitrile. The reaction is preferably carried out at temperatures of from 20° C. to 120° C.

Method C—Step 7:

After conversion of the alcohol function into a halogen, the benzyl alcohols of the formula (C-XII) can react with compounds of the formula (C-II) in a nucleophilic substitution reaction to give compounds of the formula (C-VIII). This reaction takes place under the conditions described in Step 1 and Step 2 of Method A.

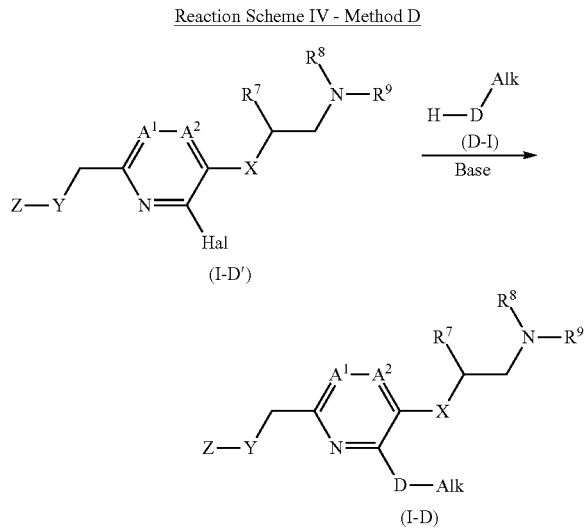

Compounds of the formula (I-D) can be prepared, for example, according to Reaction Scheme IV. The radicals $A^1$, $A^2$, X, Y, Z, $R^7$, $R^8$ and $R^9$ have the meanings mentioned above and optionally further meanings relevant for the preparation processes, which meanings are evident from the text or context. Hal represents chlorine or fluorine. D represents O or S. Alk represents optionally substituted $(C_1-C_4)$-alkyl.

The compounds of the formula (I-D') can be obtained by known preparation processes or analogously to preparation processes described in the present application. The thiols and aldehydes (D-I) and their sodium salts are known, commercially available or can be obtained by known preparation processes. In the presence of a basic reaction auxiliary such as, for example, sodium hydride, the compounds of the formula (I-D') react in a nucleophilic aromatic substitution reaction with alcohols and thiols of the formula (D-I) to give compounds of the formula (I-D). It is also possible to employ directly the sodium salts of the alcohols and thiols of the formula (D-I). In this case, the addition of a base is redundant. The reaction is carried out in the presence of an inert solvent or diluent. Examples which may be mentioned are N,N-dimethylformamide, N,N-dimethylacetamide, N-methyl-2-pyrrolidone and tetrahydrofuran. The reaction is preferably carried out at temperatures of from 0° C. to 80° C.

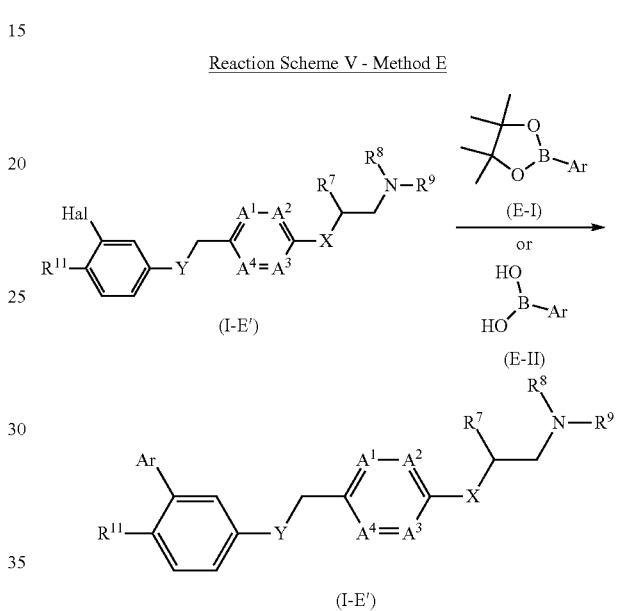

Compounds of the formula (I-E) can be prepared, for example, according to Reaction Scheme V. The radicals $A^1$, $A^2$, $A^3$, $A^4$, X, Y, $R^7$, $R^8$, $R^9$ and $R^{11}$ have the meanings mentioned above and optionally further meanings relevant for the preparation processes, which meanings are evident from the text or context. Hal represents bromine or iodine. Ar represents in each case optionally substituted phenyl, pyrid-2-yl, pyrid-3-yl, pyrid-4-yl, thiophen-2-yl or thiophen-3-yl.

In principle, the compounds of the formula (I-E') can be obtained by known preparation processes or analogously to preparation processes described in the present application. The boronic esters (E-I) and the boronic acids (E-II) are known, commercially available or can be obtained by known preparation processes.

The compounds of the formula (I-E') react in the presence of suitable coupling catalysts such as, for example, tetrakis (triphenylphosphine)palladium(0) or [1,1'-bis(diphenylphosphino)ferrocene]dichloropalladium(II) in the presence of a base such as, for example, potassium carbonate or sodium carbonate with optionally substituted arylboronic acids (E-II) or arylboronic acid pinacol esters (E-I) to give compounds of the formula (I-E) (see, for example, WO2014/201206 or WO2016/059097). The reaction is carried out in an inert solvent or diluent. By way of example, mention may be made of 1,4-dioxane, toluene or tetrahydrofuran, in each case optionally in combination with water. The reaction is preferably carried out at temperatures of from 40° C. to 120° C.

Reaction Scheme VI - Method F

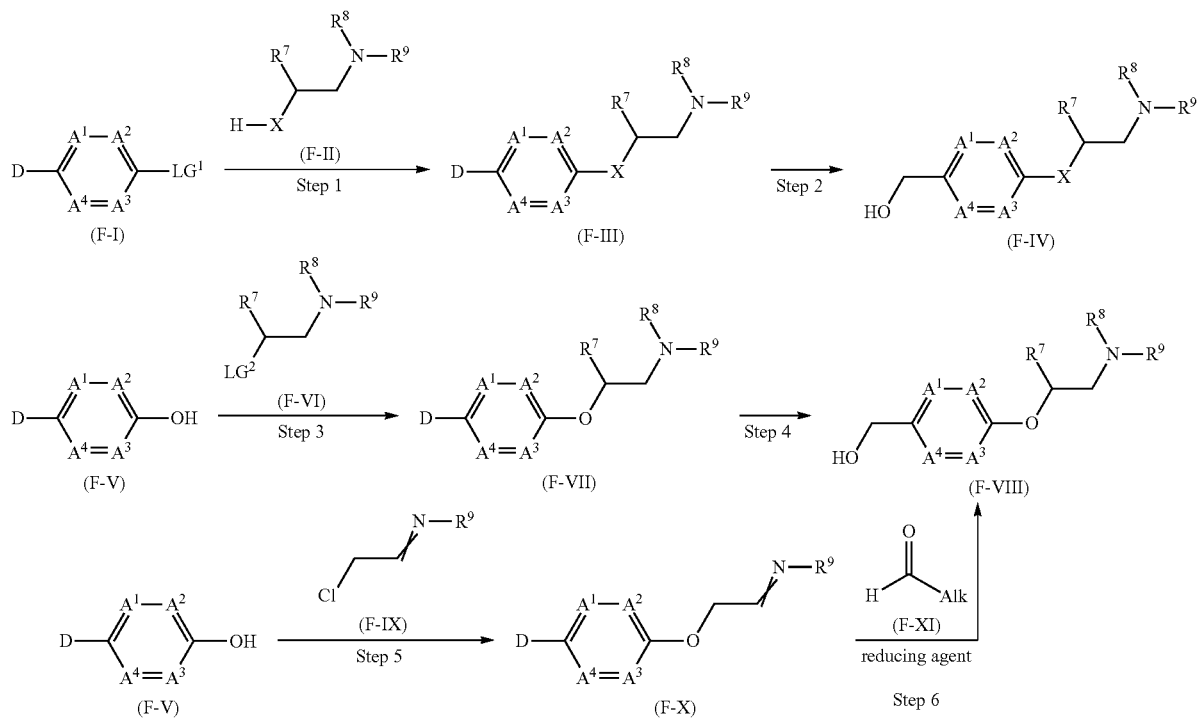

Compounds of the formulae (F-VIII) and (F-IV) can be prepared, for example, according to Reaction Scheme VI. The radicals $A^1$, $A^2$, $A^3$, $A^4$, $R^6$, $R^7$, $R^8$ and $R^9$ have the meanings mentioned above and optionally further meanings relevant for the preparation processes, which meanings are evident from the text or context. X represents O, $NR^6$ or S. LG represents chlorine or fluorine. $LG^2$ represents chlorine or bromine. Alk represents an optionally substituted ($C_1$-$C_5$)-alkyl. D represents cyano, ($C_1$-$C_3$)-alkoxycarbonyl, formyl or $CH_2OPG$. PG represents a protective group such as, for example, tert-butyldimethylsilyl. Protective groups for alcohols, their introduction and their removal are known to the person skilled in the art. A review is given, for example, in T. W. Greene, P. G. M. Wuts, *Protective Groups in Organic Synthesis,* 3' Edition, 1999 (Wiley-Interscience).

Method F—Step 1:

The compounds of the formula (F-I) and the formula (F-II) are known, commercially available or can be obtained by known preparation processes (see, for example, *Journal of Organic Chemistry,* 1957, 22, 579 for 2-[methoxy (methyl)amino]ethanol).

In the presence of a basic reaction auxiliary such as, for example, sodium hydride or potassium carbonate, the compounds of the formula (F-I) react in a nucleophilic aromatic substitution reaction with compounds of the formula (F-II) to give compounds of the formula (F-III). The reaction is carried out in the presence of an inert solvent or diluent. Examples which may be mentioned are N,N-dimethylformamide, N,N-dimethylacetamide, N-methyl-2-pyrrolidone and acetonitrile. The reaction is preferably carried out at temperatures of from 0° C. to 100° C. (see, for example, the syntheses, described in the present application, of 5-{2-[methoxy(methyl)amino]ethoxy}-3-methylpyridine-2-carbonitrile, 6-{2-[methoxy(methyl)amino]ethoxy}nicoti- naldehyde, methyl 3-methoxy-5-{2-[methoxy(methyl)amino] ethoxy}pyridine-2-carboxylate) and ethyl 5-(4-ethylp- iperazin-1-yl)-3-fluoropyridine-2-carboxylate).

Method F—Step 2:

Depending on substituent D, the compounds of the formula (F-III) can be converted in a one-step or optionally multistep process into compounds of the structure (F-IV).

If D represents cyano, the cyano function can be hydrolyzed in the presence of a base such as, for example, sodium hydroxide to yield the acid function. The reaction is carried out in the presence of an inert solvent or diluent. Examples which may be mentioned are ethanol, methanol, tetrahydrofuran and water, or optionally mixtures of these substances. The reaction is preferably carried out at temperatures of from 20° C. to 120° C. (see, for example, WO2010/043377 for the synthesis of (6-methoxypyridin-3-yl)methanol or the synthesis of methyl 5-{2-[methoxy(methyl)amino]ethoxy}-3-methylpyridine-2-carboxylate in the present application). This acid function can then be converted in the presence of a mineral acid such as, for example, sulfuric acid and an alkanol of the chain length ($C_1$-$C_3$) into compounds of the formula (F-III), in which D represents ($C_1$-$C_3$)-alkoxycarbonyl (see, for example, WO2003/084917 for the synthesis of methyl 3-bromopyridine-2-carboxylate or the synthesis of methyl 5-{2-[methoxy(methyl)amino]ethoxy}-3-methylpyridine-2-carboxylate in the present application). The reaction is preferably carried out in the presence of an excess of the ($C_1$-$C_3$)-alkanol as solvent or diluent, optionally as a mixture with another solvent or diluent. The reaction is preferably carried out at temperatures of from 40° C. to 100° C.

If D represents ($C_1$-$C_3$)-alkoxycarbonyl, the ester function can be reduced in the presence of a suitable reducing agent such as, for example, sodium borohydride or diisobutylaluminium hydride to give benzyl alcohols of the formula (F-IV). If the reaction is carried out in the presence of sodium borohydride, a suitable solvent or diluent such as, for example, ethanol or methanol is employed. Here, the reaction is preferably carried out at temperatures of from 0° C. to 50° C. If diisobutylaluminium hydride is used, the reaction is carried out in a suitable inert solvent, for example toluene or dichloromethane. Here, the reaction is preferably carried out at temperatures of from −78° C. to +30° C. (see, for example, the syntheses, described in the present application, of (5-{2-[methoxy(methyl)amino]ethoxy}-3-methylpyridin-2-yl)methanol) and (3-methoxy-5-{2-[methoxy (methyl)amino]ethoxy}pyridin-2-yl)methanol).

If D represents formyl, the formyl group can be reduced in the presence of a suitable reducing agent such as, for example, sodium borohydride to give benzyl alcohols of the formula (F-IV). If the reaction is carried out in the presence of sodium borohydride, a suitable solvent or diluent such as, for example, ethanol or methanol, optionally as a mixture with tetrahydrofuran, is employed. Here, the reaction is preferably carried out at temperatures of from 0° C. to 50° C.

If D represents —CH$_2$OPG, the protective group can be removed under various conditions, depending on its nature. The conditions for the removal of alcohol protective groups are known to the person skilled in the art. A review is given, for example, in T. W. Greene, P. G. M. Wuts, *Protective Groups in Organic Synthesis*, 3$^{rd}$ Edition, 1999 (Wiley-Interscience).

Method F—Step 3:

The halides of the formula (F-VI) are known, commercially available or can be obtained by the preparation processes described in the present application (see, for example, the preparation of 2-bromo-N-methoxy-N-methylethanamine hydrobromide (1:1)). The compounds of the formula (F-V) are known, commercially available or can be obtained by known preparation processes (see, for example, the preparation, described in the present application, of 2-({[tert-butyl(dimethyl)silyl]oxy}methyl)pyrimidin-5-ol).

In the presence of a basic reaction auxiliary such as, for example, potassium carbonate and optionally in the presence of sodium iodide, the compounds of the formula (F-VI) react in a nucleophilic substitution reaction with alcohols of the formula (F-V) to give compounds of the formula (F-VII). The reaction is carried out in the presence of an inert solvent or diluent. Examples which may be mentioned are N,N-dimethylformamide, N-methyl-2-pyrrolidone and tetrahydrofuran. The reaction is preferably carried out at temperatures of from 0° C. to 100° C. (see, for example, WO2016/040185 for the reaction of 2-bromo-N,N-dimethylethanamine with 5-brompyridin-3-ol).

Method F—Step 4:

Depending on substituent D, the compounds of the formula (F-VII) can be converted in a one-step or optionally multistep process into compounds of the structure (F-VIII). The reaction conditions correspond to those described for the reaction of compounds of the formula (F-III) into compounds of the formula (F-IV) in Step 2.

Method F—Step 5:

The compounds of the formula (F-IX) are known, commercially available or can be obtained by known preparation processes.

In the presence of a basic reaction auxiliary such as, for example, potassium carbonate or caesium carbonate, the compounds of the formula (F-V) react in a nucleophilic substitution reaction with chlorides of the formula (F-IX) to give compounds of the formula (F-X). The reaction is optionally carried out in the presence of an inert solvent or diluent. Examples which may be mentioned are N,N-dimethylformamide, N-methyl-2-pyrrolidone and acetonitrile. The reaction is preferably carried out at temperatures of from 20° C. to 120° C. (see, for example, the synthesis, described in the present application, of methyl 3-fluoro-5-[2-(methoxyimino)ethoxy]pyridine-2-carboxylate).

Method F—Step 6:

The aldehydes of the formula (F-XI) are known, commercially available or can be obtained by known preparation processes.

The compounds of the formula (F-X) can be converted in a two-step one-pot reaction into compounds of the formula (F-VIII). In the first step, the compounds of the formula (F-X) initially react in the presence of a reducing agent such as, for example, sodium cyanoborohydride to give an intermediate of the formula (F-VIII) in which R$^8$ represents hydrogen. The reaction is carried out in the presence of a solvent or diluent such as, for example, acetic acid at temperatures of from 10° C. to 80° C.

In the second step, this intermediate reacts in the presence of a reducing agent with aldehydes of the formula (F-XI) in a reductive alkylation to give compounds of the formula (F-VIII) in which R$^8$ represents (C$_1$-C$_6$)-alkyl which is optionally substituted at C$_2$ to C$_6$. The reaction is carried out in the presence of a solvent or diluent such as, for example, acetic acid at temperatures of from 10° C. to 80° C.

Reaction Scheme VII - Method G

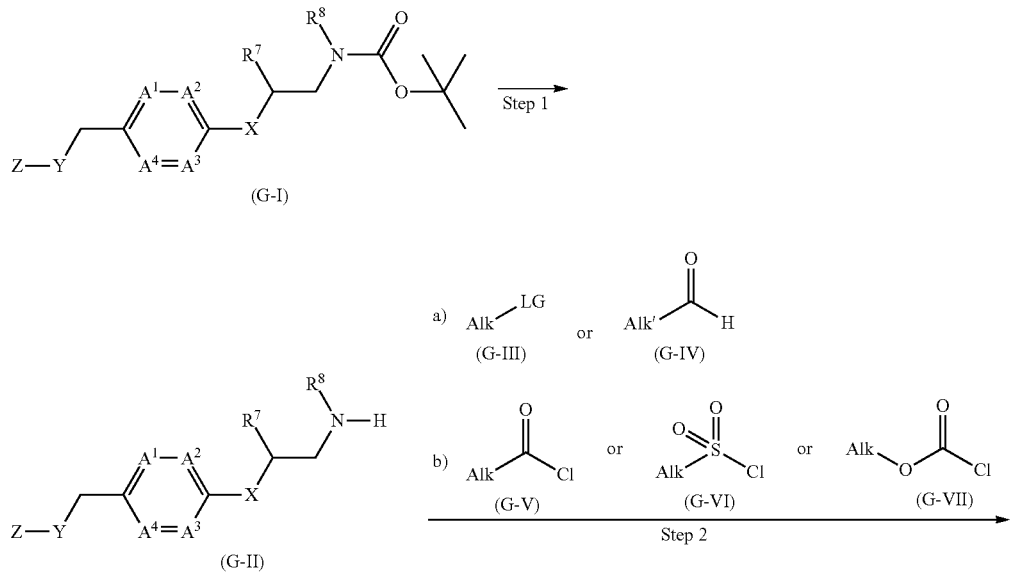

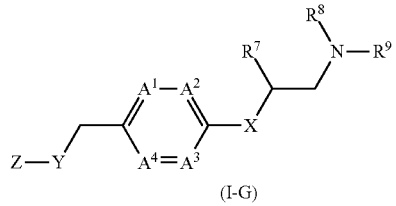

(I-G)

Compounds of the formula (I-G) can be prepared, for example, according to Reaction Scheme VII. The radicals $A^1$, $A^2$, $A^3$, $A^4$, $R^7$, $R^8$, X, Y and Z have the meanings mentioned above and optionally further meanings relevant for the preparation processes, which meanings are evident from the text or context. $R^6$ represents optionally substituted $(C_1-C_4)$-alkyl, $(C_3-C_6)$-cycloalkyl, $(C_1-C_4)$-alkanoyl or a ring closure with $R^8$ formed by 1 to 3 $CH_2$ groups. $R^5$ represents optionally substituted $(C_1-C_4)$-alkyl. $R^9$ represents optionally substituted $(C_1-C_6)$-alkyl, $(C_1-C_6)$-alkylcarbonyl, $(C_1-C_6)$-alkylsulfonyl or $(C_1-C_6)$-alkoxycarbonyl. Alk represents an optionally substituted $(C_1-C_6)$-alkyl group. Alk' represents an optionally substituted $(C_1-C_5)$-alkyl group. LG represents a leaving group such as halogen or the ester of a sulfonic acid.

Method G—Step 1:

The compounds of the formula (G-I) can be obtained by the methods shown in Reaction Schemes I and III.

The tert-butoxycarbonyl group of compounds of the formula (G-I) can be removed under acidic conditions. The acids used are preferably hydrogen chloride or trifluoroacetic acid. The reaction is optionally carried out in the presence of an inert solvent or diluent or in pure trifluoroacetic acid. Exemplary solvents which may be mentioned are 1,4-dioxane, dichloromethane and water. The reaction is preferably carried out at temperatures of from 0° C. to 60° C. (see, for example, the syntheses, described in the present application, of 5-{[(4-chloro-1-naphthyl)oxy]methyl}-2-(pyrrolidin-3-yloxy)pyridine or US2015/238641).

Method G—Step 2:

Depending on substituent $R^9$, the compounds of the formula (G-II) can be converted in a one-step process into compounds of the structure (1-G).

a) The compounds of the structure (I-G) in which $R^9$ represents optionally substituted $(C_1-C_6)$-alkyl are obtained by reacting compounds of the formula (G-II) with alkylating agents of the general structure (G-III) in the presence of a basic reaction auxiliary such as, for example, potassium carbonate or triethylamine. Preferred leaving groups LG are the halogens chlorine, bromine or iodine or the esters of a sulfonic acid such as, for example, of methanesulfonic acid or of p-toluenesulfonic acid. The reaction is optionally carried out in the presence of an inert solvent or diluent such as, for example, acetonitrile, dichloromethane or N,N-dimethylformamide. The reaction is preferably carried out at temperatures of from 0° C. to 100° C. (see, for example, WO2014/207240 or WO2014/116684).

Alternatively, compounds of the formula (G-II) react in the presence of a reducing agent such as, for example, sodium cyanoborohydride with aldehydes of the formula (G-IV) in a reductive alkylation to give compounds of the formula (I-G) in which $R^9$ represents $(C_1-C_6)$-alkyl which is optionally substituted at $C_2$ to $C_6$. The reaction is carried out in the presence of a solvent or diluent such as, for example, acetic acid at temperatures of from 10° C. to 80° C.

b) The compounds of the structure (I-G) in which $R^9$ represents optionally substituted $(C_1-C_6)$-alkylcarbonyl, $(C_1-C_6)$-alkylsulfonyl or $(C_1-C_6)$-alkoxycarbonyl are obtained by reacting compounds of the formula (G-II) with acyl chlorides of the general structure (G-V) or with sulfonyl chlorides of the general structure (G-VI) or with chloroformic esters of the general structure (G-VII). The reactions are preferably carried out in the presence of a basic reaction auxiliary such as, for example, triethylamine or diisopropylethylamine and an inert solvent or diluent such as, for example, dichloromethane, tetrahydrofuran or acetonitrile. The reactions are preferably carried out at temperatures of from 0° C. to 100° C. (see, for example, US2015/259317 for a reaction with an acyl chloride, WO2004/041264 for a reaction with a sulfonyl chloride or WO2004/089925 for a reaction with a chloroformic ester).

A further embodiment of the invention relates to intermediates and comprises the following compounds of the formula (Va) or (Vb):

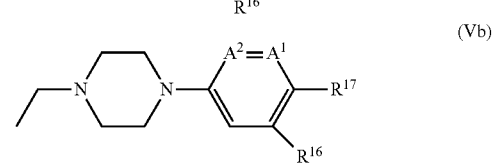

in which $A^1$ represents N or CH, $A^2$ represents N or CH, where at least $A^1$ or $A^2$ represents N and preferably $A^1$ represents N and $A^2$ represents CH, $R^{16}$ represents hydrogen, methyl, fluorine or methoxy, $R^{17}$ represents cyano, hydroxymethyl, methylcarboxy, ethylcarboxy or 3-bromophenoxymethyl, $R^{18}$ in the compounds of the formula (Va) represents a radical:

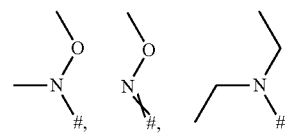

or bromine, with the proviso that the following compounds are excluded:

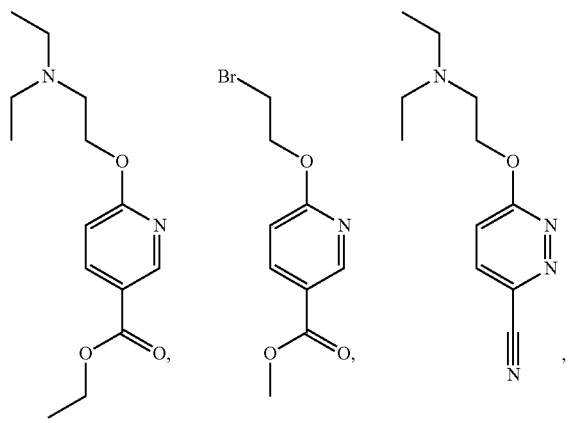

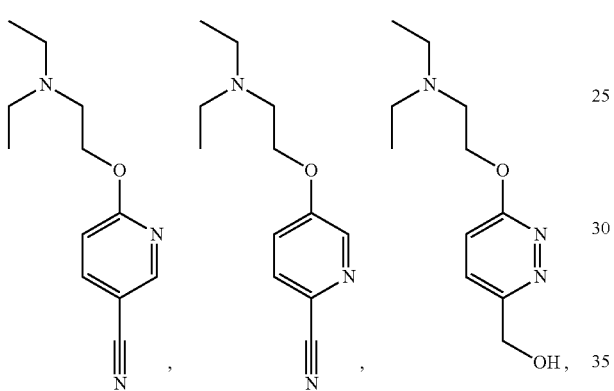

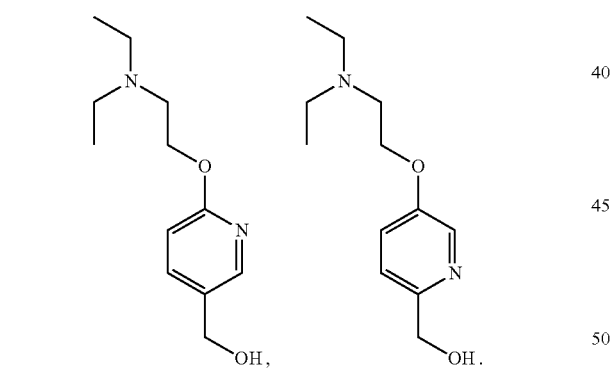

In a preferred embodiment of the invention, $R^{18}$ represents a radical:

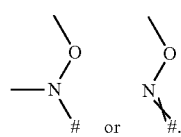

In a further preferred embodiment of the invention, the compounds of the formula (Vb) represent:

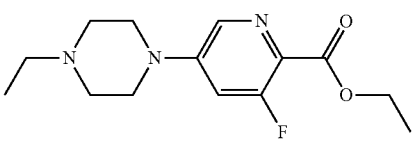
(Vb-1)

Furthermore, a particularly preferred embodiment of the invention relates to compounds of the formulae (Va-1 to Va-14) and of formula (Vb-1):

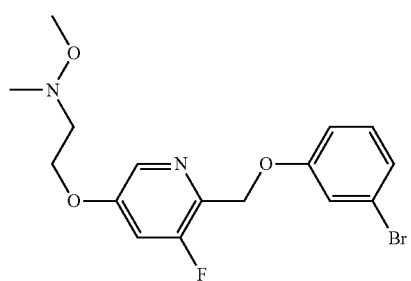
(Va-1)

(Va-2)

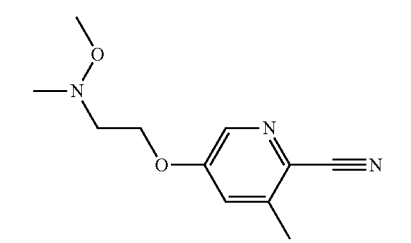
(Va-3)

(Va-4)

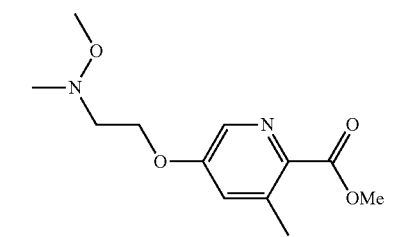

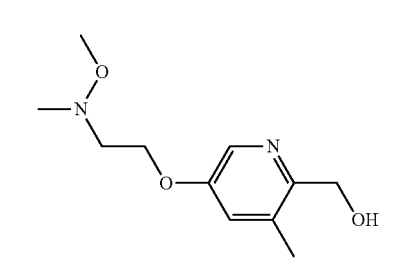

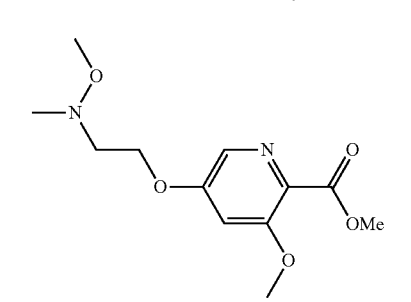
(Va-5)

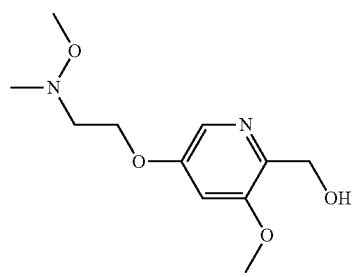
(Va-6)
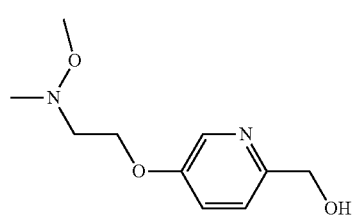
(Va-7)
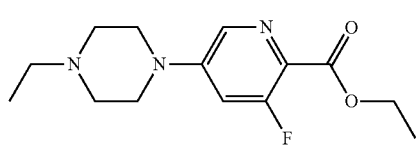
(Vb-1)
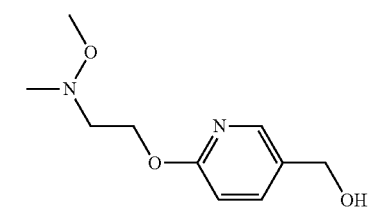
(Va-8)
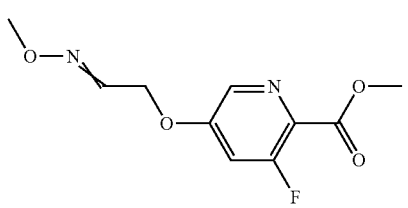
(Va-9)
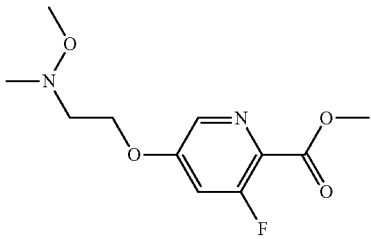
(Va-10)
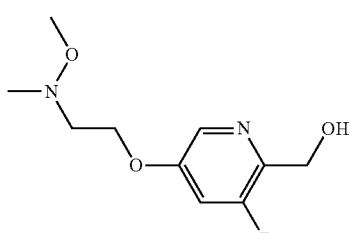
(Va-11)
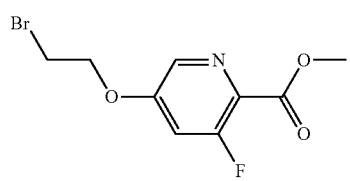
(Va-12)
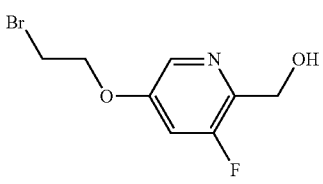
(Va-13)
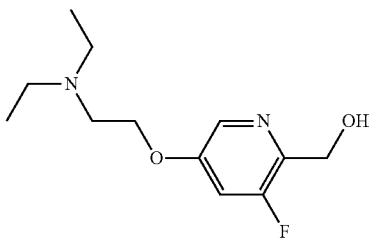
(Va-14)
The preparation processes describes above afforded inter alia the compounds of the formula (I) described in Table 1.

TABLE 1

Compounds of the formula (I-a)

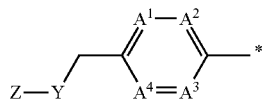

where the substituents Z, Y, $A^1$, $A^2$, $A^3$, $A^4$, and * have the following meaning:

| Ex. No. | Z | Y | $A^1$ | $A^2$ | $A^3$ | $A^4$ | * |
|---|---|---|---|---|---|---|---|
| 1 | 1,2-dichloronaphthalen-5-yl | O | CH | CH | N | CH | #-O-CH2CH2-N(OMe)(Me) |
| 2 | 1,4-dichloronaphthalen-5-yl | O | CH | CH | N | CH | #-O-CH2CH2-N(OMe)(Me) |
| 3 | 4-chloronaphthalen-1-yl | O | CH | CH | N | CF | #-O-CH2CH2-N(OMe)(Me) |
| 4 | 4-chloronaphthalen-1-yl | O | CH | CH | N | CH | #-O-(3-pyrrolidinyl)-N-acetyl |
| 5 | 4-chloronaphthalen-1-yl | O | CH | CH | N | CH | #-O-(3-pyrrolidinyl)-N-CH2CN |
| 6 | 4-chloronaphthalen-1-yl | O | CH | $CCHF_2$ | N | CH | #-O-CH2CH2-N(OMe)(Me) |
| 7 | 4-chloronaphthalen-1-yl | O | CH | CCl | N | CH | #-O-CH2CH2-N(OMe)(Me) |
| 8 | dibenzofuran-2-yl | O | CH | CH | N | CH | #-O-CH2CH2-N(OMe)(Me) |

TABLE 1-continued

Compounds of the formula (I-a)

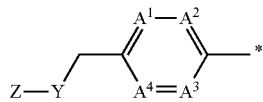

where the substituents Z, Y, A¹, A², A³, A⁴, and * have the following meaning:

| Ex. No. | Z | Y | A¹ | A² | A³ | A⁴ | * |
|---|---|---|---|---|---|---|---|
| 9 | 5,6-dichloronaphthalen-1-yl | O | CH | CH | N | CH | #-O-CH₂CH₂-N(Et)₂ |
| 10 | 2'-fluoro-3'-(trifluoromethoxy)biphenyl-5-yl | O | CH | CH | N | CH | #-O-CH₂CH₂-N(OMe)(Me) |
| 11 | 3'-(trifluoromethoxy)biphenyl-3-yl | O | CH | CH | N | CH | #-O-CH₂CH₂-N(Et)₂ |
| 12 | 3'-chloro-2-fluorobiphenyl-5-yl | O | CH | CH | N | CH | #-O-CH₂CH₂-N(Et)₂ |
| 13 | biphenyl-3-yl | O | CH | CH | N | CH | #-O-CH₂CH₂-N(OMe)(Me) |
| 14 | 4-chloro-3-(trifluoromethoxy)phenyl | O | CH | CH | N | CH | #-O-CH₂CH₂-N(Et)₂ |
| 15 | 3,4-dichlorophenyl | O | CH | CH | N | CH | #-O-CH₂CH₂-N(OMe)(Me) |
| 16 | 5,6-dichloronaphthalen-1-yl | O | CH | CH | CH | N | #-O-CH₂CH₂-N(OMe)(Me) |

TABLE 1-continued

Compounds of the formula (I-a)

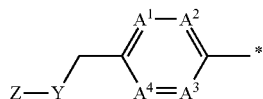

where the substituents Z, Y, A¹, A², A³, A⁴, and * have the following meaning:

| Ex. No. | Z | Y | A¹ | A² | A³ | A⁴ | * |
|---|---|---|---|---|---|---|---|
| 17 | 1,2-dichloronaphthalen-5-yl | O | CH | CH | CF | N | #-OCH₂CH₂-N(OCH₃)(CH₃) |
| 18 | 1,2-dichloronaphthalen-5-yl | O | CH | CH | CCl | N | #-OCH₂CH₂-N(OCH₃)(CH₃) |
| 19 | 4-chloronaphthalen-1-yl | O | CF | CH | CH | N | #-OCH₂CH₂-N(OCH₃)(CH₃) |
| 20 | dibenzofuran-2-yl | O | CF | CH | CH | N | #-OCH₂CH₂-N(OCH₃)(CH₃) |
| 21 | 4-bromonaphthalen-1-yl | O | CF | CH | CH | N | #-OCH₂CH₂-N(OCH₃)(CH₃) |
| 22 | 1,2-dichloronaphthalen-5-yl | O | CF | CH | CH | N | #-OCH₂CH₂-N(OCH₃)(CH₃) |
| 23 | dibenzothiophen-2-yl | O | CF | CH | CH | N | #-OCH₂CH₂-N(OCH₃)(CH₃) |
| 24 | 5-fluoronaphthalen-1-yl | O | CF | CH | CH | N | #-OCH₂CH₂-N(OCH₃)(CH₃) |

TABLE 1-continued

Compounds of the formula (I-a)

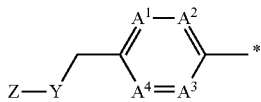

where the substituents Z, Y, A¹, A², A³, A⁴, and * have the following meaning:

| Ex. No. | Z | Y | A¹ | A² | A³ | A⁴ | * |
|---|---|---|---|---|---|---|---|
| 25 | 4-chloronaphthalen-1-yl | O | CCl | CH | CH | N | #—O—CH₂CH₂—N(CH₃)—O—CH₃ |
| 26 | 1,2-dichloronaphthalen-5-yl | O | CCl | CH | CH | N | #—O—CH₂CH₂—N(CH₃)—O—CH₃ |
| 27 | 4-chloronaphthalen-1-yl | O | CF | CH | CH | N | #—O—CH₂CH₂—N(CH₃)—CH₂CN |
| 28 | 1,2-dichloronaphthalen-5-yl | O | CF | CH | CH | N | #—O—CH₂CH₂—N(CH₃)—CH₂CN |
| 29 | dibenzofuran-2-yl | O | CF | CH | CH | N | #—O—CH₂CH₂—N(CH₃)—CH₂CN |
| 30 | dibenzofuran-2-yl | O | CCH₃ | CH | CH | N | #—O—CH₂CH₂—N(CH₃)—O—CH₃ |
| 31 | dibenzofuran-2-yl | O | CH | CH | CH | N | #—O—CH₂CH₂—N(CH₃)—O—CH₃ |
| 32 | 1,2-dichloronaphthalen-5-yl | O | CF | CH | CH | N | #—O—CH₂CH₂—N(C₂H₅)₂ |

TABLE 1-continued

Compounds of the formula (I-a)

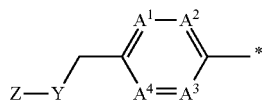

where the substituents Z, Y, A¹, A², A³, A⁴, and * have the following meaning:

| Ex. No. | Z | Y | A¹ | A² | A³ | A⁴ | * |
|---|---|---|---|---|---|---|---|
| 33 | 3,4-dichloronaphthalen-1-yl | O | CH | CH | CH | N | #—O—CH₂CH₂—N(Et)₂ |
| 34 | dibenzofuran-2-yl | O | CF | CH | CH | N | #—O—CH₂CH₂—N(Me)(tBu) |
| 35 | dibenzofuran-2-yl | O | CF | CH | CH | N | Cl⁻ #—O—CH₂CH₂—N⁺(H)(Me)(tBu) |
| 36 | 3,4-dichloronaphthalen-1-yl | O | CF | CH | CH | N | #—O—CH₂CH₂—N(Me)(tBu) |
| 37 | 3,4-dichloronaphthalen-1-yl | O | CF | CH | CH | N | Cl⁻ #—O—CH₂CH₂—N⁺(H)(Me)(tBu) |
| 38 | 3,4-dichloronaphthalen-1-yl | O | CF | CH | CH | N | #—O—CH₂CH₂—NH(tBu) |
| 39 | 3,4-dichloronaphthalen-1-yl | O | CF | CH | CH | N | #—O—CH₂CH₂—N(iPr)₂ |
| 40 | dibenzofuran-2-yl | O | CF | CH | CH | N | #—O—CH₂CH₂—N(iPr)₂ |

TABLE 1-continued

Compounds of the formula (I-a)

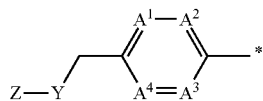

where the substituents Z, Y, A¹, A², A³, A⁴, and * have the following meaning:

| Ex. No. | Z | Y | A¹ | A² | A³ | A⁴ | * |
|---|---|---|---|---|---|---|---|
| 41 | dibenzofuran-2-yl | O | CF | CH | CH | N | -O-CH₂CH₂-N(piperidine) |
| 42 | 3,4-dichloronaphthalen-1-yl | O | CF | CH | CH | N | -O-CH₂CH₂-N(piperidine) |
| 43 | dibenzofuran-2-yl | O | CF | CH | CH | N | -O-CH₂CH₂-N(iPr)(Me) |
| 44 | 3,4-dichloronaphthalen-1-yl | O | CF | CH | CH | N | -O-CH₂CH₂-N(iPr)(Me) |
| 45 | 3,4-dichloronaphthalen-1-yl | O | CF | CH | CH | N | -N(piperazine)-Et |
| 46 | dibenzofuran-2-yl | O | CF | CH | CH | N | -N(piperazine)-Et |
| 47 | 3'-(trifluoromethoxy)-2-fluorobiphenyl-5-yl | O | CF | CH | CH | N | -O-CH₂CH₂-N(Et)₂ |
| 48 | 3'-(trifluoromethoxy)-2-chlorobiphenyl-5-yl | O | CF | CH | CH | N | -O-CH₂CH₂-N(Me)(OMe) |

TABLE 1-continued

Compounds of the formula (I-a)

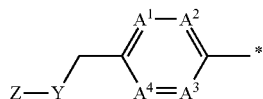

where the substituents Z, Y, A¹, A², A³, A⁴, and * have the following meaning:

| Ex. No. | Z | Y | A¹ | A² | A³ | A⁴ | * |
|---|---|---|---|---|---|---|---|
| 49 | 3-Cl, 2-F biphenyl | O | CF | CH | CH | N | #—O—CH₂CH₂—N(CH₃)—O—CH₃ |
| 50 | 3-F₃CO, 2-F biphenyl | O | CF | CH | CH | N | #—O—CH₂CH₂—N(CH₃)—O—CH₃ |
| 51 | 3-F₃CO, 2-F biphenyl | O | CF | CH | CH | N | #—O—CH₂CH₂—N(CH₃)—C(CH₃)₃ |
| 52 | 5,6-diCl naphthyl | O | CH | CH | CSCH₃ | N | #—O—CH₂CH₂—N(CH₃)—O—CH₃ |
| 53 | 3-F₃CO biphenyl | O | CF | CH | CH | N | #—O—CH₂CH₂—N(CH₃)—O—CH₃ |
| 54 | 3-CH₃CH₂O, 4-Cl phenyl | O | CF | CH | CH | N | #—O—CH₂CH₂—N(CH₃)—O—CH₃ |
| 55 | 3-F, 2-F biphenyl | O | CF | CH | CH | N | #—O—CH₂CH₂—N(CH₃)—O—CH₃ |
| 56 | 3-Cl, 2-Cl biphenyl | O | CF | CH | CH | N | #—O—CH₂CH₂—N(CH₃)—O—CH₃ |

TABLE 1-continued

Compounds of the formula (I-a)

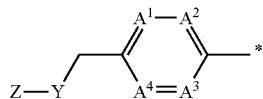

where the substituents Z, Y, A$^1$, A$^2$, A$^3$, A$^4$, and * have the following meaning:

| Ex. No. | Z | Y | A$^1$ | A$^2$ | A$^3$ | A$^4$ | * |
|---|---|---|---|---|---|---|---|
| 57 | 3-F$_3$CO, 2'-F biphenyl | O | CF | CH | CH | N | -OCH$_2$CH$_2$N(iPr)$_2$ |
| 58 | 3-H$_3$CO, 4-Cl phenyl | O | CF | CH | CH | N | -OCH$_2$CH$_2$N(OCH$_3$)(CH$_3$) |
| 59 | 3-F$_3$CO, 2'-F biphenyl | O | CCH$_3$ | CH | CH | N | -OCH$_2$CH$_2$N(OCH$_3$)(CH$_3$) |
| 60 | 3-F$_3$CO, 2'-F biphenyl | O | CF | CH | CH | N | -OCH$_2$CH$_2$N(iPr)(CH$_3$) |
| 61 | 3'-F, 2-Cl biphenyl | O | CF | CH | CH | N | -OCH$_2$CH$_2$N(OCH$_3$)(CH$_3$) |
| 62 | 3-F$_3$CO, 2'-F biphenyl | O | CF | CH | CH | N | -OCH$_2$CH$_2$NH(tBu) |
| 63 | 2-Cl biphenyl | O | CF | CH | CH | N | -OCH$_2$CH$_2$N(OCH$_3$)(CH$_3$) |
| 64 | 3-F$_3$CO biphenyl | O | CH | CH | CH | N | -OCH$_2$CH$_2$N(OCH$_3$)(CH$_3$) |

TABLE 1-continued

Compounds of the formula (I-a)

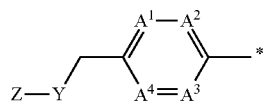

where the substituents Z, Y, $A^1$, $A^2$, $A^3$, $A^4$, and * have the following meaning:

| Ex. No. | Z | Y | $A^1$ | $A^2$ | $A^3$ | $A^4$ | * |
|---|---|---|---|---|---|---|---|
| 65 | 3-Cl, 2'-F-biphenyl | O | CH | CH | CH | N | #-O-CH2CH2-N(CH3)-OCH3 |
| 66 | 3-F3CO-biphenyl | O | CF | CH | CH | N | #-O-CH2CH2-N(CH3)-tBu |
| 67 | 3-F3CO-biphenyl | O | CF | CH | CH | N | #-O-CH2CH2-N(iPr)-tBu |
| 68 | 3-CHF2CF2O, 4-Cl-phenyl | O | CF | CH | CH | N | #-O-CH2CH2-N(CH3)-OCH3 |
| 69 | 3-F3CO-biphenyl | O | CF | CH | CH | N | #-O-CH2CH2-N(CH3)-iPr |
| 70 | biphenyl | O | CF | CH | CH | N | #-O-CH2CH2-N(CH3)-OCH3 |
| 71 | 2'-F-biphenyl | O | CF | CH | CH | N | #-O-CH2CH2-N(CH3)-OCH3 |
| 72 | 3-F3CO, 4-Cl-phenyl | O | CF | CH | CH | N | #-O-CH2CH2-N(CH3)-OCH3 |

TABLE 1-continued

Compounds of the formula (I-a)

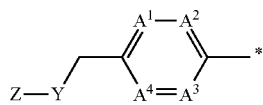

where the substituents Z, Y, A¹, A², A³, A⁴, and * have the following meaning:

| Ex. No. | Z | Y | A¹ | A² | A³ | A⁴ | * |
|---|---|---|---|---|---|---|---|
| 73 | F₃CO-, Cl- phenyl | O | CH | CH | CH | N | methoxyethyl-N(OMe)(Me) |
| 74 | 3-F₃CO-biphenyl | O | CF | CH | CH | N | methoxyethyl-NH-tBu |
| 75 | 3-F₃CO, 2'-F-biphenyl | O | CF | CH | CH | N | methoxyethyl-piperidine |
| 76 | I-, Cl- phenyl | O | CF | CH | CH | N | methoxyethyl-N(OMe)(Me) |
| 77 | 3-F₃CO, 2'-F-biphenyl | O | CF | CH | CH | N | Cl⁻ methoxyethyl-N⁺H(tBu)(Me) |
| 78 | 3-F₃CO-biphenyl | O | CF | CH | CH | N | methoxyethyl-NEt₂ |
| 79 | F₃CO-, Cl- phenyl | O | CF | CH | CH | N | methoxyethyl-N(iPr)₂ |
| 80 | 3-Cl-biphenyl | O | CF | CH | CH | N | methoxyethyl-N(OMe)(Me) |

TABLE 1-continued

Compounds of the formula (I-a)

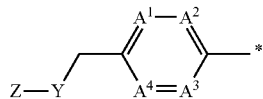

where the substituents Z, Y, A¹, A², A³, A⁴, and * have the following meaning:

| Ex. No. | Z | Y | A¹ | A² | A³ | A⁴ | * |
|---|---|---|---|---|---|---|---|
| 81 | 3-(F₃CO)-biphenyl-3-yl | O | CH | CH | CH | N | -OCH₂CH₂N(Et)₂ |
| 82 | 3'-Cl-2-F-biphenyl-5-yl | O | CH | CH | CH | N | -OCH₂CH₂N(Et)₂ |
| 83 | 3-Br-4-F-phenyl | O | CF | CH | CH | N | -OCH₂CH₂N(OMe)(Me) |
| 84 | 3-(F₃CO)-4-F-phenyl | O | CF | CH | CH | N | -OCH₂CH₂-piperidinyl |
| 85 | 3'-F-biphenyl-3-yl | O | CF | CH | CH | N | -OCH₂CH₂N(OMe)(Me) |
| 86 | 3-(H₃CO)-4-Br-phenyl | O | CF | CH | CH | N | -OCH₂CH₂N(OMe)(Me) |
| 87 | 3-(F₃CO)-biphenyl-3-yl | O | CF | CH | CH | N | -OCH₂CH₂-piperidinyl |
| 88 | 3-(F₃CO)-4-Cl-phenyl | O | CH | CH | CH | N | -OCH₂CH₂N(Et)₂ |
| 89 | 3-(F₃CO)-4-Cl-phenyl | O | CF | CH | CH | N | -OCH₂CH₂N(OMe)(Me) |

TABLE 1-continued

Compounds of the formula (I-a)

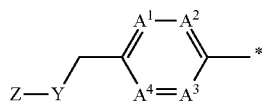

where the substituents Z, Y, A¹, A², A³, A⁴, and * have the following meaning:

| Ex. No. | Z | Y | A¹ | A² | A³ | A⁴ | * |
|---|---|---|---|---|---|---|---|
| 90 | dibenzofuran-2-yl | O | COCH₃ | CH | CH | N | #-O-CH₂CH₂-N(OCH₃)(CH₃) |
| 91 | 4-chloronaphthalen-1-yl | O | COCH₃ | CH | CH | N | #-O-CH₂CH₂-N(OCH₃)(CH₃) |
| 92 | 4-chloro-2-(trifluoromethoxy)phenyl | O | CF | CH | CH | N | #-O-CH₂CH₂-N(OC(CH₃)₃)(CH₃) |
| 93 | 3,4-dichloronaphthalen-1-yl | O | COCH₃ | CH | CH | N | #-O-CH₂CH₂-N(OCH₃)(CH₃) |
| 94 | biphenyl-3-yl | O | COCH₃ | CH | CH | N | #-O-CH₂CH₂-N(OCH₃)(CH₃) |
| 95 | 3-iodophenyl | O | CF | CH | CH | N | #-O-CH₂CH₂-N(OCH₃)(CH₃) |
| 96 | 3,4-dichloronaphthalen-1-yl | O | CH | CH | COCH₃ | N | #-O-CH₂CH₂-N(OCH₃)(CH₃) |
| 97 | 3,4-dichloronaphthalen-1-yl | O | CH | CH | COCH₂CH₃ | N | #-O-CH₂CH₂-N(OCH₃)(CH₃) |

TABLE 1-continued

Compounds of the formula (I-a)

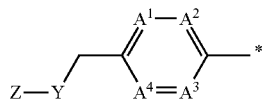

where the substituents Z, Y, $A^1$, $A^2$, $A^3$, $A^4$, and * have the following meaning:

| Ex. No. | Z | Y | $A^1$ | $A^2$ | $A^3$ | $A^4$ | * |
|---|---|---|---|---|---|---|---|
| 98 | 4-chloronaphthalen-1-yl | O | CH | N | N | CH | #-O-CH$_2$CH$_2$-N(CH$_3$)-O-CH$_3$ |
| 99 | 4-chloronaphthalen-1-yl | O | N | CH | CH | N | #-O-CH$_2$CH$_2$-N(CH$_3$)-O-CH$_3$ |

Preparation of 2-[(5-fluoro-6-{[(6-fluorobiphenyl-3-yl)oxy]methyl}pyridin-3-yl)oxy]-N-methoxy-N-methylethanamine

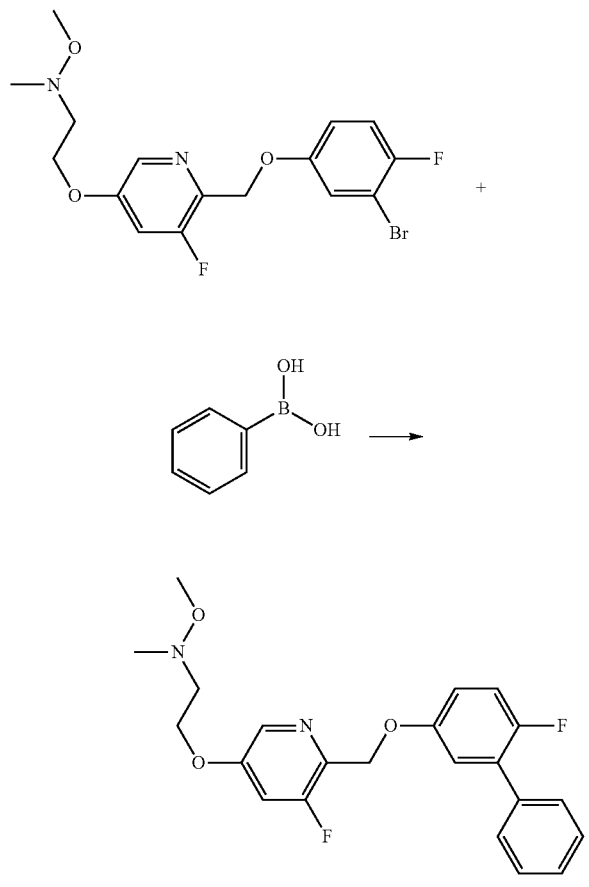

Under argon, 58 mg (0.42 mmol) of potassium carbonate, 49 mg (42 μmol) of tetrakis-(triphenylphosphine)palladium, 1 ml of water and 51 mg (0.42 mmol) of phenylboronic acid were added to a solution of 85 mg (0.21 mmol) of 2-({6-[(3-bromo-4-fluorophenoxy)methyl]-5-fluorpyridin-3-yl}oxy)-N-methoxy-N-methylethanamine in 5 ml of tetrahydrofuran. By passing through a stream of argon, the reaction mixture was freed from dissolved oxygen, and the mixture was then stirred at 80° C. overnight and silica gel was then added prior to removal of the solvent under reduced pressure. The residue was separated chromatographically initially by MPLC on silica gel (gradient: ethyl acetate/cyclohexane) and subsequently once more by HPLC (gradient: H$_2$O/acetonitrile). This gave 80 mg of 2-[(5-fluoro-6-{[(6-fluorobiphenyl-3-yl)oxy]methyl}pyridin-3-yl)oxy]-N-methoxy-N-methylethanamine.

$^1$H-NMR (400.0 MHz, d$_6$-DMSO): δ=8.2304 (2.2); 8.2263 (2.2); 7.5763 (1.4); 7.5681 (2.6); 7.5640 (1.8); 7.5471 (4.3); 7.4984 (1.9); 7.4804 (3.7); 7.4611 (2.0); 7.4291 (0.8); 7.4259 (1.4); 7.4227 (0.9); 7.4135 (0.5); 7.4076 (1.7); 7.3895 (0.6); 7.2630 (1.2); 7.2404 (1.7); 7.2374 (1.6); 7.2147 (1.5); 7.1731 (1.2); 7.1653 (1.4); 7.1570 (1.3); 7.1492 (1.4); 7.0680 (0.8); 7.0587 (1.3); 7.0503 (0.8); 7.0456 (0.8); 7.0367 (1.0); 7.0280 (0.6); 5.1873 (4.3); 5.1829 (4.6); 4.2340 (1.9); 4.2203 (4.0); 4.2066 (2.1); 3.4025 (19.6); 3.3189 (19.4); 2.9769 (1.8); 2.9633 (3.6); 2.9495 (1.8); 2.6708 (0.4); 2.5643 (16.0); 2.5643 (16.6); 2.5239 (0.9); 2.5104 (22.3); 2.5061 (46.1); 2.5016 (61.5); 2.4971 (45.7); 2.4929 (23.3); 2.3283 (0.4); 0.0079 (1.5); −0.0002 (41.0); −0.0084 (1.9).

Preparation of 2-[(6-{[(5,6-dichloro-1-naphthyl)oxy]methyl}-2-ethoxypyridin-3-yl)oxy]-N-methoxy-N-methylethanamine

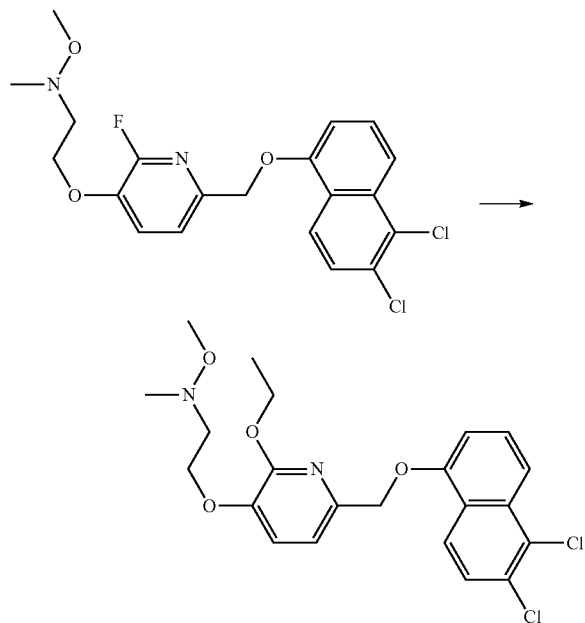

At room temperature, 9.6 mg (0.14 mmol) of sodium ethoxide were added to a solution of 20 mg (47 μmol) of 2-[(6-{[(5,6-dichloro-1-naphthyl)oxy]methyl}-2-fluoropyridin-3-yl)oxy]-N-methoxy-N-methylethanamine in 1 ml of dimethylacetamide. The reaction mixture was stirred overnight and then separated chromatographically by HPLC (gradient: $H_2O$/acetonitrile). This gave 7 mg of 2-[(6-{[(5,6-dichloro-1-naphthyl)oxy]methyl}-2-ethoxypyridin-3-yl)oxy]-N-methoxy-N-methylethanamine.

$^1$H-NMR (400.0 MHz, $d_6$-DMSO): δ=9.9594 (0.4); 8.2457 (2.4); 8.2230 (2.6); 7.7922 (1.9); 7.7708 (2.7); 7.6965 (3.2); 7.6791 (1.9); 7.6739 (3.3); 7.6593 (2.4); 7.6384 (1.3); 7.3698 (2.4); 7.3498 (2.8); 7.2878 (2.3); 7.2684 (2.1); 7.1449 (2.7); 7.1251 (2.3); 5.2364 (7.8); 4.5171 (0.3); 4.3665 (1.3); 4.3490 (4.1); 4.3315 (4.2); 4.3139 (1.4); 4.1371 (2.1); 4.1226 (4.5); 4.1080 (2.3); 3.4096 (18.6); 3.4001 (2.0); 3.3204 (31.9); 2.9799 (2.3); 2.9655 (4.6); 2.95 11 (2.3); 2.6709 (0.6); 2.5723 (16.0); 2.5558 (1.6); 2.5058 (75.0); 2.5019 (95.4); 2.4980 (72.3); 2.3286 (0.5); 1.3184 (4.2); 1.3009 (8.7); 1.2834 (4.2); 1.2308 (0.6); 0.1457 (0.5); −0.0004 (99.6); −0.1499 (0.5).

Preparation of 2-({6-[(dibenzo[b,d]furan-2-yloxy)methyl]-5-methylpyridin-3-yl}oxy)-N-methoxy-N-methylethanamine

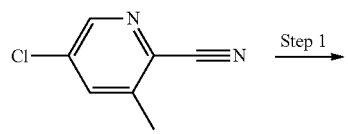

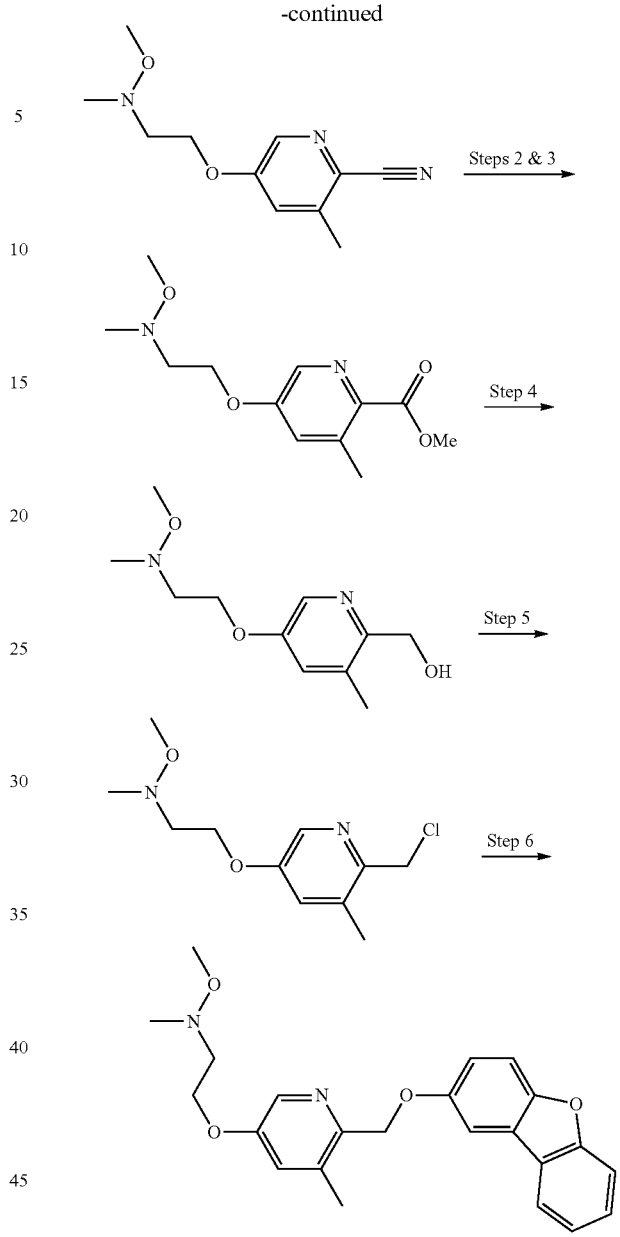

Step 1: Preparation of 5-{2-[methoxy(methyl)amino]ethoxy}-3-methylpyridine-2-carbonitrile A solution of 1.38 g (13.1 mmol) of 2-[methoxy(methyl)amino]ethanol in 4 ml of N-methyl-2-pyrrolidone was slowly added dropwise to a cooled suspension of 686 mg (15.7 mmol) of sodium hydride (55% strength dispersion in mineral oil) in 32 ml of N-methyl-2-pyrrolidone. The reaction mixture was stirred at room temperature for 30 min and a solution of 2.00 g (13.1 mmol) of 5-chloro-3-methylpyridine-2-carbonitrile in 4 ml of N-methyl-2-pyrrolidone was then added dropwise. Stirring at room temperature was continued overnight and 20 ml of ethyl acetate were then added. After 5 min, water was added and the mixture was extracted repeatedly with ethyl acetate. The combined organic phases were dried with sodium sulfate and filtered and the solvent was removed under reduced pressure. The residue was adsorbed on RP silica gel and separated chromatographically by MPLC on RP silica gel (gradient: $H_2O$/acetonitrile). This gave 1.20 g of 5-{2-[methoxy(methyl)amino]ethoxy}-3-methylpyridine-2-carbonitrile.

$^1$H-NMR (400.0 MHz, CDCl3): δ=8.7253 (0.4); 8.7197 (0.4); 8.2526 (1.8); 8.2459 (1.9); 7.7789 (0.3); 7.7733 (0.3); 7.2654 (4.4); 7.1286 (1.7); 7.1221 (1.7); 4.2396 (1.4); 4.2259 (2.9); 4.2122 (1.6); 3.9097 (0.7); 3.5168 (16.0); 3.0561 (2.1); 3.0424 (4.0); 3.0286 (2.0); 2.7222 (0.6); 2.6748 (14.6); 2.6247 (1.3); 2.5715 (0.4); 2.5393 (11.4); 2.0097 (3.7); 1.6280 (0.5); −0.0002 (3.7).

Steps 2&3: Preparation of methyl 5-{2-[methoxy(methyl)amino]ethoxy}-3-methylpyridine-2-carboxylate 2.17 g (54.3 mmol) of sodium hydroxide, 2.7 ml of water and 2.7 ml of ethanol were added to a solution of 1.20 g (5.43 mmol) of 5-{2-[methoxy(methyl)amino]ethoxy}-3-methylpyridine-2-carbonitrile in 5.4 ml of tetrahydrofuran and the mixture was stirred at 70° C. for 12 h. The reaction mixture was then diluted with water, acidified with 1 M hydrochloric acid and extracted repeatedly with ethyl acetate. The combined organic phases were dried with sodium sulfate and filtered and the solvent was removed under reduced pressure. This gave 245 mg of a residue. The aqueous phase was likewiese concentrated under reduced pressure and the residue was dried azeotropically with $CH_2Cl_2$. This gave 4.28 g of a residue, which was dissolved in 45 ml of methanol, and a catalytic amount of sulfuric acid was added. The reaction solution was heated under reflux for 5 d and the solvent was then removed under reduced pressure. Saturated $NaHCO_3$ solution was added to the residue and the solution obtained was extracted repeatedly with ethyl acetate. The combined organic phases were dried with sodium sulfate and filtered and the solvent was removed under reduced pressure. This gave 787 mg of methyl 5-{2-[methoxy(methyl)amino]ethoxy}-3-methylpyridine-2-carboxylate.

$^1$H-NMR (400.0 MHz, CDCl3): δ=8.2899 (1.8); 8.2832 (1.8); 7.2673 (4.3); 7.1065 (1.6); 7.1003 (1.6); 5.3010 (0.6); 4.2446 (1.2); 4.2311 (2.5); 4.2174 (1.4); 4.0111 (1.3); 3.9793 (1.3); 3.9549 (15.8); 3.9047 (0.5); 3.524 4 (16.0); 3.0596 (1.9); 3.0459 (3.7); 3.0322 (1.9); 2.6789 (14.2); 2.6359 (11.1); 1.6127 (0.4); −0.0002 (2.9)

Step 4: Preparation of (5-{2-[methoxy(methyl)amino]ethoxy}-3-methylpyridin-2-yl)methanol At −78° C., 14.8 ml (14.8 mmol) of a 1 M solution of diisobutylaluminium hydride were added dropwise to a solution of 750 mg (2.95 mmol) of methyl 5-{2-[methoxy(methyl)amino]ethoxy}-3-methylpyridine-2-carboxylate in 32 ml of toluene. The reaction solution was stirred at −10° C. for 60 min, 50 ml of a saturated potassium sodium tartrate solution were added and the mixture was then extracted repeatedly with ethyl acetate. The combined organic phases were dried with sodium sulfate and filtered and the solvent was removed under reduced pressure. The residue was dissolved in 10 ml of methanol and, with ice cooling, 64 mg (1.7 mmol) of sodium borohydride were added. The solution was stirred at room temperature for 2 h. The solvent was removed under reduced pressure. Water was added to the residue and the mixture was extracted repeatedly with ethyl acetate. The combined organic phases were dried with sodium sulfate and filtered and the solvent was removed under reduced pressure. This gave 498 mg of (5-{2-[methoxy(methyl)amino]ethoxy}-3-methylpyridin-2-yl)methanol.

$^1$H-NMR (400.0 MHz, CDCl3): δ=8.1296 (1.7); 8.1232 (1.8); 7.2654 (3.6); 7.1012 (1.6); 7.0955 (1.6); 4.6307 (3.8); 4.5215 (0.5); 4.1966 (1.3); 4.1829 (2.6); 4.1692 (1.4); 3.8572 (0.5); 3.5324 (16.0); 3.0446 (2.0); 3.030 8 (3.9); 3.0171 (2.0); 2.6788 (14.8); 2.2275 (0.4); 2.2064 (10.4); 1.6595 (0.9); −0.0002 (2.0).

Step 5: Preparation of 2-{[6-(chloromethyl)-5-methylpyridin-3-yl]oxy}-N-methoxy-N-methylethanamine At 0° C., 0.23 ml (1.3 mmol) of diisopropylethylamine and 34 µl (0.44 mmol) of methanesulfonyl chloride were added to a solution of 100 mg (442 µmol) of (5-{2-[methoxy(methyl)amino]ethoxy}-3-methylpyridin-2-yl)methanol in 3 ml of $CH_2Cl_2$. The reaction solution was stirred at room temperature overnight and then diluted with $CH_2Cl_2$ and washed with saturated $NaHCO_3$ solution and water. The organic phase was dried over sodium sulfate and filtered, and the solvent was removed under reduced pressure. This gave 102 mg of 2-{[6-(chloromethyl)-5-methylpyridin-3-yl]oxy}-N-methoxy-N-methylethanamine.

$^1$H-NMR (400.0 MHz, CDCl3): δ=8.1510 (1.8); 8.1442 (1.8); 7.2641 (5.4); 7.0808 (1.7); 7.0743 (1.7); 4.7037 (0.5); 4.6904 (9.1); 4.1959 (1.4); 4.1823 (2.7); 4.1686 (1.5); 3.8559 (0.5); 3.5265 (16.0); 3.0400 (2.0); 3.0263 (3.8); 3.0125 (2.0); 2.6738 (14.6); 2.4657 (0.4); 2.4289 (11.1); 1.6500 (0.9); −0.0002 (3.5)

Step 6: Preparation of 2-({6-[(dibenzo[b,d]furan-2-yloxy)methyl]-5-methylpyridin-3-yl}oxy)-N-methoxy-N-methylethanamine 61 mg (0.33 mmol) of dibenzo[b,d]furan-2-ol and 227 mg (1.64 mmol) of $K_2CO_3$ were added to a solution of 100 mg (409 µmol) of 2-{[6-(chloromethyl)-5-methylpyridin-3-yl]oxy}-N-methoxy-N-methylethanamine in 3 ml of N,N-dimethylformamide. The reaction mixture was stirred at 70° C. for 4 h and overnight at room temperature. Water was then added, and the mixture was extracted repeatedly with ethyl acetate. The combined organic phases were dried with sodium sulfate and filtered and the solvent was removed under reduced pressure. The residue was separated chromatographically by HPLC (gradient: $H_2O$/acetonitrile). This gave 93 mg of 2-({6-[(dibenzo[b,d]furan-2-yloxy)methyl]-5-methylpyridin-3-yl}oxy)-N-methoxy-N-methylethanamine.

$^1$H-NMR (400.0 MHz, CDCl3): δ=8.2065 (2.0); 8.1997 (2.0); 7.9262 (1.5); 7.9069 (1.6); 7.5833 (2.4); 7.5768 (2.5); 7.5423 (1.4); 7.5217 (2.2); 7.4626 (2.3); 7.4559 (1.0); 7.4536 (0.9); 7.4401 (3.2); 7.4172 (0.8); 7.3375 (1.2); 7.3184 (1.8); 7.3000 (0.8); 7.2610 (7.7); 7.1522 (1.4); 7.1457 (1.4); 7.1299 (1.3); 7.1233 (1.4); 7.1162 (1.9); 7.1096 (1.8); 5.2523 (8.4); 4.2062 (1.4); 4.1927 (2.7); 4.1790 (1.5); 3.8629 (0.5); 3.5287 (16.0); 3.0459 (1.9); 3.032 3 (3.8); 3.0186 (1.9); 2.6759 (14.0); 2.4599 (11.8); 2.0045 (1.6); 1.6104 (5.7); −0.0002 (5.0).

Preparation of 2-({6-[(dibenzo[b,d]furan-2-yloxy)methyl]-5-methoxypyridin-3-yl}oxy)-N-methoxy-N-methylethanamine

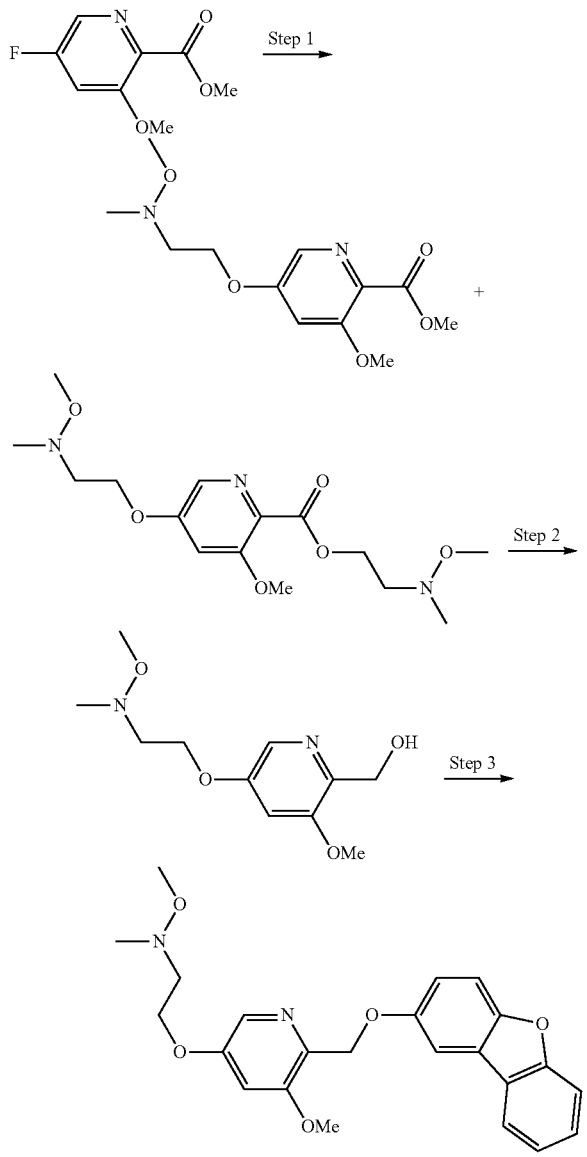

Step 1: Preparation of methyl 3-methoxy-5-{2-[methoxy(methyl)amino]ethoxy}pyridine-2-carboxylate A solution of 1.35 g (12.9 mmol) of 2-[methoxy(methyl)amino]ethanol in 10 ml of N,N-dimethylformamide was added dropwise to a suspension of 673 mg (15.4 mmol) of sodium hydride (55% strength dispersion in mineral oil) in 80 ml of N,N-dimethylformamide. The reaction solution was stirred at room temperature for 30 min, and a solution of 2.38 g (12.9 mmol) of methyl 5-fluoro-3-methoxypyridine-2-carboxylate in 10 ml of N,N-dimethylformamide was then added dropwise. The reaction mixture was stirred at room temperature overnight, water was then added and the mixture was extracted with ethyl acetate. The combined organic phases were dried with sodium sulfate and filtered and the solvent was removed under reduced pressure. The residue was separated chromatographically by HPLC (gradient: H₂O/acetonitrile). This gave 2.76 g of crude product, which was re-purified chromatographically by HPLC (gradient: H₂O/acetonitrile). This gave 1.43 g of methyl 3-methoxy-5-{2-[methoxy(methyl)amino]ethoxy}pyridine-2-carboxylate (purity about 69%) as a mixture with 2-[methoxy(methyl)amino]ethyl-3-methoxy-5-{2-[methoxy(methyl)amino]ethoxy}pyridine-2-carboxylate.

$^1$H-NMR (400.0 MHz, CDCl3): δ=8.0372 (1.9); 8.0315 (1.9); 8.0009 (0.9); 7.9951 (0.9); 7.2691 (3.6); 6.9242 (1.7); 6.9186 (1.7); 6.8404 (0.8); 6.8346 (0.8); 4.2815 (1.0); 4.2681 (1.9); 4.2547 (1.1); 3.9713 (0.6); 3.9495 (16.0); 3.9380 (6.1); 3.9351 (6.2); 3.9249 (10.7); 3.9142 (0.6); 3.5489 (0.5); 3.5312 (11.7); 3.0632 (1.4); 3.0497 (2.7); 3.0362 (1.4); 2.6847 (10.4); 2.6366 (0.4); 1.6400 (2.2); −0.0002 (3.8).

Step 2: Preparation of (3-methoxy-5-{2-[methoxy(methyl)amino]ethoxy}pyridin-2-yl)methanol At −78° C., 3.3 ml (3.3 mmol) of a 1 M solution of diisobutylaluminium hydride were added dropwise to a solution of 1.43 g (5.29 mmol) of methyl 3-methoxy-5-{2-[methoxy(methyl)amino]ethoxy}pyridine-2-carboxylate in 56 ml of toluene. The reaction solution was stirred at 0° C. overnight. At 0° C., a further 10.6 ml (10.6 mmol) of a 1 M solution of diisobutylaluminium hydride were then added. After 1 h of stirring at 0° C., 3 ml of methanol were added dropwise, followed after 5 min by 56 ml of a saturated potassium sodium tartrate solution. The mixture was extracted repeatedly with ethyl acetate. The combined organic phases were dried with sodium sulfate and filtered and the solvent was removed under reduced pressure. The residue was dissolved in 5 ml of methanol and, with ice cooling, 114 mg (3.02 mmol) of sodium borohydride were added. The solution was stirred at room temperature for 2 h. The reaction mixture was concentrated under reduced pressure, water was added and the mixture was extracted repeatedly with ethyl acetate. The combined organic phases were dried with sodium sulfate and filtered and the solvent was removed under reduced pressure. The residue was separated chromatographically by HPLC (gradient: H₂O/acetonitrile). This gave 949 mg of (3-methoxy-5-{2-[methoxy(methyl)amino]ethoxy}pyridin-2-yl)methanol.

$^1$H-NMR (400.0 MHz, CDCl3): δ=7.8658 (0.8); 7.2645 (3.4); 6.8295 (2.2); 6.8242 (2.2); 4.6788 (2.4); 4.6682 (2.5); 4.2230 (1.2); 4.2096 (2.3); 4.1962 (1.3); 4.0111 (0.5); 3.9995 (0.9); 3.9882 (0.4); 3.8247 (14.4); 3.5389 (16.0); 3.0482 (1.8); 3.0347 (3.5); 3.0212 (1.9); 2.6855 (14.5); 1.6298 (0.8); −0.0002 (3.3.)

Step 3: Preparation of 2-({6-[(dibenzo[b,d]furan-2-yloxy)methyl]-5-methoxypyridin-3-yl}oxy)-N-methoxy-N-methylethanamine 246 mg (2.06 mmol) of SOCl₂ and a catalytic amount of N,N-dimethylformamide were added to 100 mg (413 μmol) of (3-methoxy-5-{2-[methoxy(methyl)amino]ethoxy} pyridin-2-yl)methanol. The reaction mixture was stirred at room temperature for 4 h and then concentrated under reduced pressure. The residue was dissolved in 2 ml of N,N-dimethylformamide and 61 mg (0.33 mmol) of dibenzo[b,d]furan-2-ol and 285 mg (2.06 mmol) of K₂CO₃ were added. The reaction mixture was stirred at 70° C. for 4 h and at RT for 3 d, adsorbed on RP silica gel and separated chromatographically by MPLC on RP silica gel (gradient: H₂O/acetonitrile). This gave 48 mg of 2-({6-[(dibenzo[b,d]furan-2-yloxy)methyl]-5-methoxypyridin-3-yl}oxy)-N-methoxy-N-methylethanamine.

¹H-NMR (400.0 MHz, CDCl3): δ=7.9991 (2.4); 7.9934 (2.7); 7.9143 (1.4); 7.8951 (1.5); 7.6111 (2.2); 7.6049 (2.5); 7.5409 (1.3); 7.5202 (2.1); 7.4563 (2.1); 7.4506 (1.1); 7.4471 (1.0); 7.4336 (3.0); 7.4295 (2.1); 7.4115 (0.8); 7.4083 (0.8); 7.3311 (1.0); 7.3289 (1.0); 7.3104 (1.6); 7.2936 (0.7); 7.2916 (0.7); 7.2605 (8.3); 7.1897 (1.4); 7.1832 (1.5); 7.1673 (1.2); 7.1609 (1.3); 6.8950 (2.2); 6.8894 (2.5); 5.2982 (2.7); 5.2508 (8.2); 4.2445 (1.3); 4.2311 (2.5); 4.2178 (1.4); 3.8825 (14.1); 3.5365 (16.0); 3.0517 (1.8); 3.0383 (3.5); 3.0248 (1.8); 2.6834 (13.9); 1.5841 (6.1); -0.0002 (7.8).

Preparation of (5-{2-[methoxy(methyl)amino]ethoxy}pyridin-2-yl)methanol

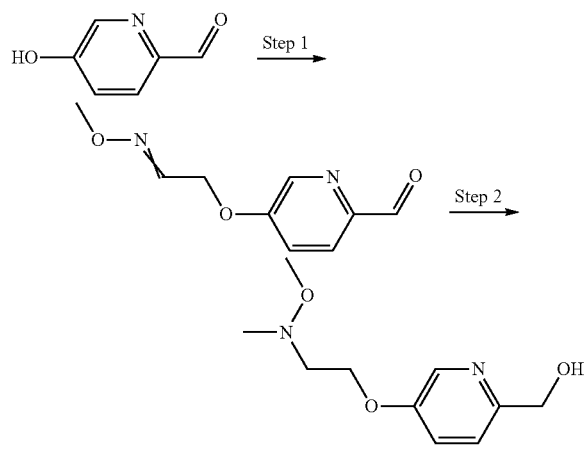

Step 1: Preparation of 5-[2-(methoxyimino)ethoxy]pyridine-2-carbaldehyde

At room temperature, 4.42 g (32.0 mmol) of K₂CO₃ and a solution of 2.41 g (22.4 mmol) of 2-chloro-N-methoxyethanimine in 30 ml of acetonitrile were added to a solution of 1.97 g (16.0 mmol) of 5-hydroxypyridine-2-carbaldehyde in 30 ml of acetonitrile. The reaction mixture was heated under reflux for 40 h and stirred at room temperature for a further 4 d. The sediment was filtered off, the filtrate was concentrated under reduced pressure and the residue was taken up in 15 ml of acetonitrile. The mixture was filtered again and the filtrate was concentrated under reduced pressure. This gave 1.91 g of 5-[2-(methoxyimino)ethoxy]pyridine-2-carbaldehyde as residue.

¹H-NMR (400.0 MHz, CDCl3): δ=10.0000 (4.9); 8.4785 (2.5); 8.4717 (2.5); 8.4568 (0.8); 8.4500 (0.8); 7.9809 (2.4); 7.9592 (2.5); 7.5613 (1.3); 7.5469 (2.6); 7.5328 (1.4); 7.3812 (1.3); 7.3743 (1.3); 7.3594 (1.2); 7.3530 (1.5); 7.3203 (0.4); 7.3136 (0.4); 7.2985 (0.4); 7.2918 (0.4); 7.2652 (6.8); 6.9597 (0.4); 6.9506 (0.8); 6.9413 (0.4); 4.9494 (1.7); 4.9403 (1.7); 4.7838 (5.2); 4.7695 (5.1); 3.9757 (5.0); 3.9550 (0.3); 3.9161 (16.0); 3.9032 (1.0); 3.8898 (0.4); 1.6375 (3.0); -0.0001 (3.9).

Step 2: Preparation of (5-{2-[methoxy(methyl)amino]ethoxy}pyridin-2-yl)methanol

At 10° C., 926 mg (14.7 mmol) of sodium cyanoborohydride were added to a solution of 1.91 g (9.83 mmol) of 5-[2-(methoxyimino)ethoxy]pyridine-2-carbaldehyde in 15 ml of acetic acid, and the mixture was stirred at room temperature for 2 h. With cooling, at 20° C. 12.1 g (147 mmol) of a 36.5% strength aqueous formaldehyde solution were then added. After 10 min, a further 926 mg (14.7 mmol) of sodium cyanoborohydride were added. The reaction mixture was stirred at room temperature overnight, and then the solvent was removed under reduced pressure. 50 ml of water were added to the residue, the pH was adjusted to 10 using a 50% strength sodium hydroxide solution and the mixture was extracted repeatedly with ethyl acetate. The combined organic phases were dried with sodium sulfate and filtered and the solvent was removed under reduced pressure. The residue was separated chromatographically by MPLC on silica gel (gradient: ethyl acetate/cyclohexane). This gave 1.08 g of 5-{2-[methoxy(methyl)amino]ethoxy}pyridin-2-yl)methanol.

¹H-NMR (400.0 MHz, CDCl3): δ=8.2963 (2.0); 8.2894 (2.0); 7.2869 (1.1); 7.2799 (1.0); 7.2697 (2.7); 7.2657 (2.0); 7.2585 (1.7); 7.2065 (2.4); 7.1852 (1.4); 4.9625 (0.5); 4.7643 (0.5); 4.7038 (7.6); 4.2049 (1.5); 4.1912 (2.9); 4.1775 (1.6); 3.5311 (16.0); 3.0514 (2.2); 3.0377 (4.2); 3.0239 (2.1); 2.6800 (15.3); -0.0002 (1.2).

Preparation of 2-{[6-{[(5,6-dichloro-1-naphthyl)oxy]methyl}-2-(methylsulfanyl)pyridin-3-yl]oxy}-N-methoxy-N-methylethanamine

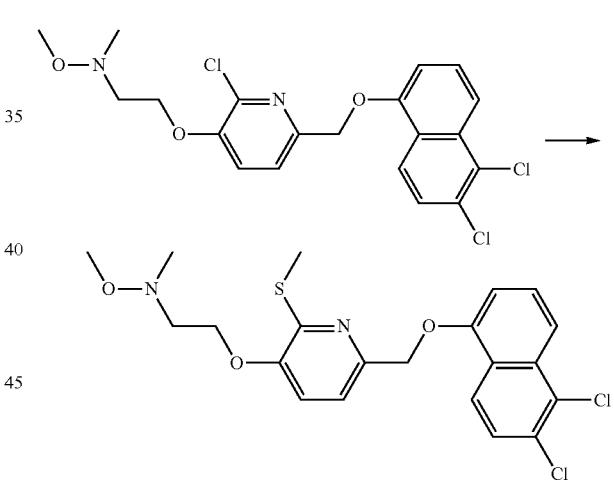

14.6 mg (0.21 mmol) of sodium methanethiolate were added to a solution of 46 mg (0.10 mmol) of 2-[(2-chloro-6-{[(5,6-dichloro-1-naphthyl)oxy]methyl}pyridin-3-yl)oxy]-N-methoxy-N-methylethanamine in dimethylacetamide and the mixture was stirred at room temperature overnight. A further 7.3 mg (0.10 mmol) of sodium methanethiolate were then added. After 2 h at room temperature, another 7.3 mg (0.10 mmol) of sodium methanethiolate were added and the reaction mixture was stirred overnight. Water was added to the reaction mixture and the mixture was extracted repeatedly with ethyl acetate. The combined organic phases were dried with sodium sulfate and filtered and the solvent was removed under reduced pressure. The residue was separated chromatographically by HPLC (gradient: H₂O/acetonitrile). This gave 3 mg of 2-{[6-{[(5,6-dichloro-1-naphthyl)oxy]methyl}-2-(methylsulfanyl)pyridin-3-yl]oxy}-N-methoxy-N-methylethanamine.

¹H-NMR (601.6 MHz, CDCl3): δ=8.2606 (1.7); 8.2455 (1.8); 7.8618 (1.6); 7.8475 (1.7); 7.5069 (1.2); 7.5011 (2.6); 7.4936 (1.8); 7.4861 (2.4); 7.4797 (1.2); 7.2589 (26.6); 7.1854 (1.7); 7.1718 (2.0); 7.0330 (2.2); 7.0193 (1.9); 6.9921 (1.7); 6.9793 (1.6); 5.3152 (6.8); 4.2239 (1.9); 4.2140 (4.0); 4.2041 (2.0); 3.5268 (16.0); 3.1054 (2.2); 3.0956 (4.4); 3.0857 (2.1); 2.6824 (14.6); 2.5371 (15.1); 1.5443 (15.4); 1.2554 (1.0); 0.0691 (3.3); 0.0051 (0.6); −0.0002 (16.0); −0.0056 (0.7).

Preparation of 2-[(5-{[(4-chloro-1-naphthyl)oxy]methyl}pyridin-2-yl)oxy]-N-methoxy-N-methyl-ethanamine

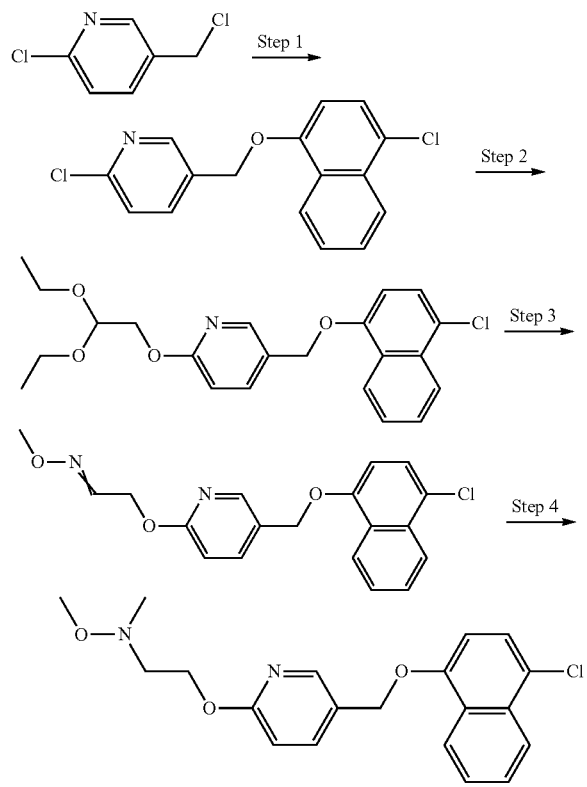

Step 1: Preparation of 2-chloro-5-{[(4-chloro-1-naphthyl)oxy]methyl}pyridine 6.22 g (34.8 mmol) of 4-chloro-1-naphthol and 14.4 g (104 mmol) of K₂CO₃ were added to a solution of 5.64 g (34.8 mmol) of 2-chloro-5-(chloromethyl)pyridine in 40 ml of N,N-dimethylformamide. The reaction mixture was stirred at 70° C. for 16 h and then concentrated under reduced pressure. The residue was dissolved in ethyl acetate and this solution was washed with water and a saturated ammonium chloride solution. The organic phase was then extracted with saturated ammonium chloride solution and the combined aqueous phases were extracted repeatedly with ethyl acetate. The organic phases were combined, washed with saturated aqueous sodium chloride solution, dried with sodium sulfate and filtered, and the solvent was removed under reduced pressure. The residue was adsorbed on silica gel and separated chromatographically by MPLC on silica gel (gradient: cyclohexane/ethyl acetate). This gave 9.72 g of 2-chloro-5-{[(4-chloro-1-naphthyl)oxy]methyl}pyridine.

¹H-NMR (400.0 MHz, d₆-DMSO): δ=8.6347 (4.5); 8.6289 (4.7); 8.2855 (3.6); 8.2647 (3.9); 8.1440 (3.6); 8.1229 (4.0); 8.0817 (2.7); 8.0759 (2.7); 8.0612 (2.9); 8.0553 (2.9); 7.7505 (1.7); 7.7325 (3.3); 7.7140 (2.2); 7.6592 (2.5); 7.6462 (6.3); 7.6409 (3.8); 7.6256 (6.5); 7.6154 (5.7); 7.5948 (5.0); 7.1313 (5.5); 7.1104 (5.1); 5.3830 (16.0); 3.3373 (32.0); 2.5096 (30.8); 2.5056 (39.6); 2.5016 (30.3); 0.0074 (0.9); −0.0002 (21.8).

Step 2: Preparation of 5-{[(4-chloro-1-naphthyl)oxy]methyl}-2-(2,2-diethoxyethoxy)pyridine 359 mg (8.22 mmol) of sodium hydride (55% strength dispersion in mineral oil) were added to a solution of 882 mg (6.58 mmol) of 2,2-diethoxyethanol in tetrahydrofuran, and the mixture was stirred at room temperature for 30 min. 1.00 g (3.29 mmol) of 2-chloro-5-{[(4-chloro-1-naphthyl)oxy]methyl}pyridine, dissolved in 20 ml of tetrahydrofuran, was then added, and the reaction solution was stirred at 60° C. for 4 h and at room temperature for 12 h. A further 359 mg (8.22 mmol) of sodium hydride (55% strength dispersion in mineral oil) were then added, and the mixture was stirred at 60° C. for a further 6 h and at room temperature overnight. Water and ethyl acetate were added to the reaction mixture and the phases were separated. The organic phase was washed with water and the aqueous phase was extracted repeatedly with ethyl acetate. The organic phases were combined and washed with saturated aqueous sodium chloride solution. The organic phases were dried with sodium sulfate and filtered and the solvent was removed under reduced pressure. The residue was adsorbed on silica gel and separated chromatographically by MPLC on silica gel (gradient: cyclohexane/ethyl acetate). This gave 128 mg of 5-{[(4-chloro-1-naphthyl)oxy]methyl}-2-(2,2-diethoxyethoxy)pyridine and 891 mg of a contaminated fraction. The latter was separated chromatographically by MPLC on RP silica gel (gradient: acetonitrile/H₂O). This gave a further 652 mg of 5-{[(4-chloro-1-naphthyl)oxy]methyl}-2-(2,2-diethoxyethoxy)pyridine.

¹H-NMR (400.0 MHz, d₆-DMSO): δ=8.3586 (1.9); 8.3534 (2.0); 8.2309 (1.4); 8.2103 (1.5); 8.1313 (1.5); 8.1105 (1.6); 7.9306 (1.2); 7.9246 (1.2); 7.9094 (1.3); 7.9034 (1.3); 7.7362 (0.7); 7.7333 (0.7); 7.7190 (1.1); 7.7158 (1.4); 7.7124 (0.8); 7.6980 (0.9); 7.6950 (0.9); 7.6373 (2.8); 7.6166 (3.5); 7.5971 (0.7); 7.5944 (0.6); 7.1480 (2.2); 7.1271 (2.0); 6.9259 (2.1); 6.9047 (2.0); 5.2679 (5.9); 4.8430 (1.1); 4.8297 (2.5); 4.8165 (1.2); 4.2634 (4.4); 4.2501 (4.2); 3.7038 (0.5); 3.6861 (1.6); 3.6798 (0.9); 3.6684 (1.8); 3.6622 (2.5); 3.6507 (0.7); 3.6445 (2.4); 3.6269 (0.7); 3.5846 (0.7); 3.5670 (2.3); 3.5608 (0.7); 3.5494 (2.4); 3.5430 (1.8); 3.5318 (0.9); 3.5254 (1.6); 3.5078 (0.5); 3.3325 (27.3); 2.5258 (0.6); 2.5122 (12.8); 2.5081 (24.9); 2.5036 (32.0); 2.4991 (23.6); 2.4951 (11.9); 1.1454 (7.9); 1.1278 (16.0); 1.1102 (7.6); 0.0079 (0.8); −0.0002 (20.6); −0.0083 (0.9).

Step 3: Preparation of 2-[(5-{[(4-chloro-1-naphthyl)oxy]methyl}pyridin-2-yl)oxy]-N-methoxyethanimine A solution of 125 mg (1.49 mmol) of O-methyl hydroxylamine hydrochloride in 3 ml of water was added to a solution of 200 mg (498 μmol) of 5-{[(4-chloro-1-naphthyl)oxy]methyl}-2-(2,2-diethoxyethoxy)pyridine in 20 ml of ethanol, and the mixture was stirred at 65° C. overnight. The solvents were then removed under reduced pressure. Water and CH$_2$Cl$_2$ were added to the reaction mixture and the phases were separated. The organic phase was washed with water, dried with sodium sulfate and filtered, and the solvent was removed under reduced pressure. The residue was adsorbed on silica gel and separated chromatographically by MPLC on silica gel (gradient: cyclohexane/ethyl acetate). This gave 160 mg of 2-[(5-{[(4-chloro-1-naphthyl)oxy]methyl}pyridin-2-yl)oxy]-N-methoxyethanimine.

$^1$H-NMR (400.0 MHz, d$_6$-DMSO): δ=8.3813 (2.0); 8.3765 (3.2); 8.2340 (2.3); 8.2131 (2.4); 8.1323 (2.4); 8.1114 (2.7); 7.9720 (0.9); 7.9659 (1.0); 7.9608 (1.3); 7.9546 (1.3); 7.9510 (1.1); 7.9446 (1.1); 7.9395 (1.3); 7.9335 (1.2); 7.7372 (1.2); 7.7344 (1.2); 7.7200 (1.8); 7.7169 (2.3); 7.6990 (1.5); 7.6960 (1.4); 7.6766 (1.2); 7.6628 (2.4); 7.6490 (1.3); 7.6398 (4.3); 7.6193 (5.6); 7.5989 (1.1); 7.5963 (1.0); 7.1515 (3.4); 7.1306 (3.2); 7.0390 (0.8); 7.0298 (1.8); 7.0208 (0.9); 6.9829 (1.5); 6.9616 (1.5); 6.9545 (2.0); 6.9332 (1.9); 5.2769 (9.9); 5.0632 (3.8); 5.0541 (3.8); 4.9043 (4.8); 4.8905 (4.8); 3.8585 (11.2); 3.7910 (16.0); 3.3331 (34.8); 2.5260 (0.9); 2.5083 (35.1); 2.5039 (45.3); 2.4994 (33.8); 1.9903 (1.2); 1.1934 (0.3); 1.1756 (0.6); 0.0078 (1.4); −0.0002 (33.0).

Step 4: 2-[(5-{[(4-Chloro-1-naphthyl)oxy]methyl}pyridin-2-yl)oxy]-N-methoxy-N-methyl-ethanamine 49 mg (0.79 mmol) of sodium cyanoborohydride were added to a solution of 140 mg (392 μmol) of 2-[(5-{[(4-chloro-1-naphthyl)oxy]methyl}pyridin-2-yl)oxy]-N-methoxyethanimine in 20 ml of acetic acid and the mixture was stirred at room temperature for 1 h. A further 49 mg (0.79 mmol) of sodium cyanoborohydride were then added. After 30 min at room temperature, 2.98 ml (39.2 mmol) of a 36.5% strength aqueous formaldehyde solution were added, and after a further 20 min 74 mg (1.2 mmol) of sodium cyanoborohydride were added. The reaction mixture was stirred at room temperature for 2 h. Saturated aqueous NaHCO$_3$ solution was then added, and the reaction mixture was extracted repeatedly with ethyl acetate. The combined organic phases were washed with a saturated aqueous sodium chloride solution, dried with sodium sulfate and filtered, and the solvent was removed under reduced pressure. The residue was adsorbed on silica gel and separated chromatographically by MPLC on silica gel (gradient: cyclohexane/ethyl acetate). This gave 78 mg of 2-[(5-{[(4-chloro-1-naphthyl)oxy]methyl}pyridin-2-yl)oxy]-N-methoxy-N-methylethanamine.

$^1$H-NMR (400.0 MHz, d$_6$-DMSO): δ=8.3630 (5.1); 8.3579 (5.5); 8.2317 (3.9); 8.2108 (4.1); 8.1311 (4.0); 8.1102 (4.3); 7.9169 (3.2); 7.9109 (3.2); 7.8956 (3.3); 7.8896 (3.3); 7.7361 (1.8); 7.7335 (2.0); 7.7160 (3.8); 7.6980 (2.3); 7.6953 (2.4); 7.6387 (6.2); 7.6180 (8.4); 7.5966 (1.7); 7.5943 (1.8); 7.1509 (5.6); 7.1300 (5.2); 6.9034 (5.4); 6.8821 (5.2); 5.2613 (16.0); 4.8123 (1.3); 4.7872 (1.6); 4.6588 (1.7); 4.4268 (5.1); 4.4124 (10.6); 4.3979 (5.4); 3.4092 (42.0); 3.3340 (86.0); 3.2821 (2.8); 2.9629 (4.6); 2.9486 (9.2); 2.9341 (4.6); 2.6773 (0.8); 2.6731 (0.6); 2.6687 (0.4); 2.5578 (0.8); 2.5082 (62.5); 2.5039 (81.9); 2.4997 (64.1); 2.3307 (0.5); 1.3969 (1.8); 1.2317 (2.8); 0.8527 (0.4); 0.0077 (0.8); −0.0002 (16.2).

Preparation of {3-[(5-{[(4-chloro-1-naphthyl)oxy]methyl}pyridin-2-yl)oxy]pyrrolidin-1-yl}acetonitrile

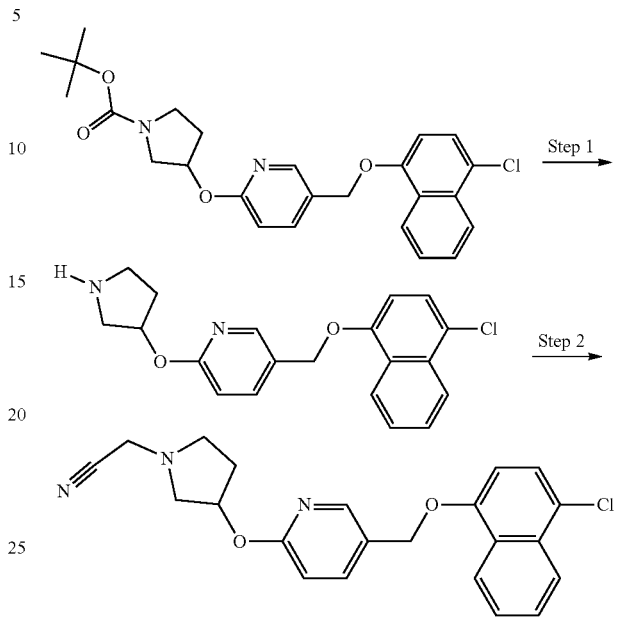

Step 1: Preparation of 5-{[(4-chloro-1-naphthyl)oxy]methyl}-2-(pyrrolidin-3-yloxy)pyridine At 0° C., 1.54 ml (6.16 mmol) of a 4 M solution of hydrochloric acid in 1,4-dioxane were added to a solution of 280 mg (615 μmol) of tert-butyl 3-[(5-{[(4-chloro-1-naphthyl)oxy]methyl}pyridin-2-yl)oxy]pyrrolidine-1-carboxylate in 6 ml of CH$_2$Cl$_2$. The reaction solution was stirred at room temperature overnight, 5 ml of water were added and the pH was adjusted to 8 using a saturated aqueous NaHCO$_3$ solution. The phases were separated and the aqueous phase was extracted twice with 5 ml of CH$_2$Cl$_2$. The combined organic phases were washed with a saturated aqueous sodium chloride solution, dried with sodium sulfate and filtered, and the solvent was removed under reduced pressure. This gave a further 249 mg of 5-{[(4-chloro-1-naphthyl)oxy]methyl}-2-(pyrrolidin-3-yloxy)pyridine.

$^1$H-NMR (400.0 MHz, d$_6$-DMSO): δ=8.3634 (1.8); 8.3580 (1.7); 8.2375 (1.3); 8.2173 (1.4); 8.1393 (1.4); 8.1186 (1.6); 7.9133 (1.1); 7.9073 (1.0); 7.8920 (1.1); 7.8860 (1.1); 7.7434 (0.7); 7.7405 (0.7); 7.7262 (1.0); 7.7229 (1.3); 7.7051 (0.9); 7.7021 (0.8); 7.6448 (2.6); 7.6241 (3.3); 7.6044 (0.6); 7.6018 (0.6); 7.1562 (2.1); 7.1353 (1.9); 6.8639 (1.8); 6.8427 (1.7); 5.4316 (0.5); 5.4174 (0.7); 5.4022 (0.4); 5.2648 (5.3); 3.5757 (16.0); 3.5001 (0.3); 3.4806 (0.4); 3.4702 (0.4); 3.3656 (2.6); 3.1757 (0.6); 3.1619 (0.6); 3.1449 (0.8); 3.1311 (0.7); 2.9862 (0.6); 2.9784 (0.4); 2.9593 (0.8); 2.9406 (0.4); 2.9270 (0.8); 2.9223 (0.8); 2.8958 (1.0); 2.8838 (0.6); 2.8750 (0.5); 2.8635 (0.5); 2.8569 (0.4); 2.5318 (0.8); 2.5183 (17.8); 2.5140 (35.3); 2.5095 (47.3); 2.5050 (34.4); 2.5007 (16.0); 2.0926 (0.4); 2.0759 (0.5); 2.0575 (0.6); 2.0415 (0.5); 1.8551 (0.4); 1.8380 (0.4); 1.8210 (0.4).

Step 2: Preparation of {3-[(5-{[(4-chloro-1-naphthyl)oxy]methyl}pyridin-2-yl)oxy]pyrrolidin-1-yl}acetonitrile 35 μl (0.25 mmol) of triethylamine and 18 μl (0.25 mmol) of bromoacetonitrile were added to a solution of 90 mg (0.25 mmol) of 5-{[(4-chloro-1-naphthyl)oxy]methyl}-2-(pyrrolidin-3-yloxy)pyridine in 3 ml of tetrahydrofuran, and the mixture was stirred at 70° C. for 30 min. The solvent was then removed under reduced pressure. The residue was adsorbed on silica gel and separated chromatographically by MPLC on silica gel (gradient: cyclohexane/ethyl acetate). This gave 75 mg of 3-[(5-{[(4-chloro-1-naphthyl)oxy]methyl}pyridin-2-yl)oxy]pyrrolidin-1-yl}acetonitrile.

$^1$H-NMR (400.0 MHz, d$_6$-DMSO): δ=8.3569 (3.4); 8.3518 (3.4); 8.3142 (4.9); 8.2335 (2.5); 8.2124 (2.7); 8.1313 (2.6); 8.1106 (2.9); 7.9180 (2.2); 7.9119 (2.1); 7.8967 (2.2); 7.8906 (2.2); 7.7358 (1.2); 7.7328 (1.4); 7.7187 (1.8); 7.7154 (2.5); 7.7119 (1.4); 7.6976 (1.6); 7.6945 (1.6); 7.6371 (5.9); 7.6164 (7.2); 7.5985 (1.2); 7.5958 (1.2); 7.1484 (3.9); 7.1275 (3.6); 6.8863 (3.6); 6.8650 (3.5); 5.7544 (3.1); 5.4337 (0.4); 5.4264 (0.9); 5.4188 (1.0); 5.4112 (1.2); 5.4074 (1.3); 5.3999 (1.1); 5.3921 (0.9); 5.3850 (0.5); 5.2594 (10.2); 3.8567 (16.0); 3.3186 (33.8); 3.2947 (1.9); 3.0038 (1.5); 2.9886 (1.6); 2.9775 (2.0); 2.9623 (1.8); 2.8469 (0.6); 2.8263 (1.3); 2.8108 (1.4); 2.7907 (0.8); 2.7530 (1.7); 2.7463 (1.7); 2.7267 (1.4); 2.7201 (1.4); 2.6757 (0.3); 2.6712 (0.5); 2.6667 (0.4); 2.5830 (0.8); 2.5628 (1.6); 2.5464 (1.6); 2.5420 (1.2); 2.5249 (1.9); 2.5111 (25.9); 2.5067 (53.8); 2.5022 (74.6); 2.4977 (57.1); 2.4934 (28.5); 2.3698 (0.4); 2.3506 (0.8); 2.3356 (1.5); 2.3164 (1.4); 2.3016 (0.9); 2.2820 (0.4); 2.0742 (1.4); 1.9166 (0.4); 1.9096 (0.5); 1.8961 (0.7); 1.8821 (0.8); 1.8750 (0.8); 1.8605 (0.6); 1.8472 (0.4); 1.8408 (0.4); −0.0002 (6.6).

Preparation of 2-[5-{[(4-chloro-1-naphthyl)oxy]methyl}-6-fluoropyridin-2-yl)oxy]-N-methoxy-N-methylethanamine

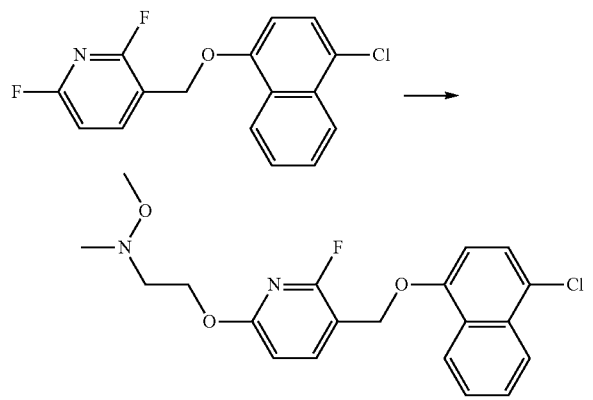

43 mg (0.98 mmol) of sodium hydride (55% strength dispersion in mineral oil) were added to a solution of 52 mg (0.49 mmol) of 2-[methoxy(methyl)amino]ethanol in 3 ml of tetrahydrofuran and 0.5 ml of N,N-dimethylformamide. A solution of 100 mg (327 mmol) of 3-{[(4-chloro-1-naphthyl)oxy]methyl}-2,6-difluoropyridine in 3 ml of tetrahydrofuran was added dropwise. The reaction mixture was stirred at room temperature for 2 d, ice was added and the mixture was then extracted with ethyl acetate. The combined organic phases were washed with a saturated aqueous sodium chloride solution, dried with sodium sulfate and filtered, and the solvent was removed under reduced pressure. The residue was adsorbed on RP silica gel and separated chromatographically by MPLC on RP silica gel (gradient: H$_2$O/acetonitrile). This gave 7 mg of 2-[(5-{[(4-chloro-1-naphthyl)oxy]methyl}-6-fluoropyridin-2-yl)oxy]-N-methoxy-N-methylethanamine.

$^1$H-NMR (400.0 MHz, d$_6$-DMSO): δ=8.3185 (0.4); 8.2012 (3.8); 8.1806 (4.1); 8.1441 (2.6); 8.1346 (4.3); 8.1235 (3.5); 8.1186 (3.5); 8.1138 (5.0); 8.0986 (2.6); 7.7379 (2.0); 7.7351 (2.0); 7.7207 (3.0); 7.7176 (3.8); 7.7141 (2.1); 7.6997 (2.6); 7.6967 (2.4); 7.6441 (6.7); 7.6338 (3.0); 7.6312 (3.0); 7.6234 (7.6); 7.6165 (2.7); 7.6133 (4.0); 7.6105 (2.9); 7.5956 (1.9); 7.5930 (1.8); 7.1689 (6.1); 7.1480 (5.6); 6.8636 (4.3); 6.8431 (4.2); 5.2692 (16.0); 5.2479 (0.4); 4.3869 (4.7); 4.3729 (9.7); 4.3588 (5.1); 3.8703 (3.1); 3.4562 (0.4); 3.4080 (45.7); 3.3516 (5.1); 3.3445 (5.1); 3.2886 (0.4); 3.2287 (0.3); 2.9594 (4.3); 2.9454 (8.5); 2.9314 (4.4); 2.6770 (0.7); 2.6724 (0.9); 2.6680 (0.7); 2.5584 (37.8); 2.5257 (2.1); 2.5120 (53.0); 2.5079 (106.6); 2.5034 (139.2); 2.4989 (102.1); 2.4949 (52.0); 2.3874 (0.4); 2.3346 (0.7); 2.3302 (1.0); 2.3256 (0.7); 1.2984 (0.5); 1.2584 (0.8); 1.2318 (2.7); 0.1460 (0.3); 0.0079 (2.7); −0.0002 (78.0); −0.0084 (3.4); −0.1496 (0.4).

Preparation of (6-{2-[methoxy(methyl)amino]ethoxy}pyridin-3-yl)methanol

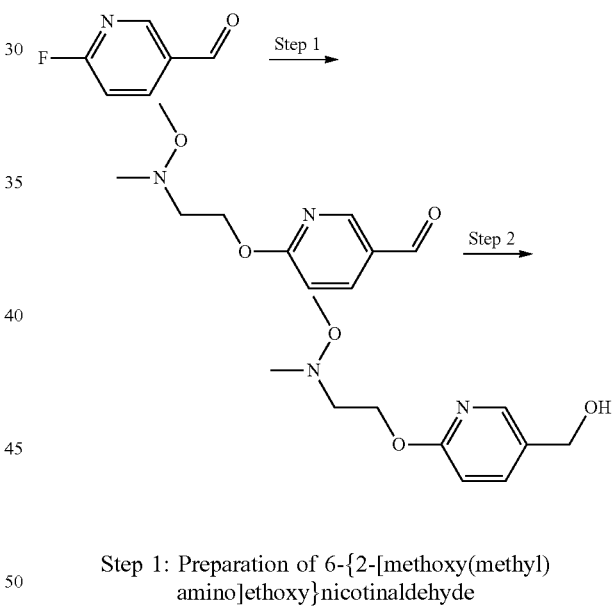

Step 1: Preparation of 6-{2-[methoxy(methyl)amino]ethoxy}nicotinaldehyde

With stirring at room temperature, 686 mg (15.7 mmol) of sodium hydride (55% strength dispersion in mineral oil) were added to a solution of 1.64 g (13.1 mmol) of 6-fluoronicotinaldehyde in 30 ml of acetonitrile. After 10 min at room temperature, a solution of 1.38 g (13.1 mmol) of 2-[methoxy(methyl)amino]ethanol in 5 ml of acetonitrile was added dropwise. Stirring of the reaction mixture was continued overnight, ethyl acetate and water were then added and the mixture was extracted repeatedly with ethyl acetate. The combined organic phases were dried with sodium sulfate and filtered and the solvent was removed under reduced pressure. The residue was separated chromatographically by MPLC on RP silica gel (gradient: H$_2$O/acetonitrile). This gave 50 mg of 6-{2-[methoxy(methyl)amino]ethoxy}nicotinaldehyde.

¹H-NMR (400.0 MHz, d₆-DMSO): δ=9.9600 (16.0); 8.7610 (8.6); 8.7555 (8.3); 8.3457 (1.0); 8.1297 (5.1); 8.1241 (4.9); 8.1081 (5.5); 8.1024 (5.9); 8.0814 (0.6); 8.0752 (0.5); 8.0607 (0.4); 7.6942 (0.5); 7.6887 (0.5); 7.6727 (0.6); 7.6671 (0.5); 7.2136 (0.7); 7.2067 (0.6); 7.1927 (0.6); 7.1859 (0.5); 7.0042 (7.5); 6.9826 (7.2); 6.8655 (0.9); 6.8443 (0.8); 5.3751 (2.9); 5.1906 (0.6); 5.1765 (1.0); 5.1623 (0.5); 4.8916 (0.4); 4.5316 (7.1); 4.5175 (14.4); 4.5033 (7.6); 4.4439 (1.6); 4.4299 (1.5); 3.4326 (0.9); 3.4004 (56.2); 3.3517 (0.7); 3.3210 (24.3); 2.9809 (6.7); 2.9668 (12.9); 2.9526 (6.7); 2.9050 (0.4); 2.6761 (0.5); 2.6720 (0.6); 2.5761 (1.0); 2.5563 (50.5); 2.5068 (89.3); 2.5025 (113.6); 2.4984 (85.1); 2.3338 (0.5); 2.3295 (0.7); 2.0957 (0.8); 2.0391 (1.0); 0.0038 (9.9); −0.0004 (50.2).

Step 2: Preparation of (6-{2-[methoxy(methyl) amino]ethoxy}pyridin-3-yl)methanol A solution of 100 mg (476 μmol) of 6-{2-[methoxy (methyl)amino]ethoxy}nicotinaldehyde was dissolved in a mixture of 15 ml of methanol and 25 ml of tetrahydrofuran, and 27 mg (0.71 mmol) of sodium borohydride were added at 0° C. The reaction solution was stirred at room temperature for 1 h. Water was then added, the organic solvents were removed under reduced pressure and the aqueous phase was extracted repeatedly with ethyl acetate. The combined organic phases were dried with sodium sulfate and filtered and the solvent was removed under reduced pressure. This gave 90 mg of 6-{2-[methoxy(methyl)amino]ethoxy} pyridin-3-yl)methanol.

¹H-NMR (400.0 MHz, d₆-DMSO): δ=6.7875 (0.4); 6.7660 (0.3); 5.1460 (0.5); 4.4268 (0.7); 4.4128 (0.6); 4.3792 (0.4); 4.3647 (0.8); 4.3501 (0.4); 3.3975 (3.3); 3.3805 (1.3); 3.3196 (12.3); 3.3030 (4.8); 3.2951 (0.5); 3.2853 (3.6); 2.9374 (0.4); 2.9228 (0.7); 2.9083 (0.3); 2.6950 (16.0); 2.5447 (2.8); 2.5236 (0.4); 2.5103 (8.4); 2.5059 (17.3); 2.5014 (23.1); 2.4968 (16.9); 2.4926 (8.6); 2.1965 (1.8); 2.1765 (3.5); 2.1560 (2.4); 1.9887 (1.4); 1.9379 (0.9); 1.9203 (2.2); 1.9174 (1.8); 1.9117 (0.5); 1.9017 (2.5); 1.8914 (0.4); 1.8819 (2.0); 1.8621 (0.6); 1.3551 (0.5); 1.2351 (0.4); 1.1924 (0.4); 1.1746 (0.7); 1.1568 (0.4); −0.0001 (2.2).

Preparation of 6-fluoro-3'-(trifluoromethoxy)biphenyl-3-ol

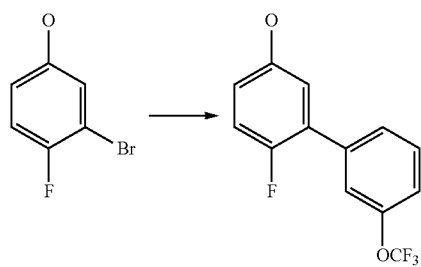 [SMILES: Oc1ccc(F)c(Br)c1 ; Oc1ccc(F)c(-c2cccc(OC(F)(F)F)c2)c1]

By introduction of a stream of argon, a mixture of 5.0 g (26 mmol) of 3-bromo-4-fluorophenol, 7.00 g (34.0 mmol) of [3-(trifluoromethoxy)phenyl]boronic acid, 7.60 g (55.0 mmol) of potassium carbonate, 35 ml of tetrahydrofuran and 7 ml of water was freed from dissolved oxygen, and 0.50 g (0.43 mmol) of tetrakis(triphenylphosphine)palladium was then added. The reaction mixture was stirred at 80° C. overnight and then concentrated under reduced pressure, and the pH was adjusted to 1 using 1 M hydrochloric acid. Water and ethyl acetate were added, the phases were separated and the aqueous phase was extracted repeatedly with ethyl acetate. The combined organic phases were washed with a saturated aqueous sodium chloride solution, dried with sodium sulfate and filtered, and the solvent was removed under reduced pressure. The residue was separated chromatographically by MPLC on RP silica gel (gradient: H₂O/ acetonitrile). This gave 4.85 g of 6-fluoro-3'-(trifluoromethoxy)biphenyl-3-ol.

¹H-NMR (400.0 MHz, d₆-DMSO): δ=8.3185 (1.1); 7.6289 (0.4); 7.6203 (1.7); 7.6006 (4.7); 7.5807 (3.6); 7.5675 (0.4); 7.5484 (2.9); 7.5453 (3.0); 7.5287 (1.6); 7.5257 (1.5); 7.4457 (3.0); 7.4083 (1.8); 7.4056 (1.9); 7.4028 (1.6); 7.3882 (1.5); 7.3855 (1.6); 7.3826 (1.4); 7.1303 (2.2); 7.1081 (2.7); 7.1037 (2.5); 7.0815 (2.6); 6.8504 (2.1); 6.8429 (2.6); 6.8339 (2.1); 6.8264 (2.6); 6.7931 (1.5); 6.7833 (2.0); 6.7755 (1.3); 6.7710 (1.4); 6.7614 (1.6); 6.7535 (1.0); 2.5257 (0.5); 2.5123 (15.4); 2.5079 (32.4); 2.5034 (43.5); 2.4989 (31.4); 2.4945 (15.1); 2.0760 (16.0); 0.0080 (0.7); −0.0002 (21.3); −0.0085 (0.8).

Preparation of 2-chloro-5-{[(4-chloro-1-naphthyl) oxy]methyl}pyrimidine

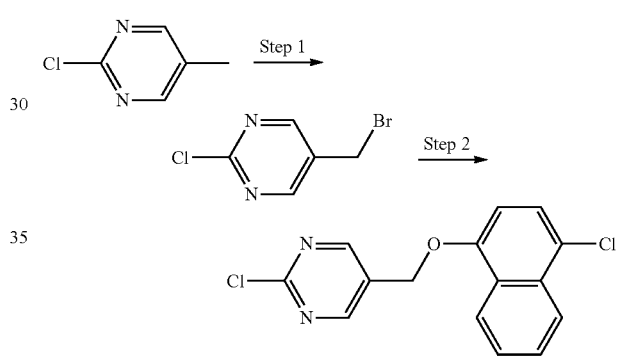

Step 1: Preparation of 5-(bromomethyl)-2-chloropyrimidine

A solution of 200 mg (1.56 mmol) of 2-chloro-5-methylpyrimidine, 277 mg (1.56 mmol) of N-bromosuccinimide and 26 mg (0.16 mmol) of 2,2'-azobis(2-methylpropionitrile) in 17.6 ml of chlorobenzene was heated under reflux for 16 h. The reaction solution was then washed with an aqueous Na₂SO₃ solution and with saturated aqueous NaHCO₃ solution, dried with sodium sulfate and filtered and the solvent was removed under reduced pressure. The residue was separated chromatographically by MPLC on silica gel (gradient: cyclohexane/ethyl acetate). This gave 76 mg of 5-(bromomethyl)-2-chloropyrimidine.

¹H-NMR (400.0 MHz, d₆-DMSO): δ=8.9119 (1.1); 8.8913 (15.0); 8.8619 (0.7); 8.8222 (1.3); 8.6390 (1.4); 5.5539 (0.5); 5.3766 (0.9); 4.8528 (2.2); 4.7481 (16.0); 4.7234 (1.3); 3.3281 (67.0); 2.6718 (0.4); 2.5248 (0.8); 2.5114 (23.6); 2.5071 (48.7); 2.5027 (64.9); 2.4983 (46.7); 2.4941 (22.6); 2.3295 (0.4); 2.2725 (2.8); 2.2461 (0.6); 1.4376 (0.4); −0.0002 (0.7).

Step 2: Preparation of 2-chloro-5-{[(4-chloro-1-naphthyl)oxy]methyl}pyrimidine A suspension of 38 mg (0.21 mmol) of 4-chloro-1-naphthol and 60 mg (0.43 mmol) of potassium carbonate in 1 ml of acetonitrile was stirred at room temperature for 1 h. The mixture was cooled to 0° C., and a solution of 76 mg (0.27 mmol) of 5-(bromomethyl)-2-chloropyrimidine in acetonitrile was added dropwise. The reaction mixture was stirred at room temperature overnight, and water and a saturated NaHCO$_3$ solution were then added. The mixture was extracted repeatedly with ethyl acetate. The combined organic phases were washed with water and a saturated aqueous sodium chloride solution, dried with sodium sulfate and filtered, and the solvent was removed under reduced pressure. The residue was separated chromatographically by MPLC on silica gel (gradient: cyclohexane/ethyl acetate). This gave 70 mg of 2-chloro-5-{[(4-chloro-1-naphthyl)oxy]methyl}pyrimidine.

$^1$H-NMR (400.0 MHz, d$_6$-DMSO): δ=9.0173 (16.0); 8.9478 (1.4); 8.8875 (0.4); 8.3103 (2.7); 8.2893 (2.8); 8.1476 (2.8); 8.1269 (3.1); 7.7565 (1.4); 7.7534 (1.6); 7.7393 (2.2); 7.7359 (2.9); 7.7323 (1.5); 7.7183 (2.0); 7.7150 (1.9); 7.6608 (6.9); 7.6439 (1.8); 7.6402 (8.3); 7.6231 (1.4); 7.6202 (1.3); 7.1554 (4.4); 7.1485 (0.6); 7.1345 (4.1); 7.1276 (0.5); 5.4057 (11.9); 5.3819 (1.1); 4.8531 (0.5); 3.3215 (34.5); 2.6719 (0.4); 2.5254 (1.0); 2.5206 (1.5); 2.5120 (25.1); 2.5075 (54.3); 2.5029 (73.9); 2.4983 (52.7); 2.4938 (24.5); 2.3297 (0.4); 0.1459 (0.4); 0.0080 (3.4); −0.0002 (106.7); −0.0085 (3.6); −0.1498 (0.4).

Preparation of 4-chloro-3-methoxyphenol and 2-chloro-5-methoxyphenol

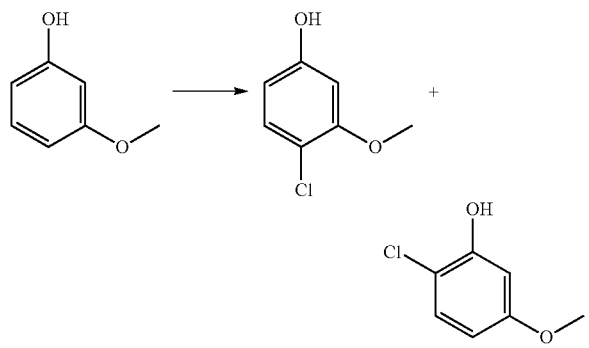

At 0° C., 342 mg (2.54 mmol) of sulfuryl chloride were added to a solution of 300 mg (2.42 mmol) of 3-methoxyphenol in 2 ml of CH$_2$Cl$_2$. The reaction solution was stirred at 0° C. for 1 h, and water and CH$_2$Cl$_2$ were then added. The phases were separated and the aqueous phase was extracted repeatedly with CH$_2$Cl$_2$. The combined organic phases were washed with a saturated aqueous sodium chloride solution, dried with sodium sulfate and filtered, and the solvent was removed under reduced pressure. The residue was adsorbed on RP silica gel and separated chromatographically by MPLC on RP silica gel (gradient: H$_2$O/acetonitrile). This gave 125 mg of 4-chloro-3-methoxyphenol and 194 mg of 2-chloro-5-methoxyphenol.

4-Chloro-3-methoxyphenol $^1$H-NMR (400.0 MHz, d$_6$-DMSO): δ=9.6746 (2.2); 7.1593 (2.9); 7.1379 (3.1); 7.0630 (0.3); 7.0428 (0.5); 6.5162 (2.7); 6.5096 (2.8); 6.3642 (1.8); 6.3576 (1.7); 6.3484 (0.4); 6.3427 (1.7); 6.3362 (1.7); 6.3152 (0.4); 6.3094 (0.4); 3.7876 (0.8); 3.7744 (16.0); 3.7390 (0.5); 3.6885 (0.6); 3.6800 (2.9); 3.3248 (6.3); 2.5240 (0.4); 2.5064 (18.8); 2.5021 (24.2); 2.4978 (17.3); 2.0253 (0.4); 0.0078 (0.5); −0.0002 (11.6); −0.0073 (0.4).

2-Chloro-5-methoxyphenol $^1$H-NMR (400.0 MHz, d$_6$-DMSO): δ=10.1114 (4.9); 7.2062 (2.6); 7.1843 (2.8); 6.5256 (2.6); 6.5185 (2.9); 6.4149 (1.6); 6.4077 (1.4); 6.3929 (1.5); 6.3857 (1.3); 3.6893 (16.0); 3.3297 (3.7); 2.5112 (4.3); 2.5071 (8.6); 2.5028 (11.2); 2.4984 (7.9).

Preparation of 5-[2-(diethylamino)ethoxy]pyridine-2-carbaldehyde

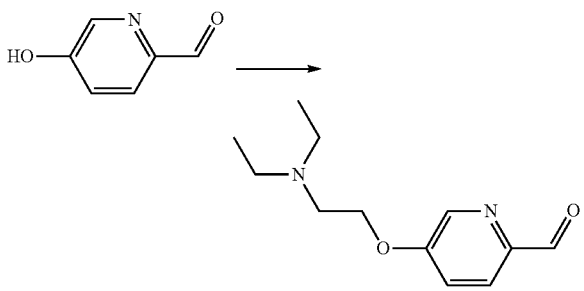

A suspension of 1.0 g (8.1 mmol) of 5-hydroxypyridine-2-carbaldehyde and 3.4 g (25 mmol) of K$_2$CO$_3$ in 25 ml of N,N-dimethylformamide was stirred at 65° C. for 2 h. At 30° C., 13 mg (81 μmol) of potassium iodide and 2.43 g (9.14 mmol) of 2-bromo-N,N-diethylethanamine hydrobromide (1:1) were then added and the reaction mixture was stirred at 65° C. for 16 h. A further 1.27 g (4.87 mmol) of 2-bromo-N,N-diethylethanamine hydrobromide (1:1), 1.7 g (12 mmol) of potassium carbonate and 13 mg (81 μmol) of potassium iodide were then added and the mixture was stirred at 65° C. for a further 20 h. The reaction mixture was filtered through kieselguhr and the solvent was removed under reduced pressure. The residue was separated chromatographically by MPLC on RP silica gel (gradient: H$_2$O/acetonitrile). After removal of the solvent under reduced pressure, water was added to the residue and the mixture was extracted repeatedly with ethyl acetate. The combined organic phases were dried with sodium sulfate and filtered and the solvent was removed under reduced pressure. This gave 803 mg of 5-[2-(diethylamino)ethoxy]pyridine-2-carbaldehyde.

$^1$H-NMR (400.0 MHz, d$_6$-DMSO): δ=9.8858 (4.6); 8.4862 (2.4); 8.4793 (2.5); 7.9378 (2.3); 7.9161 (2.6); 7.6092 (1.2); 7.6024 (1.3); 7.5874 (1.1); 7.5807 (1.1); 4.2358 (2.2); 4.2208 (4.6); 4.2059 (2.3); 3.3230 (10.4); 2.8232 (2.2); 2.8083 (4.5); 2.7933 (2.2); 2.5739 (2.3); 2.5561 (7.3); 2.5383 (7.5); 2.5205 (3.2); 2.5073 (16.8); 2.5030 (22.2); 2.4987 (17.2); 0.9826 (8.0); 0.9649 (16.0); 0.9471 (7.7); −0.0002 (20.2).

Preparation of ethyl 5-(4-ethylpiperazin-1-yl)-3-fluoropyridine-2-carboxylate

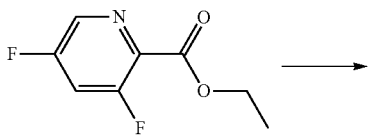

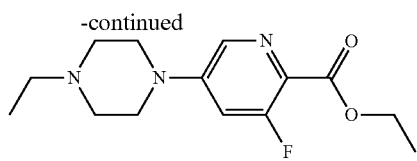

In a microwave reactor, a suspension of 1.98 g (17.4 mmol) of 1-ethylpiperazine, 2.50 g (13.4 mmol) of ethyl 3,5-difluoropyridine-2-carboxylate and 2.40 g (17.4 mmol) of potassium carbonate in 21 ml of N,N-dimethylacetamide was heated at 70° C. for 2 h. Water was then added to the reaction mixture and the mixture was extracted repeatedly with ethyl acetate. The combined organic phases were dried with sodium sulfate and filtered and the solvent was removed under reduced pressure. The residue was separated chromatographically by MPLC on silica gel (gradient: cyclohexane/ethyl acetate+1% v/v triethylamine). This gave 1.46 g of ethyl 5-(4-ethylpiperazin-1-yl)-3-fluoropyridine-2-carboxylate.

$^1$H-NMR (400.0 MHz, d$_6$-DMSO): δ=8.2421 (2.7); 8.2374 (4.2); 7.2262 (2.2); 7.2203 (2.2); 7.1891 (2.2); 7.1832 (2.2); 4.2963 (2.2); 4.2786 (7.0); 4.2608 (7.1); 4.2431 (2.3); 3.4222 (6.1); 3.4097 (7.9); 3.3967 (6.4); 3.3230 (23.9); 2.9455 (4.4); 2.7859 (3.6); 2.5080 (21.5); 2.5036 (28.6); 2.4992 (21.7); 2.4833 (6.8); 2.4705 (8.4); 2.4579 (6.3); 2.3926 (1.9); 2.3746 (6.1); 2.3566 (6.2); 2.3387 (2.1); 1.9587 (3.8); 1.3048 (7.7); 1.2870 (16.0); 1.2693 (7.5); 1.0464 (6.7); 1.0284 (13.9); 1.0105 (6.4); 0.0079 (0.8); −0.0002 (18.1); −0.0082 (0.8).

Preparation of 2-[(6-{[(5,6-dichloro-1-naphthyl)oxy]methyl}-2-fluoropyridin-3-yl)oxy]-N-methoxy-N-methylethanamine

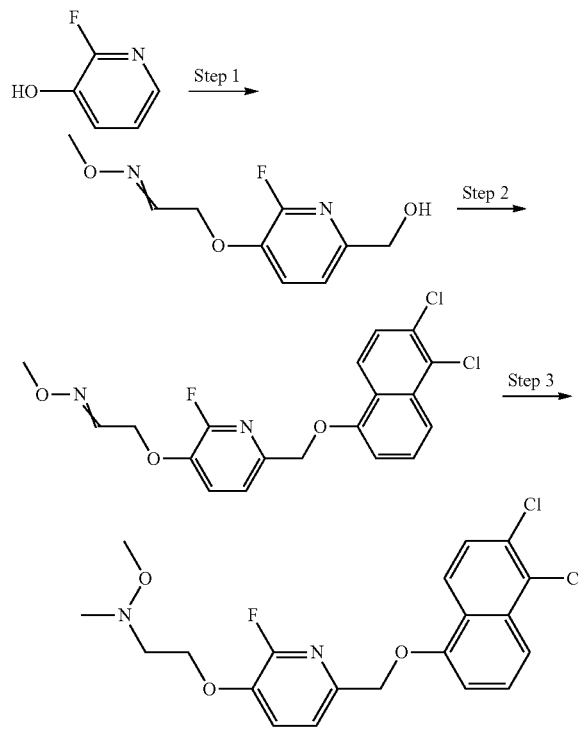

Step 1: Preparation of {6-fluoro-5-[2-(methoxyimino)ethoxy]pyridin-2-yl}methanol 334 mg (3.97 mmol) of sodium bicarbonate were added to a solution of 300 mg (2.65 mmol) of 2-fluoropyridin-3-ol in 2.3 ml of water, and the mixture was stirred at room temperature for 15 min. After heating to 90° C., a little at a time 696 μl (9.28 mmol) of a 37% strength aqueous formaldehyde solution were added and the mixture was stirred at 90° C. for 2.5 h and at room temperature for a further 16 h. After addition of 2 g of ice, the mixture was adjusted to pH 1 using 6 N aqueous hydrochloric acid and extracted repeatedly with ethyl acetate. The combined organic extracts were dried over sodium sulfate and filtered, and the solvent was removed under reduced pressure. The residue was taken up in dichloromethane and filtered and the solvent was removed under reduced pressure. The intermediate 2-fluoro-6-(hydroxymethyl)pyridin-3-ol obtained in this manner was dissolved in 9 ml of acetonitrile, 579 mg (4.19 mmol) of potassium carbonate and 413 mg (3.07 mmol, purity 80%) of 2-chloro-N-methoxyethanimine were added and the mixture was then heated under reflux for 4 h and stirred at room temperature for a further 16 h. After removal of the sediment by filtration, the filtrate was adsorbed on silica gel and separated chromatographically by MPLC on silica gel (gradient: cyclohexane/ethyl acetate). This gave 205 mg of an (E,Z) isomer mixture of {6-fluoro-5-[2-(methoxyimino)ethoxy]pyridin-2-yl}methanol.

$^1$H-NMR (400.0 MHz, d$_6$-DMSO): δ=7.7277 (0.9); 7.7073 (1.0); 7.7015 (1.0); 7.6810 (1.0); 7.6596 (1.1); 7.6456 (2.5); 7.6316 (1.2); 7.6227 (0.4); 7.6167 (0.4); 7.5963 (0.4); 7.3251 (1.6); 7.3048 (1.4); 7.1226 (0.4); 7.1133 (0.9); 7.1040 (0.4); 5.4528 (0.7); 5.4500 (1.3); 5.4382 (1.6); 5.4352 (2.8); 5.4235 (0.8); 5.4205 (1.4); 4.9464 (1.8); 4.9371 (1.8); 4.7654 (4.5); 4.7514 (4.4); 4.4156 (4.5); 4.4009 (4.4); 3.8674 (5.9); 3.7989 (16.0); 3.3316 (17.6); 2.5251 (0.4); 2.5112 (9.1); 2.5072 (18.1); 2.5028 (23.6); 2.4983 (17.5); −0.0002 (4.4).

Step 2: Preparation of 2-[(6-{[(5,6-dichloro-1-naphthyl)oxy]methyl}-2-fluoropyridin-3-yl)oxy]-N-methoxyethanimine 194 μl (2.66 mmol) of thionyl chloride and a catalytic amount of N,N-dimethylformamide were added to a solution of 190 mg (0.88 mmol) of an (E,Z) isomer mixture of {6-fluoro-5-[2-(methoxyimino)ethoxy]pyridin-2-yl}methanol in 6 ml of toluene. The reaction mixture was stirred at room temperature for 3.5 h and then concentrated under reduced pressure. The residue was dissolved in 6 ml of N,N-dimethylformamide and 246 mg (1.15 mmol) of 5,6-dichloro-1-naphthol and 368 mg (2.66 mmol) of potassium carbonate were added. The reaction mixture was stirred at 70° C. for 50 min and then concentrated under reduced pressure. The residue was taken up in dichloromethane, adsorbed on silica gel and separated chromatographically by MPLC on silica gel (gradient: cyclohexane/ethyl acetate). This gave 332 mg of an (E,Z) isomer mixture of 2-[(6-{[(5,6-dichloro-1-naphthyl)oxy]methyl}-2-fluoropyridin-3-yl)oxy]-N-methoxyethanimine.

$^1$H-NMR (400.0 MHz, d$_6$-DMSO): δ=8.2461 (1.6); 8.2385 (0.8); 8.2236 (1.8); 8.2158 (0.9); 8.1528 (0.4); 8.1300 (0.4); 7.8100 (1.9); 7.8011 (0.8); 7.7885 (2.7); 7.7808 (0.8); 7.7752 (0.8); 7.7546 (0.9); 7.7077 (3.1); 7.6876 (3.4); 7.6849 (3.5); 7.6688 (4.6); 7.6549 (1.2); 7.6479 (1.4); 7.6134 (0.6); 7.5859 (1.7); 7.5663 (2.1); 7.5548 (0.4); 7.5472 (0.6); 7.5357 (0.4); 7.2592 (2.2);

7.2397 (2.0); 7.1517 (0.5); 7.1424 (1.1); 7.1331 (0.5); 7.0119 (0.3); 5.2828 (7.5); 4.9992 (2.0); 4.9899 (2.0); 4.8222 (4.0); 4.8083 (3.9); 3.8747 (6.9); 3.8067 (16.0); 3.3316 (25.0); 2.6729 (0.3); 2.5260 (0.9); 2.5125 (20.4); 2.5083 (41.0); 2.5038 (53.8); 2.4993 (39.3); 2.4950 (19.3); 2.3305 (0.4); 1.3971 (0.4); 0.0079 (0.6); −0.0002 (16.4); −0.0084 (0.6).

Step 3: 2-[(6-{[(5,6-Dichloro-1-naphthyl)oxy]methyl}-2-fluoropyridin-3-yl)oxy]-N-methoxy-N-methylethanamine 68 mg (1.08 mmol) of sodium cyanoborohydride were added to a solution of 295 mg (0.72 mmol) of an (E,Z) isomer mixture of 2-[(6-{[(5,6-dichloro-1-naphthyl)oxy]methyl}-2-fluoropyridin-3-yl)oxy]-N-methoxyethanimine in 6.2 ml of acetic acid. After 30 min at room temperature, 1.08 ml (14.4 mmol) of a 37% strength aqueous formaldehyde solution were added, and after a further 5 min 68 mg (1.08 mmol) of sodium cyanoborohydride were added. The reaction mixture was stirred at room temperature for 30 min and concentrated under reduced pressure. The residue was taken up in dichloromethane, adsorbed on silica gel and separated chromatographically by MPLC on silica gel (gradient: cyclohexane/ethyl acetate). This gave 236 mg of 2-[(6-{[(5,6-dichloro-1-naphthyl)oxy]methyl}-2-fluoropyridin-3-yl)oxy]-N-methoxy-N-methylethanamine.

$^1$H-NMR (400.0 MHz, d$_6$-DMSO): δ=8.2363 (2.0); 8.2351 (2.0); 8.2136 (2.2); 8.2124 (2.2); 7.8066 (1.6); 7.7851 (3.2); 7.7646 (1.2); 7.7589 (1.0); 7.7384 (1.1); 7.7052 (3.3); 7.6877 (1.6); 7.6825 (3.2); 7.6679 (2.1); 7.6468 (1.3); 7.5581 (2.0); 7.5379 (1.7); 7.2605 (1.9); 7.2413 (1.8); 5.2740 (6.6); 4.2559 (1.9); 4.2421 (4.0); 4.2282 (2.0); 3.4043 (19.9); 3.3348 (27.4); 2.9998 (1.7); 2.9861 (3.5); 2.9722 (1.7); 2.5742 (16.0); 2.5273 (0.4); 2.5139 (10.8); 2.5095 (22.1); 2.5050 (29.0); 2.5005 (21.1); 2.4961 (10.3); 1.3968 (0.4); 0.0079 (0.5); −0.0002 (15.7); −0.0084 (0.5).

Preparation of 2-[(6-{[(5,6-dichloro-1-naphthyl)oxy]methyl}-5-fluoropyridin-3-yl)oxy]-N-methoxy-N-methylethanamine

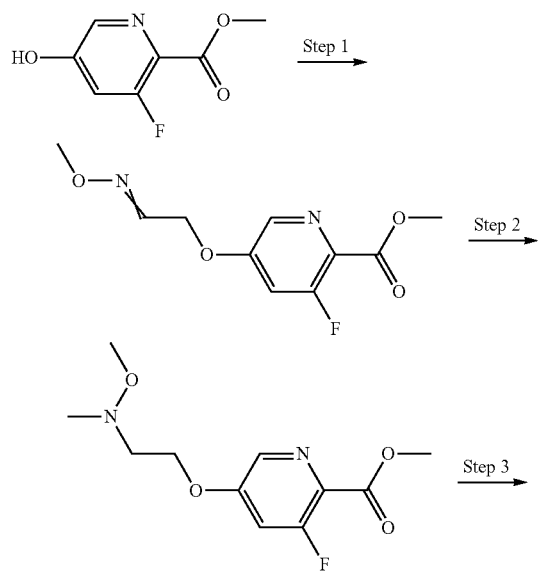

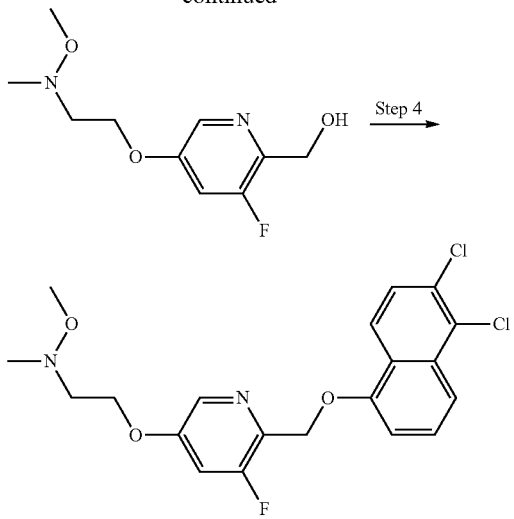

Step 1: Preparation of methyl 3-fluoro-5-[2-(methoximino)ethoxy]pyridine-2-carboxylate At room temperature, 18.39 g (133 mmol) of potassium carbonate and 59.1 ml (44.4 mmol) of a 0.75 M solution of 2-chloro-N-methoxyethanimine in acetonitrile were added to a solution of 7.59 g (44.4 mmol) of methyl 3-fluoro-5-hydroxypyridine-2-carboxylate in 253 ml of acetonitrile. The reaction mixture was heated under reflux for 27 h and stirred at room temperature for a further 3 d. After removal of the sediment by filtration, the filtrate was concentrated under reduced pressure. This gave 5.17 g of an (E,Z) isomer mixture of methyl 3-fluoro-5-[2-(methoxyimino)ethoxy]pyridine-2-carboxylate.

$^1$H-NMR (400.0 MHz, d$_6$-DMSO): δ=8.3132 (1.5); 8.3107 (1.6); 8.3074 (1.7); 8.3004 (0.7); 8.2977 (0.7); 8.2942 (0.7); 7.6847 (1.0); 7.6710 (3.1); 7.6648 (1.2); 7.6574 (1.1); 7.6391 (1.0); 7.6331 (1.1); 7.6238 (0.4); 7.6178 (0.4); 7.5925 (0.4); 7.5864 (0.4); 7.1439 (0.4); 7.1344 (0.8); 7.1251 (0.4); 5.0357 (1.5); 5.0263 (1.5); 4.8625 (4.0); 4.8488 (3.9); 3.8787 (5.0); 3.8551 (16.0); 3.8083 (14.4); 3.3195 (2.3); 2.5068 (17.8); 2.5024 (23.4); 2.4981 (17.5); 0.0079 (0.6); −0.0002 (18.6); −0.0085 (0.9).

Step 2: Preparation of methyl 3-fluoro-5-{2-[methoxy(methyl)amino]ethoxy}pyridine-2-carboxylate 2.01 g (32.0 mmol) of sodium cyanoborohydride were added to a solution of 5.17 g of an (E,Z) isomer mixture of methyl 3-fluoro-5-[2-(methoxyimino)ethoxy]pyridine-2-carboxylate in 180 ml of acetic acid.

After 1 h at room temperature, 32.0 ml (427 mmol) of a 37% strength aqueous formaldehyde solution were added, and after a further 15 min 2.01 g (32.0 mmol) of sodium cyanoborohydride were added. The reaction mixture was stirred at room temperature for 1 h and then concentrated under reduced pressure. The residue was taken up in dichloromethane, adsorbed on silica gel and separated chromatographically by MPLC on silica gel (gradient: cyclohexane/ethyl acetate). This gave 4.61 g of methyl 3-fluoro-5-{2-[methoxy(methyl)amino]ethoxy}pyridine-2-carboxylate.

$^1$H-NMR (400.0 MHz, d$_6$-DMSO): δ=8.2901 (1.6); 8.2874 (2.2); 8.2844 (2.2); 8.2817 (2.1); 7.6473 (1.3);

7.6414 (1.4); 7.6153 (1.3); 7.6094 (1.4); 4.2890 (2.2); 4.2754 (4.2); 4.2617 (2.2); 3.8498 (16.0); 3.4048 (19.4); 3.3192 (5.5); 2.9915 (1.8); 2.9779 (3.7); 2.9643 (1.9); 2.5678 (16.0); 2.5202 (0.5); 2.5112 (8.5); 2.5070 (18.4); 2.5025 (25.4); 2.4981 (19.5); 1.9893 (0.4); 1.9092 (6.7); 0.0079 (0.6); −0.0002 (18.8); −0.0083 (0.9).

Step 3: Preparation of (3-fluoro-5-{2-[methoxy(methyl)amino]ethoxy}pyridin-2-yl)methanol At 10° C., 2.78 g (73.6 mmol) of sodium borohydride were added to a solution of 7.84 g (30.4 mmol) of methyl 3-fluoro-5-{2-[methoxy(methyl)amino]ethoxy}pyridine-2-carboxylate in 78 ml of ethanol, and the reaction mixture was stirred at 10° C. for 1 h and then at room temperature for a further 16 h. After addition of 100 ml of water with ice cooling, the mixture was stirred at room temperature for 20 min. Subsequently, most of the ethanol was removed under reduced pressure and the residue was extracted repeatedly with ethyl acetate. The combined organic phases were washed with a saturated aqueous sodium chloride solution, dried with sodium sulfate and filtered, and the filtrate was concentrated under reduced pressure. This gave 5.31 g of (3-fluoro-5-{2-[methoxy(methyl)amino]ethoxy}pyridin-2-yl)methanol.

$^1$H-NMR (400.0 MHz, d$_6$-DMSO): δ=8.1383 (2.4); 8.1339 (2.4); 7.4605 (1.4); 7.4548 (1.4); 7.4312 (1.4); 7.4254 (1.4); 5.1829 (1.2); 5.1683 (2.5); 5.1537 (1.2); 4.5150 (2.9); 4.5095 (3.0); 4.5004 (2.9); 4.4950 (2.8); 4.2006 (2.3); 4.1868 (4.6); 4.1730 (2.4); 3.4028 (18.6); 3.3203 (16.8); 2.9662 (2.1); 2.9525 (4.1); 2.9386 (2.1); 2.5626 (16.0); 2.5058 (38.8); 2.5016 (49.8); 2.4974 (37.0); −0.0002 (8.2).

Step 4: Preparation of 2-[(6-{[(5,6-dichloro-1-naphthyl)oxy]methyl}-5-fluoropyridin-3-yl)oxy]-N-methoxy-N-methylethanamine 20 ml (273 mmol) of thionyl chloride and a catalytic amount of N,N-dimethylformamide were added to 1.0 g (4.34 mmol) of (3-fluoro-5-{2-[methoxy(methyl)amino]ethoxy}pyridin-2-yl)methanol. The reaction mixture was stirred at room temperature for 80 min and then concentrated under reduced pressure. The residue was dissolved in 26 ml of N,N-dimethylformamide and 787 mg (3.69 mmol) of 5,6-dichloro-1-naphthol and 2.55 g (18.5 mmol) of potassium carbonate were added. The reaction mixture was stirred at 70° C. for 4 h 20 min and for a further 15 h at room temperature and then concentrated under reduced pressure. The residue was taken up in dichloromethane, adsorbed on silica gel and separated chromatographically by MPLC on silica gel (gradient: cyclohexane/ethyl acetate). This gave 1.16 g of 2-[(6-{[(5,6-dichloro-1-naphthyl)oxy]methyl}-5-fluoropyridin-3-yl)oxy]-N-methoxy-N-methylethanamine.

$^1$H-NMR (400.0 MHz, d$_6$-DMSO): δ=8.2575 (2.3); 8.2531 (2.4); 8.0842 (2.2); 8.0615 (2.5); 7.8056 (1.7); 7.7842 (2.6); 7.7031 (1.6); 7.6833 (2.3); 7.6593 (3.7); 7.6365 (3.1); 7.6107 (1.4); 7.6047 (1.3); 7.5811 (1.4); 7.5752 (1.4); 7.3719 (2.2); 7.3525 (1.9); 5.3891 (4.6); 5.3853 (4.7); 4.2479 (2.0); 4.2342 (4.2); 4.2204 (2.1); 3.4116 (19.6); 3.3190 (60.2); 2.9871 (1.9); 2.9735 (3.7); 2.9597 (1.9); 2.6759 (0.5); 2.6712 (0.7); 2.6670 (0.5); 2.5718 (16.0); 2.5244 (2.2); 2.5108 (43.8); 2.5066 (86.7); 2.5022 (117.2); 2.4978 (89.0); 2.3336 (0.5); 2.3291 (0.7); 2.3247 (0.5); 1.9000 (0.4); 0.0079 (1.3); −0.0001 (31.9); −0.0081 (1.4).

Preparation of {[2-({6-[(dibenzo[b,d]furan-2-yloxy)methyl]-5-fluoropyridin-3-yl}oxy)ethyl](methyl)amino}acetonitrile

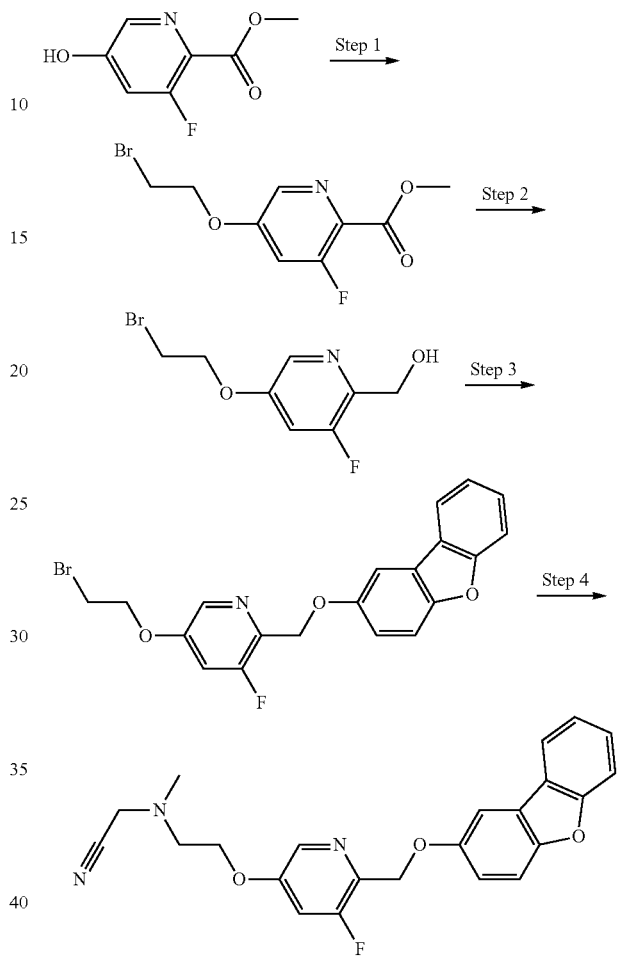

Step 1: Preparation of methyl 5-(2-bromoethoxy)-3-fluoropyridine-2-carboxylate

At room temperature, 7.07 g (51.1 mmol) of potassium carbonate and 8.9 ml (103 mmol) of 1,2-dibromoethane were added to a solution of 3.50 g (20.5 mmol) of methyl 3-fluoro-5-hydroxypyridine-2-carboxylate in 100 ml of acetonitrile. The reaction mixture was stirred at 80° C. overnight, then adsorbed on silica gel and separated chromatographically by MPLC on silica gel (gradient: cyclohexane/ethyl acetate). This gave 1.96 g of methyl 5-(2-bromoethoxy)-3-fluoropyridine-2-carboxylate.

$^1$H-NMR (400.0 MHz, d$_6$-DMSO): δ=8.3079 (1.6); 8.3054 (1.8); 8.3021 (1.8); 7.6591 (1.2); 7.6532 (1.2); 7.6275 (1.2); 7.6215 (1.2); 4.5409 (2.1); 4.5277 (2.7); 4.5142 (2.3); 3.8715 (2.4); 3.8545 (16.0); 3.8449 (2.6); 3.3192 (14.1); 2.5107 (13.3); 2.5064 (27.3); 2.5019 (37.7); 2.4975 (28.6); 2.4932 (14.4); 1.3979 (0.8); 0.0080 (0.4); −0.0002 (10.4); −0.0083 (0.5).

Step 2: Preparation of [5-(2-bromoethoxy)-3-fluoropyridin-2-yl]methanol

With ice cooling, 3.19 g (84.4 mmol) of sodium borohydride were added to a solution of 9.39 g (33.8 mmol) of methyl 5-(2-bromoethoxy)-3-fluoropyridine-2-carboxylate in 300 ml of ethanol, and the reaction mixture was stirred with ice cooling for 1 h and then at room temperature overnight. After addition of 250 ml of water with ice cooling, the mixture was stirred at room temperature for 40 min, most of the ethanol was removed under reduced pressure and the residue was extracted repeatedly with ethyl acetate. The combined organic phases were washed with a saturated aqueous sodium chloride solution, dried with sodium sulfate and filtered, and the filtrate was concentrated under reduced pressure. This gave 5.96 g of [5-(2-bromo-ethoxy)-3-fluoropyridin-2-yl]methanol (purity 88%).

$^1$H-NMR (400.0 MHz, d$_6$-DMSO): δ=8.1532 (11.0); 8.1489 (10.9); 8.1037 (0.9); 8.0999 (0.9); 7.4823 (6.6); 7.4763 (6.8); 7.4532 (6.7); 7.4473 (6.8); 7.3980 (0.6); 7.3921 (0.6); 7.3686 (0.6); 7.3625 (0.6); 6.5251 (0.4); 5.2083 (5.5); 5.1936 (11.9); 5.1789 (6.3); 5.1624 (1.1); 5.1480 (0.5); 4.5215 (12.7); 4.5161 (14.0); 4.5069 (13.8); 4.5016 (13.5); 4.4908 (1.7); 4.4486 (11.6); 4.4354 (15.8); 4.4218 (12.8); 4.3831 (0.6); 4.3710 (0.8); 4.3578 (0.7); 4.1452 (0.6); 4.1279 (1.7); 4.1104 (1.7); 4.0930 (0.6); 3.9835 (0.7); 3.9703 (0.8); 3.9581 (0.6); 3.8396 (13.2); 3.8260 (16.0); 3.8128 (12.1); 3.3216 (53.4); 2.6750 (0.7); 2.6709 (0.9); 2.5061 (112.3); 2.5017 (151.1); 2.4974 (118.2); 2.3326 (0.6); 2.3286 (0.8); 1.3559 (1.8); 1.3385 (3.6); 1.3210 (1.7); 0.1459 (0.6); 0.0079 (5.5); −0.0002 (130.8); −0.1497 (0.6).

Step 3: Preparation of 5-(2-bromoethoxy)-2-[(dibenzo[b,d]furan-2-yloxy)methyl]-3-fluoropyridine 11.1 ml (152 mmol) of thionyl chloride and a catalytic amount of N,N-dimethylformamide were added to 516 mg (2.06 mmol) of [5-(2-bromoethoxy)-3-fluoropyridin-2-yl]methanol. The reaction mixture was stirred at room temperature for 80 min and then concentrated under reduced pressure. The residue was dissolved in 14 ml of N,N-dimethylformamide and 388 mg (2.10 mmol) of dibenzo[b,d]furan-2-ol and 1.43 g (10.3 mmol) of potassium carbonate were added. The reaction mixture was stirred at 70° C. for 2 h 40 min and then concentrated under reduced pressure. The residue was taken up in dichloromethane, adsorbed on silica gel and separated chromatographically by MPLC on silica gel (gradient: cyclohexane/ethyl acetate). This gave 120 mg of 5-(2-bromoethoxy)-2-[(dibenzo[b,d]furan-2-yloxy)methyl]-3-fluoropyridine.

$^1$H-NMR (400.0 MHz, d$_6$-DMSO): δ=8.2654 (7.9); 8.2602 (7.8); 8.1324 (5.7); 8.1134 (6.2); 7.8764 (9.5); 7.8698 (9.6); 7.6849 (6.7); 7.6643 (8.7); 7.6304 (10.0); 7.6131 (5.3); 7.6079 (15.2); 7.5841 (4.8); 7.5781 (4.6); 7.5414 (3.2); 7.5384 (3.2); 7.5205 (6.1); 7.5025 (3.4); 7.4996 (3.2); 7.4159 (4.5); 7.3969 (7.2); 7.3785 (3.2); 7.1949 (5.8); 7.1883 (5.6); 7.1726 (5.2); 7.1659 (5.1); 5.2553 (15.8); 5.2507 (16.0); 4.4973 (7.8); 4.4843 (10.2); 4.4706 (8.4); 4.4321 (0.5); 4.4199 (0.6); 4.4066 (0.5); 4.0096 (0.6); 3.9968 (0.7); 3.9842 (0.5); 3.8650 (8.7); 3.8513 (10.3); 3.8383 (7.9); 3.5441 (0.3); 3.5294 (0.4); 3.3607 (1876.4); 2.6834 (1.1); 2.6791 (1.5); 2.6747 (1.1); 2.5321 (3.9); 2.5187 (89.6); 2.5143 (185.4); 2.5099 (255.8); 2.5055 (190.1); 2.5013 (91.8); 2.3411 (1.0); 2.3368 (1.4); 2.3327 (1.0); 1.4029 (0.4); 1.2389 (0.3).

Step 4: {[2-{6-[(Dibenzo[b,d]furan-2-yloxy)methyl]-5-fluoropyridin-3-yl}oxy)ethyl](methyl)amino}acetonitrile 99 mg (1.41 mmol) of (methylamino)acetonitrile were added to a solution of 117 mg (0.28 mmol) of 5-(2-bromo-ethoxy)-2-[(dibenzo[b,d]furan-2-yloxy)methyl]-3-fluoro-pyridine in 2 ml of dimethylformamide, and the mixture was stirred at 80° C. for 4 h. The reaction mixture was then adsorbed on silica gel and separated chromatographically by MPLC on silica gel (gradient: cyclohexane/ethyl acetate). This gave 95 mg of {[2-({6-[(dibenzo[b,d]furan-2-yloxy)methyl]-5-fluoropyridin-3-yl}oxy)ethyl](methyl)amino}acetonitrile.

$^1$H-NMR (400.0 MHz, d$_6$-DMSO): δ=8.2459 (2.6); 8.2408 (2.7); 8.0776 (2.6); 8.0549 (2.9); 7.8046 (1.9); 7.7832 (2.9); 7.7018 (1.8); 7.6818 (2.6); 7.6614 (5.2); 7.6389 (3.4); 7.5845 (1.5); 7.5786 (1.5); 7.5550 (1.5); 7.5491 (1.5); 7.3692 (2.5); 7.3496 (2.2); 5.3903 (5.1); 5.3868 (5.2); 4.2442 (2.3); 4.2307 (4.4); 4.2171 (2.3); 3.8084 (10.6); 3.3201 (14.6); 2.8214 (2.3); 2.8079 (4.2); 2.7943 (2.2); 2.6761 (0.4); 2.6717 (0.6); 2.6678 (0.4); 2.5247 (1.3); 2.5069 (68.8); 2.5026 (94.4); 2.4983 (71.4); 2.3426 (16.0); 2.3298 (0.8); 0.0078 (1.2); −0.0002 (33.8); −0.0077 (1.4).

Preparation of 2-[(6-{[(5,6-dichloro-1-naphthyl)oxy]methyl}-5-fluoropyridin-3-yl)oxy]-N,N-diethyl-ethanamine

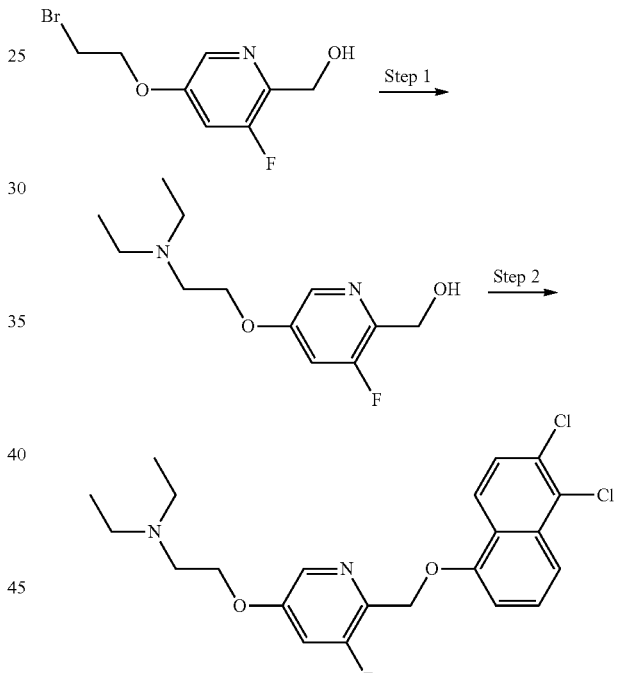

Step 1: Preparation of {5-[2-(diethylamino)ethoxy]-3-fluoropyridin-2-yl}methanol 918 µl (8.88 mmol) of diethylamine were added to a solution of 740 mg (2.96 mmol) of [5-(2-bromoethoxy)-3-fluoropyridin-2-yl]methanol in 2 ml of dimethylformamide, and the mixture was stirred at 75° C. for 5 h. The reaction mixture was separated chromatographically by MPLC on RP silica gel (gradient: water/acetonitrile). This gave 613 mg of {5-[2-(diethylamino)ethoxy]-3-fluoropyridin-2-yl}methanol.

$^1$H-NMR (400.0 MHz, d$_6$-DMSO): δ=8.1056 (2.0); 8.1019 (2.0); 7.4256 (1.2); 7.4196 (1.2); 7.3961 (1.2); 7.3901 (1.3); 5.1802 (0.5); 5.1657 (0.9); 5.1512 (0.5); 4.5038 (2.1); 4.4959 (2.1); 4.1224 (2.1); 4.1074 (4.6); 4.0923 (2.2); 3.3237 (7.8); 2.7819 (2.2); 2.7669 (4.4); 2.7518 (2.0); 2.5614 (2.3); 2.5436 (7.3); 2.5258 (7.9); 2.5064 (26.0); 2.5019 (33.3); 2.4974 (24.8); 1.9039 (1.0);

0.9769 (7.9); 0.9592 (16.0); 0.9414 (7.5); 0.0079 (1.1); −0.0002 (28.0); −0.0083 (1.3).

Step 2: Preparation of 2-[(6-{(5,6-dichloro-1-naphthyl)oxy]methyl}-5-fluoropyridin-3-yl)oxyl-N,N-diethylethanamine 1.0 ml (13.7 mmol) of thionyl chloride and a catalytic amount of N,N-dimethylformamide were added to a solution of 634 mg (2.62 mmol) of {5-[2-(diethylamino)ethoxy]-3-fluoropyridin-2-yl}methanol in 30 ml of dichloromethane, and the mixture was stirred at room temperature for 90 min. After addition of 30 ml of toluene, the reaction mixture was concentrated under reduced pressure. The residue was dissolved in 12 ml of N,N-dimethylformamide and one sixth of this solution was added to 79 mg (0.37 mmol) of 5,6-dichloro-1-naphthol and 428 mg (1.31 mmol) of caesium carbonate. The reaction mixture was stirred at 80° C. overnight and then separated chromatographically by MPLC on RP silica gel (gradient: water/acetonitrile). This gave 144 mg of 2-[(6-{[(5,6-dichloro-1-naphthyl)oxy]methyl}-5-fluoropyridin-3-yl)oxy]-N,N-diethylethanamine.

$^1$H-NMR (400.0 MHz, d$_6$-DMSO): δ=8.2239 (2.2); 8.2196 (2.2); 8.0771 (2.1); 8.0544 (2.3); 7.8029 (1.6); 7.7815 (2.3); 7.7006 (1.5); 7.6807 (2.1); 7.6591 (4.2); 7.6363 (2.8); 7.5745 (1.2); 7.5687 (1.3); 7.5449 (1.2); 7.5391 (1.2); 7.3669 (2.0); 7.3476 (1.8); 5.3842 (4.2); 5.3808 (4.4); 4.1683 (1.9); 4.1533 (4.1); 4.1383 (2.0); 3.3230 (39.8); 2.8013 (1.8); 2.7865 (3.8); 2.7714 (1.8); 2.6720 (0.4); 2.6675 (0.3); 2.5675 (2.1); 2.5497 (6.7); 2.5319 (7.2); 2.5071 (57.4); 2.5027 (75.6); 2.4983 (56.7); 2.3294 (0.4); 2.3249 (0.3); 0.9792 (7.8); 0.9615 (16.0); 0.9437 (7.5); 0.0078 (2.3); −0.0002 (54.0); −0.0081 (2.7).

Preparation of N-{2-[(6-{[(5,6-dichloro-1-naphthyl)oxy]methyl}-5-fluoropyridin-3-yl)oxy]ethyl}-N,2-dimethylpropan-2-aminium chloride and N-{2-[(6-{[(5,6-dichloro-1-naphthyl)oxy]methyl}-5-fluoropyridin-3-yl)oxy]ethyl}-N,2-dimethylpropan-2-amine 1.0 ml (13.7 mmol) of thionyl chloride and a catalytic amount of N,N-dimethylformamide were added to a solution of 596 mg (2.33 mmol) of (5-{2-[tert-butyl(methyl)amino]ethoxy}-3-fluoropyridin-2-yl)methanol in 20 ml of dichloromethane, and the mixture was stirred at room temperature for 90 min. After addition of 30 ml of toluene, the reaction mixture was concentrated under reduced pressure. The residue was dissolved in 12 ml of N,N-dimethylformamide and one sixth of this solution was added to 70 mg (0.33 mmol) of 5,6-dichloro-1-naphthol and 378 mg (1.16 mmol) of caesium carbonate. The reaction mixture was stirred at 80° C. overnight and then separated chromatographically by MPLC on RP silica gel (gradient: water/acetonitrile). The solid precipitated in the injection syringe after addition of ethanol and water during the liquid injection of the reaction mixture into the MPLC was re-dissolved by addition of acetonitrile and 1 N aqueous hydrochloric acid. This gave 99 mg of N-{2-[(6-{[(5,6-dichloro-1-naphthyl)oxy]methyl}-5-fluoropyridin-3-yl)oxy]ethyl}-N,2-dimethylpropan-2-aminium chloride (purity 78%) and 29 mg of N-{2-[(6-{[(5,6-dichloro-1-naphthyl)oxy]methyl}-5-fluoropyridin-3-yl)oxy]ethyl}-N,2-dimethylpropan-2-amine.

N-{2-[(6-{[(5,6-Dichloro-1-naphthyl)oxy]methyl}-5-fluoropyridin-3-yl)oxy]ethyl}-N,2-dimethylpropan-2-aminium chloride (purity 78%)

$^1$H-NMR (400.0 MHz, d$_6$-DMSO): δ=9.6357 (0.4); 8.3034 (1.2); 8.2990 (1.2); 8.0670 (1.2); 8.0443 (1.3); 7.8101 (1.0); 7.7885 (1.4); 7.7061 (0.8); 7.6863 (1.3); 7.6764 (1.9); 7.6653 (0.8); 7.6537 (2.2); 7.6362 (0.5); 7.6235 (1.3); 7.3742 (1.2); 7.3549 (1.0); 5.7570 (0.8); 5.4187 (2.5); 5.2320 (0.6); 4.5213 (1.4); 4.5096 (1.0); 3.8081 (0.4); 3.7953 (0.4); 3.7817 (0.4); 3.7708 (0.4); 3.3260 (52.0); 2.8122 (2.7); 2.8002 (2.9); 2.6758 (0.3); 2.6716 (0.4); 2.5068 (60.7); 2.5024 (79.5); 2.4980 (60.3); 2.3292 (0.4); 2.3249 (0.4); 1.3720 (16.0); 0.1460 (0.3); 0.0077 (3.4); −0.0002 (73.8); −0.0083 (4.0); −0.1498 (0.3).

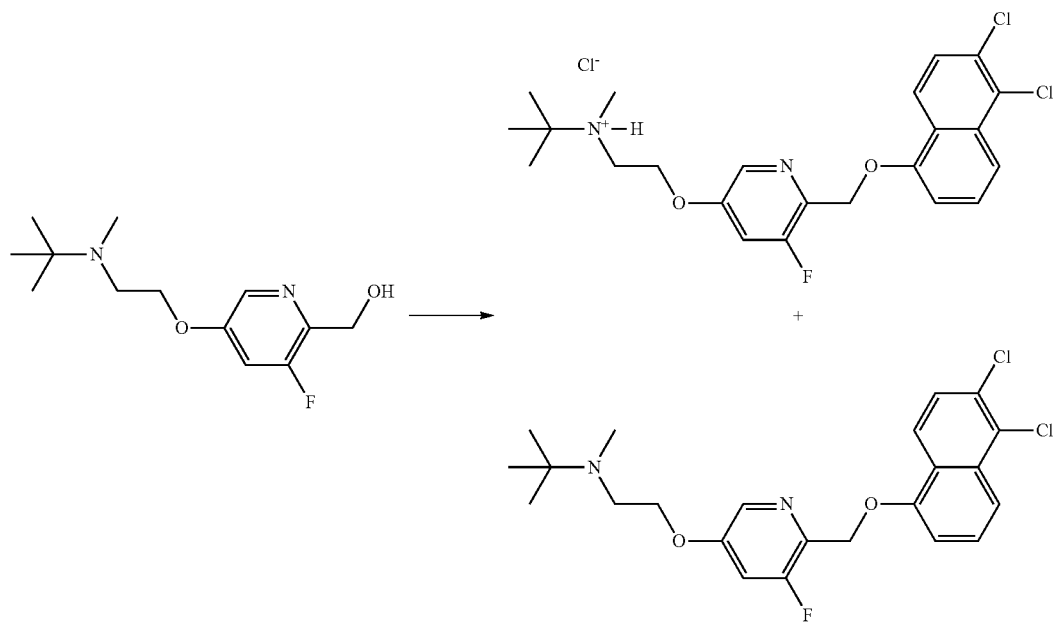 [SMILES: CN(CCOc1cnc(CO)c(F)c1)C(C)(C)C ; CN(CCOc1cnc(COc2cccc3c(Cl)c(Cl)ccc23)c(F)c1)C(C)(C)C ; C[NH+](CCOc1cnc(COc2cccc3c(Cl)c(Cl)ccc23)c(F)c1)C(C)(C)C ; [Cl-]]

N-{2-[(6-{[(5,6-Dichloro-1-naphthyl)oxy]methyl}-5-fluoropyridin-3-yl)oxy]ethyl}-N,2-dimethylpropan-2-amine ¹H-NMR (400.0 MHz, d₆-DMSO): δ=8.2188 (1.1); 8.2144 (1.1); 8.0759 (1.0); 8.0532 (1.2); 7.8031 (0.8); 7.7816 (1.2); 7.7000 (0.8); 7.6800 (1.1); 7.6602 (2.0); 7.6378 (1.4); 7.5625 (0.6); 7.5566 (0.6); 7.5326 (0.6); 7.5268 (0.6); 7.3651 (1.0); 7.3459 (0.9); 5.3811 (2.2); 4.1263 (0.8); 4.1109 (1.6); 4.0956 (0.8); 3.3230 (51.0); 2.7359 (0.7); 2.7206 (1.4); 2.7050 (0.7); 2.6712 (0.4); 2.5064 (54.4); 2.5021 (71.6); 2.4977 (54.5); 2.3288 (0.4); 2.2272 (4.9); 1.0083 (16.0); 0.0077 (2.8); −0.0003 (64.9).

Preparation of 2-[(2-{[(4-chloro-1-naphthyl)oxy]methyl}pyrimidin-5-yl)oxy]-N-methoxy-N-methylethanamine

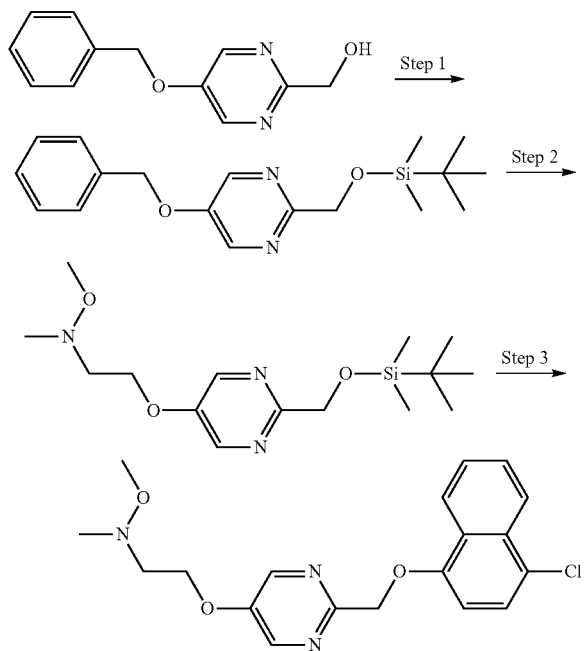

Step 1: Preparation of 5-(benzyloxy)-2-({[tert-butyl(dimethyl)silyl]oxy}methyl)pyrimidine 616 mg (4.10 mmol) of tert-butyldimethylsilyl chloride were added to a solution of 744 mg (3.44 mmol) of [5-(benzyloxy)pyrimidin-2-yl]methanol (D. Bensen et al, WO2014/043272) and 341 mg (5.0 mmol) of imidazole in 3.5 ml of N,N-dimethylformamide, and the mixture was stirred at room temperature for 30 min. After addition of ethyl acetate, the mixture was washed with a saturated aqueous sodium chloride solution, dried with magnesium sulfate and filtered, and the filtrate was concentrated under reduced pressure. The residue was taken up in dichloromethane, adsorbed on silica gel and separated chromatographically by MPLC on silica gel (gradient: cyclohexane/ethyl acetate). This gave 0.83 g of 5-(benzyloxy)-2-({[tert-butyl(dimethyl)silyl]oxy}methyl)pyrimidine.

¹H-NMR (400.0 MHz, CDCl3): δ=8.3222 (3.5); 7.2949 (1.8); 7.2883 (1.2); 7.2807 (1.3); 7.1373 (2.4); 5.0288 (2.9); 4.7408 (3.4); 1.4579 (1.2); 0.8133 (0.7); 0.8061 (16.0); 0.7990 (0.9); 0.0076 (0.4); −0.0002 (11.7); −0.0079 (0.5); −0.1235 (2.7).

Step 2: Preparation of 2-{[2-({[tert-butyl(dimethyl)silyl]oxy}methyl)pyrimidin-5-yl]oxy}-N-methoxy-N-methylethanamine In an H-Cube® hydrogenation reactor, a solution of 470 mg (1.42 mmol) of 5-(benzyloxy)-2-({[tert-butyl(dimethyl)silyl]oxy}methyl)pyrimidine in 40 ml of methanol was hydrogenated over 10% Pd/C at 1 bar using a flow rate of 2 ml/min. The reaction solution was then concentrated under reduced pressure. This gave 328 mg of unpurified 2-({[tert-butyl(dimethyl)silyl]oxy}methyl)pyrimidin-5-ol as intermediate. 224 mg (1.62 mmol) of potassium carbonate and 202 mg (0.81 mmol) of 2-bromo-N-methoxy-N-methylethanamine hydrobromide (1:1) were added to a solution of 150 mg of the unpurified intermediate 2-({[tert-butyl(dimethyl)silyl]oxy}methyl)pyrimidin-5-ol in 1.5 ml of N,N-dimethylformamide, and the mixture was stirred at 50° C. for 15 h. After addition of a further 62 mg (0.25 mmol) of 2-bromo-N-methoxy-N-methylethanamine hydrobromide (1:1), the reaction solution was stirred at 50° C. for another 3 h and then concentrated under reduced pressure. Water was added to the residue and the mixture was extracted repeatedly with ethyl acetate. The combined organic phases were washed with a saturated aqueous sodium chloride solution, dried with sodium sulfate and filtered, and the filtrate was concentrated under reduced pressure. The crude product was separated chromatographically by MPLC on silica gel (gradient: cyclohexane/ethyl acetate). This gave 43 mg of 2-{[2-({[tert-butyl(dimethyl)silyl]oxy}methyl)pyrimidin-5-yl]oxy}-N-methoxy-N-methylethanamine.

¹H-NMR (400.0 MHz, d₆-DMSO): δ=8.5493 (3.9); 4.7338 (3.3); 4.2697 (0.7); 4.2559 (1.5); 4.2421 (0.8); 3.3996 (6.2); 3.3184 (2.0); 2.9778 (0.7); 2.9640 (1.3); 2.9502 (0.7); 2.5641 (5.3); 2.5066 (8.9); 2.5021 (12.5); 2.4978 (9.6); 0.8740 (16.0); 0.8639 (1.7); 0.0677 (0.5); 0.0602 (11.7); 0.0439 (1.0); −0.0002 (8.8); −0.0080 (0.4).

Step 3: Preparation of 2-[(2-{[(4-chloro-1-naphthyl)oxy]methyl}pyrimidin-5-yl)oxy]-N-methoxy-N-methylethanamine 250 μl (0.25 mmol) of a 1 M solution of tetrabutylammonium fluoride in tetrahydrofuran were added to a solution of 40 mg (0.12 mmol) of 2-{[2-({[tert-butyl(dimethyl)silyl]oxy}methyl)pyrimidin-5-yl]oxy}-N-methoxy-N-methylethanamine in 0.7 ml of tetrahydrofuran, and the mixture was stirred at room temperature for 30 min. After addition of saturated aqueous ammonium chloride solution, the mixture was extracted repeatedly with ethyl acetate, the combined organic phases were dried over magnesium sulfate and filtered and the filtrate was concentrated under reduced pressure. The residue was dissolved in 1 ml of toluene, and 25 μl (0.34 mmol) of thionyl chloride and a catalytic amount of N,N-dimethylformamide were added. The reaction mixture was stirred at room temperature for 2 h and then concentrated under reduced pressure. The residue was dissolved in 1 ml of N,N-dimethylformamide and 27 mg (0.15 mmol) of 4-chloro-1-naphthol and 47 mg (0.34 mmol) of potassium carbonate were added. The reaction mixture was stirred at 70° C. for 2 h and then concentrated under reduced pressure. The residue was taken up in dichloromethane, adsorbed on silica gel and separated chromatographically by MPLC on silica gel (gradient: cyclohexane/ethyl acetate).

This gave 28 mg of 2-[(2-{[(4-chloro-1-naphthyl)oxy]methyl}pyrimidin-5-yl)oxy]-N-methoxy-N-methyl-ethanamine.

$^1$H-NMR (400.0 MHz, d$_6$-DMSO): δ=8.6301 (12.6); 8.3049 (1.5); 8.2842 (1.6); 8.1276 (1.6); 8.1072 (1.8); 7.7419 (0.8); 7.7388 (0.8); 7.7247 (1.2); 7.7214 (1.6); 7.7178 (0.8); 7.7037 (1.1); 7.7005 (1.0); 7.6548 (1.1); 7.6520 (1.1); 7.6342 (1.6); 7.6311 (1.1); 7.6166 (0.8); 7.6138 (0.7); 7.5759 (2.8); 7.5551 (3.0); 7.0297 (2.6); 7.0087 (2.4); 5.4358 (8.1); 4.2925 (2.0); 4.2788 (4.2); 4.2650 (2.1); 3.3999 (20.0); 3.3213 (5.2); 2.9859 (1.8); 2.9723 (3.7); 2.9586 (1.8); 2.5655 (16.0); 2.5251 (0.7); 2.5202 (1.1); 2.5115 (15.9); 2.5071 (33.7); 2.5025 (47.0); 2.4980 (34.8); 2.4937 (16.6); 0.0080 (0.3); −0.0002 (10.8); −0.0085 (0.4).

Preparation of
2-bromo-N-methoxy-N-methylethanamine
hydrobromide (1:1)

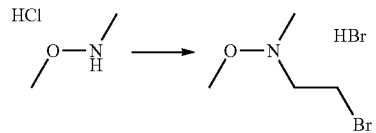

At 0° C., 463 g (2.46 mol) of 1,2-dibromoethane were slowly added to a suspension of 100 g (1.02 mol) of N-methoxymethanamine hydrochloride (1:1) and 435 g (3.15 mol) of potassium carbonate in 1 l of acetonitrile. The mixture was then stirred at 0° C. for 20 min, at room temperature for 70 h and at 50° C. for 24 h. The sediment was filtered off and the filtrate was concentrated under reduced pressure. The residue was treated with a solution of hydrogen chloride in diethyl ether. The precipitated solid was filtered off and washed with diethyl ether. At 0° C., the hydrochloride obtained in this manner was dissolved in a solution of hydrogen bromide in acetic acid and stirred for 10 min. The acetic acid was then removed under reduced pressure. The residue was dissolved in dichloromethane and filtered and the filtrate was concentrated. This gave 22 g of 2-bromo-N-methoxy-N-methylethanamine hydrobromide (1:1).

2-Bromo-N-methoxy-N-methylethanamine
hydrochloride (1:1)

$^1$H-NMR (300.0 MHz, d$_6$-DMSO): δ=3.61 (t, J=6.9 Hz, 2H), 3.55 (s, 3H), 3.14 (t, J=6.9 Hz, 2H), 2.67 (s, 3H) ppm.

NMR Data of Selected Examples
NMR Peak List Method

The 1H-NMR data of selected examples and synthesis intermediates are noted in the form of 1H-NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore takes the form of:
δ$_1$ (intensity$_1$); δ$_2$ (intensity$_2$); ... ; δ$_i$ (intensity$_i$); ... ; δ$_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form the subject-matter of the invention, and/or peaks of impurities.

In the reporting of compound signals in the delta range of solvents and/or water, our lists of 1H NMR peaks show the usual solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

| Example |
| --- |
| 1: $^1$H-NMR(400.0 MHz, d$_6$-DMSO): δ = 8.3682(5.1); 8.3625(5.2); 8.3181(0.4); 8.1644(5.2); 8.1416(5.8); 7.9202(3.4); 7.9141(3.3); 7.8989(3.5); 7.8928(3.5); 7.8027(3.8); 7.7813(5.8); 7.7092(4.0); 7.6894(5.2); 7.6673(10.2); 7.6443(7.3); 7.3154(4.8); 7.2963(4.3); 6.9035(5.8); 6.8823(5.6); 6.0677(1.0); 6.0513 (2.3); 6.0349(1.0); 5.2800(16.0); 4.8119(2.1); 4.7868(2.3); 4.6582(2.5); 4.4271(5.5); 4.4126(11.7); 4.3981(5.8); 4.3040(4.5); 4.2877 (4.4); 3.4089(48.4); 3.3286(91.4); 3.2818(4.0); 2.9628(4.7); 2.9485(9.8); 2.9340(4.8); 2.6768(0.6); 2.6723(0.9); 2.6679(0.6); 2.5578 (41.0); 2.5256(2.1); 2.5207(3.2); 2.5120(48.1); 2.5077(98.0); 2.5031(130.4); 2.4986(95.8); 2.4943(47.2); 2.3344(0.6); 2.3300(0.9); 2.3254 (0.6); 1.9897(0.4); 0.1460(0.8); 0.0080(5.7); −0.0002(164.9); −0.0085(6.0); −0.1496(0.8) |
| 2: $^1$H-NMR(400.0 MHz, d$_6$-DMSO): δ = 8.3630(5.1); 8.3579(5.5); 8.2317(3.9); 8.2108(4.1); 8.1311(4.0); 8.1102(4.3); 7.9169(3.2); 7.9109(3.2); 7.8956(3.3); 7.8896(3.3); 7.7361(1.8); 7.7335(2.0); 7.7160(3.8); 7.6980(2.3); 7.6953(2.4); 7.6387(6.2); 7.6180(8.4); 7.5966(1.7); 7.5943(1.8); 7.1509(5.6); 7.1300 (5.2); 6.9034(5.4); 6.8821(5.2); 5.2613(16.0); 4.8123(1.3); 4.7872(1.6); 4.6588(1.7); 4.4268(5.1); 4.4124(10.6); 4.3979(5.4); 3.4092 (42.0); 3.3340(86.0); 3.2821(2.8); 2.9629(4.6); 2.9486(9.2); 2.9341(4.6); 2.6773(0.4); 2.6731(0.6); 2.6687(0.4); 2.5578(36.3); 2.5082 (62.5); 2.5039(81.9); 2.4997(64.1); 2.3307(0.5); 1.3969(1.8); 1.2317(2.8); 0.8527(0.4); 0.0077(0.8); −0.0002(16.2) |

-continued

| Example |
|---|
| 3: $^1$H-NMR(400.0 MHz, d$_6$-DMSO): δ = <br>8.3185(0.4); 8.2012(3.8); 8.1806(4.1); 8.1441(2.6); 8.1346(4.3); 8.1235(3.5); 8.1186(3.5); 8.1138(5.0); 8.0986(2.6); 7.7379(2.0); 7.7351(2.0); 7.7207(3.0); 7.7176(3.8); 7.7141(2.1); 7.6997(2.6); 7.6967(2.4); 7.6441(6.7); 7.6338(3.0); 7.6312(3.0); 7.6234(7.6); 7.6165 (2.7); 7.6133(4.0); 7.6105(2.9); 7.5956(1.9); 7.5930(1.8); 7.1689(6.1); 7.1480(5.6); 6.8636(4.3); 6.8431(4.2); 5.2692(16.0); 5.2479(0.4); 4.3869(4.7); 4.3729(9.7); 4.3588(5.1); 3.8703(3.1); 3.4562(0.4); 3.4080(45.7); 3.3516(5.1); 3.3445(5.1); 3.2886(0.4); 3.2287(0.3); 2.9594(4.3); 2.9454(8.5); 2.9314(4.4); 2.6770(0.7); 2.6724(0.9); 2.6680(0.7); 2.5584(37.8); 2.5257(2.1); 2.5120(53.0); 2.5079(106.6); 2.5034(139.2); 2.4989(102.1); 2.4949(52.0); 2.3874(0.4); 2.3346(0.7); 2.3302(1.0); 2.3256(0.7); 1.2984(0.5); 1.2584(0.8); 1.2318(2.7); 0.1460(0.3); 0.0079(2.7); −0.0002(78.0); −0.0084(3.4); −0.1496(0.4) |
| 4: $^1$H-NMR(400.0 MHz, d$_6$-DMSO): δ = <br>8.7828(0.3); 8.3787(3.9); 8.3135(0.4); 8.2345(3.1); 8.2135(3.3); 8.1323(3.1); 8.1216(0.5); 8.1113(3.4); 7.9396(1.3); 7.9336(1.4); 7.9289(1.6); 7.9226(1.6); 7.9186(1.5); 7.9122(1.5); 7.9076(1.6); 7.9014(1.5); 7.7353(1.6); 7.7178(2.5); 7.6972(1.9); 7.6385(5.2); 7.6182 (6.4); 7.5978(1.4); 7.1552(2.5); 7.1493(2.9); 7.1343(2.3); 7.1283(2.6); 6.9164(2.2); 6.8994(2.8); 6.8955(2.4); 6.8783(2.5); 5.7538(15.6); 5.6080(0.5); 5.6025(0.9); 5.5969(1.0); 5.5910(0.9); 5.5853(0.5); 5.5249(0.8); 5.5199(1.0); 5.5140(1.3); 5.5090(1.0); 5.5030(0.7); 5.3798(1.2); 5.2723(7.7); 5.2687(8.4); 3.8665(0.8); 3.8546(0.9); 3.8370(1.1); 3.8252(1.0); 3.6564(0.3); 3.6488(0.4); 3.6312(1.0); 3.6244 (1.0); 3.6088(1.0); 3.6019(1.3); 3.5904(1.6); 3.5809(1.1); 3.5719(2.5); 3.5593(2.9); 3.5391(2.5); 3.5243(0.6); 3.5158(0.6); 3.5062(0.6); 3.3835(0.5); 3.3648(0.7); 3.3596(0.8); 3.3213(136.8); 3.3179(114.0); 2.6753(0.8); 2.6709(1.1); 2.6664(0.8); 2.5238(3.4); 2.5106(70.5); 2.5063(140.5); 2.5018(185.4); 2.4973(135.6); 2.4929(67.1); 2.3329(0.9); 2.3285(1.2); 2.3244(0.8); 2.3193(0.4); 2.2901(0.3); 2.2795 (0.7); 2.2674(0.6); 2.2554(0.8); 2.2440(0.6); 2.2328(0.4); 2.2210(0.4); 2.1919(0.7); 2.1808(0.8); 2.1707(1.2); 2.1585(0.8); 2.1467(1.0); 2.1348(0.9); 2.1242(0.4); 2.1123(0.3); 2.0909(0.6); 2.0834(0.5); 2.0737(0.6); 2.0675(0.4); 1.9764(16.0); 1.9303(13.8); 1.2932(0.4); 1.2338(0.5); 0.0079(0.8); −0.0001(21.3); −0.0083(0.8) |
| 5: $^1$H-NMR(400.0 MHz, d$_6$-DMSO): δ = <br>8.3569(3.4); 8.3518(3.4); 8.3142(4.9); 8.2335(2.5); 8.2124(2.7); 8.1313(2.6); 8.1106(2.9); 7.9180(2.2); 7.9119(2.1); 7.8967(2.2); 7.8906(2.2); 7.7358(1.2); 7.7328(1.4); 7.7187(1.8); 7.7154(2.5); 7.7119(1.4); 7.6976(1.6); 7.6945(1.6); 7.6371(5.9); 7.6164(7.2); 7.5985 (1.2); 7.5958(1.2); 7.1484(3.9); 7.1275(3.6); 6.8863(3.6); 6.8650(3.5); 5.7544(3.1); 5.4337(0.4); 5.4264(0.9); 5.4188(1.0); 5.4112(1.2); 5.4074(1.3); 5.3999(1.1); 5.3921(0.9); 5.3850(0.5); 5.2594(10.2); 3.8567(16.0); 3.3186(33.8); 3.2947(1.9); 3.0038(1.5); 2.9886(1.6); 2.9775(2.0); 2.9623(1.8); 2.8469(0.6); 2.8263(1.3); 2.8108(1.4); 2.7907(0.8); 2.7530(1.7); 2.7463(1.7); 2.7267(1.4); 2.7201(1.4); 2.6757(3.2); 2.6712(0.5); 2.6667(0.4); 2.5830(0.8); 2.5628(1.6); 2.5464(1.6); 2.5420(1.2); 2.5249(1.9); 2.5111(25.9); 2.5067(53.8); 2.5022 (74.6); 2.4977(57.1); 2.4934(28.5); 2.3698(0.4); 2.3506(0.8); 2.3356(1.5); 2.3164(1.4); 2.3016(0.9); 2.2820(0.4); 2.0742(1.4); 1.9166 (0.4); 1.9096(0.5); 1.8961(0.7); 1.8821(0.8); 1.8750(0.8); 1.8605(0.6); 1.8472(0.4); 1.8408(0.4); −0.0002(6.6) |
| 6: $^1$H-NMR(400.0 MHz, d$_6$-DMSO): δ = <br>8.5420(2.1); 8.2339(1.6); 8.2138(1.8); 8.1539(2.1); 8.1369(1.8); 8.1161(1.9); 7.7406(0.7); 7.7378(0.8); 7.7235(1.1); 7.7204(1.6); 7.7026(1.0); 7.6996(1.1); 7.6473(3.4); 7.6266(4.3); 7.6079(0.7); 7.6053(0.8); 7.2144(1.0); 7.1569(2.5); 7.1359(2.3); 7.0776(2.2); 6.9407 (1.1); 5.3367(6.6); 4.5456(2.2); 4.5311(4.8); 4.5166(2.4); 3.4051(19.0); 3.3241(19.0); 3.0037(2.1); 2.9893(4.3); 2.9747(2.0); 2.5644 (16.0); 2.5263(0.5); 2.5128(11.1); 2.5085(23.9); 2.5040(34.0); 2.4997(26.8); 1.3974(0.3); 1.2314(0.6); 0.0081(1.4); −0.0002(42.7) |
| 7: $^1$H-NMR(601.6 MHz, d$_6$-DMSO): δ = <br>8.3415(2.4); 8.3381(2.5); 8.2473(1.5); 8.2337(1.6); 8.1303(1.6); 8.1168(4.4); 8.1136(3.1); 7.7321(0.8); 7.7301(0.8); 7.7206(1.1); 7.7184(1.5); 7.7161(0.9); 7.7066(1.0); 7.7046(0.9); 7.6356(3.7); 7.6258(1.1); 7.6218(4.0); 7.6121(0.8); 7.6103(0.8); 7.1365(2.4); 7.1226 (2.3); 5.2736(6.5); 4.5246(2.2); 4.5150(4.7); 4.5054(2.3); 3.4189(19.7); 3.3156(8.6); 3.0036(1.8); 2.9940(3.7); 2.9844(1.8); 2.5725 (16.0); 2.5113(4.3); 2.5083(9.0); 2.5053(12.3); 2.5023(9.1); 2.4993(4.4); −0.0002(3.4) |
| 8: $^1$H-NMR(400.0 MHz, d$_6$-DMSO): δ = <br>8.3577(0.6); 8.3447(0.6); 8.3159(5.5); 8.3106(5.1); 8.1411(4.1); 8.1219(4.4); 8.0992(0.3); 8.0927(0.4); 7.9100(0.4); 7.9043(0.4); 7.8884(0.4); 7.8833(0.5); 7.8676(3.1); 7.8616(3.3); 7.8529(6.5); 7.8465(5.1); 7.8407(3.6); 7.6752(4.6); 7.6546(5.9); 7.6263(6.0); 7.6040 (6.6); 7.5300(2.2); 7.5103(4.1); 7.4920(2.3); 7.4077(3.0); 7.3891(4.9); 7.3710(2.2); 7.2226(0.4); 7.2155(0.8); 7.2018(0.4); 7.1843(3.6); 7.1778(3.4); 7.1620(3.2); 7.1555(3.1); 6.9541(0.7); 6.9328(0.6); 6.8792(5.3); 6.8579(5.1); 5.4036(2.0); 5.1675(2.1); 5.1493(16.0); 4.4156(4.8); 4.4012(10.1); 4.3867(5.1); 3.4009(39.3); 3.3207(78.2); 2.9537(4.6); 2.9394(9.1); 2.9249(4.5); 2.6707(1.6); 2.5506(34.4); 2.5056(220.0); 2.5017(280.2); 2.4975(205.6); 2.3284(1.6); 1.2338(0.5); 1.0542(1.4); −0.0003(52.8) |
| 9: $^1$H-NMR(400.0 MHz, d$_6$-DMSO): δ = <br>8.3553(3.4); 8.3498(3.5); 8.1588(3.6); 8.1362(3.6); 7.9089(2.0); 7.9029(2.0); 7.8876(2.1); 7.8816(2.1); 7.8008(2.4); 7.7793(3.6); 7.7073(2.4); 7.6875(3.2); 7.6666(6.6); 7.6440(4.4); 7.4947(0.4); 7.3123(3.0); 7.2930(2.7); 6.8694(3.5); 6.8482(3.3); 5.7590(0.6); 5.2763 (9.7); 5.2439(0.6); 4.3405(2.3); 4.3248(4.7); 4.3091(2.4); 4.0567(0.4); 4.0388(1.0); 4.0210(1.1); 4.0032(0.4); 3.3237(22.6); 3.2048(0.5); 3.1873(0.5); 2.8913(0.7); 2.7764(1.5); 2.7623(2.4); 2.7324(1.0); 2.6764(0.4); 2.6721 (0.5); 2.6676(0.4); 2.5632(1.8); 2.5463(4.1); 2.5262(5.1); 2.5075(64.9); 2.5031(83.5); 2.4986(62.1); 2.3338(0.4); 2.3299(0.5); 2.3256(0.4); 1.9900(4.5); 1.2983(0.4); 1.2578(0.5); 1.2306(0.6); 1.1932(1.2); 1.1754(2.2); 1.1576(1.1); 1.0387(0.5); 1.0202(0.4); 1.0027(0.4); 0.9824(8.2); 0.9646(16.0); 0.9469(8.1); 0.9239 (0.7); 0.0076(0.4); −0.0002(9.3) |
| 10: $^1$H-NMR(400.0 MHz, d$_6$-DMSO): δ = <br>8.3568(0.6); 8.3167(0.4); 8.2989(0.7); 8.2934(0.7); 8.2648(5.3); 8.2595(5.4); 8.0953(0.4); 8.0890(0.4); 7.8613(0.4); 7.8558(0.4); 7.8404(0.5); 7.8345(0.5); 7.8183(3.2); 7.8125(3.1); 7.7971(3.3); 7.7911(3.2); 7.6523(0.8); 7.6326(5.8); 7.6261(4.6); 7.6180(10.7); 7.5425 (5.1); 7.4331(2.6); 7.4230(2.2); 7.3075(2.7); 7.2845(4.2); 7.2589(3.3); 7.2174(2.1); 7.2098(3.3); 7.2014(3.4); 7.1938(3.3); 7.1063(1.9); 7.0975(2.2); 7.0887(2.1); 7.0841(1.8); 7.0753(2.4); 7.0666(1.3); 6.9446(0.7); 6.9234(0.7); 6.8681(5.5); 6.8469(5.3); 5.4001(2.2); 5.1213(2.2); 5.1038(16.0); 4.4109(5.0); 4.3964(10.6); 4.3820(5.3); 3.3978(43.2); 3.3216(55.9); 2.9501(4.8); 2.9356(9.6); 2.9212(4.7); 2.6759(0.8); 2.6715(1.0); 2.6674(0.8); 2.5487(37.1); 2.5067(137.5); 2.5025(176.7); 2.4982(128.8); 2.3290(1.0); 1.2341(0.7); 1.0540 (3.3); 0.0078(1.5); −0.0002(37.0) |
| 11: $^1$H-NMR(400.0 MHz, d$_6$-DMSO): δ = <br>8.2745(2.1); 8.2689(2.2); 7.8237(1.3); 7.8177(1.3); 7.8024(1.4); 7.7964(1.4); 7.7459(1.2); 7.7256(1.5); 7.6538(1.9); 7.6157(1.4); 7.5956(2.5); 7.5757(1.3); 7.4299(1.0); 7.4102(2.3); 7.3900(1.9); 7.3828(1.2); 7.3620(1.0); 7.3458(2.2); 7.3408(1.6); 7.3068(1.6); 7.2874 (1.2); 7.0779(1.1); 7.0728(1.1); 7.0581(1.0); 7.0525(1.0); 6.8375(2.3); 6.8163(2.2); 5.1410(6.4); 4.3241(2.2); 4.3083(4.6); 4.2924(2.2); 3.3235(20.0); 2.7629(2.0); 2.7471(4.2); 2.7313(2.1); 2.5532(2.2); 2.5354(7.0); 2.5174(9.1); 2.5114(16.7); 2.5072(32.3); 2.5027(43.3); 2.4985(33.2); 1.9924(0.3); 0.9729(7.9); 0.9552(16.0); 0.9374(7.7); 0.0079(1.6); −0.0002(39.1) |
| 12: $^1$H-NMR(400.0 MHz, d$_6$-DMSO): δ = <br>8.2510(2.3); 8.2456(2.5); 7.8046(1.4); 7.7988(1.4); 7.7834(1.4); 7.7774(1.5); 7.6196(2.4); 7.5468(0.5); 7.5310(2.8); 7.5131(3.0); 7.4961(2.2); 7.4928(2.7); 7.4865(1.1); 7.4794(0.5); 7.4747(0.6); 7.2915(1.2); 7.2686(1.7); 7.2431(1.4); 7.2003(1.2); 7.1926(1.4); 7.1844 (1.3); 7.1766(1.3); 7.0865(0.8); 7.0777(1.3); 7.0691(0.8); 7.0643(0.7); 7.0556(1.0); 7.0466(0.6); 6.8330(2.5); 6.8118(2.4); 5.0942(7.1); 4.3213(2.3); 4.3054(4.7); 4.2896(2.3); 3.3235(21.3); 2.7603(2.2); 2.7445(4.5); 2.7287(2.1); 2.5514(2.4); 2.5336(7.5); 2.5069(31.4); 2.5026(41.4); 2.4985(33.7); 0.9714(8.0); 0.9536(16.0); 0.9359(7.6); 0.0078(1.6); −0.0002(35.0) |

| Example |
|---|
| 13: $^1$H-NMR(400.0 MHz, d$_6$-DMSO): δ = 8.2824(5.7); 8.2777(6.0); 7.8343(3.1); 7.8286(3.2); 7.8131(3.2); 7.8073(3.3); 7.6765(6.7); 7.6579(8.4); 7.6192(1.0); 7.6029(0.9); 7.5972(0.8); 7.4801(3.9); 7.4612(8.1); 7.4420(5.0); 7.4285(0.9); 7.4050(2.5); 7.3858(7.8); 7.3674(5.9); 7.3502(1.6); 7.3064(0.4); 7.2825 (5.7); 7.2571(4.3); 7.2380(3.2); 7.1174(0.7); 7.0960(0.6); 7.0335(3.0); 7.0280(2.9); 7.0131(2.7); 7.0076(2.6); 6.8712(5.7); 6.8500(5.5); 5.1300(16.0); 5.0934(1.3); 5.0603(0.5); 4.4136(5.1); 4.3992(10.4); 4.3848(5.5); 4.3687(0.5); 3.4006(35.7); 3.3209(33.5); 2.9524(4.8); 2.9380(9.4); 2.9237(4.8); 2.6708(0.6); 2.5501(32.7); 2.5017(91.7); 2.3285(0.5); −0.0002(37.4) |
| 14: $^1$H-NMR(400.0 MHz, d$_6$-DMSO): δ = 8.2560(2.2); 8.2507(2.2); 7.8067(1.3); 7.8007(1.3); 7.7854(1.4); 7.7794(1.4); 7.6128(2.7); 7.5904(3.0); 7.2262(1.7); 7.2230(1.8); 7.1475(1.6); 7.1404(1.4); 7.1250(1.4); 7.1179(1.3); 6.8295(2.3); 6.8083(2.2); 5.0954(7.0); 4.3210(2.2); 4.3052(4.7); 4.2894(2.3); 3.3225 (13.3); 2.8913(0.8); 2.7577(2.2); 2.7418(4.4); 2.7318(1.1); 2.7260(2.1); 2.5506(2.3); 2.5328(7.3); 2.5252(1.3); 2.5070(26.5); 2.5027 (34.8); 2.4982(27.7); 2.4731(0.4); 0.9710(8.0); 0.9532(16.0); 0.9354(7.7); 0.9238(0.4); 0.0077(1.4); −0.0002(33.2); −0.0083(1.5) |
| 15: $^1$H-NMR(400.0 MHz, d$_6$-DMSO): δ = 10.1255(3.7); 8.5176(0.7); 8.5125(0.7); 8.3133(1.0); 8.2521(4.4); 8.2469(4.6); 7.9513(1.1); 7.9366(0.6); 7.9306(0.5); 7.7996(3.0); 7.7936(2.9); 7.7783(3.1); 7.7723(3.1); 7.5811(1.0); 7.5637(1.3); 7.5593(1.2); 7.5449(6.8); 7.5366(0.7); 7.5226(7.3); 7.4010(3.1); 7.3791 (3.4); 7.3724(1.6); 7.3652(1.6); 7.3476(6.6); 7.3404(6.9); 7.0780(0.7); 7.0706(0.7); 7.0575(4.1); 7.0503(4.0); 7.0352(3.5); 7.0279(3.4); 6.9771(3.0); 6.9701(3.3); 6.8626(5.2); 6.8414(5.0); 6.7806(2.0); 6.7736(1.8); 6.7586(1.8); 6.7516(1.7); 6.5776(0.7); 5.2005(3.0); 5.1944(1.4); 5.0763(16.0); 4.4088(4.9); 4.3944(10.3); 4.3799(5.2); 3.8554(2.5); 3.3989(43.8); 3.3814(0.4); 3.3145(135.2); 2.9689(0.4); 2.9485(4.5); 2.9340(9.2); 2.9196(4.5); 2.8910(5.4); 2.7320(4.4); 2.6749(1.6); 2.6704(2.3); 2.6659(1.6); 2.5584(2.0); 2.5488(36.8); 2.5237(5.2); 2.5102(125.4); 2.5058(255.3); 2.5013(342.6); 2.4968(257.0); 2.4925(129.2); 2.4464(0.7); 2.4364(0.5); 2.4308(0.5); 2.4041 (0.4); 2.3785(0.4); 2.3326(1.8); 2.3281(2.4); 2.3236(1.8); 2.1187(1.0); 1.6615(0.4); 1.6359(0.4); 1.6221(0.4); 1.6088(0.4); 1.5962(0.3); 1.5755(0.5); 1.5501(0.4); 1.5224(0.4); 1.4765(0.5); 1.4705(0.5); 1.3825(0.5); 1.3699(1.2); 1.3614(0.6); 1.3365(1.3); 1.2702(2.2); 1.2355(10.6); 1.1693(5.5); 1.1466(0.9); 1.1371(0.9); 1.1254(0.9); 1.1054(0.7); 1.0919(0.9); 1.0482(0.8); 1.0160(0.9); 1.0000(0.8); 0.9907 (0.4); 0.9797(0.9); 0.9656(3.9); 0.9380(0.6); 0.9301(0.6); 0.9216(0.7); 0.9086(0.8); 0.9011(0.7); 0.8539(4.1); 0.8362(3.2); 0.8102(1.6); 0.7549(0.4); 0.1461(1.0); 0.0080(7.8); −0.0002(245.8); −0.0085(9.5); −0.1496(1.1) |
| 16: $^1$H-NMR(400.0 MHz, d$_6$-DMSO): δ = 8.3453(2.5); 8.3383(2.6); 8.2325(2.3); 8.2098(2.6); 7.7974(1.8); 7.7759(2.6); 7.6988(3.1); 7.6835(1.7); 7.6761(3.0); 7.6634(2.4); 7.6426(1.3); 7.6082(1.9); 7.5867(2.9); 7.5077(1.7); 7.5005(1.7); 7.4862(1.2); 7.4789(1.2); 7.2737(2.3); 7.2542(2.1); 5.3373(7.9); 4.7326 (0.3); 4.2089(2.2); 4.1950(4.6); 4.1811(2.5); 3.4095(18.5); 3.3270(30.8); 2.9837(2.1); 2.9698(4.2); 2.9559(2.2); 2.6720(0.4); 2.5731 (16.0); 2.5070(47.5); 2.5029(61.3); 2.4987(48.0); 2.3296(0.4); −0.0002(41.4) |
| 17: $^1$H-NMR(400.0 MHz, d$_6$-DMSO): δ = 8.2363(2.0); 8.2351(2.0); 8.2136(2.2); 8.2124(2.2); 7.8066(1.6); 7.7851(3.2); 7.7646(1.2); 7.7589(1.0); 7.7384(1.1); 7.7052(3.3); 7.6877(1.6); 7.6825(3.2); 7.6679(2.1); 7.6468(1.3); 7.5581(2.0); 7.5379(1.7); 7.2605(1.9); 7.2413(1.8); 5.2740(6.6); 4.2559(1.9); 4.2421 (4.0); 4.2282(2.0); 3.4043(19.9); 3.3348(27.4); 2.9998(1.7); 2.9861(3.5); 2.9722(1.7); 2.5742(16.0); 2.5273(0.4); 2.5139(10.8); 2.5095 (22.1); 2.5050(29.0); 2.5005(21.1); 2.4961(10.3); 1.3968(0.4); 0.0079(0.5); −0.0002(15.7); −0.0084(0.5) |
| 18: $^1$H-NMR(400.0 MHz, d$_6$-DMSO): δ = 8.2408(2.2); 8.2181(2.4); 7.8110(1.7); 7.7894(2.4); 7.7145(1.8); 7.7070(3.4); 7.6932(4.6); 7.6844(3.3); 7.6725(2.3); 7.6511(4.5); 7.6302(1.7); 7.2630(2.1); 7.2436(1.9); 5.3214(7.4); 4.3047(0.4); 4.2884(0.4); 4.2748(2.0); 4.2609(4.3); 4.2468(2.2); 3.4152(19.1); 3.3319 (26.4); 3.0247(2.0); 3.0108(4.0); 2.9968(2.0); 2.6728(0.3); 2.5893(16.0); 2.5082(37.4); 2.5039(49.2); 2.4995(37.6); 1.9901(1.0); 1.1757(0.5); −0.0002(7.8) |
| 19: $^1$H-NMR(400.0 MHz, d$_6$-DMSO): δ = 8.2574(1.9); 8.2554(2.2); 8.2515(2.2); 8.1547(1.6); 8.1345(1.8); 8.1262(1.8); 8.1051(1.8); 7.7268(0.8); 7.7237(0.9); 7.7095(1.2); 7.7062(1.6); 7.7026(0.9); 7.6885(1.0); 7.6854(1.0); 7.6320(2.8); 7.6114(4.0); 7.6018(1.6); 7.5989(1.3); 7.5952(1.7); 7.5921(1.2); 7.5780 (2.1); 7.5727(1.6); 7.2083(2.6); 7.1873(2.4); 5.3679(4.5); 5.3640(4.6); 4.2478(2.0); 4.2340(4.1); 4.2203(2.1); 3.4127(19.5); 3.3195(8.5); 2.9877(1.8); 2.9741(3.7); 2.9602(1.9); 2.5724(16.0); 2.5254(0.6); 2.5121(12.1); 2.5078(24.4); 2.5033(32.1); 2.4988(23.8); 2.4944 (11.9); 2.0411(0.4); 0.0080(0.4); −0.0002(12.7); −0.0084(0.5) |
| 20: $^1$H-NMR(400.0 MHz, d$_6$-DMSO): δ = 8.2437(2.3); 8.2381(2.1); 8.1232(1.6); 8.1042(1.6); 7.8680(2.6); 7.8614(2.6); 7.6765(1.8); 7.6559(2.4); 7.6214(2.7); 7.5991(3.0); 7.5885(1.3); 7.5825(1.3); 7.5590(1.3); 7.5531(1.3); 7.5332(0.9); 7.5299(1.0); 7.5148(1.3); 7.5120(1.7); 7.4942(1.0); 7.4910(1.0); 7.4082 (1.1); 7.4063(1.2); 7.3875(1.9); 7.3708(0.8); 7.3687(0.9); 7.1882(1.7); 7.1815(1.6); 7.1659(1.5); 7.1592(1.5); 5.2391(4.2); 5.2344(4.4); 4.2428(1.9); 4.2291(4.0); 4.2153(2.1); 3.4087(20.5); 3.3180(40.5); 2.9839(1.8); 2.9703(3.6); 2.9566(1.8); 2.6753(0.5); 2.6708(0.6); 2.6664(0.5); 2.5693(16.0); 2.5499(0.4); 2.5241(1.8); 2.5106(36.0); 2.5062(74.9); 2.5017(104.0); 2.4972(79.2); 2.4928(39.7); 2.3331 (0.4); 2.3285(0.6); 2.3239(0.4); 1.2343(0.3); 0.0079(1.0); −0.0002(28.9); −0.0085(1.2) |
| 21: $^1$H-NMR(400.0 MHz, d$_6$-DMSO): δ = 8.2562(2.0); 8.2542(2.2); 8.2503(2.2); 8.1442(1.6); 8.1241(1.7); 8.0807(1.7); 8.0597(1.9); 7.8079(2.9); 7.7872(3.2); 7.7219(0.8); 7.7189(0.9); 7.7047(1.2); 7.7014(1.6); 7.6978(0.9); 7.6836(1.0); 7.6804(1.0); 7.6087(1.5); 7.6027(2.4); 7.5882(1.0); 7.5848(1.7); 7.5796 (1.7); 7.5732(1.4); 7.5673(0.9); 7.5645(0.8); 7.1682(2.6); 7.1473(2.4); 5.7551(0.5); 5.3679(4.3); 5.3639(4.4); 4.2470(1.9); 4.2332(4.0); 4.2194(2.0); 3.4113(20.4); 3.3185(33.7); 2.9867(1.8); 2.9731(3.5); 2.9594(1.7); 2.6759(0.4); 2.6712(0.5); 2.6667(0.4); 2.5713(16.0); 2.5245(1.5); 2.5111(30.8); 2.5067(63.0); 2.5021(86.4); 2.4976(64.8); 2.4932(31.8); 2.3334(0.4); 2.3290(0.5); 2.3243(0.4); 0.0080(0.8); −0.0001(23.0); −0.0083(0.9) |
| 22: $^1$H-NMR(400.0 MHz, d$_6$-DMSO): δ = 8.2575(2.3); 8.2531(2.4); 8.0842(2.2); 8.0615(2.5); 7.8056(1.7); 7.7842(2.6); 7.7031(1.6); 7.6833(2.3); 7.6593(3.7); 7.6365(3.1); 7.6107(1.4); 7.6047(1.3); 7.5811(1.4); 7.5752(1.4); 7.3719(2.2); 7.3525(1.9); 5.3891(4.6); 5.3853(4.7); 4.2479(2.0); 4.2342(4.2); 4.2204 (2.1); 3.4116(19.6); 3.3190(60.2); 2.9871(1.9); 2.9735(3.7); 2.9597(1.9); 2.6759(0.5); 2.6712(0.7); 2.6670(0.5); 2.5718(16.0); 2.5244 (2.2); 2.5108(43.8); 2.5066(86.7); 2.5022(117.2); 2.4978(89.0); 2.3336(0.5); 2.3291(0.7); 2.3247(0.5); 1.9000(0.4); 0.0079(1.3); −0.0001(31.9); −0.0081(1.4) |
| 23: $^1$H-NMR(400.0 MHz, d$_6$-DMSO): δ = 8.3749(1.1); 8.3699(0.8); 8.3622(1.1); 8.3522(1.1); 8.2536(2.2); 8.2495(2.2); 8.0976(2.3); 8.0914(2.4); 8.0051(1.2); 7.9985(0.8); 7.9950(1.2); 7.9876(0.9); 7.9828(1.3); 7.9751(0.3); 7.9183(2.6); 7.8964(2.8); 7.5962(1.3); 7.5902(1.2); 7.5668(1.3); 7.5608(1.2); 7.5275 (0.4); 7.5148(2.3); 7.5097(1.6); 7.5046(1.8); 7.5024(1.7); 7.4972(1.5); 7.4920(2.4); 7.4795(0.4); 7.2324(1.4); 7.2261(1.4); 7.2105(1.4); 7.2042(1.4); 5.7552(0.8); 5.2892(3.8); 5.2847(3.9); 4.2445(1.9); 4.2308(4.0); 4.2170(2.1); 3.4087(20.1); 3.3207(33.6); 2.9842(1.8); 2.9705(3.6); 2.9567(1.8); 2.8908(0.6); 2.7316(0.5); 2.6711(0.4); 2.5691(16.0); 2.5246(1.0); 2.5196(1.5); 2.5110(23.6); 2.5066(50.7); 2.5020(71.6); 2.4975(53.7); 2.4932(25.9); 2.3289(0.4); 2.3244(0.3); −0.0002(6.3) |

-continued

| Example |
|---|

24: $^1$H-NMR(400.0 MHz, d$_6$-DMSO): δ =
8.2584(2.4); 8.2542(2.4); 7.8974(1.9); 7.8764(2.1); 7.6321(1.4); 7.6105(3.6); 7.6041(1.6); 7.5802(1.4); 7.5741(1.6); 7.5698(1.9); 7.5502(2.2); 7.5295(1.1); 7.4767(0.6); 7.4622(0.8); 7.4570(1.3); 7.4426(1.2); 7.4364(0.9); 7.4221(0.8); 7.3719(1.2); 7.3541(0.8); 7.3456 (1.2); 7.3267(0.8); 7.3083(2.1); 7.2892(1.8); 5.7555(0.4); 5.3716(4.8); 5.3679(4.9); 4.2491(2.0); 4.2353(4.2); 4.2216(2.2); 3.4128(19.6); 3.3197(21.3); 2.9883(1.9); 2.9747(3.8); 2.9610(1.9); 2.6712(0.5); 2.6667(0.4); 2.5725(16.0); 2.5065(61.6); 2.5021(85.0); 2.4978 (64.4); 2.3334(0.4); 2.3290(0.5); −0.0002(6.4)

25: $^1$H-NMR(400.0 MHz, d$_6$-DMSO): δ =
8.3391(3.2); 8.3327(3.4); 8.1797(1.7); 8.1590(1.8); 8.1266(1.8); 8.1057(2.0); 7.7517(3.0); 7.7453(3.0); 7.7278(0.8); 7.7248(0.9); 7.7105 (1.2); 7.7073(1.6); 7.6895(1.0); 7.6865(1.0); 7.6266(2.9); 7.6184(1.2); 7.6157(1.2); 7.6059(3.3); 7.6015(1.2); 7.5979(1.7); 7.5801 (0.8); 7.5777(0.8); 7.1867(2.7); 7.1657(2.5); 5.3920(7.8); 4.2614(2.0); 4.2476(4.1); 4.2338(2.1); 3.4131(20.3); 3.3212(25.3); 2.9832 (1.8); 2.9695(3.7); 2.9558(1.8); 2.6719(0.4); 2.5710(16.0); 2.5249(1.0); 2.5114(23.1); 2.5070(49.0); 2.5024(68.8); 2.4980(51.6); 2.4938 (25.0); 2.3293(0.4); 0.0079(0.4); −0.0002(10.7); −0.0085(0.4)

26: $^1$H-NMR(400.0 MHz, d$_6$-DMSO): δ =
8.3409(3.2); 8.3345(3.4); 8.3152(0.4); 8.1070(2.3); 8.0844(2.6); 7.8031(1.8); 7.7815(2.7); 7.7538(3.0); 7.7475(3.1); 7.6984(1.6); 7.6784(2.4); 7.6648(3.5); 7.6575(1.5); 7.6421(3.1); 7.3507(2.2); 7.3316(2.0); 5.4132(8.0); 4.2614(2.0); 4.2477(4.2); 4.2341(2.2); 3.4127 (19.5); 3.3192(21.4); 2.9827(2.0); 2.9690(3.9); 2.9555(1.9); 2.6712(0.9); 2.5708(16.0); 2.5062(110.3); 2.5019(150.1); 2.4976(115.0); 2.3328(0.6); 2.3291(0.7); 0.0077(0.8); −0.0002(20.4)

27: $^1$H-NMR(400.0 MHz, d$_6$-DMSO): δ =
8.2420(2.7); 8.2368(2.6); 8.1482(1.9); 8.1259(4.1); 8.1045(2.3); 8.0787(0.6); 7.7272(0.9); 7.7246(1.0); 7.7069(1.8); 7.6891(1.1); 7.6863(1.2); 7.6318(3.1); 7.6112(3.9); 7.5965(1.8); 7.5761(2.4); 7.5524(1.4); 7.5465(1.5); 7.2055(3.0); 7.1845(2.7); 5.3686(5.1); 5.3651 (5.4); 4.5718(1.0); 4.3877(1.5); 4.2425(2.2); 4.2289(4.4); 4.2153(2.3); 3.8070(10.2); 3.3200(44.7); 3.0008(2.4); 2.8201(2.3); 2.8152 (2.4); 2.8066(4.3); 2.7931(2.2); 2.6710(0.7); 2.6666(0.6); 2.5241(1.7); 2.5062(88.9); 2.5017(126.0); 2.4974(99.5); 2.3413(16.0); 2.3289 (1.0); 2.2877(0.4); 0.0079(1.8); −0.0003(55.6); −0.0082(2.5)

28: $^1$H-NMR(400.0 MHz, d$_6$-DMSO): δ =
8.2459(2.6); 8.2408(2.7); 8.0776(2.6); 8.0549(2.9); 7.8046(1.9); 7.7832(2.9); 7.7018(1.8); 7.6818(2.6); 7.6614(5.2); 7.6389(3.4); 7.5845(1.5); 7.5786(1.5); 7.5550(1.5); 7.5491(1.5); 7.3692(2.5); 7.3496(2.2); 5.3903(5.1); 5.3868(5.2); 4.2442(2.3); 4.2307(4.4); 4.2171 (2.3); 3.8084(10.6); 3.3201(14.6); 2.8214(2.3); 2.8079(4.2); 2.7943(2.2); 2.6761(0.4); 2.6717(0.6); 2.6678(0.4); 2.5247(1.3); 2.5069 (68.8); 2.5026(94.4); 2.4983(71.4); 2.3426(16.0); 2.3298(0.8); 0.0078(1.2); −0.0002(33.8); −0.0077(1.4)

29: $^1$H-NMR(400.0 MHz, d$_6$-DMSO): δ =
8.2324(2.5); 8.2271(2.7); 8.1230(1.9); 8.1039(2.1); 7.8677(3.1); 7.8611(3.2); 7.6765(2.2); 7.6559(2.9); 7.6209(3.2); 7.5985(3.6); 7.5629(1.5); 7.5570(1.5); 7.5333(2.5); 7.5294(2.0); 7.5124(2.0); 7.4942(1.1); 7.4914(1.1); 7.4078(1.5); 7.3888(2.4); 7.3705(1.1); 7.1869 (1.8); 7.1803(1.8); 7.1646(1.7); 7.1580(1.7); 5.7549(0.4); 5.2407(5.0); 5.2364(5.2); 4.2388(2.2); 4.2253(4.3); 4.2117(2.3); 3.8055(10.4); 3.3197(18.6); 2.8180(2.2); 2.8045(4.2); 2.7909(2.2); 2.6757(0.5); 2.6714(0.6); 2.6671(0.5); 2.5245(1.5); 2.5066(79.4); 2.5022(109.8); 2.4979(82.8); 2.3404(16.0); 2.3290(1.2); 0.0079(1.3); −0.0002(39.8); −0.0079(1.6)

30: $^1$H-NMR(400.0 MHz, CDCl$_3$): δ =
8.2065(2.0); 8.1997(2.0); 7.9262(1.5); 7.9069(1.6); 7.5833(2.4); 7.5768(2.5); 7.5423(1.4); 7.5217(2.2); 7.4626(2.3); 7.4559(1.0); 7.4536(0.9); 7.4401(3.2); 7.4172(0.8); 7.3375(1.2); 7.3184(1.8); 7.3000(0.8); 7.2610(7.7); 7.1522(1.4); 7.1457(1.4); 7.1299(1.3); 7.1233 (1.4); 7.1162(1.9); 7.1096(1.8); 5.2523(8.4); 4.2062(1.4); 4.1927(2.7); 4.1790(1.5); 3.8629(0.5); 3.5287(16.0); 3.0459(1.9); 3.0323(3.8); 3.0186(1.9); 2.6759(14.0); 2.4599(11.8); 2.0045(1.6); 1.6104(5.7); −0.0002(5.0)

31: $^1$H-NMR(400.0 MHz, CDCl$_3$): δ =
8.3769(2.0); 8.3697(2.1); 7.9042(1.4); 7.8849(1.5); 7.5447(1.4); 7.5240(2.1); 7.5073(2.3); 7.5008(3.9); 7.4777(3.7); 7.4551(3.2); 7.4396(1.4); 7.4369(1.4); 7.4192(0.8); 7.4161(0.7); 7.3344(1.1); 7.3154(1.7); 7.3006(1.5); 7.2945(1.7); 7.2793(1.1); 7.2720(1.1); 7.2611 (7.1); 7.1498(1.4); 7.1432(1.3); 7.1275(1.2); 7.1209(1.2); 5.2499(7.4); 4.2145(1.3); 4.2009(2.7); 4.1872(1.5); 3.5300(16.0); 3.5175(0.4); 3.4761(0.4); 3.0549(2.0); 3.0412(3.7); 3.0274(1.9); 2.9545(1.1); 2.8839(1.1); 2.6793(14.1); 1.6102(4.4); 1.2555(0.6); 0.9208(0.6); −0.0002(3.6)

32: $^1$H-NMR(400.0 MHz, d$_6$-DMSO): δ =
8.2239(2.2); 8.2196(2.2); 8.0771(2.1); 8.0544(2.3); 7.8029(1.6); 7.7815(2.3); 7.7006(1.5); 7.6807(2.1); 7.6591(4.2); 7.6363(2.8); 7.5745(1.2); 7.5687(1.3); 7.5449(1.2); 7.5391(1.2); 7.3669(2.0); 7.3476(1.8); 5.3842(4.2); 5.3808(4.4); 4.1683(1.9); 4.1533(4.1); 4.1383 (2.0); 3.3230(39.8); 2.8013(1.8); 2.7865(3.8); 2.7714(1.8); 2.6720(0.4); 2.6675(0.3); 2.5675(2.1); 2.5497(6.7); 2.5319(7.2); 2.5071(57.4); 2.5027(75.6); 2.4983(56.7); 2.3294(0.4); 2.3249(0.3); 0.9792(7.8); 0.9615(16.0); 0.9437(7.5); 0.0078(2.3); −0.0002(54.0); −0.0081(2.7)

33: $^1$H-NMR(400.0 MHz, d$_6$-DMSO): δ =
8.3143(3.0); 8.3071(3.0); 8.2285(2.6); 8.2058(2.9); 7.7954(2.1); 7.7739(3.0); 7.6976(3.9); 7.6800(2.1); 7.6750(3.9); 7.6602(2.7); 7.6392(1.5); 7.5932(2.2); 7.5718(3.2); 7.4760(1.9); 7.4687(1.9); 7.4546(1.4); 7.4472(1.4); 7.2663(2.5); 7.2470(2.3); 5.3328(8.9); 4.1265 (2.1); 4.1114(4.3); 4.0963(2.2); 3.3268(102.8); 2.7997(1.6); 2.7846(3.0); 2.7697(1.5); 2.6765(0.4); 2.6718(0.5); 2.6677(0.4); 2.5726 (1.8); 2.5549(5.0); 2.5371(5.4); 2.5074(65.8); 2.5030(86.3); 2.4986(64.2); 2.3344(0.4); 2.3296(0.5); 2.3253(0.4); 0.9853(8.0); 0.9676 (16.0); 0.9498(7.7); 0.0076(2.2); −0.0001(50.7); −0.0082(2.6)

34: $^1$H-NMR(400.0 MHz, d$_6$-DMSO): δ =
8.2074(0.9); 8.1210(0.7); 8.1021(0.8); 8.0766(0.5); 8.0541(0.5); 7.8635(1.2); 7.8571(1.2); 7.8031(0.4); 7.7817(0.6); 7.6999(0.4); 7.6769(1.0); 7.6559(1.2); 7.6377(0.6); 7.6192(1.2); 7.5968(1.3); 7.5330(1.0); 7.5115(0.2); 7.4939(0.5); 7.4073(0.6); 7.3882(0.9); 7.3672 (0.6); 7.3459(0.4); 7.1854(0.7); 7.1788(0.7); 7.1631(0.6); 7.1564(0.6); 5.3846(1.0); 5.2348(1.8); 5.2313(1.8); 4.1224(0.8); 4.1071(1.5); 4.0917(0.8); 3.3215(25.5); 2.7331(0.8); 2.7181(1.6); 2.7032(0.8); 2.6714(0.4); 2.5066(49.3); 2.5022(63.5); 2.4978(46.9); 2.3292(0.4); 2.2264(5.6); 1.0064(16.0); 0.0078(3.0); −0.0002(61.6); −0.0085(2.8)

35: $^1$H-NMR(400.0 MHz, d$_6$-DMSO): δ =
8.2924(1.1); 8.2875(1.1); 8.1219(0.8); 8.1029(0.9); 7.8707(1.2); 7.8642(1.3); 7.6815(0.9); 7.6604(1.2); 7.6352(0.6); 7.6269(1.6); 7.6045(1.8); 7.5363(0.4); 7.5180(0.8); 7.4992(0.4); 7.4123(0.6); 7.3934(1.0); 7.3746(0.5); 7.1862(0.7); 7.1798(0.7); 7.1638(0.7); 7.1572 (0.7); 5.2718(2.1); 5.2686(2.1); 4.5248(0.8); 4.5135(1.3); 4.5012(0.7); 3.7673(0.3); 3.3262(45.3); 2.8103(2.7); 2.7981(2.7); 2.6719(0.3); 2.5066(46.0); 2.5025(59.6); 2.4984(45.0); 2.3293(0.4); 1.3683(16.0); 0.0074(2.5); −0.0002(48.8); −0.0071(2.7)

36: $^1$H-NMR(400.0 MHz, d$_6$-DMSO): δ =
8.2188(1.1); 8.2144(1.1); 8.0759(1.0); 8.0532(1.2); 7.8031(0.8); 7.7816(1.2); 7.7000(0.8); 7.6800(1.1); 7.6602(2.0); 7.6378(1.4); 7.5625(0.6); 7.5566(0.6); 7.5326(0.6); 7.5268(0.6); 7.3651(1.0); 7.3459(0.9); 5.3811(2.2); 4.1263(0.8); 4.1109(1.6); 4.0956(0.8); 3.3230 (51.0); 2.7359(0.7); 2.7206(1.4); 2.7050(0.7); 2.6712(0.4); 2.5064(54.4); 2.5021(71.6); 2.4977(54.5); 2.3288(0.4); 2.2272(4.9); 1.0083 (16.0); 0.0077(2.8); −0.0003(64.9)

37: $^1$H-NMR(400.0 MHz, d$_6$-DMSO): δ =
9.6357(0.4); 8.3034(1.2); 8.2990(1.2); 8.0670(1.2); 8.0443(1.3); 7.8101(1.0); 7.7885(1.4); 7.7061(0.8); 7.6863(1.3); 7.6764(1.9); 7.6653(0.8); 7.6537(2.2); 7.6362(0.5); 7.6235(1.3); 7.3742(1.2); 7.3549(1.0); 5.5570(0.8); 5.4187(2.5); 5.2320(0.6); 4.5213(1.4); 4.5096

-continued (1.0); 3.8081(0.4); 3.7953(0.4); 3.7817(0.4); 3.7708(0.4); 3.3260(52.0); 2.8122(2.7); 2.8002(2.9); 2.6758(0.3); 2.6716(0.4); 2.5068 (60.7); 2.5024(79.5); 2.4980(60.3); 2.3292(0.4); 2.3249(0.4); 1.3720(16.0); 0.1460(0.3); 0.0077(3.4); −0.0002(73.8); −0.0083(4.0); −0.1498(0.3)

38: $^1$H-NMR(400.0 MHz, d$_6$-DMSO): δ =
8.2372(0.9); 8.2319(0.9); 8.0784(0.8); 8.0557(0.9); 7.8028(0.6); 7.7813(0.9); 7.7006(0.6); 7.6802(0.8); 7.6587(1.5); 7.6358(1.0); 7.5627(0.5); 7.5570(0.5); 7.5331(0.5); 7.5273(0.5); 7.3661(0.8); 7.3467(0.7); 5.3820(1.8); 4.1287(0.7); 4.1143(1.5); 4.0997(0.8); 3.3241 (13.0); 2.8546(0.8); 2.5075(17.2); 2.5032(22.8); 2.4989(17.5); 1.0437(16.0); 0.9913(0.4); −0.0002(15.9)

39: $^1$H-NMR(400.0 MHz, d$_6$-DMSO): δ =
8.2072(1.3); 8.2029(1.3); 8.0748(1.2); 8.0521(1.4); 7.8022(0.9); 7.7808(1.4); 7.6993(0.9); 7.6794(1.2); 7.6582(2.5); 7.6355(1.6); 7.5510(0.7); 7.5451(0.7); 7.5214(0.7); 7.5157(0.7); 7.3653(1.2); 7.3460(1.0); 5.3819(2.6); 5.3787(2.6); 4.0399(1.0); 4.0231(2.1); 4.0064 (1.1); 3.3234(48.2); 3.0440(0.4); 3.0275(1.1); 3.0111(1.5); 2.9948(1.1); 2.9781(0.4); 2.8059(1.1); 2.7892(2.1); 2.7724(1.0); 2.6717(0.3); 2.5069(46.3); 2.5026(59.2); 2.4983(44.7); 2.3292(0.3); 0.9833(16.0); 0.9670(15.8); −0.0002(29.6)

40: $^1$H-NMR(400.0 MHz, d$_6$-DMSO): δ =
8.1954(1.2); 8.1908(1.2); 8.1205(0.9); 8.1020(1.0); 7.8628(1.4); 7.8562(1.5); 7.6764(1.0); 7.6559(1.4); 7.6190(1.5); 7.5966(1.7); 7.5295(1.2); 7.5235(0.8); 7.5118(1.0); 7.4999(0.8); 7.4939(1.2); 7.4060(0.7); 7.3875(1.1); 7.3694(0.5); 7.1840(0.9); 7.1774(0.9); 7.1617 (0.8); 7.1551(0.8); 5.2327(2.4); 5.2283(2.5); 4.0363(1.0); 4.0196(2.1); 4.0027(1.0); 3.3223(30.4); 3.0419(0.4); 3.0257(1.1); 3.0093(1.5); 2.9929(1.1); 2.9766(0.4); 2.8025(1.1); 2.7858(2.1); 2.7691(1.0); 2.5067(39.0); 2.5023(51.5); 2.4979(38.6); 0.9816(16.0); 0.9653 (15.7); 0.0078(1.4); −0.0002(34.1); −0.0081(1.5)

41: $^1$H-NMR(400.0 MHz, d$_6$-DMSO): δ =
8.3156(0.4); 8.2202(8.0); 8.2161(7.8); 8.1213(5.7); 8.1022(5.9); 7.8651(9.3); 7.8585(9.5); 7.6760(6.6); 7.6555(8.5); 7.6193(9.5); 7.5969(10.7); 7.5597(4.6); 7.5538(4.6); 7.5297(7.7); 7.5243(5.1); 7.5113(6.1); 7.4936(3.3); 7.4904(3.4); 7.4055(4.5); 7.3869(7.0); 7.3680 (3.2); 7.1846(5.7); 7.1780(5.7); 7.1623(5.2); 7.1556(5.4); 5.2350(15.4); 5.2305(16.0); 4.2097(7.0); 4.1952(14.8); 4.1806(7.3); 3.3241 (469.6); 2.6765(7.5); 2.6709(4.5); 2.6623(13.8); 2.6478(6.3); 2.5240(6.8); 2.5105(130.9); 2.5062(266.3); 2.5017(357.5); 2.4972 (267.6); 2.4928(135.0); 2.4181(10.1); 2.3515(0.4); 2.3449(0.5); 2.3328(1.6); 2.3284(2.2); 2.3240(1.6); 1.5094(2.9); 1.4951(8.0); 1.4810 (12.8); 1.4677(10.6); 1.4543(4.5); 1.3924(2.4); 1.3779(4.7); 1.3648(5.1); 0.1455(2.0); 0.0075(17.1); −0.0006(444.8); −0.0088(19.9); −0.1503(2.0)

42: $^1$H-NMR(601.6 MHz, d$_6$-DMSO): δ =
19.9783(1.6); 8.2312(7.6); 8.2281(7.5); 8.0748(8.2); 8.0596(9.0); 7.7987(7.0); 7.7844(9.2); 7.6920(6.5); 7.6789(8.5); 7.6648(5.8); 7.6517(13.7); 7.6367(13.3); 7.5695(4.5); 7.5655(4.4); 7.5498(4.5); 7.5459(4.4); 7.3627(7.7); 7.3500(7.1); 5.7506(1.5); 5.3847(16.0); 5.3821(15.9); 4.2114(4.2); 4.2024(8.3); 4.1927(4.4); 3.3067(438.5); 2.6661(6.0); 2.6130(2.3); 2.5223(3.9); 2.5191(4.7); 2.5161(4.4); 2.5073(132.5); 2.5042(290.9); 2.5012(411.2); 2.4981(292.1); 2.4951(133.3); 2.4207(6.4); 2.3855(2.9); 1.4915(6.6); 1.4822(9.8); 1.4730 (8.0); 1.3697(4.0); 0.0964(1.7); 0.0052(13.0); −0.0002(462.9); −0.0057(14.5); −0.1000(1.8)

43: $^1$H-NMR(400.0 MHz, d$_6$-DMSO): δ =
8.2123(2.2); 8.2083(2.3); 8.1219(1.6); 8.1037(1.7); 7.8660(2.5); 7.8595(2.6); 7.6768(1.8); 7.6563(2.3); 7.6205(2.6); 7.5982(2.8); 7.5483(1.3); 7.5425(1.3); 7.5333(0.9); 7.5301(1.0); 7.5186(1.5); 7.5126(2.9); 7.4943(0.9); 7.4912(0.9); 7.4063(1.2); 7.3878(2.0); 7.3689 (0.9); 7.1866(1.6); 7.1800(1.5); 7.1643(1.4); 7.1576(1.4); 5.2348(4.3); 5.2303(4.6); 4.1569(1.9); 4.1419(4.2); 4.1269(2.0); 3.3246(61.2); 2.8417(0.4); 2.8256(1.0); 2.8093(1.3); 2.7928(1.0); 2.7764(0.4); 2.7314(1.8); 2.7164(3.6); 2.7015(1.7); 2.6715(0.4); 2.5070(47.6); 2.5025(63.5); 2.4981(48.7); 2.3290(0.4); 2.2011(13.7); 0.9526(16.0); 0.9362(15.8); 0.1461(0.3); 0.0077(3.3); −0.0003(70.5); −0.1496(0.3)

44: $^1$H-NMR(601.6 MHz, d$_6$-DMSO): δ =
8.2221(2.1); 8.2194(2.0); 8.0750(2.0); 8.0599(2.2); 7.7991(1.7); 7.7848(2.3); 7.6921(1.6); 7.6790(2.1); 7.6649(1.4); 7.6527(3.6); 7.6377(3.4); 7.5565(1.2); 7.5525(1.2); 7.5369(1.2); 7.5329(1.2); 7.3619(1.9); 7.3493(1.8); 5.3839(4.1); 5.3812(4.1); 4.1572(1.9); 4.1472 (4.1); 4.1373(2.0); 3.3061(60.1); 2.8332(0.3); 2.8224(0.8); 2.8113(1.1); 2.8006(0.8); 2.7900(0.3); 2.7309(1.4); 2.7209(2.9); 2.7108(1.4); 2.6130(0.5); 2.5224(0.9); 2.5192(1.0); 2.5162(1.0); 2.5074(29.5); 2.5044(64.4); 2.5013(90.7); 2.4983(64.0); 2.4952(29.0); 2.3855 (0.5); 2.2033(11.7); 0.9525(16.0); 0.0965(0.4); 0.0053(3.2); −0.0002(108.5); −0.0057(3.3); −0.1003(0.4)

45: $^1$H-NMR(400.0 MHz, d$_6$-DMSO): δ =
9.8139(0.6); 8.3462(0.3); 8.2000(5.2); 8.0747(5.3); 8.0520(5.9); 7.9530(0.4); 7.7919(3.9); 7.7705(5.8); 7.6953(3.7); 7.6754(5.1); 7.6525(8.6); 7.6295(6.6); 7.5328(0.4); 7.3693(5.0); 7.3501(4.4); 7.3249(2.5); 7.3195(2.4); 7.2912(2.6); 7.2859(2.4); 5.3230(10.9); 5.3199 (11.0); 3.5125(0.6); 3.5000(0.7); 3.4877(0.6); 3.4221(0.3); 3.4081(0.4); 3.3219(219.8); 3.3084(8.2); 3.2958(9.4); 3.2832(7.1); 3.2416 (0.5); 3.2279(0.4); 2.8908(2.3); 2.7316(2.0); 2.6755(1.3); 2.6709(1.8); 2.6665(1.3); 2.5241(6.9); 2.5108(110.7); 2.5064(218.3); 2.5019 (286.9); 2.4974(212.0); 2.4931(107.5); 2.4745(8.6); 2.3956(1.9); 2.3775(5.4); 2.3595(5.6); 2.3415(2.2); 2.3334(1.9); 2.3287(2.0); 2.3242(1.4); 2.3090(0.5); 2.3019(0.5); 2.0226(0.4); 1.2980(0.9); 1.2855(0.4); 1.2580(1.3); 1.2487(0.4); 1.2331(0.5); 1.0503(7.8); 1.0324 (16.0); 1.0145(7.6); 0.1457(0.6); 0.0076(5.0); −0.0004(125.4); −0.0086(5.1); −0.1498(0.6)

46: $^1$H-NMR(400.0 MHz, d$_6$-DMSO): δ =
9.9870(1.3); 8.3450(0.6); 8.3393(0.8); 8.1868(3.1); 8.1656(0.5); 8.1451(0.5); 8.1203(2.3); 8.1024(2.4); 7.9529(2.4); 7.8917(0.7); 7.8852(0.7); 7.8599(3.7); 7.8534(3.9); 7.7514(0.7); 7.7292(0.8); 7.7220(0.5); 7.7016(0.7); 7.6748(2.7); 7.6542(3.4); 7.6133(4.0); 7.5909 (4.2); 7.5432(0.6); 7.5310(1.3); 7.5277(1.5); 7.5099(2.4); 7.4921(1.4); 7.4889(1.3); 7.4589(0.6); 7.4051(1.9); 7.3865(3.0); 7.3675(1.4); 7.3347(0.5); 7.3101(1.6); 7.3046(1.7); 7.2772(1.8); 7.2713(1.9); 7.2561(0.5); 7.2496(0.4); 7.1770(2.3); 7.1704(2.2); 7.1617(0.6); 7.1547(2.0); 7.1480(2.0); 7.1295(0.4); 6.6915(0.5); 6.6860(0.5); 5.1773(6.2); 5.1735(6.4); 4.0380(0.4); 4.0202(0.4); 3.3232(111.6); 3.2989 (4.4); 3.2869(5.5); 3.2742(4.4); 3.1834(0.4); 3.1717(0.4); 3.1590(0.3); 2.8906(2.0); 2.7312(14.2); 2.6756(0.6); 2.6712(0.9); 2.6666 (0.7); 2.5107(57.8); 2.5065(115.6); 2.5021(153.8); 2.4976(113.4); 2.4933(58.0); 2.4166(0.9); 2.3950(1.7); 2.3773(3.3); 2.3593(3.2); 2.3407(1.5); 2.3335(1.2); 2.3289(1.3); 2.3239(1.4); 2.3085(0.8); 2.3047(0.9); 2.0229(0.4); 1.9890(1.6); 1.9093(0.3); 1.7677(0.6); 1.2983 (0.4); 1.2582(0.6); 1.1927(0.4); 1.1749(0.8); 1.1572(0.4); 1.0487(5.3); 1.0308(10.9); 1.0128(5.1); 0.9946(1.0); 0.9908(0.8); 0.9849(0.5); 0.9769(1.7); 0.9589(0.8); −0.0002(9.0)

47: $^1$H-NMR(400.0 MHz, d$_6$-DMSO): δ =
8.1917(2.5); 8.1869(2.5); 7.6312(3.3); 7.6181(4.5); 7.5419(3.0); 7.5357(1.7); 7.5118(1.4); 7.5058(1.4); 7.4287(1.1); 7.2980(1.3); 7.2751(1.9); 7.2492(1.8); 7.2452(1.6); 7.2373(1.6); 7.2291(1.4); 7.2212(1.4); 7.1122(0.9); 7.1031(1.4); 7.0944(0.9); 7.0899(0.8); 7.0807 (1.1); 7.0720(0.6); 5.2010(4.8); 5.1969(5.0); 4.1566(2.0); 4.1417(4.2); 4.1267(2.0); 3.3220(64.4); 2.7917(1.8); 2.7770(3.4); 2.7621(1.7); 2.6713(0.7); 2.6666(0.6); 2.5609(2.0); 2.5431(6.2); 2.5251(8.3); 2.5065(97.0); 2.5021(125.6); 2.4978(93.4); 2.3334(0.5); 2.3290(0.7); 2.3246(0.5); 1.2327(0.4); 0.9732(7.9); 0.9555(16.0); 0.9377(7.6); 0.1461(0.4); 0.0076(3.8); −0.0003(86.7); −0.0078(4.0); −0.1496(0.4)

48: $^1$H-NMR(400.0 MHz, d$_6$-DMSO): δ =
8.2215(2.6); 8.2198(2.7); 8.2161(2.6); 7.6364(0.8); 7.6306(0.4); 7.6167(1.8); 7.5947(1.6); 7.5789(1.5); 7.5733(1.3); 7.5494(1.5); 7.5438(1.3); 7.5030(4.0); 7.4813(3.3); 7.4408(4.4); 7.4243(1.3); 7.1504(2.2); 7.1433(3.3); 7.1292(2.1); 7.1216(1.0); 7.1074(1.6); 7.0998 (1.1); 5.2043(5.2); 4.2338(2.1); 4.2203(4.3); 4.2065(2.2); 3.4021(19.5); 3.3195(13.8); 2.9769(2.0); 2.9633(4.0); 2.9497(2.0); 2.8912 (0.6); 2.7320(0.6); 2.6710(0.6); 2.5643(16.0); 2.5062(90.2); 2.5020(103.9); 2.4977(70.8); 2.3288(0.6); 0.0000(7.0)

-continued

| Example |
|---|
| 49: $^1$H-NMR(400.0 MHz, d$_6$-DMSO): δ = 8.2284(2.4); 8.2243(2.4); 7.6277(2.5); 7.5787(1.4); 7.5729(1.4); 7.5495(1.9); 7.5430(2.0); 7.5322(3.0); 7.5133(2.9); 7.4960(2.8); 7.4911(2.6); 7.4858(1.2); 7.4777(0.5); 7.4727(0.6); 7.4675(0.4); 7.2864(1.2); 7.2636(1.8); 7.2378(1.6); 7.2317(1.4); 7.2239(1.5); 7.2157 (1.3); 7.2079(1.4); 7.0972(0.8); 7.0882(1.3); 7.0795(0.9); 7.0748(0.8); 7.0659(1.0); 7.0573(0.6); 5.1994(4.8); 5.1955(4.8); 4.2356(2.1); 4.2219(4.2); 4.2081(2.2); 4.0379(0.3); 3.4030(19.0); 3.3178(17.8); 2.9779(2.0); 2.9643(3.9); 2.9506(1.9); 2.6748(0.4); 2.6707(0.5); 2.6662(0.4); 2.5649(16.0); 2.5059(70.7); 2.5016(90.3); 2.4974(67.2); 2.3328(0.4); 2.3284(0.6); 1.9887(1.3); 1.3975(2.0); 1.1925(0.4); 1.1748(0.7); 1.1569(0.3); −0.0002(55.6) |
| 50: $^1$H-NMR(400.0 MHz, d$_6$-DMSO): δ = 8.3105(0.6); 8.2279(2.2); 8.2237(2.2); 7.6330(3.0); 7.6202(3.8); 7.5792(1.3); 7.5733(1.3); 7.5499(3.1); 7.5446(2.1); 7.4409(0.6); 7.4305(1.0); 7.4150(0.5); 7.3015(1.2); 7.2788(1.7); 7.2758(1.5); 7.2526(1.9); 7.2424(1.4); 7.2342(1.2); 7.2264(1.3); 7.1183(0.8); 7.1090 (1.2); 7.1006(0.8); 7.0958(0.7); 7.0868(0.9); 7.0782(0.5); 5.2072(4.1); 5.2032(4.2); 4.2370(1.9); 4.2233(4.0); 4.2095(2.0); 4.0399(0.6); 4.0221(0.6); 3.4049(19.8); 3.3230(5.3); 2.9796(1.8); 2.9660(3.7); 2.9522(1.8); 2.5667(16.0); 2.5267(0.4); 2.5132(8.7); 2.5089(17.9); 2.5044(23.6); 2.4999(17.2); 2.4956(8.5); 1.9903(2.5); 1.3968(6.3); 1.1940(0.7); 1.1762(1.3); 1.1584(0.7); 0.0079(0.8); −0.0002(22.0); −0.0084(0.8) |
| 51: $^1$H-NMR(400.0 MHz, d$_6$-DMSO): δ = 8.1869(1.0); 8.1828(1.0); 7.6309(1.4); 7.6178(1.9); 7.5447(0.9); 7.5284(0.6); 7.5231(0.6); 7.4993(0.6); 7.4932(0.6); 7.4287(0.5); 7.2967(0.5); 7.2739(0.8); 7.2709(0.7); 7.2479(0.8); 7.2450(0.7); 7.2363(0.7); 7.2280(0.6); 7.2203(0.6); 7.1112(0.4); 7.1020(0.6); 7.0935 (0.4); 7.0888(0.3); 7.0798(0.5); 5.2007(2.0); 5.1968(2.0); 4.1153(0.7); 4.0995(1.5); 4.0841(0.8); 3.3214(27.8); 2.7259(0.7); 2.7103(1.4); 2.6949(0.7); 2.6710(0.4); 2.5064(44.2); 2.5020(58.1); 2.4976(43.3); 2.3287(0.3); 2.2201(5.0); 1.0006(16.0); 0.0078(1.4); −0.0002(33.0); −0.0079(1.6) |
| 52: $^1$H-NMR(601.6 MHz, CDCl$_3$): δ = 8.2606(1.7); 8.2455(1.8); 7.8618(1.6); 7.8475(1.7); 7.5069(1.2); 7.5011(2.6); 7.4936(1.8); 7.4861(2.4); 7.4797(1.2); 7.2589(26.6); 7.1854(1.7); 7.1718(2.0); 7.0330(2.2); 7.0193(1.9); 6.9921(1.7); 6.9793(1.6); 5.3152(6.8); 4.2239(1.9); 4.2140(4.0); 4.2041(2.0); 3.5268 (16.0); 3.1054(2.2); 3.0956(4.4); 3.0857(2.1); 2.6824(14.6); 2.5371(15.1); 1.5443(15.4); 1.2554(1.0); 0.0691(3.3); 0.0051(0.6); −0.0002(16.0); −0.0056(0.7) |
| 53: $^1$H-NMR(400.0 MHz, d$_6$-DMSO): δ = 8.2352(2.6); 8.2294(2.8); 7.7460(1.4); 7.7261(1.9); 7.6561(2.4); 7.6161(1.6); 7.5960(2.8); 7.5812(1.7); 7.5759(2.8); 7.5519(1.4); 7.5462(1.4); 7.4251(1.1); 7.4055(2.7); 7.3844(4.0); 7.3784(3.9); 7.3629(1.2); 7.3073(2.0); 7.2885(1.4); 7.0919(1.4); 7.0860(1.4); 7.0716 (1.3); 7.0654(1.3); 5.2406(4.9); 5.2372(5.0); 4.2383(2.2); 4.2246(4.4); 4.2109(2.3); 3.4048(18.8); 3.3206(40.4); 2.9804(2.0); 2.9668 (4.1); 2.9530(2.0); 2.6715(0.5); 2.5666(16.0); 2.5064(63.4); 2.5023(84.2); 2.3289(0.5); −0.0002(5.2) |
| 54: $^1$H-NMR(400.0 MHz, d$_6$-DMSO): δ = 8.2232(2.2); 8.2191(2.2); 7.5725(1.3); 7.5665(1.3); 7.5430(1.3); 7.5371(1.2); 7.3059(3.0); 7.2840(3.3); 6.7956(2.4); 6.7888(2.6); 6.6528(1.6); 6.6460(1.4); 6.6310(1.4); 6.6241(1.4); 5.1373(4.3); 5.1328(4.3); 4.2323(1.9); 4.2185(4.0); 4.2047(2.0); 4.1110(1.1); 4.0936 (3.6); 4.0761(3.6); 4.0587(1.1); 3.4042(20.4); 3.3208(28.5); 2.9767(1.8); 2.9630(3.6); 2.9494(1.8); 2.6710(0.3); 2.5655(16.0); 2.5242 (1.2); 2.5106(23.4); 2.5063(47.5); 2.5018(62.6); 2.4973(44.7); 2.4930(21.5); 2.3286(0.4); 1.9888(1.0); 1.3517(3.8); 1.3343(8.0); 1.3169 (3.7); 1.1749(0.5); 0.0079(2.6); −0.0003(66.7); −0.0085(2.8) |
| 55: $^1$H-NMR(400.0 MHz, d$_6$-DMSO): δ = 8.2290(2.0); 8.2248(2.1); 8.2116(0.6); 7.5788(1.2); 7.5729(1.2); 7.5538(0.6); 7.5495(1.3); 7.5433(1.4); 7.5354(1.1); 7.5189(1.1); 7.5144(0.7); 7.4996(0.8); 7.4299(2.5); 7.4270(2.1); 7.4078(1.8); 7.2865(1.2); 7.2821(0.7); 7.2773(0.6); 7.2730(0.6); 7.2637(1.8); 7.2603 (2.3); 7.2530(1.0); 7.2379(1.9); 7.2296(1.6); 7.2215(1.3); 7.2133(1.2); 7.2055(1.3); 7.0988(0.8); 7.0895(1.2); 7.0810(0.8); 7.0762(0.7); 7.0675(0.9); 7.0587(0.6); 5.1970(4.0); 5.1924(4.2); 4.2353(1.9); 4.2215(3.9); 4.2077(2.0); 3.4034(20.3); 3.3187(11.7); 2.9779(1.8); 2.9642(3.5); 2.9504(1.7); 2.5651(16.0); 2.5243(0.8); 2.5194(1.3); 2.5109(19.8); 2.5065(41.0); 2.5019(54.3); 2.4974(39.0); 2.4930(18.9); 2.3286(0.3); 1.3974(0.8); 0.0079(1.4); −0.0002(43.1); −0.0085(1.6) |
| 56: $^1$H-NMR(400.0 MHz, d$_6$-DMSO): δ = 8.2224(2.2); 8.2182(2.2); 7.5789(1.2); 7.5730(1.3); 7.5494(1.3); 7.5435(1.3); 7.5050(2.8); 7.4990(4.8); 7.4917(5.7); 7.4884(5.6); 7.4797(0.6); 7.4745(0.5); 7.4661(3.0); 7.4282(1.2); 7.4236(1.2); 7.4208(1.2); 7.4139(1.0); 7.4085(0.9); 7.4054(0.7); 7.4023(0.7); 7.1313 (1.9); 7.1240(3.3); 7.1122(2.2); 7.1046(1.0); 7.0905(1.7); 7.0829(1.2); 5.1973(4.0); 5.1930(4.3); 4.2343(1.9); 4.2205(3.9); 4.2067(2.0); 3.4025(20.5); 3.3206(13.3); 2.9767(1.7); 2.9630(3.5); 2.9493(1.8); 2.5643(16.0); 2.5245(0.6); 2.5109(18.2); 2.5065(39.1); 2.5021 (53.2); 2.4976(39.1); 2.4932(19.4); −0.0002(1.3) |
| 57: $^1$H-NMR(400.0 MHz, d$_6$-DMSO): δ = 8.1747(1.3); 8.1698(1.3); 7.6300(1.7); 7.6169(2.3); 7.5415(1.2); 7.5163(0.7); 7.5106(0.7); 7.4867(0.7); 7.4808(0.7); 7.4273(0.6); 7.2956(0.6); 7.2726(0.9); 7.2702(0.9); 7.2468(0.9); 7.2424(0.8); 7.2343(0.8); 7.2262(0.7); 7.2183(0.8); 7.1093(0.4); 7.1002(0.7); 7.0917 (0.5); 7.0872(0.4); 7.0780(0.6); 7.0694(0.3); 5.1998(2.4); 5.1960(2.6); 4.0291(1.0); 4.0125(2.1); 3.9959(1.1); 3.3220(19.5); 3.0369(0.4); 3.0203(1.1); 3.0041(1.5); 2.9877(1.1); 2.9714(0.4); 2.7956(1.1); 2.7790(2.1); 2.7622(1.0); 2.5069(30.6); 2.5025(41.0); 2.4981(31.9); 0.9755(16.0); 0.9591(15.8); 0.0078(1.2); −0.0002(26.4) |
| 58: $^1$H-NMR(400.0 MHz, d$_6$-DMSO): δ = 8.2274(2.3); 8.2230(2.4); 8.1437(0.7); 8.1392(0.7); 7.5757(1.3); 7.5701(1.3); 7.5463(1.3); 7.5407(1.3); 7.4547(0.4); 7.4485(0.4); 7.4253(0.5); 7.4196(0.6); 7.3143(2.5); 7.2925(2.7); 6.8153(2.3); 6.8087(2.6); 6.6680(1.4); 6.6614(1.4); 6.6462(1.4); 6.6396(1.3); 5.1479 (4.5); 5.1441(4.8); 4.2344(2.0); 4.2208(4.0); 4.2071(2.3); 4.1970(1.0); 4.1827(1.4); 4.1688(0.6); 4.1557(0.4); 4.1164(0.5); 3.8423(0.4); 3.8252(13.9); 3.7615(0.9); 3.4918(1.5); 3.4866(1.6); 3.4050(19.5); 3.3879(1.9); 3.3753(1.6); 3.3666(0.6); 3.3525(0.9); 3.3222(8.1); 2.9781(2.0); 2.9647(4.4); 2.9516(3.3); 2.9383(1.2); 2.9135(0.4); 2.6707(0.5); 2.5663(16.0); 2.5415(1.6); 2.5056(69.1); 2.5017(89.8); 2.4978(71.8); 2.3284(0.5); 2.1399(8.2); 1.2346(0.8); −0.0002(6.8) |
| 59: $^1$H-NMR(400.0 MHz, CDCl$_3$): δ = 8.1852(2.0); 8.1785(2.0); 7.4807(0.4); 7.4663(3.6); 7.4488(2.1); 7.4295(0.6); 7.3884(1.8); 7.2613(9.6); 7.2274(0.9); 7.2100(0.8); 7.1062(1.9); 7.0987(2.1); 7.0887(1.7); 7.0800(1.3); 7.0685(2.0); 7.0439(1.6); 7.0089(0.9); 7.0000(1.3); 6.9915(0.8); 6.9867(0.6); 6.9781 (0.7); 6.9691(0.4); 5.1702(8.1); 4.2028(1.4); 4.1891(2.7); 4.1755(1.5); 3.8616(0.5); 3.5267(16.0); 3.0449(2.0); 3.0312(3.8); 3.0175(1.9); 2.6755(14.1); 2.4267(11.7); 1.5856(7.7); 1.1956(0.4); 0.0703(0.5); −0.0002(6.2) |
| 60: $^1$H-NMR(400.0 MHz, d$_6$-DMSO): δ = 8.1926(2.2); 8.1888(2.2); 7.6313(2.8); 7.6184(3.8); 7.5469(2.0); 7.5366(1.5); 7.5306(1.3); 7.5069(1.2); 7.5010(1.3); 7.4399(0.6); 7.4301(1.0); 7.2980(1.1); 7.2753(1.6); 7.2723(1.5); 7.2493(1.6); 7.2454(1.4); 7.2372(1.4); 7.2291(1.2); 7.2213(1.2); 7.1126(0.8); 7.1033 (1.2); 7.0949(0.8); 7.0902(0.7); 7.0812(0.9); 7.0724(0.6); 5.2002(4.2); 5.1960(4.3); 4.1495(1.9); 4.1345(4.0); 4.1195(2.0); 3.3235(86.6); 2.8369(0.4); 2.8204(1.0); 2.8040(1.3); 2.7876(1.0); 2.7709(0.4); 2.7247(1.7); 2.7098(3.5); 2.6948(1.7); 2.6758(0.4); 2.6713(0.6); 2.6668(0.4); 2.5066(68.5); 2.5022(90.5); 2.4977(68.7); 2.3333(0.4); 2.3288(0.5); 2.3244(0.4); 2.1958(13.6); 0.9480(16.0); 0.9316(15.7); 0.1460(0.5); 0.0078(4.4); −0.0002(102.1); −0.0084(5.0); −0.1497(0.4) |

-continued

Example

61: $^1$H-NMR(400.0 MHz, d$_6$-DMSO): δ =
8.2221(2.1); 8.2186(2.1); 8.2165(2.1); 7.6128(1.1); 7.6054(1.1); 7.5787(1.1); 7.5729(1.1); 7.5492(1.1); 7.5429(1.4); 7.5264(0.5); 7.5219(0.8); 7.5063(0.9); 7.5021(0.6); 7.4879(1.7); 7.4755(1.2); 7.4668(1.8); 7.4534(1.3); 7.3101(0.7); 7.3048(0.8); 7.2977(1.2); 7.2894 (0.6); 7.2848(1.3); 7.2789(2.0); 7.2624(0.8); 7.2560(0.6); 7.2419(0.4); 7.1239(1.0); 7.1171(2.4); 7.1129(2.0); 7.1080(0.9); 7.1006(0.7); 7.0914(1.2); 7.0852(1.0); 7.0784(0.6); 5.1949(2.7); 5.1906(2.8); 5.1518(1.6); 5.1474(1.6); 4.2331(1.8); 4.2194(3.8); 4.2056(1.9); 3.4028(19.2); 3.3207(25.8); 2.9762(1.8); 2.9625(3.6); 2.9488(1.8); 2.6711(0.4); 2.5644(16.0); 2.5243(0.9); 2.5107(27.1); 2.5064(56.0); 2.5020(74.1); 2.4975(52.8); 2.4933(25.4); 2.3288(0.4); −0.0001(1.6)
62: $^1$H-NMR(400.0 MHz, d$_6$-DMSO): δ =
8.2058(0.9); 8.2014(0.9); 7.6317(1.2); 7.6187(1.6); 7.5487(0.8); 7.5295(0.5); 7.5239(0.5); 7.5001(0.5); 7.4944(0.5); 7.4285(0.4); 7.2984(0.4); 7.2750(0.6); 7.2491(0.7); 7.2387(0.5); 7.2307(0.5); 7.2230(0.5); 7.1050(0.5); 7.0823(0.4); 5.2020(1.7); 5.1987(1.7); 4.1173 (0.7); 4.1027(1.5); 4.0882(0.8); 3.3233(6.8); 2.8589(0.5); 2.8458(0.8); 2.8330(0.5); 2.5073(14.7); 2.5031(18.8); 2.4989(14.3); 1.1322 (0.3); 1.0378(16.0); 0.9945(0.5); −0.0002(13.3)
63: $^1$H-NMR(400.0 MHz, d$_6$-DMSO): δ =
8.2228(2.5); 8.2190(2.6); 7.5774(1.4); 7.5715(1.3); 7.5478(1.4); 7.5424(1.3); 7.4880(0.8); 7.4722(3.6); 7.4486(5.8); 7.4429(5.9); 7.4264(2.6); 7.4090(1.4); 7.4006(0.4); 7.3922(0.4); 7.0805(3.7); 7.0723(2.6); 7.0651(2.1); 7.0576(0.7); 5.1881(4.6); 5.1849(4.6); 5.1516 (0.5); 4.2326(2.1); 4.2189(4.4); 4.2052(2.2); 3.9033(5.3); 3.4019(18.5); 3.3203(53.9); 3.1749(0.4); 3.1617(0.3); 2.9756(2.0); 2.9620 (4.0); 2.9484(2.0); 2.6706(1.1); 2.5637(16.0); 2.5056(155.7); 2.5017(193.2); 2.3284(1.1); 1.2362(0.4); 0.0001(4.3)
64: $^1$H-NMR(400.0 MHz, CDCl$_3$): δ =
8.3620(2.1); 8.3550(2.1); 7.5060(0.9); 7.4863(1.9); 7.4732(1.8); 7.4613(1.6); 7.4516(2.2); 7.4415(2.2); 7.4219(1.0); 7.4043(2.0); 7.3825(1.0); 7.3628(2.0); 7.3429(1.3); 7.3005(1.4); 7.2934(1.4); 7.2790(1.2); 7.2718(1.2); 7.2609(6.5); 7.2064(3.0); 7.2018(2.5); 7.1801 (2.1); 7.1600(1.2); 7.0158(1.1); 7.0107(1.0); 6.9957(1.0); 6.9900(0.9); 5.2100(7.1); 5.1371(0.4); 4.2130(1.4); 4.1995(2.8); 4.1858(1.6); 3.5295(16.0); 3.0543(2.1); 3.0406(3.9); 3.0268(2.0); 2.6795(14.0); 1.5948(4.6); 1.2550(0.5); −0.0002(3.2)
65: $^1$H-NMR(400.0 MHz, CDCl$_3$): δ =
8.3545(2.0); 8.3476(2.0); 7.5140(1.9); 7.4450(1.6); 7.4232(2.5); 7.4053(1.2); 7.4004(1.3); 7.3832(0.8); 7.3637(2.2); 7.3520(1.6); 7.3471(3.3); 7.3422(1.4); 7.3324(0.4); 7.3276(0.4); 7.2997(1.4); 7.2924(1.3); 7.2782(1.1); 7.2707(1.3); 7.2627(9.4); 7.0882(0.9); 7.0656 (1.7); 7.0406(2.0); 7.0316(1.3); 7.0237(1.1); 7.0159(1.2); 6.9478(0.8); 6.9391(1.1); 6.9305(0.8); 6.9254(0.6); 6.9171(0.8); 6.9082(0.5); 5.1486(7.2); 4.2143(1.3); 4.2008(2.6); 4.1871(1.4); 3.5291(16.0); 3.0549(1.9); 3.0411(3.7); 3.0273(1.9); 2.9569(0.5); 2.8850(0.4); 2.6797(14.1); 2.0454(0.3); 1.6117(10.1); 1.2558(0.6); 0.9214(0.4); −0.0002(4.5)
66: $^1$H-NMR(400.0 MHz, d$_6$-DMSO): δ =
8.1958(0.9); 8.1915(0.9); 7.7452(0.5); 7.7246(0.6); 7.6530(0.8); 7.6150(0.6); 7.5949(1.0); 7.5750(0.5); 7.5327(0.5); 7.5268(0.5); 7.5031(0.5); 7.4973(0.5); 7.4214(0.4); 7.4018(1.0); 7.3812(1.5); 7.3754(1.2); 7.3701(0.8); 7.3636(0.4); 7.3056(0.7); 7.2855(0.5); 7.0861 (0.5); 7.0815(0.5); 7.0657(0.4); 7.0611(0.4); 5.2362(1.6); 5.2321(1.7); 4.1174(0.7); 4.1018(1.4); 4.0862(0.7); 3.3230(25.8); 2.7278(0.6); 2.7128(1.3); 2.6976(0.6); 2.5066(27.6); 2.5021(36.4); 2.4976(27.0); 2.2220(4.8); 1.0024(16.0); 0.0080(0.8); −0.0002(22.8); −0.0083 (1.1)
67: $^1$H-NMR(400.0 MHz, d$_6$-DMSO): δ =
8.1841(1.3); 8.1797(1.3); 7.7438(0.7); 7.7232(1.0); 7.6496(1.2); 7.6145(0.8); 7.5944(1.5); 7.5745(0.8); 7.5205(0.7); 7.5147(0.7); 7.4911(0.8); 7.4852(0.8); 7.4205(0.6); 7.4007(1.4); 7.3803(2.1); 7.3745(1.7); 7.3687(1.2); 7.3044(1.0); 7.2841(0.7); 7.0846(0.7); 7.0790 (0.7); 7.0641(0.6); 7.0593(0.6); 5.2355(2.5); 5.2316(2.6); 4.0318(1.0); 4.0153(2.1); 3.9985(1.0); 3.3221(19.9); 3.0394(0.4); 3.0227(1.0); 3.0065(1.3); 2.9901(1.0); 2.9737(0.4); 2.7986(0.9); 2.7821(1.8); 2.7655(0.9); 2.5069(28.2); 2.5025(37.4); 2.4981(28.2); 0.9781(16.0); 0.9618(15.8); 0.0079(1.0); −0.0002(25.8); −0.0082(1.2)
68: $^1$H-NMR(400.0 MHz, d$_6$-DMSO): δ =
8.2305(0.8); 8.2177(2.5); 8.2134(2.6); 7.5983(0.4); 7.5832(1.6); 7.5774(1.7); 7.5689(3.0); 7.5537(1.9); 7.5472(3.9); 7.4180(0.5); 7.3984(0.5); 7.3898(0.5); 7.3858(0.5); 7.1369(3.0); 7.1289(2.5); 7.1219(1.2); 7.1068(2.0); 7.0998(1.4); 7.0890(0.4); 6.9972(0.7); 6.8684 (1.4); 6.8614(0.8); 6.7394(0.7); 6.7325(0.4); 5.2855(1.0); 5.2029(4.9); 5.1994(5.0); 4.2306(2.9); 4.2174(4.5); 4.2038(2.3); 3.4069(5.7); 3.4002(17.8); 3.3571(0.5); 3.3197(26.8); 2.9737(2.5); 2.9604(4.2); 2.9469(2.2); 2.6752(0.4); 2.6716(0.5); 2.5630(16.0); 2.5063(71.1); 2.5022(86.3); 2.4986(66.7); 2.3290(0.6); 2.1406(0.7); 1.2333(0.3); 1.0551(1.0); 0.1461(0.4); −0.0003(76.8); −0.1494(0.4)
69: $^1$H-NMR(400.0 MHz, d$_6$-DMSO): δ =
8.2012(2.1); 8.1969(2.1); 7.7444(1.2); 7.7248(1.5); 7.6537(1.9); 7.6151(1.4); 7.5949(2.5); 7.5750(1.3); 7.5402(1.2); 7.5342(1.2); 7.5106(1.2); 7.5046(1.2); 7.4224(1.0); 7.4025(2.3); 7.3818(3.5); 7.3760(3.0); 7.3631(1.0); 7.3054(1.6); 7.2859(1.1); 7.0873(1.1); 7.0824 (1.1); 7.0671(1.0); 7.0623(1.0); 5.2356(4.0); 5.2316(4.1); 4.1519(1.9); 4.1369(4.0); 4.1218(2.0); 3.3227(66.7); 2.8382(0.4); 2.8219(1.0); 2.8055(1.4); 2.7891(1.0); 2.7728(0.4); 2.7267(1.7); 2.7118(3.5); 2.6968(1.7); 2.6754(0.4); 2.6710(0.5); 2.6665(0.3); 2.5105(26.3); 2.5064(51.5); 2.5019(68.5); 2.4975(52.1); 2.3289(0.4); 2.1972(13.8); 0.9493(16.0); 0.9329(15.7); 0.1456(0.4); 0.0078(3.5); −0.0003 (77.2); −0.0084(4.0); −0.1499(0.4)
70: $^1$H-NMR(400.0 MHz, d$_6$-DMSO): δ =
8.2399(2.5); 8.2358(2.6); 7.6755(3.4); 7.6563(3.9); 7.5811(1.4); 7.5752(1.5); 7.5515(1.4); 7.5458(1.5); 7.4789(1.8); 7.4606(3.9); 7.4412(2.4); 7.3985(1.2); 7.3859(1.6); 7.3787(2.9); 7.3675(2.1); 7.3590(2.0); 7.3494(0.8); 7.3108(2.6); 7.3066(2.1); 7.2567(2.0); 7.2374 (1.5); 7.0452(1.4); 7.0398(1.4); 7.0247(1.2); 7.0201(1.2); 5.2181(5.4); 4.2368(2.2); 4.2232(4.4); 4.2094(2.3); 3.4042(18.3); 3.3182(14.2); 2.9787(2.0); 2.9652(4.0); 2.9513(2.0); 2.6701(0.4); 2.5653(16.0); 2.5054(55.6); 2.5012(74.4); 2.4972(59.0); 2.3277(0.5); 0.0074 (1.9); −0.0002(43.0)
71: $^1$H-NMR(400.0 MHz, d$_6$-DMSO): δ =
8.2304(2.2); 8.2263(2.2); 7.5763(1.4); 7.5681(2.6); 7.5640(1.8); 7.5471(4.3); 7.4984(1.9); 7.4804(3.7); 7.4611(2.0); 7.4291(0.8); 7.4259(1.4); 7.4227(0.9); 7.4135(0.5); 7.4076(1.7); 7.3895(0.6); 7.2630(1.2); 7.2404(1.7); 7.2374(1.6); 7.2147(1.5); 7.1731(1.2); 7.1653 (1.4); 7.1570(1.3); 7.1492(1.4); 7.0680(0.8); 7.0587(1.3); 7.0503(0.8); 7.0456(0.8); 7.0367(1.0); 7.0280(0.6); 5.1873(4.3); 5.1829(4.6); 4.2340(1.9); 4.2203(4.0); 4.2066(2.1); 3.4025(19.6); 3.3189(19.4); 2.9769(1.8); 2.9633(3.6); 2.9495(1.8); 2.6708(0.4); 2.5643(16.0); 2.5409(36.2); 2.5239(0.9); 2.5104(22.3); 2.5061(46.1); 2.5016(61.5); 2.4971(45.7); 2.4929(23.3); 2.3283(0.4); 0.0079(1.5); −0.0002(41.0); −0.0084(1.9)
72: $^1$H-NMR(400.0 MHz, d$_6$-DMSO): δ =
8.2219(2.1); 8.2178(2.1); 8.2162(2.1); 7.6083(2.9); 7.5858(4.5); 7.5798(1.4); 7.5561(1.3); 7.5501(1.3); 7.2664(1.2); 7.2634(1.6); 7.2598(1.8); 7.2568(1.6); 7.1697(1.7); 7.1625(1.5); 7.1472(1.5); 7.1400(1.4); 5.2136(4.3); 5.2091(4.5); 4.2319(1.9); 4.2182(4.0); 4.2044 (2.0); 3.4006(19.7); 3.3191(17.2); 2.9742(1.8); 2.9606(3.6); 2.9469(1.8); 2.5633(16.0); 2.5246(0.6); 2.5111(16.6); 2.5067(34.8); 2.5022 (46.6); 2.4977(34.1); 2.4933(16.9); 0.0079(1.2); −0.0002(34.3); −0.0085(1.4)
73: $^1$H-NMR(400.0 MHz, CDCl$_3$): δ =
8.3509(2.2); 8.3439(2.2); 7.4043(1.7); 7.3830(2.4); 7.3484(2.4); 7.3261(2.7); 7.2941(1.5); 7.2869(1.5); 7.2725(1.2); 7.2619(8.0); 6.9842(1.7); 6.9811(1.8); 6.8920(1.5); 6.8850(1.3); 6.8697(1.4); 6.8626(1.2); 5.1194(8.6); 4.2128(1.5); 4.1992(3.0); 4.1857(1.6); 3.5287 (16.0); 3.0542(2.1); 3.0405(4.1); 3.0268(2.1); 2.6801(14.5); 1.5757(4.9); −0.0002(4.0)

-continued

Example

74: ¹H-NMR(400.0 MHz, d₆-DMSO): δ =
8.2142(0.9); 8.2102(0.9); 7.7448(0.5); 7.7254(0.7); 7.6562(0.8); 7.6155(0.6); 7.5954(1.0); 7.5755(0.5); 7.5340(0.5); 7.5282(0.5); 7.5044(0.5); 7.4988(0.5); 7.4233(0.4); 7.4035(0.9); 7.3830(1.4); 7.3777(1.4); 7.3608(0.4); 7.3065(0.7); 7.2875(0.5); 7.0889(0.5); 7.0833 (0.5); 7.0684(0.4); 7.0630(0.4); 5.2369(1.7); 5.2339(1.8); 4.1196(0.7); 4.1051(1.5); 4.0906(0.8); 3.3231(6.2); 2.8607(0.5); 2.8477(0.8); 2.5069(16.4); 2.5026(21.0); 2.4985(16.2); 1.0388(16.0); −0.0002(14.4)

75: ¹H-NMR(400.0 MHz, d₆-DMSO): δ =
8.3163(0.4); 8.2018(8.1); 8.1979(8.2); 7.6515(0.8); 7.6313(10.5); 7.6184(14.4); 7.6005(0.5); 7.5485(11.6); 7.5432(10.0); 7.5190(4.7); 7.5131(4.8); 7.4400(2.4); 7.4287(3.6); 7.2975(4.2); 7.2747(6.1); 7.2717(5.7); 7.2487(6.4); 7.2458(5.6); 7.2376(5.1); 7.2295(4.6); 7.2216(4.8); 7.1115(2.9); 7.1022(4.5); 7.0938(3.0); 7.0890(2.7); 7.0804(3.5); 7.0714(2.1); 5.2944(0.4); 5.2013(15.2); 5.1970(16.0); 4.2036(6.0); 4.1892(12.3); 4.1747(6.3); 3.3233(298.1); 2.6715(6.4); 2.6576(8.9); 2.6433(4.6); 2.5665(0.3); 2.5246(5.7); 2.5111(113.4); 2.5068(233.9); 2.5023(316.0); 2.4978(238.1); 2.4935(122.0); 2.4151(9.7); 2.3334(1.6); 2.3290(2.1); 2.3246(1.6); 1.5067(2.8); 1.4927 (7.9); 1.4788(12.4); 1.4653(10.2); 1.4520(4.4); 1.3777(4.9); 1.3648(5.2); 0.1460(1.6); 0.0080(14.3); −0.0002(382.2); −0.0084(18.7); −0.1497(1.7)

76: ¹H-NMR(400.0 MHz, d₆-DMSO): δ =
8.2183(2.2); 8.2141(2.2); 7.6110(3.0); 7.6036(3.1); 7.5733(1.3); 7.5674(1.2); 7.5439(1.3); 7.5379(1.3); 7.4737(3.1); 7.4515(3.5); 7.1070(1.7); 7.0996(1.7); 7.0848(1.5); 7.0774(1.5); 5.1509(4.4); 5.1463(4.5); 4.2318(2.0); 4.2181(4.1); 4.2043(2.1); 3.4036(20.2); 3.3179 (37.6); 2.9756(1.8); 2.9619(3.6); 2.9482(1.8); 2.6754(0.4); 2.6707(0.5); 2.6662(0.4); 2.5647(16.0); 2.5239(1.5); 2.5107(27.8); 2.5062 (56.4); 2.5017(77.1); 2.4972(58.0); 2.4929(28.6); 2.3328(0.3); 2.3286(0.4); 2.3239(0.3); 0.0078(0.8); −0.0002(19.3); −0.0083(0.7)

77: ¹H-NMR(400.0 MHz, d₆-DMSO): δ =
8.2715(1.2); 8.2678(1.3); 7.6359(1.6); 7.6225(3.1); 7.5935(0.6); 7.5886(0.6); 7.5553(1.3); 7.4356(0.7); 7.3054(0.7); 7.2827(1.0); 7.2567(1.0); 7.2453(0.8); 7.2371(0.8); 7.2294(0.8); 7.1110(0.5); 7.1017(0.9); 7.0934(0.5); 7.0885(0.5); 7.0796(0.6); 7.0710(0.4); 5.2333 (2.4); 4.5080(0.8); 4.4966(1.5); 4.4853(0.9); 3.8146(0.4); 3.8012(0.6); 3.7666(0.4); 3.3245(89.8); 2.8089(2.8); 2.7966(2.8); 2.6710(0.7); 2.5061(92.1); 2.5018(120.1); 2.4975(90.8); 2.3287(0.7); 1.3635(16.0); 1.3346(0.5); 1.2859(0.3); 1.2759(0.4); 1.2607(0.4); 0.1458(0.5); 0.0077(5.3); −0.0002(106.9); −0.1498(0.5)

78: ¹H-NMR(400.0 MHz, d₆-DMSO): δ =
8.2004(2.9); 8.1956(3.0); 7.7443(1.6); 7.7249(2.2); 7.6529(2.7); 7.6153(1.9); 7.5950(3.4); 7.5751(1.8); 7.5453(1.6); 7.5397(1.7); 7.5160(1.6); 7.5101(1.6); 7.4222(1.4); 7.4024(3.1); 7.3817(5.0); 7.3760(4.2); 7.3637(1.4); 7.3052(2.3); 7.2858(1.6); 7.0869(1.6); 7.0817 (1.6); 7.0669(1.4); 7.0612(1.4); 5.2364(5.6); 5.2325(5.8); 4.1597(2.0); 4.1448(4.2); 4.1297(2.1); 3.3225(106.7); 2.7944(1.6); 2.7797(3.0); 2.7653(1.6); 2.6753(0.6); 2.6711(0.8); 2.6670(0.5); 2.5627(1.9); 2.5452(5.4); 2.5266(6.7); 2.5062(112.4); 2.5019(147.5); 2.4976 (111.2); 2.3286(0.8); 2.3242(0.6); 1.2325(0.4); 0.9755(8.0); 0.9577(16.0); 0.9399(7.7); 0.1458(0.5); 0.0072(4.4); −0.0003(99.7); −0.1499(0.5)

79: ¹H-NMR(400.0 MHz, d₆-DMSO): δ =
8.1711(1.4); 8.1657(1.4); 7.5798(1.8); 7.5242(0.7); 7.5183(0.8); 7.4946(0.7); 7.4888(0.8); 7.2579(1.1); 7.2546(1.2); 7.1613(0.9); 7.1541(0.9); 7.1388(0.9); 7.1316(0.8); 5.2069(2.7); 5.2029(2.9); 4.0289(1.0); 4.0124(2.1); 3.9958(1.1); 3.3205(22.6); 3.0376 (0.4); 3.0214(0.9); 3.0050(1.2); 2.9888(0.9); 2.9724(0.4); 2.7935(0.9); 2.7770(1.7); 2.7606(0.8); 2.6711(0.3); 2.5063(41.9); 2.5019 (56.4); 2.4975(44.0); 2.3289(0.3); 0.9756(16.0); 0.9593(15.8); 0.0078(1.5); −0.0003(37.1)

80: ¹H-NMR(400.0 MHz, d₆-DMSO): δ =
8.2373(2.4); 8.2321(2.4); 7.7484(1.6); 7.7439(3.0); 7.7398(2.0); 7.6616(1.4); 7.6424(1.8); 7.5830(1.4); 7.5771(1.4); 7.5535(1.4); 7.5476(1.4); 7.5073(1.1); 7.4876(2.6); 7.4683(1.8); 7.4396(1.9); 7.4366(1.6); 7.4193(1.0); 7.4093(1.2); 7.3894(2.5); 7.3689(2.9); 7.3630 (2.6); 7.3584(2.0); 7.2887(1.8); 7.2693(1.3); 7.0715(1.3); 7.0661(1.3); 7.0512(1.2); 7.0457(1.1); 5.2353(4.6); 5.2313(4.9); 4.2381(2.1); 4.2245(4.2); 4.2107(2.2); 3.4045(19.0); 3.3176(23.4); 2.9795(2.0); 2.9659(3.9); 2.9522(2.0); 2.6745(0.5); 2.6700(0.6); 2.6658(0.5); 2.5658(16.0); 2.5055(78.8); 2.5011(104.0); 2.4968(79.7); 2.3324(0.4); 2.3279(0.6); 2.3233(0.5); 0.1457(0.3); 0.0078(3.5); −0.0003(67.5)

81: ¹H-NMR(400.0 MHz, d₆-DMSO): δ =
8.2834(2.7); 8.2766(2.7); 7.7355(1.4); 7.7159(1.9); 7.6390(2.4); 7.6132(1.6); 7.5931(2.8); 7.5732(1.4); 7.5016(1.5); 7.4803(3.4); 7.4499(2.1); 7.4429(2.0); 7.4284(1.0); 7.4203(1.9); 7.3998(2.6); 7.3800(3.1); 7.3526(2.2); 7.3475(2.7); 7.3433(2.0); 7.2960(2.0); 7.2764 (1.4); 7.0730(1.4); 7.0680(1.4); 7.0526(1.2); 7.0476(1.2); 5.1979(8.2); 4.1121(2.1); 4.0970(4.4); 4.0819(2.2); 3.3227(32.6); 2.8907(1.5); 2.7889(1.8); 2.7739(3.5); 2.7588(1.7); 2.7314(1.5); 2.6713(0.4); 2.5639(2.1); 2.5462(6.0); 2.5284(6.7); 2.5064(52.7); 2.5022(68.7); 2.4980(53.2); 2.3292(0.4); 0.9772(8.0); 0.9595(16.0); 0.9417(7.6); −0.0002(39.7)

82: ¹H-NMR(400.0 MHz, d₆-DMSO): δ =
8.2766(2.8); 8.2700(2.7); 7.6122(2.8); 7.5412(0.6); 7.5271(3.3); 7.5096(3.5); 7.4895(4.1); 7.4827(1.5); 7.4684(4.0); 7.4477(2.4); 7.4407(2.2); 7.4262(0.9); 7.4191(0.9); 7.2820(1.3); 7.2590(2.0); 7.2565(1.8); 7.2334(1.6); 7.2005(1.4); 7.1928(1.6); 7.1845(1.5); 7.1768 (1.5); 7.0853(0.9); 7.0761(1.5); 7.0676(1.0); 7.0629(0.9); 7.0538(1.2); 7.0452(0.7); 5.1540(8.8); 4.1121(2.1); 4.0970(4.4); 4.0819(2.2); 3.3226(30.0); 2.8906(1.0); 2.7875(1.8); 2.7726(3.4); 2.7575(1.7); 2.7313(1.0); 2.6713(0.4); 2.5635(2.0); 2.5459(5.8); 2.5280(6.6); 2.5065(54.7); 2.5022(70.0); 2.4978(53.0); 2.3287(0.4); 0.9770(8.0); 0.9593(16.0); 0.9415(7.7); −0.0002(40.4)

83: ¹H-NMR(400.0 MHz, d₆-DMSO): δ =
8.2217(2.1); 8.2175(2.1); 7.5758(1.2); 7.5699(1.2); 7.5464(1.2); 7.5404(1.3); 7.4155(1.4); 7.4079(1.5); 7.4014(1.4); 7.3937(1.4); 7.3305(1.3); 7.3082(2.5); 7.2864(1.6); 7.0916(0.8); 7.0821(1.2); 7.0742(0.9); 7.0688(0.8); 7.0595(0.9); 7.0513(0.6); 5.1463(4.4); 5.1416 (4.6); 4.2327(2.0); 4.2190(4.1); 4.2052(2.1); 3.4037(19.8); 3.3178(11.4); 2.9760(1.8); 2.9623(3.6); 2.9486(1.8); 2.6706(0.3); 2.5648 (16.0); 2.5240(0.9); 2.5103(20.0); 2.5061(41.0); 2.5016(54.4); 2.4971(39.9); 2.4928(19.9); 0.0078(1.5); −0.0002(42.3); −0.0084(1.8)

84: ¹H-NMR(400.0 MHz, d₆-DMSO): δ =
8.1977(7.8); 8.1938(7.7); 7.6042(10.6); 7.5817(11.8); 7.5549(4.6); 7.5490(4.5); 7.5253(4.6); 7.5193(4.6); 7.2610(6.1); 7.2574(6.5); 7.2544(5.5); 7.1643(6.2); 7.1571(5.4); 7.1418(5.5); 7.1346(5.0); 5.2091(15.5); 5.2046(16.0); 4.2008(7.0); 4.1863(14.8); 4.1718(7.2); 3.3223(177.0); 2.6673(7.6); 2.6530(13.7); 2.6385(6.5); 2.5246(4.1); 2.5111(79.8); 2.5068(161.4); 2.5022(214.8); 2.4977(159.4); 2.4934(79.6); 2.4113(9.9); 2.3337(3.8); 2.3291(4.4); 2.3245(1.1); 1.5042(2.7); 1.4897(7.6); 1.4760(12.3); 1.4626(10.2); 1.4493(4.4); 1.4272(0.4); 1.3916(2.4); 1.3763(4.6); 1.3636(4.8); 1.3499(2.7); 0.1459(1.2); 0.0079(10.9); −0.0002(277.7); −0.0085(12.2); −0.1498(1.2)

85: ¹H-NMR(400.0 MHz, d₆-DMSO): δ =
8.3166(1.8); 8.2379(2.1); 8.2338(2.1); 7.5832(1.2); 7.5773(1.2); 7.5525(2.1); 7.5473(3.0); 7.5282(3.0); 7.5249(2.7); 7.5038(1.1); 7.4878(1.0); 7.4686(0.4); 7.4097(1.1); 7.3899(2.3); 7.3696(2.7); 7.3638(2.2); 7.3587(1.7); 7.3001(1.6); 7.2799(1.1); 7.2239(0.4); 7.2188 (0.7); 7.2136(0.5); 7.1990(1.0); 7.1949(0.8); 7.1731(0.4); 7.1784(0.5); 7.1728(0.4); 7.0731(1.1); 7.0670(1.2); 7.0528(1.0); 7.0482(1.0); 5.2311(4.0); 5.2267(4.2); 4.2379(1.9); 4.2242(3.9); 4.2104(2.0); 3.4049(26.4); 3.3190(13.0); 3.2952(0.8); 2.9795(1.8); 2.9659(3.6); 2.9522(1.8); 2.6747(0.4); 2.6704(0.5); 2.6660(0.4); 2.5660(16.0); 2.5235(1.3); 2.5101(31.1); 2.5058(63.5); 2.5013(84.4); 2.4968(62.1); 2.4925(31.1); 2.3325(0.4); 2.3280(0.5); 2.3237(0.4); 1.4862(0.6); 0.0080(2.1); −0.0002(56.0); −0.0084(2.5)

86: ¹H-NMR(400.0 MHz, d₆-DMSO): δ =
8.2255(2.6); 8.2199(2.6); 7.5717(1.2); 7.5659(1.3); 7.5421(1.2); 7.5366(1.3); 7.4518(2.9); 7.4301(3.2); 6.7893(2.3); 6.7828(2.6); 6.6318(1.6); 6.6253(1.5); 6.6099(1.5); 6.6035(1.5); 5.1457(5.1); 5.1187(0.4); 4.2330(2.1); 4.2194(4.2); 4.2058(2.2); 3.8184(15.2); 3.8064

| Example |
|---|
| (1.0); 3.7621(0.8); 3.4049(19.3); 3.3750(143.9); 3.3649(121.2); 3.3631(127.5); 3.3602(136.8); 3.3574(126.4); 2.9777(2.0); 2.9642 (4.2); 2.9503(2.3); 2.6734(0.4); 2.5661(16.0); 2.5395(0.4); 2.5260(1.6); 2.5083(53.7); 2.5040(71.4); 2.4996(52.8); 2.3304(0.4); 1.0552 (0.9); −0.0002(40.5) |
| 87: $^1$H-NMR(400.0 MHz, d$_6$-DMSO): δ = 8.2104(8.0); 8.2063(8.1); 7.7440(4.4); 7.7246(6.0); 7.6544(7.4); 7.6153(5.3); 7.5951(9.6); 7.5752(5.0); 7.5527(4.4); 7.5470(4.5); 7.5231(4.4); 7.5173(4.5); 7.4217(3.9); 7.4019(8.7); 7.3815(14.2); 7.3760(11.7); 7.3635(3.8); 7.3606(3.8); 7.3053(6.2); 7.2851(4.3); 7.0861(4.4); 7.0817(4.2); 7.0659(3.9); 7.0612(3.8); 5.2367(15.1); 5.2327(16.0); 4.2063(5.2); 4.1919(10.4); 4.1776(5.4); 3.3214(118.9); 2.6713(5.4); 2.6596(7.8); 2.6452(4.2); 2.5106(94.3); 2.5064(191.6); 2.5020(257.6); 2.4975(197.0); 2.4161(9.2); 2.3331(1.3); 2.3287 (1.7); 2.3242(1.3); 1.5081(2.7); 1.4941(7.6); 1.4806(11.7); 1.4674(9.7); 1.4542(4.2); 1.3783(4.7); 1.3656(5.0); 0.1457(1.3); 0.0078(12.2); −0.0003(308.0); −0.0085(16.0); −0.1498(1.4) |
| 88: $^1$H-NMR(400.0 MHz, d$_6$-DMSO): δ = 8.2751(2.4); 8.2685(2.4); 7.5974(3.0); 7.5749(3.4); 7.4882(1.2); 7.4669(3.4); 7.4469(2.2); 7.4399(2.1); 7.4254(0.8); 7.4183(0.8); 7.2310(1.9); 7.2276(2.0); 7.1410(1.8); 7.1338(1.5); 7.1185(1.6); 7.1113(1.4); 5.1533(8.5); 4.1123(2.1); 4.0971(4.4); 4.0820(2.2); 3.3246 (26.5); 2.7864(1.7); 2.7714(3.3); 2.7562(1.6); 2.5636(1.9); 2.5460(5.6); 2.5282(6.1); 2.5076(29.1); 2.5031(37.3); 2.4987(27.5); 0.9772 (8.0); 0.9595(16.0); 0.9417(7.6); 0.0079(1.0); −0.0002(22.5); −0.0084(1.0) |
| 89: $^1$H-NMR(400.0 MHz, d$_6$-DMSO): δ = 8.2208(2.9); 8.2174(2.8); 7.5806(1.5); 7.5750(1.4); 7.5509(1.5); 7.5456(1.4); 7.4655(1.2); 7.4412(2.2); 7.4170(1.4); 7.2678(1.3); 7.2568(1.3); 7.1466(1.0); 7.1380(1.5); 7.1297(1.0); 7.1239(0.9); 7.1151(1.2); 7.1067(0.6); 5.1735(5.8); 5.1702(5.8); 4.2314(2.4); 4.2179 (4.6); 4.2042(2.4); 3.4015(18.5); 3.3203(19.6); 2.9745(2.4); 2.9612(4.3); 2.9476(2.2); 2.6719(0.4); 2.5639(16.0); 2.5022(79.0); 2.3289 (0.5); 2.1396(0.5); −0.0003(5.8) |
| 90: $^1$H-NMR(400.0 MHz, CDCl$_3$): δ = 7.9991(2.4); 7.9934(2.7); 7.9143(1.4); 7.8951(1.5); 7.6111(2.2); 7.6049(2.5); 7.5409(1.3); 7.5202(2.1); 7.4563(2.1); 7.4506(1.1); 7.4471(1.0); 7.4336(3.0); 7.4295(2.1); 7.4115(0.8); 7.4083(0.8); 7.3311(1.0); 7.3289(1.0); 7.3104(1.6); 7.2936(0.7); 7.2916(0.7); 7.2605 (8.3); 7.1897(1.4); 7.1832(1.5); 7.1673(1.2); 7.1609(1.3); 6.8950(2.2); 6.8894(2.5); 5.2982(2.7); 5.2508(8.2); 4.2445(1.3); 4.2311(2.5); 4.2178(1.4); 3.8825(14.1); 3.5365(16.0); 3.0517(1.8); 3.0383(3.5); 3.0248(1.8); 2.6834(13.9); 1.5841(6.1); −0.0002(7.8) |
| 91: $^1$H-NMR(400.0 MHz, CDCl$_3$): δ = 8.3169(1.0); 8.3156(1.1); 8.2959(1.1); 8.2945(1.1); 8.1787(1.1); 8.1576(1.2); 7.9816(2.2); 7.9758(2.3); 7.5960(0.6); 7.5928(0.6); 7.5789(0.8); 7.5754(1.2); 7.5717(0.6); 7.5578(0.8); 7.5545(0.8); 7.4901(0.8); 7.4872(0.8); 7.4730(0.6); 7.4695(1.1); 7.4661(0.9); 7.4561 (2.2); 7.4523(0.8); 7.4491(0.6); 7.4354(2.3); 7.2608(8.4); 6.9779(2.0); 6.9572(1.8); 6.8945(1.9); 6.8887(1.9); 5.3119(6.8); 4.2513(1.0); 4.2379(1.9); 4.2244(1.1); 3.8448(12.9); 3.5443(16.0); 3.0581(1.5); 3.0446(3.0); 3.0310(1.6); 2.6982(0.4); 2.6885(13.3); 1.5994(3.0); −0.0002(7.9) |
| 92: $^1$H-NMR(400.0 MHz, d$_6$-DMSO): δ = 8.1830(0.9); 8.1788(0.8); 7.6034(1.1); 7.5809(1.2); 7.5353(0.5); 7.5295(0.5); 7.5056(0.5); 7.5001(0.5); 7.2616(0.7); 7.2581(0.7); 7.1631(0.6); 7.1560(0.6); 7.1406(0.6); 7.1335(0.5); 5.2085(1.7); 5.2043(1.8); 4.1146(0.7); 4.0992(1.5); 4.0837(0.7); 3.3229(34.3); 2.7233 (0.6); 2.7082(1.1); 2.6925(0.5); 2.5064(31.1); 2.5020(41.5); 2.4975(30.7); 2.2194(4.2); 1.0004(16.0); 0.0079(1.0); −0.0002(25.2); −0.0083(1.2) |
| 93: $^1$H-NMR(400.0 MHz, CDCl$_3$): δ = 8.1801(1.7); 8.1575(1.8); 7.9828(2.4); 7.9770(2.5); 7.8378(1.5); 7.8162(1.7); 7.5315(1.2); 7.5115(1.7); 7.4905(1.2); 7.4211(2.6); 7.3984(2.4); 7.2607(7.7); 7.1157(1.7); 7.0963(1.6); 6.8980(2.2); 6.8923(2.2); 5.3209(7.6); 5.2984(0.5); 4.2530(1.2); 4.2397(2.4); 4.2263 (1.4); 3.8462(13.9); 3.5441(16.0); 3.5306(0.4); 3.0593(1.8); 3.0458(3.4); 3.0323(1.8); 2.6891(14.0); 1.6428(0.5); 1.2543(0.4); −0.0002(7.4) |
| 94: $^1$H-NMR(400.0 MHz, CDCl$_3$): δ = 7.9898(2.3); 7.9840(2.4); 7.5949(1.7); 7.5915(2.3); 7.5738(2.5); 7.5722(2.4); 7.5712(2.4); 7.4384(1.4); 7.4341(0.6); 7.4203(2.8); 7.4172(1.6); 7.4008(1.6); 7.3563(1.0); 7.3514(0.7); 7.3482(1.2); 7.3451(0.7); 7.3365(2.1); 7.3298(1.5); 7.3247(0.5); 7.3165(1.5); 7.3117 (0.6); 7.3084(0.4); 7.3032(1.2); 7.2978(1.7); 7.2931(1.4); 7.2593(7.8); 7.1876(0.9); 7.1854(1.2); 7.1840(1.2); 7.1815(1.0); 7.1686(0.8); 7.1663(1.0); 7.1647(1.0); 7.1625(0.8); 7.0589(0.8); 7.0569(0.9); 7.0526(0.9); 7.0506(0.9); 7.0384(0.8); 7.0364(0.8); 7.0321(0.8); 7.0300(0.8); 6.8786(2.1); 6.8728(2.1); 5.2129(7.5); 4.2383(1.0); 4.2250(2.1); 4.2115(1.2); 3.8548(13.3); 3.5347(16.0); 3.0481(1.6); 3.0346 (3.1); 3.0212(1.6); 2.6817(13.6); 2.0037(2.6); 1.5799(4.1); −0.0002(7.1) |
| 95: $^1$H-NMR(400.0 MHz, d$_6$-DMSO): δ = 8.2213(2.3); 8.2162(2.2); 7.5729(1.3); 7.5670(1.4); 7.5434(1.3); 7.5376(1.4); 7.4138(2.7); 7.3248(1.5); 7.3115(1.0); 7.3074(1.8); 7.1053(0.8); 7.0844(2.4); 7.0670(3.4); 7.0630(2.8); 7.0463(0.4); 7.0411(0.6); 5.1368(4.8); 5.1327(5.2); 4.2328(2.1); 4.2191(4.3); 4.2054 (2.2); 3.4046(18.8); 3.3177(23.1); 2.9764(2.0); 2.9629(3.9); 2.9492(2.0); 2.6746(0.4); 2.6703(0.5); 2.5652(16.0); 2.5057(60.7); 2.5014 (80.9); 2.4972(62.3); 2.3319(0.3); 2.3281(0.5); 0.0077(2.4); −0.0002(54.6) |
| 96: $^1$H-NMR(400.0 MHz, d$_6$-DMSO): δ = 8.2540(1.6); 8.2315(1.8); 7.7973(1.2); 7.7758(1.8); 7.7004(2.3); 7.6854(1.2); 7.6777(2.2); 7.6654(1.7); 7.6445(0.9); 7.3819(1.6); 7.3620(1.9); 7.2945(1.6); 7.2753(1.4); 7.1674(1.8); 7.1476(1.6); 5.7569(16.0); 5.2505(5.2); 4.1336(1.4); 4.1193(3.0); 4.1050(1.5); 3.8785 (11.7); 3.4033(13.2); 3.3195(26.2); 2.9761(1.4); 2.9619(2.8); 2.9477(1.4); 2.6709(0.6); 2.5695(11.2); 2.5061(74.3); 2.5018(96.5); 2.4976(71.2); 2.3285(0.6); 1.2335(0.6); 0.1462(0.6); 0.0073(6.2); −0.0001(126.0); −0.1496(0.6) |
| 97: $^1$H-NMR(400.0 MHz, d$_6$-DMSO): δ = 9.9594(0.4); 8.2457(2.4); 8.2230(2.6); 7.7922(1.9); 7.7708(2.7); 7.6965(3.2); 7.6791(1.9); 7.6739(3.3); 7.6593(2.4); 7.6384(1.3); 7.3698(2.4); 7.3498(2.8); 7.2878(2.3); 7.2684(2.1); 7.1449(2.7); 7.1251(2.3); 5.2364(7.8); 4.5171(0.3); 4.3665(1.3); 4.3490(4.1); 4.3315 (4.2); 4.3139(1.4); 4.1371(2.1); 4.1226(4.5); 4.1080(2.3); 3.4096(18.6); 3.4001(2.0); 3.3204(31.9); 2.9799(2.3); 2.9655(4.6); 2.9511 (2.3); 2.6709(0.6); 2.5723(16.0); 2.5558(1.6); 2.5058(75.0); 2.5019(95.4); 2.4980(72.3); 2.3286(0.5); 1.3184(4.2); 1.3009(8.7); 1.2834 (4.2); 1.2308(0.6); 0.1457(0.5); −0.0004(99.6); −0.1499(0.5) |
| 98: $^1$H-NMR(400.0 MHz, d$_6$-DMSO): δ = 8.8265(10.2); 8.2428(1.7); 8.2224(1.9); 8.1369(1.8); 8.1159(2.0); 7.7393(0.9); 7.7217(1.6); 7.7036(1.1); 7.6554(2.7); 7.6350(3.9); 7.6179(1.7); 7.6001(0.9); 7.1752(2.6); 7.1544(2.4); 5.7563(0.6); 5.2934(7.3); 4.4866(2.3); 4.4722(4.7); 4.4579(2.4); 3.9492(1.2); 3.4105 (18.4); 3.3537(0.5); 3.3216(84.3); 2.9878(2.0); 2.9736(4.1); 2.9592(2.0); 2.6713(0.4); 2.5655(16.0); 2.5067(54.7); 2.5023(69.9); 2.4980 (50.8); 2.3293(0.4); 0.0080(0.9); 0.0000(19.5) |
| 99: $^1$H-NMR(400.0 MHz, d$_6$-DMSO): δ = 8.6301(12.6); 8.3049(1.5); 8.2842(1.6); 8.1276(1.6); 8.1072(1.8); 7.7419(0.8); 7.7388(0.8); 7.7247(1.2); 7.7214(1.6); 7.7178(0.8); 7.7037(1.1); 7.7005(1.0); 7.6548(1.1); 7.6520(1.1); 7.6342(1.6); 7.6311(1.1); 7.6166(0.8); 7.6138(0.7); 7.5759(2.8); 7.5551(3.0); 7.0297 (2.6); 7.0087(2.4); 5.4358(8.1); 4.2925(2.0); 4.2788(4.2); 4.2650(2.1); 3.3999(20.0); 3.3213(5.2); 2.9859(1.8); 2.9723(3.7); 2.9586(1.8); 2.5655(16.0); 2.5251(0.7); 2.5202(1.1); 2.5115(15.9); 2.5071(33.7); 2.5025(47.0); 2.4980(34.8); 2.4937(16.6); 0.0080(0.3); −0.0002(10.8); −0.0085(0.4) |

BIOLOGICAL EXAMPLES

*Ctenocephalides felis*—In Vitro Contact Tests with Adult Cat Fleas

For the coating of the test tubes, 9 mg of active compound are first dissolved in 1 ml of acetone p.a. and then diluted to the desired concentration with acetone p.a. 250 µl of the solution are distributed homogeneously on the inner walls and the base of a 25 ml glass tube by turning and rocking on an orbital shaker (rocking rotation at 30 rpm for 2 h). With 900 ppm of active compound solution and internal surface area 44.7 cm$^2$, given homogeneous distribution, an area-based dose of 5 µg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm$^2$. 100% efficacy means that all the fleas were dead or moribund. 0% efficacy means that no fleas were harmed.

In this test, for example, the following compounds from the preparation examples show an efficacy of 100% at an application rate of 5 µg/cm$^2$ (=500 g/ha): 1, 2, 9, 13, 16, 19, 20, 21, 22, 23, 24, 32, 37, 39, 44, 48, 49, 53, 54, 55, 56, 57, 59, 60, 61, 62, 63, 64, 65, 68, 69, 70, 71, 72, 75, 76, 78, 86, 89, 99

*Rhipicephalus sanguineus*—In Vitro Contact Tests with Adult Brown Dog Ticks

For the coating of the test tubes, 9 mg of active compound are first dissolved in 1 ml of acetone p.a. and then diluted to the desired concentration with acetone p.a. 250 µl of the solution are distributed homogeneously on the inner walls and the base of a 25 ml glass tube by turning and rocking on an orbital shaker (rocking rotation at 30 rpm for 2 h). With 900 ppm of active compound solution and internal surface area 44.7 cm$^2$, given homogeneous distribution, an area-based dose of 5 µg/cm$^2$ is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the base of the tube and incubated on a hotplate at 45-50° C. for not more than 5 min. Ticks which remain motionless on the base or move in such an uncoordinated manner that they are unable to deliberately avoid the heat by climbing upwards are considered to be dead or moribund.

A substance shows good activity against *Rhipicephalus sanguineus* if, in this test, an efficacy of at least 80% was achieved at an application rate of 5 µg/cm$^2$. An efficacy of 100% means that all the ticks were dead or moribund. 0% efficacy means that none of the ticks were harmed.

In this test, for example, the following compounds from the preparation examples show an efficacy of 100% at an application rate of 5 µg/cm$^2$ (=500 g/ha): 1, 2, 9, 13, 16, 19, 20, 21, 22, 23, 24, 27, 28, 31, 48, 49, 53, 54, 55, 56, 57, 59, 60, 61, 62, 63, 64, 65, 68, 69, 70, 71, 72, 75, 76, 78, 80, 86, 89, 99

*Boophilus microplus*—Dip Test

Test animals: cattle ticks (*Boophilus microplus*) Parkhurst strain, SP-resistant Solvent: dimethyl sulfoxide 10 mg of active compound are dissolved in 0.5 ml of dimethyl sulfoxide. To produce a suitable formulation, the active compound solution is diluted with water to the concentration desired in each case.

This active compound formulation is pipetted into tubes. 8-10 engorged adult female cattle ticks (*Boophilus microplus*) are transferred into a further tube with holes. The tube is immersed into the active compound formulation, and all the ticks are completely wetted. After the liquid has run out, the ticks are transferred on filter disks into plastic dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 100 ppm: 19, 54, 86, 99

In this test, for example, the following compounds from the preparation examples show an efficacy of 95% at an application rate of 100 ppm: 16, 58

In this test, for example, the following compounds from the preparation examples show an efficacy of 90% at an application rate of 100 ppm: 55

In this test, for example, the following compounds from the preparation examples show an efficacy of 80% at an application rate of 100 ppm: 23

*Boophilus microplus*—Injection Test

Solvent: dimethyl sulfoxide

To produce a suitable active compound formulation, 10 mg of active compound are mixed with 0.5 ml of solvent and the concentrate is diluted to the desired concentration with solvent.

1 µl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 µg/animal: 1, 2, 4, 5, 13, 16, 17, 18, 19, 20, 21, 22, 23, 24, 25, 27, 28, 29, 30, 31, 32, 36, 38, 44, 47, 48, 49, 53, 54, 55, 56, 58, 59, 60, 61, 63, 64, 65, 68, 70, 71, 72, 76, 80, 86, 89, 90, 91, 93, 99

In this test, for example, the following compounds from the preparation examples show an efficacy of 95% at an application rate of 20 µg/animal: 57

In this test, for example, the following compounds from the preparation examples show an efficacy of 90% at an application rate of 20 µg/animal: 9, 39

In this test, for example, the following compounds from the preparation examples show an efficacy of 85% at an application rate of 20 µg/animal: 69

In this test, for example, the following compounds from the preparation examples show an efficacy of 80% at an application rate of 20 µg/animal: 33, 34, 37, 73, 81, 83, 94

*Ctenocephalides felis*—Oral Test

Solvent: dimethyl sulfoxide

To produce a suitable active compound formulation, 10 mg of active compound are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound formulation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: 4, 29

In this test, for example, the following compounds from the preparation examples show an efficacy of 95% at an application rate of 100 ppm: 20, 63, 68, 72

In this test, for example, the following compounds from the preparation examples show an efficacy of 90% at an application rate of 100 ppm: 22, 55, 61

In this test, for example, the following compounds from the preparation examples show an efficacy of 80% at an application rate of 100 ppm: 2, 19, 21, 81

*Lucilia cuprina* Test

Solvent: dimethyl sulfoxide

To produce a suitable active compound formulation, 10 mg of active compound are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active compound formulation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: 1, 2, 4, 5, 16, 20, 21, 22, 23, 28, 29, 31, 48, 49, 53, 54, 55, 56, 59, 61, 63, 68, 70, 71, 72, 80, 93, 99

In this test, for example, the following compounds from the preparation examples show an efficacy of 98% at an application rate of 100 ppm: 19

In this test, for example, the following compounds from the preparation examples show an efficacy of 90% at an application rate of 100 ppm: 65, 77

In this test, for example, the following compounds from the preparation examples show an efficacy of 80% at an application rate of 100 ppm: 38, 90, 91

*Musca domestica* Test

Solvent: dimethyl sulfoxide

To produce a suitable active compound formulation, 10 mg of active compound are mixed with 0.5 ml of dimethyl sulfoxide, and the concentrate is diluted with water to the desired concentration.

Vessels containing a sponge treated with sugar solution and the desired concentration of active compound formulation are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 80% at an application rate of 100 ppm: 4

*Meloidogyne incognita* Test

Solvent: 125.0 parts by weight of acetone

To produce a suitable active compound formulation, 1 part by weight of active compound is mixed with the stated amount of solvent and the concentrate is diluted to the desired concentration with water.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples show an efficacy of 90% at an application rate of 20 ppm: 4

*Myzus persicae*—Spray Test

Solvent: 78 parts by weight of acetone 1.5 parts by weight of dimethylformamide

Emulsifier: alkylaryl polyglycol ether

To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active compound formulation of the desired concentration.

After 5 days, the efficacy in % is determined. 100% means that all the aphids have been killed; 0% means that no aphids have been killed.

In this test, for example, the following compounds from the preparation examples show an efficacy of 90% at an application rate of 500 g/ha: 10, 48, 50, 53, 59

In this test, for example, the following compounds from the preparation examples show an efficacy of 90% at an application rate of 100 g/ha: 39

*Nezara viridula*—Spray Test

Solvent: 78.0 parts by weight of acetone 1.5 parts by weight of dimethylformamide Emulsifier: alkylaryl polyglycol ether To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Barley plants (*Hordeum vulgare*) infected with larvae of the Southern green shield bug (*Nezara viridula*) are srayed with an active compound formulation of the desired concentration.

After 4 days, the efficacy in % is determined. 100% means that all of the shield bugs have been killed; 0% means that none of the shield bugs have been killed.

In this test, for example, the following compounds from the preparation examples show an efficacy of 100% at an application rate of 500 g/ha: 50

*Nilaparvata lugens* Test

Solvent: 78.0 parts by weight of acetone
1.5 parts by weight of dimethylformamide
Emulsifier: alkylaryl polyglycol ether To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Rice plants (*Oryza sativa*) are sprayed with the active compound formulation of the desired concentration and then infected with the brown planthopper (*Nilaparvata lugens*).

After 4 days, the efficacy in % is determined. 100% means that all of the planthoppers have been killed; 0% means that none of the planthoppers have been killed.

In this test, for example, the following compounds from the preparation examples show an efficacy of 100% at an application rate of 500 g/ha: 20, 50, 53

In this test, for example, the following compounds from the preparation examples show an efficacy of 90% at an application rate of 500 g/ha: 22

*Phaedon cochleariae*—Spray Test

Solvent: 78.0 parts by weight of acetone
1.5 parts by weight of dimethylformamide
Emulsifier: alkylaryl polyglycol ether To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active compound formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: 1, 2, 4, 5, 8, 10, 11, 13, 19, 20, 21, 22, 23, 27, 29, 31, 33, 34, 36, 37, 38, 39, 40, 43, 44, 45, 47, 48, 49, 50, 52, 53, 54, 56, 57, 58, 60, 62, 64, 66, 69, 70, 76, 79, 80, 98, 99

In this test, for example, the following compounds from the preparation examples show an efficacy of 83% at an application rate of 500 g/ha: 9, 16, 30, 35, 51, 55, 59, 67, 71, 77, 82, 91

In this test, for example, the following compounds from the preparation examples show an efficacy of 100% at an application rate of 100 g/ha: 63

*Spodoptera frugiperda*—Spray Test

Solvent: 78.0 parts by weight of acetone
1.5 parts by weight of dimethylformamide
Emulsifier: alkylaryl polyglycol ether To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active compound formulation of the desired concentration and, after drying, populated with caterpillars of the fall armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 500 g/ha: 1, 2, 4, 8, 9, 10, 11, 12, 18, 19, 20, 21, 22, 23, 25, 27, 29, 31, 32, 33, 34, 36, 37, 38, 39, 42, 44, 45, 47, 48, 49, 50, 51, 52, 53, 54, 55, 56, 57, 58, 59, 60, 61, 62, 63, 65, 66, 67, 68, 71, 74, 77, 78, 81, 99

In this test, for example, the following compounds from the preparation examples show an efficacy of 83% at an application rate of 500 g/ha: 5, 16, 24, 46, 64, 69, 72, 75, 80, 85, 86, 90

*Tetranychus urticae*—Spray Test, OP-Resistant

Solvent: 78.0 Parts by Weight of Acetone
1.5 parts by weight of dimethylformamide
Emulsifier: alkylaryl polyglycol ether To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active compound formulation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 500 g/ha: 1, 7, 10, 11, 12, 30, 48, 49, 50, 51, 53, 54, 55, 56, 58, 59, 63, 65, 72, 73, 83, 84, 89

In this test, for example, the following compounds from the preparation examples show an efficacy of 90% at an application rate of 500 g/ha: 2, 13, 21, 23, 27, 32, 34, 41, 47, 61, 62, 64, 68, 70, 75, 87

In this test, for example, the following compounds from the preparation examples shows an efficacy of 90% at an application rate of 100 g/ha: 44, 76

*Anopheles* Test (ANPHGB Surface Treatment)

Solvent: acetone+2000 ppm rapeseed oil methyl ester (RME)

To produce an appropriate active compound formulation, the active compound is dissolved in the solvent (2 mg/ml). The active compound formulation is pipetted onto a glazed tile and, after it has dried off, adult mosquitoes of the species *Anopheles gambiae* strain RSPH (homozygot kdr) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 80-100% at an application rate of 100 mg/m$^2$: 1, 2, 3, 5, 6, 11, 16, 17, 18, 19, 20, 21, 22, 23, 24, 34, 53, 70, 76, 90, 95, 98, In this test, for example, the following compounds from the preparation examples show efficacy of 80-100% at an application rate of 20 mg/m$^2$: 1, 2, 3, 5, 8, 10, 12, 13, 16, 17, 18, 19, 20, 21, 22, 23, 24, 25, 26, 28, 29, 30, 31, 48, 49, 50, 53, 54, 55, 56, 58, 59, 64, 65, 68, 70, 71, 72, 73, 76, 80, 85, 89, 93, 95, 96, 98, 99

*Anopheles* Test (ANPHFU Surface Treatment)

Solvent: acetone+2000 ppm rapeseed oil methyl ester (RME)

To produce an appropriate active compound formulation, the active compound is dissolved in the solvent (2 mg/ml). The active compound formulation is pipetted onto a glazed tile and, after it has dried off, adult mosquitoes of the species *Anopheles funestus* strain FUMOZ-R (Hunt et al., *Med Vet Entomol.* 2005 Sep.; 19 (3):271-5) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 80-100% at an application rate of 100 mg/m$^2$: 1, 2, 3, 6, 15, 18, 19, 20, 21, 22, 23, 24, 53, 70, 76, 90, In this test, for example, the following compounds from the preparation examples show efficacy of 80-100% at an application rate of 20 mg/m$^2$:1, 2, 3, 5, 10, 18, 19, 20, 21, 22, 23, 25, 28, 30, 31, 48, 49, 50, 53, 54, 55, 56, 58, 59, 64, 65, 68, 70, 71, 72, 73, 76, 80, 85, 86, 89, 96, 99

*Aedes* Test (AEDSAE Surface Treatment)

Solvent: acetone+2000 ppm rapeseed oil methyl ester (RME)

To produce an appropriate active compound formulation, the active compound is dissolved in the solvent (2 mg/ml). The active compound formulation is pipetted onto a glazed tile and, after it has dried off, adult mosquitoes of the species *Aedes aegypti* strain MONHEIM are placed onto the treated tile. The exposure time is 30 minutes. 24 hours after contact with the treated surface, mortality in % is determined. 100% means that all mosquitoes have been killed; 0% means that none of the mosquitoes have been killed.

In this test, for example, the following compounds from the preparation examples show efficacy of 80-100% at an application rate of 100 mg/m$^2$:1, 2, 3, 11, 14, 15, 16, 18, 19, 20, 21, 22, 23, 24, 53, 70, 76, 83, 90, 94, 95, In this test, for example, the following compounds from the preparation examples show efficacy of 80-100% at an application rate of 20 mg/m$^2$:1, 2, 8, 10, 11, 13, 16, 18, 19, 20, 21, 22, 23, 24, 28, 30, 31, 48, 49, 50, 53, 54, 55, 56, 58, 59, 61, 63, 64, 65, 68, 70, 71, 72, 73, 76, 80, 83, 85, 86, 89, 90, 91, 94, 96, 97, 99

The invention claimed is:

1. A compound of the formula (I)

(I)

wherein

Z represents optionally substituted naphthyl, dibenzo[b,d]furanyl, dibenzo[b,d]thiophenyl, carbazolyl, indanyl, benzothiophenyl, benzofuranyl, indolyl, fluorenyl, phenanthrenyl, anthracenyl, or represents a phenyl of the substructure formula (II)

(II)

and the substituted phenyl of the substructure formula (II) may optionally carry up to two further substituents selected from the group consisting of halogen, cyano, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylsulfanyl, ($C_3$-$C_6$)-cycloalkyl, and ($C_3$-$C_6$)-halocycloalkyl, Y represents O or S, $A^1$ represents N or —$CR^1$, $A^2$ represents N or —$CR^2$, $A^3$ represents N or —$CR^3$, $A^4$ represents N or —$CR^4$, where at least one and at most two of the atoms $A_1$, $A_2$, $A_3$ and $A_4$ in the aromatic ring represents N, X represents oxygen, sulfanyl, sulfinyl, sulfonyl, —$CH_2$, carbonyl, —CHOH, or —$NR^6$, $R^1$, $R_2$, $R^3$ and $R^4$ each independently of one another represent hydrogen, halogen, nitro, cyano, aminocarbonyl, or aminosulfonyl, in each case optionally substituted ($C_1$-$C_4$)-alkyl, ($C_2$-$C_4$)-alkenyl, ($C_2$-$C_4$)-alkynyl, ($C_3$-$C_6$)-cycloalkyl, ($C_1$-$C_4$)-alkoxy, ($C_2$-$C_4$)-alkenyloxy, ($C_2$-$C_4$)-alkynyloxy, ($C_3$-$C_6$)-cycloalkoxy, N-mono-($C_1$-$C_4$)-alkylamino, N-mono-($C_3$-$C_6$)-cycloalkylamino, N,N-di-($C_1$-$C_4$)-alkylamino, N,N-di-($C_3$-$C_6$)-cycloalkylamino, N,N—($C_3$-$C_6$)-cycloalkyl-($C_1$-$C_4$)-alkylamino, N—($C_1$-$C_4$)-alkanoylamino, N—($C_3$-$C_6$)-cycloalkanoylamino, N—($C_1$-$C_4$)-alkanoyl-N—($C_1$-$C_4$)-alkylamino, N—($C_3$-$C_6$)-cycloalkanoyl-N—($C_1$-$C_4$)-alkylamino, N—($C_3$-$C_6$)-cycloalkanoyl-N—($C_3$-$C_6$)-cycloalkylamino, N—($C_1$-$C_4$)-alkanoyl-N—($C_3$-$C_6$)-cycloalkylamino, ($C_1$-$C_4$)-alkoxycarbonyl, ($C_3$-$C_6$)-cycloalkoxycarbonyl, ($C_1$-$C_4$)-alkanoyl, ($C_3$-$C_6$)-cycloalkanoyl, ($C_1$-$C_4$)-alkylsulfanyl, ($C_1$-$C_4$)-alkylsulfinyl, ($C_1$-$C_4$)-alkylsulfonyl, ($C_3$-$C_6$)-cycloalkylsulfanyl, ($C_3$-$C_6$)-cycloalkylsulfinyl, ($C_3$-$C_6$)-cycloalkylsulfonyl, N—($C_1$-$C_4$)-alkylaminocarbonyl, N—($C_3$-$C_6$)-cycloalkylaminocarbonyl, N,N-di-($C_1$-$C_4$)-alkylaminocarbonyl, N,N-di-($C_3$-$C_6$)-cycloalkylaminocarbonyl, N,N—($C_3$-$C_6$)-cycloalkyl-($C_1$-$C_4$)-alkylaminocarbonyl, —CH=N—O—[($C_1$-$C_4$)-alkyl], —CH=N—O—[($C_3$-$C_6$)-cycloalkyl], —C[($C_1$-$C_4$)-alkyl]=N—O—[($C_1$-$C_4$)-alkyl], —C[($C_3$-$C_6$)-cycloalkyl]=N—O—[($C_1$-$C_4$)-alkyl], —C[($C_1$-$C_4$)-alkyl]=N—O—[($C_3$-$C_6$)-cycloalkyl], or —C[($C_3$-$C_6$)-cycloalkyl]=N—O—[($C_3$-$C_6$)-cycloalkyl], $R^6$ represents hydrogen or optionally substituted ($C_1$-$C_4$)-alkyl, ($C_3$-$C_6$)-cycloalkyl, ($C_1$-$C_4$)-alkanoyl, or a ring closure with $R^8$ formed by 1 to 3 $CH_2$ groups, $R^7$ represents hydrogen, or optionally substituted ($C_1$-$C_4$)-alkyl, or ($C_3$-$C_6$)-cycloalkyl, or, in the case that $R^8$ and $R^9$ do not form a ring closure, a ring closure with $R^8$ formed by 1 to 3 $CH_2$ groups, $R^8$ represents hydrogen or represents optionally substituted ($C_1$-$C_4$)-alkyl, ($C_2$-$C_4$)-alkenyl, ($C_2$-$C_4$)-alkynyl, ($C_3$-$C_6$)-cycloalkyl, or together with $R^6$ or $R^7$ is closed in a ring formed by 1 to 3 $CH_2$ groups or together with $R^9$ is closed in 4- to 6-membered heterocyclic ring which, in the case of a 5- to 6-membered heterocyclic ring, may comprise further heteroatoms, and which is optionally mono- or polysubstituted by identical or different halogen substituents, cyano or by $(C_1-C_4)$-alkyl, $(C_3-C_6)$-cycloalkyl, or $(C_1-C_4)$-alkoxy, each of which is optionally mono- or polysubstituted by identical or different halogen substituents, $R^9$ represents:
  optionally substituted: $(C_1-C_4)$-alkyl, $(C_3-C_6)$-cycloalkyl, $(C_2-C_4)$-alkenyl, $(C_2-C_4)$-alkynyl, N-mono-$(C_1-C_4)$-alkylamino, N,N-di-$(C_1-C_4)$-alkylamino, $(C_1-C_4)$-alkoxy, $(C_2-C_4)$-alkenyloxy, $(C_2-C_4)$-alkynyloxy, $(C_3-C_6)$-cycloalkoxy, $(C_1-C_4)$-alkylcarbonyl, $(C_1-C_4)$-alkylsulfinyl, $(C_1-C_4)$-alkylsulfonyl, or $(C_1-C_4)$-alkoxycarbonyl, in the case that $R^7$ represents hydrogen, or optionally substituted: $(C_1-C_4)$-alkyl, or $(C_3-C_6)$-cycloalkyl, or in the case that $R^7$ together with $R^8$ forms a 5- or 6-membered ring,
  optionally substituted: $(C_1-C_4)$-alkyl, $(C_3-C_6)$-cycloalkyl, $(C_2-C_4)$-alkenyl, $(C_2-C_4)$-alkynyl, N-mono-$(C_1-C_4)$-alkylamino, N,N-di-$(C_1-C_4)$-alkylamino, $(C_1-C_4)$-alkoxy, $(C_2-C_4)$-alkenyloxy, $(C_2-C_4)$-alkynyloxy, $(C_3-C_6)$-cycloalkoxy, $(C_1-C_4)$-alkylsulfinyl, or $(C_1-C_4)$-alkylsulfonyl, in the case that $R^7$ forms a 4-membered ring together with $R^8$, or
  $R^8$ and $R^9$ represent a 4- to 6-membered heterocyclic ring closure which, in the case of a 5- to 6-membered heterocyclic ring, may comprise further heteroatoms and is optionally mono- or polysubstituted by identical or different halogen substituents, cyano or by $(C_1-C_4)$-alkyl, $(C_3-C_6)$-cycloalkyl, or $(C_1-C_4)$-alkoxy, each of which is optionally mono- or polysubstituted by identical or different halogen substituents, $R^{10}$ represents halogen, nitro, cyano, —$SF_5$ or represents phenyl, pyrid-2-yl, pyrid-3-yl, pyrid-4-yl, thiophen-2-yl, thiophen-3-yl, $(C_1-C_4)$-alkyl, $(C_1-C_4)$-alkenyl, $(C_1-C_4)$-alkynyl, $(C_3-C_6)$-cycloalkyl, $(C_1-C_4)$-alkoxy, $(C_2-C_4)$-alkenyloxy, $(C_2-C_4)$-alkynyloxy, $(C_3-C_6)$-cycloalkoxy, $(C_1-C_4)$-alkylsulfanyl, $(C_1-C_4)$-alkylsulfinyl, $(C_1-C_4)$-alkylsulfonyl, $(C_3-C_6)$-cycloalkylsulfanyl, $(C_3-C_6)$-cycloalkylsulfinyl, $(C_3-C_6)$-cycloalkylsulfonyl, —CH=N—O—[$(C_1-C_4)$-alkyl], or —C[$(C_1-C_4)$-alkyl]=N—O—[$(C_1-C_4)$-alkyl], optionally mono- or polysubstituted by identical or different substituents from the group consisting of halogen, cyano, nitro, —$SF_5$, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkoxy, $(C_1-C_4)$-haloalkoxy, $(C_2-C_4)$-alkenyloxy, $(C_2-C_4)$-haloalkenyloxy, $(C_2-C_4)$-alkynyloxy, $(C_3-C_6)$-cycloalkoxy, $(C_3-C_6)$-halocycloalkoxy, $(C_3-C_6)$-cyclo alkyl, $(C_3-C_6)$-halocycloalkyl, $(C_1-C_4)$-alkylsulfanyl, $(C_1-C_4)$-alkylsulfinyl, $(C_1-C_4)$-alkylsulfonyl, $(C_1-C_4)$-haloalkylsulfonyl, $(C_1-C_4)$-haloalkylsulfanyl, $(C_1-C_4)$-haloalkylsulfinyl, $(C_3-C_6)$-cycloalkylsulfanyl, $(C_3-C_6)$-cycloalkylsulfinyl, $(C_3-C_6)$-cycloalkylsulfonyl, $C_6$-, $C_{10}$-, $C_{14}$-aryl, $C_6$-, $C_{10}$-, $C_{14}$-aryloxy, benzyl, benzyloxy, benzylthio, $C_6$-, $C_{10}$-, $C_{14}$-arylthio, $C_6$-, $C_{10}$-, $C_{14}$-arylamino, benzylamino, heterocyclyl, and trialkylsilyl, and $R^{11}$ represents hydrogen, halogen, cyano or nitro or represents in each case optionally substituted $(C_1-C_4)$-alkyl, $(C_3-C_5)$-cycloalkyl, $(C_1-C_4)$-alkoxy, $(C_1-C_4)$-alkylsulfanyl, $(C_1-C_4)$-alkylsulfinyl, $(C_1-C_4)$-alkylsulfonyl, —CH=N—O—[$(C_1-C_4)$-alkyl], or —C[$(C_1-C_4)$-alkyl]=N—O—[$(C_1-C_4)$-alkyl], and/or a salt, metal complex, N-oxide and tautomeric form of the compound of formula (I), with the proviso, that the compound 1-[4-(6-{2-[3-(chloromethyl)phenyl]ethyl}pyridin-3-yl)piperazin-1-yl]ethanone is excluded.

2. The compound according to claim 1, wherein

Z represents optionally substituted naphthyl, dibenzo[b,d]furanyl, dibenzo[b,d]thiophenyl, indan-4-yl, benzothiophen-4-yl, benzofuran-4-yl, or indol-4-yl, or represents substituted phenyl of the substructure formula (II) and the phenyl of the substructure formula (II) carries no further substituents apart from $R^{10}$ and $R^{11}$, Y represents O or S, $R^1$, $R^2$, $R^3$ and $R^4$ each independently of one another represent a substituent selected from the group consisting of hydrogen, halogen, nitro, and cyano, or represent $(C_1-C_4)$-alkyl, $(C_2-C_4)$-alkenyl, $(C_2-C_4)$-alkynyl, $(C_3-C_6)$-cycloalkyl, $(C_1-C_4)$-alkoxy, $(C_2-C_4)$-alkenyloxy, $(C_2-C_4)$-alkynyloxy, $(C_3-C_6)$-cycloalkoxy, $(C_1-C_4)$-alkoxycarbonyl, $(C_3-C_6)$-cycloalkoxycarbonyl, N-mono-$(C_1-C_4)$-alkylamino, N,N-di-$(C_1-C_4)$-alkylamino, $(C_1-C_4)$-alkylsulfanyl, $(C_1-C_4)$-alkylsulfinyl, $(C_1-C_4)$-alkylsulfonyl, $(C_3-C_6)$-cycloalkylsulfanyl, $(C_3-C_6)$-cycloalkylsulfinyl, or $(C_3-C_6)$-cycloalkylsulfonyl, each of which is optionally mono- or polysubstituted by identical or different substituents from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy, $(C_3-C_6)$-cycloalkyl, and $(C_3-C_6)$-halocycloalkyl, $R^6$ represents hydrogen or represents $(C_1-C_4)$-alkyl, $(C_3-C_4)$-cycloalkyl, or $(C_1-C_4)$-alkanoyl, optionally mono- or polysubstituted by identical or different halogen substituents, or a ring closure with $R^8$ formed by 1 to 3 $CH_2$ groups, $R^7$ represents hydrogen or represents $(C_1-C_4)$-alkyl, or $(C_3-C_4)$-cycloalkyl, optionally mono- or polysubstituted by identical or different halogen substituents, or, in the case that $R^8$ and $R^9$ do not form a ring closure, a ring closure with $R^8$ formed by 1 to 3 $CH_2$ groups, $R^8$ represents hydrogen or represents $(C_1-C_4)$-alkyl, $(C_2-C_4)$-alkenyl, $(C_2-C_4)$-alkynyl, or $(C_3-C_4)$-cycloalkyl, optionally mono- or polysubstituted by identical or different substituents from the group consisting of halogen, nitro, and cyano, or a ring closure together with $R^6$ or $R^7$ formed by 1 to 3 $CH_2$ groups, or a 4- to 6-membered heterocyclic ring closure together with $R^9$ which, in the case of a 5- to 6-membered heterocyclic ring, may comprise further heteroatoms selected from the group consisting of N and O and which is optionally mono- or polysubstituted by identical or different substituents from the group consisting of halogen, $(C_1-C_4)$-alkyl, and $(C_1-C_4)$-haloalkyl, $R^9$ represents:
  optionally substituted: $(C_1-C_4)$-alkyl, $(C_2-C_4)$-alkenyl, $(C_3-C_4)$-cycloalkyl, $(C_1-C_4)$-alkoxy, $(C_2-C_4)$-alkenyloxy, $(C_3-C_6)$-cycloalkoxy, $(C_1-C_4)$-alkylcarbonyl, $(C_1-C_4)$-alkylsulfinyl, $(C_1-C_4)$-alkylsulfonyl, or $(C_1-C_4)$-alkoxycarbonyl, each of which is optionally mono- or polysubstituted by identical or different substituents from the group consisting of halogen, cyano, nitro, and $(C_3-C_6)$-cycloalkyl, in the case that $R^7$ represents hydrogen or $(C_1-C_4)$-alkyl, or $(C_3-C_4)$-cycloalkyl, optionally mono- or polysubstituted by identical or different halogen substituents, or in the case that $R^7$ with $R^8$ forms a 5- or 6-membered ring, ($C_1$-$C_4$)-alkyl, ($C_2$-$C_4$)-alkenyl, ($C_3$-$C_4$)-cycloalkyl, ($C_1$-$C_4$)-alkoxy, ($C_2$-$C_4$)-alkenyloxy, ($C_3$-$C_4$)-cycloalkoxy, ($C_1$-$C_4$)-alkylsulfinyl, or ($C_1$-$C_4$)-alkylsulfonyl, in each case optionally mono- or polysubstituted by identical or different substituents from the group consisting of halogen, cyano, nitro, and ($C_3$-$C_6$)-cycloalkyl, in the case that $R^7$ forms a 4-membered ring together with $R^8$, or $R^8$ and $R^9$ represent a 4- to 6-membered heterocyclic ring closure which, in the case of a 5- to 6-membered heterocyclic ring, may contain further heteroatoms selected from the group consisting of N and O, and which is optionally mono- or polysubstituted by identical or different substituents from the group consisting of halogen, ($C_1$-$C_4$)-alkyl, and ($C_1$-$C_4$)-haloalkyl, $R^{10}$ represents halogen or represents phenyl, pyrid-2-yl, pyrid-3-yl, pyrid-4-yl, thiophen-2-yl, thiophen-3-yl, ($C_1$-$C_4$)-alkyl, ($C_1$-$C_4$)-alkenyl, ($C_1$-$C_4$)-alkynyl, ($C_3$-$C_6$)-cyclo alkyl, ($C_1$-$C_4$)-alkoxy, ($C_2$-$C_4$)-alkenyloxy, ($C_2$-$C_4$)-alkynyloxy, ($C_3$-$C_6$)-cycloalkoxy, ($C_1$-$C_4$)-alkylsulfanyl, ($C_1$-$C_4$)-alkylsulfinyl, ($C_1$-$C_4$)-alkylsulfonyl, ($C_3$-$C_6$)-cycloalkylsulfanyl, ($C_3$-$C_6$)-cycloalkylsulfinyl, ($C_3$-$C_6$)-cycloalkylsulfonyl, —CH═N—O—[($C_1$-$C_4$)-alkyl], or —C[($C_1$-$C_4$)-alkyl]═N—O—[($C_1$-$C_4$)-alkyl], optionally mono- or polysubstituted by identical or different substituents from the group consisting of halogen, cyano, nitro, ($C_1$-$C_4$)-alkyl, ($C_1$-$C_4$)-haloalkyl, ($C_1$-$C_4$)-alkoxy, ($C_1$-$C_4$)-haloalkoxy, ($C_3$-$C_6$)-cycloalkyl, and ($C_3$-$C_6$)-halocycloalkyl, and $R^{11}$ represents hydrogen, halogen, cyano or nitro, or represents ($C_1$-$C_4$)-alkyl, ($C_1$-$C_4$)-alkoxy, ($C_1$-$C_4$)-alkylsulfanyl, ($C_1$-$C_4$)-alkylsulfinyl, ($C_1$-$C_4$)-alkylsulfonyl, ($C_3$-$C_5$)-cycloalkyl, —CH═N—O—($C_1$-$C_4$)-alkyl], or —C[($C_1$-$C_4$)-alkyl]═N—O—[($C_1$-$C_4$)-alkyl], optionally mono- or polysubstituted by identical or different substituents from the group consisting of halogen, cyano, nitro, ($C_1$-$C_4$)-alkoxy, and ($C_3$-$C_6$)-cycloalkyl.

3. The compound according to claim 1 wherein

Z represents naphthyl, dibenzo[b,d]furanyl, dibenzo[b,d]thiophenyl, optionally mono- or polysubstituted by identical or different substituents from the group consisting of halogen, cyano, nitro, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylsulfanyl, ($C_1$-$C_4$)-haloalkylsulfanyl, ($C_3$-$C_6$)-cycloalkyl, ($C_3$-$C_6$)-halocycloalkyl, ($C_1$-$C_4$)-alkylcarbonyl, and ($C_1$-$C_4$)-haloalkylcarbonyl, or Z represents substituted phenyl of the substructure formula (II), at least one of the atoms $A_3$ or $A_4$ in the aromatic ring represents nitrogen, $R^1$, $R^2$, $R^3$ and $R^4$ each independently of one another represent a substituent selected from the group consisting of hydrogen, halogen, ($C_1$-$C_4$)-alkyl, ($C_1$-$C_4$)-haloalkyl, ($C_2$-$C_4$)-alkenyl, ($C_2$-$C_4$)-haloalkenyl, ($C_1$-$C_4$)-alkoxy, ($C_1$-$C_4$)-haloalkoxy, ($C_3$-$C_6$)-cycloalkyl, ($C_3$-$C_6$)-halocycloalkyl, ($C_1$-$C_4$)-alkylsulfanyl, ($C_1$-$C_4$)-alkylsulfinyl, and ($C_1$-$C_4$)-alkylsulfonyl, $R^6$ represents hydrogen, ($C_1$-$C_4$)-alkyl or a ring closure with $R^8$ formed by 1 to 3 $CH_2$ groups, $R^7$ represents hydrogen, ($C_1$-$C_4$)-alkyl, ($C_3$-$C_4$)-cycloalkyl or, in the case that $R^8$ and $R^9$ do not form a ring closure, a ring closure with $R^8$ formed by 1 to 3 $CH_2$ groups, $R^8$ represents hydrogen or represents ($C_1$-$C_4$)-alkyl, ($C_2$-$C_4$)-alkenyl, ($C_2$-$C_4$)-alkynyl, or ($C_3$-$C_4$)-cycloalkyl, optionally mono- or polysubstituted by identical or different substituents from the group consisting of halogen and a ring closure together with $R^6$ or $R^7$ formed by 1 to 3 $CH_2$ groups, and a 4- to 6-membered heterocyclic ring closure together with $R^9$ which is formed by 3 to 5 $CH_2$ groups and which is optionally mono- or polysubstituted by identical or different substituents from the group consisting of halogen, ($C_1$-$C_4$)-alkyl, and ($C_1$-$C_4$)-haloalkyl, $R^9$ represents:

($C_1$-$C_4$)-alkyl, ($C_3$-$C_6$)-cycloalkyl, ($C_1$-$C_6$)-alkoxy, or ($C_1$-$C_6$)-alkylcarbonyl, each of which is optionally mono- or polysubstituted by identical or different substituents from the group consisting of halogen, cyano, nitro, and ($C_3$-$C_6$)-cycloalkyl, in the case that $R^7$ represents hydrogen, ($C_1$-$C_4$)-alkyl, or ($C_3$-$C_4$)-cycloalkyl, in the case that $R^7$ together with $R^8$ forms a 5- or 6-membered ring, or ($C_1$-$C_4$)-alkyl, ($C_3$-$C_4$)-cycloalkyl, or ($C_1$-$C_4$)-alkoxy, each of which is optionally mono- or polysubstituted by identical or different substituents from the group consisting of halogen, cyano, nitro, and ($C_3$-$C_6$)-cycloalkyl, in the case that $R^7$ together with $R^8$ forms a 4-membered ring, or $R^8$ and $R^9$ represent a 4- to 6-membered heterocyclic ring closure which is formed by 3 to 5 $CH_2$ groups and which is optionally mono- or polysubstituted by identical or different substituents from the group consisting of halogen, ($C_1$-$C_4$)-alkyl, and ($C_1$-$C_4$)-haloalkyl, $R^{10}$ represents halogen or represents phenyl, pyrid-2-yl, pyrid-3-yl, pyrid-4-yl, thiophen-2-yl, or thiophen-3-yl, optionally mono- or polysubstituted by identical or different substituents from the group consisting of halogen, cyano, nitro, ($C_1$-$C_4$)-alkyl, ($C_1$-$C_4$)-haloalkyl, ($C_1$-$C_4$)-alkoxy, ($C_1$-$C_4$)-haloalkoxy, ($C_3$-$C_6$)-cycloalkyl, and ($C_3$-$C_6$)-halocycloalkyl, or represents ($C_1$-$C_4$)-alkyl, ($C_1$-$C_4$)-alkenyl, ($C_1$-$C_4$)-alkynyl, ($C_3$-$C_6$)-cycloalkyl, ($C_1$-$C_4$)-alkoxy, ($C_2$-$C_4$)-alkenyloxy, ($C_2$-$C_4$)-alkynyloxy, ($C_3$-$C_6$)-cycloalkoxy, ($C_1$-$C_4$)-alkylsulfanyl, ($C_1$-$C_4$)-alkylsulfinyl, ($C_1$-$C_4$)-alkylsulfonyl, ($C_3$-$C_6$)-cycloalkylsulfanyl, ($C_3$-$C_6$)-cycloalkylsulfinyl, ($C_3$-$C_6$)-cycloalkylsulfonyl, —CH═N—O—[($C_1$-$C_4$)-alkyl], or —C[($C_1$-$C_4$)-alkyl]═N—O—[($C_1$-$C_4$)-alkyl, optionally mono- or polysubstituted by identical or different substituents from the group consisting of halogen, cyano, and nitro, and $R^{11}$ represents hydrogen, halogen, cyano or nitro or represents ($C_1$-$C_4$)-alkyl, ($C_1$-$C_4$)-alkoxy, ($C_1$-$C_4$)-alkylsulfanyl, ($C_1$-$C_4$)-alkylsulfinyl, ($C_1$-$C_4$)-alkylsulfonyl, or ($C_3$-$C_5$)-cycloalkyl, optionally mono- or polysubstituted by identical or different substituents from the group consisting of halogen, cyano, and ($C_3$-$C_6$)-cycloalkyl.

4. The compound according to claim 1 wherein

Z represents naphthyl, dibenzo[b,d]furanyl, dibenzo[b,d]thiophenyl, optionally mono- or polysubstituted by identical or different substituents from the group consisting of halogen, cyano, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylsulfanyl, ($C_1$-$C_4$)-haloalkylsulfanyl, and ($C_3$-$C_6$)-cycloalkyl, or Z represents substituted phenyl of the substructure formula (II), Y represents oxygen, and X represents oxygen or —$NR^6$.

5. The compound according to claim 1 wherein
Z represents naphthyl which is optionally mono- or polysubstituted by identical or different substituents from the group consisting of halogen, cyano, $(C_1-C_4)$-alkyl, and $(C_1-C_4)$-haloalkyl, or represents unsubstituted dibenzo[b,d]furanyl or dibenzo[b,d]thiophenyl, or Z represents substituted phenyl of the substructure formula (II),
$R^1$, $R^2$, $R^3$ and $R^4$ represent a substituent selected from the group consisting of hydrogen, halogen, $(C_1-C_4)$-alkyl, $(C_1-C_4)$-haloalkyl, $(C_1-C_4)$-alkoxy and $(C_1-C_4)$-alkylsulfanyl,
$R^6$ represents hydrogen, $(C_1-C_3)$-alkyl, or a ring closure with $R^8$ formed by 1 to 2 $CH_2$ groups,
$R^7$ represents hydrogen or, in the case that $R^8$ and $R^9$ do not form a ring closure, a ring closure with $R^8$ formed by 1 to 3 $CH_2$ groups,
$R^8$ represents hydrogen or represents $(C_1-C_4)$-alkyl, optionally mono- or polysubstituted by identical or different halogen substituents, or a ring closure together with $R^6$ formed by 1 to 2 $CH_2$ groups or a ring closure together with $R^7$ formed by 1 to 3 $CH_2$ groups or a 4- to 6-membered heterocyclic ring closure together with $R^9$ which is formed by 3 to 5 $CH_2$ groups and which is optionally mono- or polysubstituted by identical or different substituents from the group consisting of halogen, $(C_1-C_4)$-alkyl, and $(C_1-C_4)$-haloalkyl,
$R^9$ represents:
$(C_1-C_6)$-alkyl, $(C_3-C_6)$-cycloalkyl, or $(C_1-C_6)$-alkoxy, each of which is optionally mono- or polysubstituted by identical or different substituents from the group consisting of halogen, cyano and $(C_3-C_6)$-cycloalkyl, or
$R^8$ and $R^9$ represent a 4- to 6-membered heterocyclic ring closure which is formed by 3 to 5 $CH_2$ groups and which is optionally mono- or polysubstituted by identical or different substituents from the group consisting of halogen, $(C_1-C_4)$-alkyl, and $(C_1-C_4)$-haloalkyl,
$R^{10}$ represents halogen, $(C_1-C_4)$-alkyl, $(C_1-C_4)$-alkoxy, or $(C_1-C_4)$-haloalkoxy or represents phenyl which is optionally mono- or polysubstituted by identical or different substituents from the group consisting of halogen, cyano, $(C_1-C_4)$-alkyl, $(C_1-C_4)$-haloalkyl, $(C_1-C_4)$-alkoxy and $(C_1-C_4)$-haloalkoxy, and
$R^{11}$ represents hydrogen, halogen, nitro or cyano or represents $(C_1-C_4)$-alkyl, $(C_3-C_5)$-cycloalkyl, or $(C_1-C_4)$-alkoxy, optionally mono- or polysubstituted by identical or different halogen substituents.
6. The compound according to claim 1 wherein
Z represents a naphthyl of the substructure formula (III):

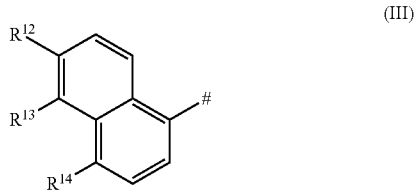

(III)

or represents unsubstituted dibenzo[b,d]furanyl or dibenzo[b,d]thiophenyl, or represents substituted phenyl of the substructure formula (II),
$R^1$ represents hydrogen, halogen, $(C_1-C_4)$-alkyl, or $(C_1-C_4)$-alkoxy,
$R^2$ represents hydrogen, halogen or $(C_1-C_4)$-haloalkyl,
$R^3$ represents hydrogen, halogen, $(C_1-C_4)$-alkoxy or $(C_1-C_4)$-alkylsulfanyl,
$R^4$ represents hydrogen or halogen,
$R^6$ represents hydrogen, or represents a piperazine ring closure with $R^8$,
$R^7$ represents hydrogen, or represents a pyrrolidine ring closure with $R^8$,
$R^8$ represents hydrogen, $(C_1-C_4)$-alkyl or represents a piperazine ring closure together with $R^6$ or represents a pyrrolidine ring closure together with $R^7$ or represents a piperidine ring closure together with $R^9$,
$R^9$ represents $(C_1-C_4)$-alkyl or $(C_1-C_4)$-alkoxy, each of which is optionally mono- or polysubstituted by identical or different substituents from the group consisting of halogen and cyano, or
$R^8$ and $R^9$ represent a piperidine ring closure,
$R^{10}$ represents halogen, $(C_1-C_4)$-alkyl, $(C_1-C_4)$-alkoxy, or $(C_1-C_4)$-haloalkoxy or represents a phenyl of the substructure formula (IV):

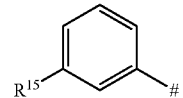

(IV)

$R^{11}$ represents hydrogen or halogen or represents $(C_1-C_4)$-alkyl or $(C_1-C_4)$-alkoxy, optionally mono- or polysubstituted by identical or different halogen substituents,
$R^{12}$, $R^{13}$ and $R^{14}$ each independently of one another represent hydrogen or halogen, and
$R^{15}$ represents hydrogen, halogen, cyano, $(C_1-C_4)$-alkyl, $(C_1-C_4)$-haloalkyl, $(C_1-C_4)$-alkoxy, or $(C_1-C_4)$-haloalkoxy.

7. The compound of claim 1, wherein one and only one of the atoms A1, A2, A3 and A4 in the aromatic ring represents N.

8. The compound of claim 1, wherein two and only two of the atoms A1, A2, A3 and A4 in the aromatic ring represents N.

9. A formulation comprising a compound according to claim 1 and at least one auxiliary.

10. The formulation according to claim 9, additionally comprising a further agrochemical active compound.

11. A method of controlling one or more animal pests, comprising bringing a compound of formula (I) according to claim 1 or a formulation thereof into contact with the animal pests.

12. A product comprising a compound of formula (I) according to claim 1 or a formulation thereof for controlling one or more animal pests.

13. The product according to claim 12, where the animal pests are mosquitoes.

14. A method of controlling one or more animal pests, comprising bringing a compound according to claim 1 or a formulation thereof into contact with a habitat of the animal pests.

15. A formulation comprising a compound according to claim 1 and at least one pharmaceutically acceptable excipient.

16. A method comprising treating a plant with a compound of formula (I) according to claim 1 or a formulation thereof.

17. A method comprising treating a seed with a compound of formula (I) according to claim 1 or a formulation thereof.

18. A method of controlling animal parasites, the method comprising treating an animal with an effective amount of a compound of formula (I) according to claim 1 or a formulation thereof.

19. The method of claim 18, wherein the animal has an ectoparasitic infection.

20. The method of claim 18, wherein the animal has an endoparasitic infection.

21. A product comprising a compound according to claim 1 or a formulation thereof for preparing one or more medicaments for controlling ectoparasites on animals.

* * * * *